United States Patent [19]

Kimura

[11] Patent Number: 4,593,090
[45] Date of Patent: Jun. 3, 1986

[54] NOVEL NITROSOUREA COMPOUNDS, METHOD FOR PREPARING SAME, AND PHARMACEUTICAL COMPOSITION CONTAINING SAME

[75] Inventor: Akira Kimura, Kamakura, Japan

[73] Assignee: Gogo Kimura, Kamakura, Japan

[21] Appl. No.: 381,731

[22] Filed: May 24, 1982

[30] Foreign Application Priority Data

Jun. 3, 1981 [JP] Japan .................................. 56-84446

[51] Int. Cl.$^4$ ............................................. C07H 15/04
[52] U.S. Cl. .................................. 536/17.4; 536/17.3; 536/17.7; 536/17.2; 536/17.8
[58] Field of Search .................... 536/17.3, 17.4, 17.7, 536/17.8, 17.9; 424/180

[56] References Cited

U.S. PATENT DOCUMENTS

| | | | |
|---|---|---|---|
| 4,057,684 | 11/1977 | Kimura et al. | 536/17.7 |
| 4,086,415 | 4/1978 | Suami et al. | 536/17.5 |
| 4,273,766 | 6/1981 | Stanek | 536/17.7 |
| 4,472,573 | 9/1984 | Morikawa et al. | 536/17.7 |

FOREIGN PATENT DOCUMENTS

| | | | |
|---|---|---|---|
| 0056458 | 7/1982 | European Pat. Off. | 536/17.7 |
| 0062329 | 10/1982 | European Pat. Off. | 536/17.7 |
| 2087876 | 6/1982 | United Kingdom | 536/17.7 |

OTHER PUBLICATIONS

Morikawa et al., "Chem. Pharm. Bull.", vol. 30, 1982, pp. 2386–2392.
Johnson et al., "Cancer Treatment Reviews", vol. 2, 1975, pp. 1–6.
Kimura et al., Japan J. Cancer Chemother 8 (5), 730–734 (1981).
Harada et al. ibid. 8 (5), 735–742 (1981).
Kanamaru et al., ibid. 10 (8), 1831–1837 (1983).
Masaoka et al., ibid. 10 (6), 1518–1523 (1983).

Primary Examiner—Johnnie R. Brown
Attorney, Agent, or Firm—Wegner & Bretschneider

[57] ABSTRACT

The invention provides pharmaceutically active agents of the structural formula

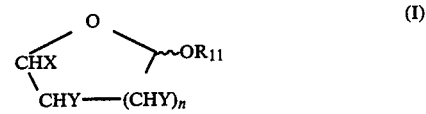

(I)

wherein
n is 1 or 2;
X is Z if n is 1 and X is $CH_2Y$, $CH_2OH$ or OH if n is 2;
Y is OH if n is 1 and, if n is 2, one of the radicals Y is Z and all other radicals Y are OH;

$$Z \text{ is } -NR_{12}-CON-CH_2-CH_2Cl; \atop \text{NO}$$

$R_{11}$ is
a $C_3$–$C_{10}$ linear or branched alkyl;
a $C_3$–$C_5$ linear or branched alkenyl or alkynyl;
a $C_2$–$C_4$ linear or branched alkyl substituted by $C_1$–$C_4$ alkoxy, methoxymethoxy, methoxyethoxy, or hydroxyethoxy radicals;
$C_{3-8}$ cycloalkyl;
$C_{1-3}$ alkyl substituted with $C_{3-8}$ cycloalkyl groups;
benzyl;
benzyl having 1 to 3 substituents selected from the group consisting of $C_{1-4}$ alkyl, $C_{1-4}$ alkoxy and cyclopropyl;
phenethyl;
tetrahydrofurfuryl, furfuryl;
morpholinoethyl, morpholinopropyl;
piperidinoethyl; and
$R_{12}$ is a $C_1$–$C_{10}$ linear or branched alkyl;
$C_3$–$C_5$ linear or branched alkenyl or alkynyl;
$C_{1-6}$ hydroxyalkyl;
$C_{2-4}$ linear or branched alkyl substituted by $C_{1-4}$ alkoxy or $C_{1-4}$ hydroxyalkoxy;
$C_{3-8}$ cycloalkyl;
$C_{1-3}$ alkyl substituted by a $C_{3-8}$ cycloalkyl radical;
benzyl, chlorobenzyl;
benzyl having 1 to 3 substituents selected from the group consisting of $C_{1-4}$ alkyl and $C_{1-4}$ alkoxy;
tetrahydrofurfuryl;
furfuryl;
morpholino;
morpholinoethyl;
morpholinopropyl;
thiophen-2-yl-methyl;
pyridylethyl; and
piperidinoethyl.

18 Claims, No Drawings

NOVEL NITROSOUREA COMPOUNDS, METHOD FOR PREPARING SAME, AND PHARMACEUTICAL COMPOSITION CONTAINING SAME

BACKGROUND OF THE INVENTION

1. Field of the Invention

The present invention relates to a novel compounds having pharmaceutical activity. More particularly, it relates to novel aldohexopyranose-, aldopentopyranose-, and aldopentofuranose-nitrosourea compounds having excellent anti-tumor activity and good safety (low toxicity), and to methods for the preparation thereof as well as pharmaceutical compositions containing said compounds. It also relates to the nitrosourea compounds having excellent diuresis activity. It further relate to the nitrosourea compounds having excellent anti-tumor and diuresis activity.

2. Description of the Prior Art

There have been known a number of carcinostatic nitroso compounds of monosaccharides and their preparation methods. These compounds are regarded to have outstanding carcinostatic activity which possess a $C_1$–$C_4$ n-alkyl substituted for the hydrogen of the 1-positioned hydroxyl group of monosaccharide and also possess a 2-chloroethylnitrosourea group attached to any one of the 2-, 3-, and 6-positioned carbon of monosaccharide. These known compounds include, for example 3-($C_1$–$C_4$ n-alkyl α- or β-D-glucopyranose-6- or 2-yl)-1-(2-chloroethyl)-1-nitrosourea (Japan Pat. Nos. 902,656 and 1,023,948; U.S. Pat. Nos. 4,057,684 and 4,156,777; Can. Pat. No. 1,044,228; Brit. Pat. No. 1,499,760; Fr. Pat. No. 75 21144; Ger. Pat. No. 2,530,416; Swit. Pat. No. 610,334; USSR Pat. No. 670,225; Span. Pat. No. 465,846; Hung. Pat. No. 172,906; etc.), 3-(methyl-α-D-glucopyranose-3-yl)-1-(2-chloroethyl)-1-nitrosourea (Japan Laid-Open Pat. No. 4324/1980; J. of Antibiotics, 33, 517–519/1980), 3-n-butyl or methyl-3-(methyl-α-D-glucopyranose-6-yl)-1-(2-chloroethyl)-1-nitrourea, 3-(2-hydroxyethyl)-3-(methyl-α-D-glucopyranose-6-yl)-1-(2-chloroethyl)-1-nitrosourea, 3-methyl-3-(methyl-α-D-mannopyranose-6-yl)-1-(2-chloroethyl)-1-nitrosourea, and 3-methyl-3-(methyl-β-D-ribofuranose-5-yl)-1-(2-chloroethyl)-1-nitrosourea (Japan Laid-Open Pat. No. 157,527/1979).

SUMMARY OF THE INVENTION

An object of the present invention is to provide novel monosaccharide compounds for anti-tumor agents.

A further object of the present invention is to provide novel nitrosourea compounds for diuretic agents.

According to one aspect of the present invention, there is provided a compound of the structural formula

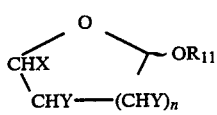  (I)

wherein
n is 1 or 2;
X is $CH_2Y$, where n is 1 and
X is $CH_2Y$ or H where n is 2, and,
one of the radicals Y is Z and all other radicals Y are OH;

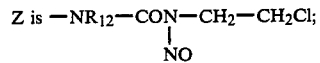

$R_{11}$ is
a $C_3$–$C_{10}$ linear or branched alkyl;
a $C_3$–$C_5$ linear or branched alkenyl or alkynyl;
a $C_2$–$C_4$ linear or branched alkyl substituted by $C_1$–$C_4$ alkoxy, methoxymethoxy, methoxyethoxy, or hydroxyethoxy radicals;
$C_{3-8}$ cycloalkyl;
$C_{1-3}$ alkyl substituted with $C_{3-8}$ cycloalkyl groups;
benzyl;
benzyl having 1 to 3 substituents selected from the group consisting of $C_{1-4}$ alkyl, $C_{1-4}$ alkoxy and cyclopropyl;
phenethyl;
tetrahydrofurfuryl, furfuryl;
morpholinoethyl, morpholinopropyl;
piperidinoethyl; and
$R_{12}$ is
a $C_1$–$C_{10}$ linear or branched alkyl;
$C_3$–$C_5$ linear or branched alkenyl or alkynyl;
$C_{1-6}$ hydroxyalkyl;
$C_{2-4}$ linear or branched alkyl substituted by $C_{1-4}$ alkoxy or $C_{1-4}$ hydroxyalkoxy;
$C_{3-8}$ cycloalkyl;
$C_{1-3}$ alkyl substituted by a $C_{3-8}$ cycloalkyl radical;
benzyl, chlorobenzyl;
benzyl having 1 to 3 substituents selected from the group consisting of $C_{1-4}$ alkyl and $C_{1-4}$ alkoxy;
tetrahydrofurfuryl;
furfuryl;
morpholino;
morpholinoethyl;
morpholinopropyl;
thiophen-2-yl-methyl;
pyridylethyl; and
piperidinoethyl.

Another aspect of the present invention, there is provided a process for preparing the above-mentioned compounds.

A further aspect of the present invention, there is provided an anti-tumor pharmaceutical composition containing a tumor inhibiting dose of at least one compound of the above-mentioned compounds.

A still further aspect of the present invention, there is provided a diuresis pharmaceutical composition containing a diuretic dose of at least one compound of the above-mentioned compounds.

A still further aspect of the present invention, there is provided a tumor inhibiting and diuretic dose of at least one compound of the above-mentioned compounds.

DETAILED DESCRIPTION OF THE PREFERRED EMBODIMENTS

The present inventor researched chemical structures of said known 2-chloroethylnitrosourea derivatives of monosaccharides, particularly, in detail, effects of kinds of aliphatic, alicyclic, and aromatic groups substituted for the hydrogen of the hydroxyl group in the 1-position of aldohexopyranose, aldopentopyranose, and aldopentofuranose as well as effects of kinds of aliphatic, alicyclic, and aromatic groups substituted for the hydrogen attached to the 3-positioned nitrogen of 2-chloroethylnitrosourea group. As a result, the inventor has found a number of novel aldohexopyranose-, aldopentopyranose-, and aldopentofuranose-(2-chloroethyl)-nitrosourea derivatives having excellent antitumor activity, or diuresis activity, or both with low toxicity. This fact is quite difficult to anticipate from the natures of known 2-chloroethylnitrosourea derivatives of the prior art.

The compounds of this invention can be structurally represented by the formula

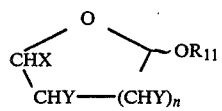 (I)

wherein n is 1 or 2;

X is $CH_2$ if n is 1 and X is $CH_2Y$, or H if n is 2;

one of the radicals Y is Z and all other radicals Y are OH;

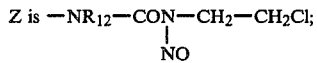

$R_{11}$ is a $C_3$–$C_{10}$ linear or branched alkyl;

a $C_3$–$C_5$ linear or branched alkenyl or alkynyl;

a $C_2$–$C_4$ linear or branched alkyl substituted by $C_1$–$C_4$ akoxy, methoxymethoxy, methoxyethoxy, or hydroxyethoxy radicals;

$C_{3-8}$ cycloalkyl;

$C_{1-3}$ alkyl substituted with $C_{3-8}$ cycloalkyl groups;

benzyl;

benzyl having 1 to 3 substituents selected from the group consisting of $C_{1-4}$ alkyl, $C_{1-4}$ alkoxy and cyclopropyl phenethyl;

tetrahydrofurfuryl, furfuryl;

morpholinoethyl, morpholinopropyl;

piperidinoethyl; and $R_{12}$ is a $C_1$–$C_{10}$ linear or branched alkyl;

$C_3$–$C_5$ linear or branched alkenyl or alkynyl;

$C_{1-6}$ hydroxyalkyl;

$C_{2-4}$ linear or branched alkyl substituted by $C_{1-4}$ alkoxy or $C_{1-4}$ hydroxyalkoxy;

$C_{3-8}$ cycloalkyl;

$C_{1-3}$ alkyl substituted by a $C_{3-8}$ cycloalkyl radical;

benzyl, chlorobenzyl;

benzyl having 1 to 3 substituents selected from the group consisting of $C_{1-4}$ alkyl and $C_{1-4}$ alkoxy;

tetrahydrofurfuryl;

furfuryl;

morpholino;

morpholinoethyl;

morpholinopropyl;

thiophen-2-yl-methyl;

pyridylethyl; and piperidinoethyl.

The novel compounds of Formula (I) above of this invention include aldohexopyranose-, aldopentopyranose-, and aldopentofuranose-nitrosourea compounds represented by the following formulae Ia, Ib and Ic, respectively:

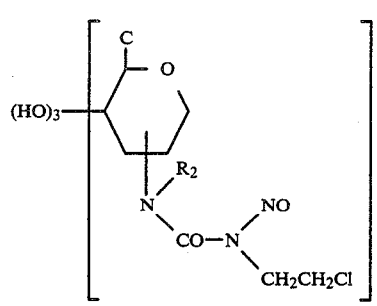

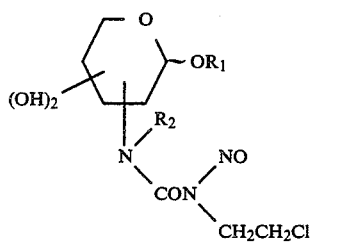

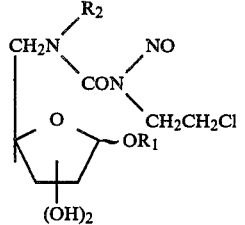

$R_1$ is Formulae Ia, Ib and Ic represents a radical selected from the group consisting of $C_3$–$C_{10}$ linear or branched alkyls; $C_3$–$C_5$ linear or branched alkenyls and alkynyls; $C_2$–$C_4$ linear or branched alkyls substituted by $C_1$–$C_3$ alkoxy, methoxymethoxy, methoxy-ethoxy, or 2-hydroxyethoxy; methyl, ethyl, and propyl having $C_3$–$C_8$ alicyclic radical; $C_3$–$C_8$ alicyclic radicals; benzyl; benzyls having 1 to 3 substituents selected from $C_1$–$C_4$ alkyls, alkoxys, or cyclopropyl; phenylethyl; tetrahydrofurfuryl; furfuryl; ethyl and propyl radicals having morpholino; and piperidino-ethyl; and $R_2$ represents a radical selected from the group consisting of $C_1$–$C_{10}$ linear or branched alkyls; $C_3$–$C_5$ linear or branched alkenyls and alkynyls; $C_1$–$C_6$ hydroxyalkyls; $C_2$–$C_4$ linear or branched alkyls having $C_1$–$C_4$ alkoxy or hydroxyalkoxy; methyl, ethyl, and propyl having $C_3$–$C_8$ alicyclic radical; $C_3$–$C_8$ alicyclic radicals; benzyl; chlorobenzyls; benzyls having 1 to 3 substituents selected from $C_1$–$C_4$ alkyls and alkoxys; tetrahydrofurfuryl; furfuryl; morpholino-radicals; ethyl and propyl having morpholino-radicals; piperidino-ethyl, pyridyl-ethyl; and thiophene-2-yl-methyl.

Said compounds of this invention exist each in two forms of stereoisomers, namely α- and β-anomers. Either each of thse anomers or mixture thereof exhibits excellent biological activity.

Structural formulae of subject compounds of this invention and of relating compounds are shown in the Tables using the nomenclature of "Diagramatic Hand Book of Saccharide Chemistry" (M. Mizuno & K. Nishizawa, published by Kyoritsu Pub. Co. Aug. 15, 1971). The present compounds will be described below in further detail.

The compounds of Formula Ia are nitrosourea derivatives of aldohexopyranoses and as D-glucopyranose, D- or L-galactopyranose, D-mannopyranose, D-altropyranose, D-talopyranose, D-fucopyranose, L-rhamnopyranose and the like. These derivatives have the substituent $R_1$ in place of the hydrogen of the hydroxyl group attached to the 1-positioned anomeric carbon of monosaccharide structure; the substituent

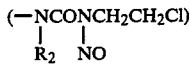

in place of any one of the hydroxyl groups attached to the 2-, 3-, 4- and 6-positioned carbons of monosaccharide structure; and three hydroxyl groups attached to the other three carbons of monosaccharide structure. The group attached to the 6-positioned carbon, although represented by (—C) in Formula Ia for simplification, is

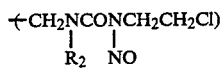

or (—CH$_2$OH) when expressed exactly. This 6-positioned carbon is found above the 6-membered ring of the pyranose type is the case of nitrosourea compounds of α-aldohexopyranoses (e.g. D-glucopyranose, D-galactopyranose, D-mannopyranose, D-altropyranose, D-talopyranose, and D-fucopyranose) and below the 6-membered ring in the case of nitrosourea compounds of L-aldohexopyranoses (e.g. L-galactopyranose and L-rhamnopyranose).

The compounds of Formula Ib are nitrosourea derivatives of aldopentopyranoses such as D-xylopyranose, D- or L-orabinopyranose, L-lyxopyranose, and the like, having the substituent $R_1$ in place of the hydrogen of the hydroxyl group attached to the 1-positioned anomeric carbon; the substituent

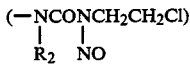

in place of any one of the hydroxyl groups attached to the 2-, 3-, and 4-position carbons; and two hydroxyl groups attached to the other two carbons.

The compounds of Formula Ic are nitrosourea derivatives of aldopentofuranoses such as D-ribofuranose, D-arabinofuranose, D-xylofuranose, L-lyxofuranose, and the like, having the substituents $R_1$ in place of the hydrogen of the hydroxyl group attached to the 1-positioned anomeric carbon; the substituent

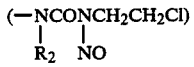

in place of the hydroxyl group attached to the 5-positioned carbon; and two hydroxyl groups attached to the other two carbons in the 2- and 3-position. The substituent

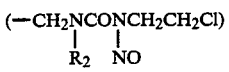

in the 5-position is found above the 5-membered ring of furanose type in the case of nitrosourea derivatives of D-aldopentofuranose (e.g. D-ribofuranose, D-arabinofuranose, and D-xylofuranose) and below the 5-membered ring in the case of nitrosourea derivatives of L-aldopentofuranoses (e.g. L-lyxofuranose).

The meaning, positions, and combining modes of substituents are the same as described above, referring to the substituents $R_1$ and

(the meaning of $R_3$ will be explained later), the hydroxy groups, and the 6-positioned (—C), in the respective formulae IIa, IIb and IIc, later shown, of secondary amine derivatives of aldohexopyranose, aldopentopyranose, and aldopentofuranose; and referring to the substituents $R_1$ and

the hydroxyl groups, and the 6-positioned (—C) in the respective formulae Va, Vb and Vc, later shown, of chloroethylurea derivatives of aldohexopyranose, aldopentopyranose, and aldopentofuranose.

Typical examples of $R_1$ are the following: linear alkyls such as n-propyl, n-butyl, n-pentyl, n-hexyl, n-heptyl, n-octyl, n-nonyl, and n-decyl; branched alkyls such as isopropyl, isobutyl, sec-butyl, tert-butyl, isopentyl, neopentyl, 1-methylbutyl, 1-ethylpropyl, tert-pentyl, 2-methylpentyl, isohexyl, 3,3-dimethyl-n-butyl, 5-methylhexyl, 2-methylheptyl, 2,2-dimethylhexyl, and 2-ethylhexyl; linear or branched alkenyls such as 2-n-propenyl, 2-methyl-2-n-propenyl, 2-n-butenyl, 3-n-butenyl, and 2-methyl-3-n-butenyl; linear or branched alkynyls such as 2-n-propynyl, 2-n-butynyl, 3-n-butynyl, and 2-methyl-3-n-butynyl; $C_2$–$C_4$ linear or branched alkyls substituted by lower alkoxy group (methoxy, ethoxy, or propoxy), methoxymethoxy, or 2-hydroxyethoxy, such as 2-methoxyethyl, 2-methoxy-n-propyl, 3-methoxy-n-propyl, 1-methyl-2-methoxyethyl, 2,3-dimethoxy-n-propyl, 3-methoxy-n-butyl, 2-ethoxyethyl, 3-ethoxy-n-propyl, 3-(n-propoxy)-n-propyl, 2-(methoxymethoxy)ethyl, 2-(2-methoxyethoxy)ethyl, 2-(2-hydroxyethoxy)ethyl, and 2,2-diethoxyethyl; alicyclic radicals such as cyclopropylmethyl, α-methylcyclopropylmethyl, 2-cyclopropylethyl, cyclobutylmethyl, cyclobutylethyl, cyclopentylmethyl, cyclopentylethyl, 3-cyclopentyl-n-propyl, cyclohexylmethyl, cyclohexylethyl, cyclopropyl, cyclopentyl, cyclohexyl, cycloheptyl, and cyclooctyl; benzyl; substituted benzyls such as monomethylbenzyls (e.g. p-methylbenzyl and α-methylbenzyl), monoethylbenzyls (e.g. α-ethylbenzyl), monopropylbenzyls (e.g. p-n-propylbenzyl), α-cyclopropylbenzyl, trimethylbenzyls (e.g. 2,4,6-trimethylbenzyl), monomethoxybenzyls (e.g. p-methoxybenzyl), monoethoxybenzyls (e.g. p-ethoxybenzyl), dimethoxybenzyls (e.g. 2,3-dimethoxybenzyl), trimethoxybenzyls (e.g. 3,4,5-trimethoxybenzyl), monochlorobenzyls (e.g. p-chlorobenzyl), and monoitrobenzyls (e.g. p-nitrobenzyl); phenylethyl; tetrahydrofurfuryl; furfuryl; 2-morpholinoethyl; 3-morpholinopropyl; 1-morpholinopropyl; amd 2-piperidinoethyl.

Typical examples of $R_2$ are the following: linear alkyls such as methyl, ethyl, n-propyl, n-butyl, n-pentyl, n-hexyl, n-heptyl, n-octyl, n-nonyl, and n-decyl; branched alkyls such as isopropyl, isobutyl, sec-butyl, tert-butyl, isopentyl, neopentyl, 1-methylbutyl, 1-ethylpropyl, tert-pentyl, 2-methylpentyl, isohexyl, 3,3-dimethylbutyl, 5-methylhexyl, 2-methylheptyl, 2,2-dimethylhexyl, and 2-ethylhexyl; linear or branched alkenyls such as 2-n-propenyl, 2-methyl-2-n-propenyl, 2-n-butenyl, 3-n-butenyl, and 2-methyl-3-n-butenyl; linear or branched alkynyls such as 2-n-propynyl, 2-n-butynyl, 3-n-butynyl, and 2-methyl-3-n-butynyl; hydroxyl-having $C_2$–$C_5$ linear or branched alkyls such as 2-hydroxyethyl, 2-hydroxy-n-propyl, 3-hydroxy-n-propyl, 2-hydroxy-1-methylethyl, 1-hydroxy-n-butyl, 2-hydroxy-n-butyl, 4-hydroxy-n-butyl, 2-hydroxy-1-ethyl-n-propyl, 3-hydroxy-2-ethyl-n-propyl and 2,2-dimethyl-3-hydroxypropyl; $C_2$–$C_4$ linear or branched alkyls substituted by a lower alkoxy (such as methoxy, ethoxy, or propoxy), methoxymethoxy, or 2-hydroxyethoxy, such as 2-methoxyethyl, 2-methoxy-n-propyl, 3-methoxy-n-propyl, 1-methyl-2-methoxyethyl, 2,2-dimethoxyethyl, 2,3-dimethoxy-n-propyl, 1-methoxy-n-butyl, 3-methoxy-n-butyl, 2-ethoxyethyl, 3-ethoxy-n-propyl, 3-(n-propoxy)-n-propyl, 3-isopropyloxy-n-propyl, 2-(methoxymethoxy)ethyl, 2-(2-hydroxyethoxy)ethyl, and 2,2-diethoxyethyl; alicyclic radicals such as cyclopropylmethyl, cyclopropylethyl, cyclobutylmethyl, cyclobutylethyl, cyclopentylmethyl, cyclopentylethyl, cyclohexylmethyl, cyclohexylethyl, cyclopropyl, cyclopentyl, cyclohexyl, cycloheptyl, and cyclooctyl; benzyl; substituted benzyls such as monomethylbenzyls (e.g. p-methylbenzyl and α-methylbenzyl), monoethylbenzyls (e.g. α-ethylbenzyl), monopropylbenzyls (e.g. p-n-propylbenzyl), trimethylbenzyls (e.g. 2,4,6-trimethylbenzyl), monomethoxybenzyls (e.g. p-methoxybenzyl), monoethoxybenzyls (e.g. p-ethoxybenzyl), dimethoxybenzyls (2,3-dimethoxybenzyl), trimethoxybenzyls (e.g. 3,4,5-trimethoxybenzyl), monochlorobenzyls (e.g. p-chlorobenzyl), and mononitrobenzyls (e.g. p-nitrobenzyl); phenylethyl; tetrahydrofurfuryl; furfuryl; morpholino; 2-morpholinoethyl; 3-morpholinopropyl; 2-piperidinoethyl; 2-(4-pyridyl)ethyl; and thiophene-2-yl-methyl.

The nitrosourea compounds of Formula I according to this invention are new compounds provided with desirable biological activity. These compounds generally have low water-solubility but increased oil-solubility. These compounds can be generally synthesized by the following methods.

Synthetic method 1

The nitrosourea compounds of aldohexopyranose, aldopentopyranose, and aldopentofuranose represented by Formulae Ia, Ib and Ic, respectively, can be synthesized by reaction of secondary amine derivatives of aldohexopyranose, aldopentopyranose, and aldopentofuranose represented by the following formulae IIa, IIb and IIc:

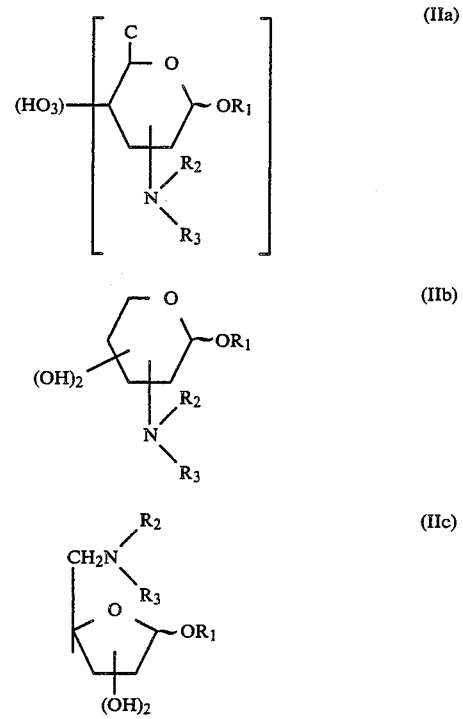

wherein $R_1$ and $R_2$ are as defined above, and $R_3$ represents hydrogen or hydroacid addition salt, with an ortho- or parasubstituted phenyl N-(2-chloroethyl)-N-nitrosocarbamate compound of the following formula III:

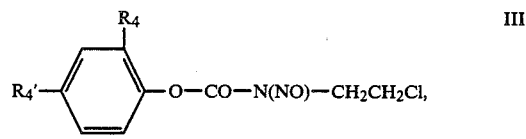

wherein one of the radicals $R_4$ and $R_4'$ is hydrogen and the other is either nitro or cyano.

The above secondary amine derivatives of Formulae IIa, IIb and IIc can be synthesized by known methods. For example, among IIa compounds, an aldohexopyranose substituted by

at the 6-position can be synthesized, as expressed by the following equation by reaction of $R_2NH_2$ with a 6-O-tosyl-, 6-O-mesyl-, or 6-halogeno-6-deoxy compound at 60°–100° C., and among IIc compounds, an aldopentofuranose substituted by

at the 5-position can be synthesized by similar reaction of $R_2NH_2$ with a 5-O-tosyl, 5-O-mesyl-, or 5-halogeno- 5-deoxy compound, easily in good yields. Similarly, 2- and

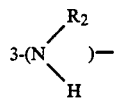

substituted compounds of IIa, IIb and IIc can be synthesized in good yields by thermal decomposition reactions of $R_2NH_2$ with 2- and 3-anhydro compounds, thereby causing rearrangement of the 2- or 3-positioned bond. Further, 2-, 3- and

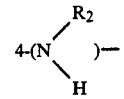

substituted compounds of IIa, IIb and IIc can be also obtained in good yields by thermal decomposition reactions of $R_2NH_2$ with halogenated corresponding monosaccharides (e.g. iodides), causing rearrangement reactions. Furthermore, intended products can be obtained by thermal hydrolysis of 4- $R_2$ substituted amino-4-deoxy-2,3-anhydro compounds in dilute aqueous alkali or dilute acetic acid, causing rearrangements. Examples by synthetic methods for the compounds of IIa, IIb and IIc are shown by the following equations (A) to (T):

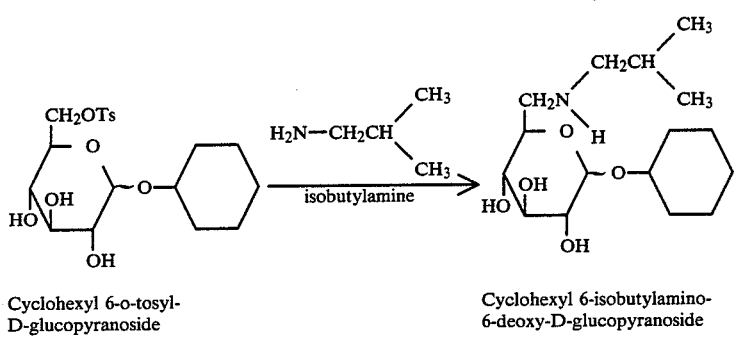

(A)

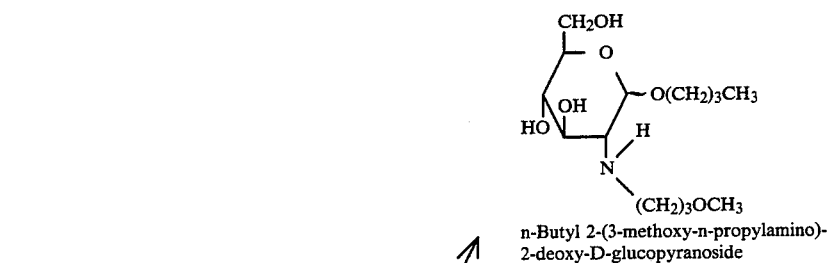

(B)

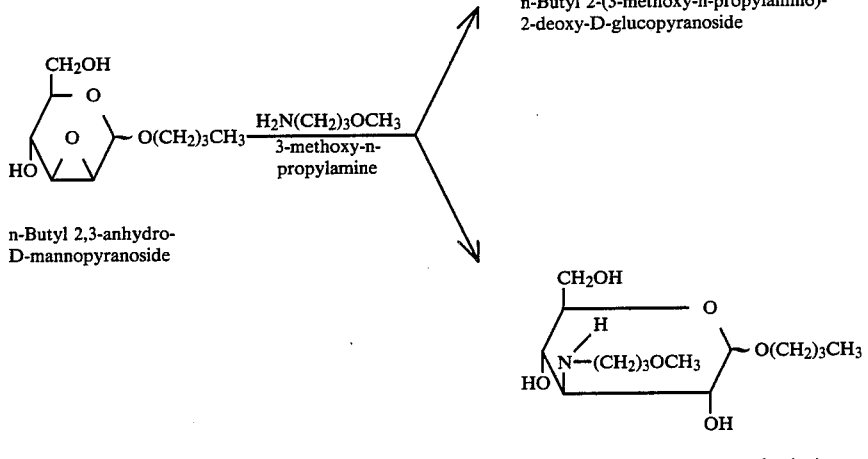

(C)

-continued
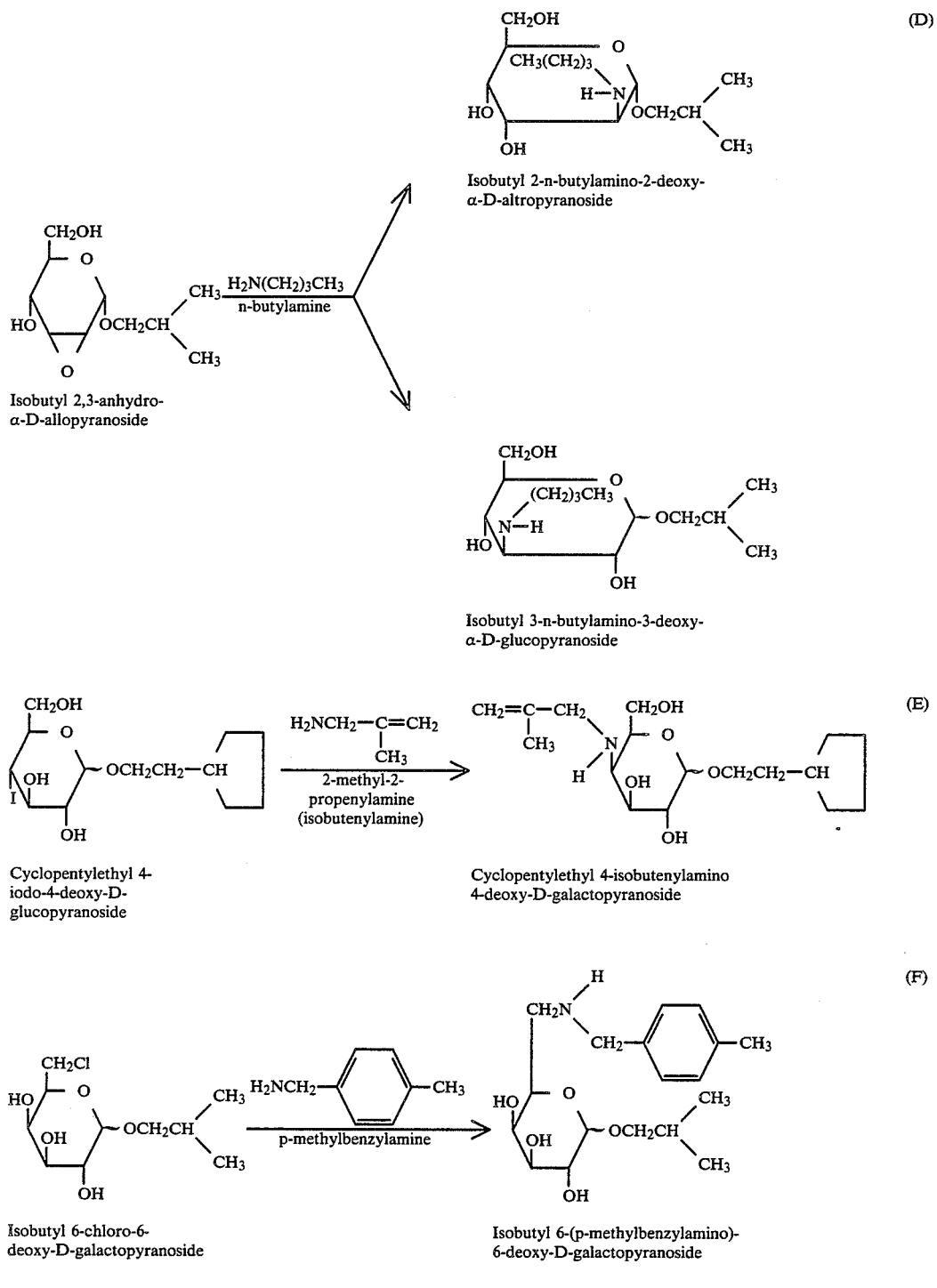
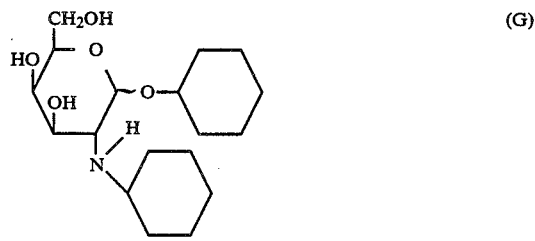

-continued

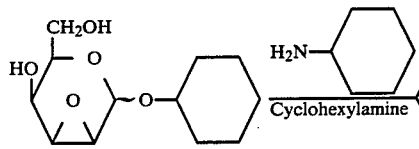
Cyclohexyl 2,3-
anhydro-D-talopyranoside

Cyclohexyl 2-cyclohexylamino-
2-deoxy-D-galactopyranoside

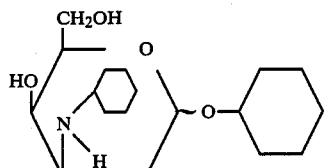
Cyclohexyl 3-cyclohexylamino-
3-deoxy-D-galactopyranoside

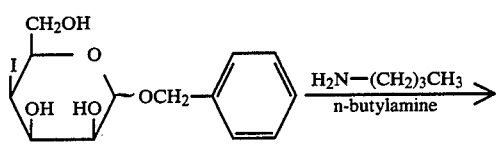
Benzyl 4-iodo-4-deoxy-
D-talopyranoside

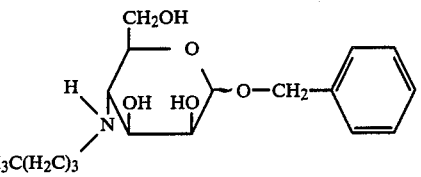 (H)
Benzyl 4-n-butylamino-4-deoxy-
D-mannopyranoside

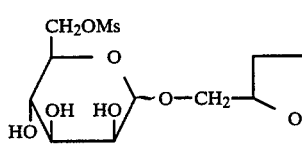
Tetrahydrofurfuryl 6-O—
mesyl-D-mannopyranoside

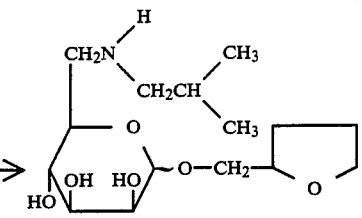 (I)
Tetrahydrofurfuryl 6-isobutylamino-
6-deoxy-D-mannopyranoside

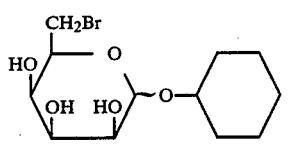
Cyclohexyl 6-bromo-6-deoxy-
D-talopyranoside

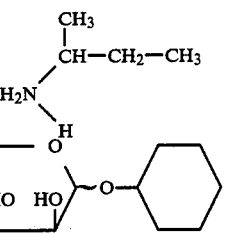 (J)
Cyclohexyl 6-sec-butylamino-6-
deoxy-D-talopyranoside

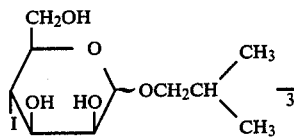
Isobutyl 4-iodo-4-deoxy-
D-mannopyranoside

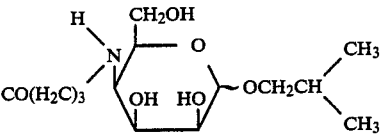 (K)
Isobutyl 4-(3-methoxy-n-propyl-
amino)-4-deoxy-D-talopyranoside

-continued

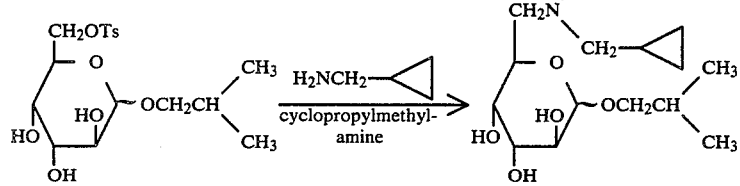

Isobutyl 6-O—tosyl-D-altropyranoside → Isobutyl 6-cyclopropylmethyl-amino-6-deoxy-D-altropyranoside (L)

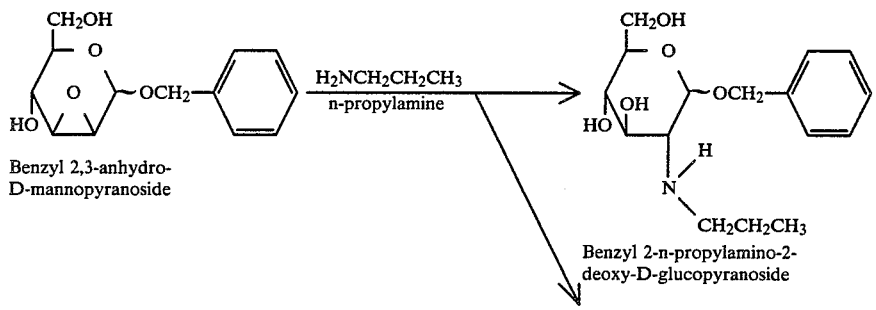

Benzyl 2,3-anhydro-D-mannopyranoside → Benzyl 2-n-propylamino-2-deoxy-D-glucopyranoside (M)

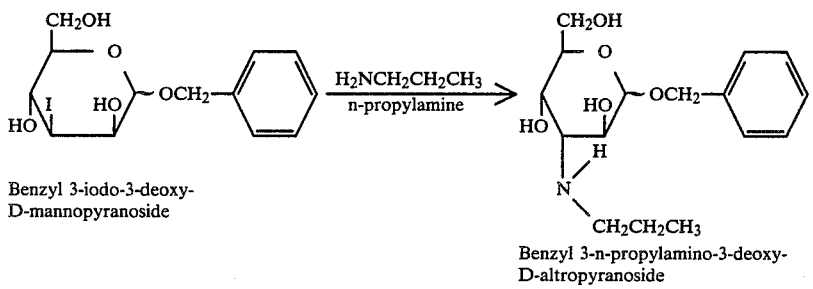

Benzyl 3-iodo-3-deoxy-D-mannopyranoside → Benzyl 3-n-propylamino-3-deoxy-D-altropyranoside (N)

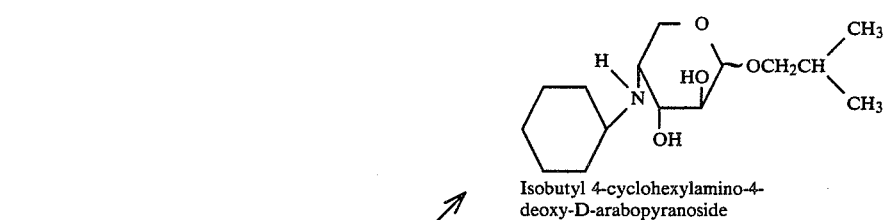

Isobutyl 4-cyclohexylamino-4-deoxy-D-arabopyranoside (O)

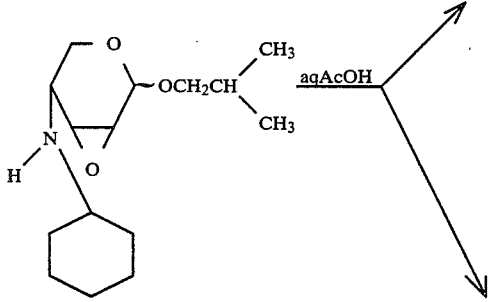

Isobutyl 2,3-anhydro-4-cyclohexylamino-4-deoxy-D-ribopyranoside

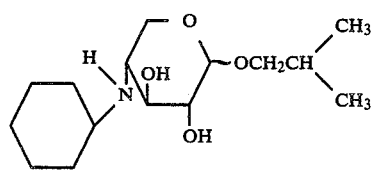

Isobutyl 4-cyclohexylamino-4-deoxy-D-xylopyranoside

-continued
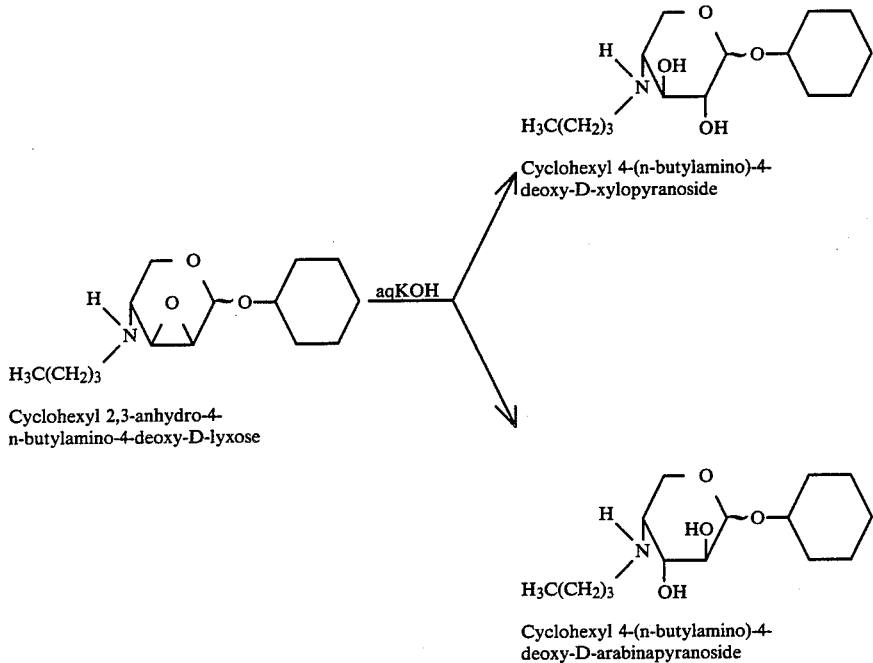
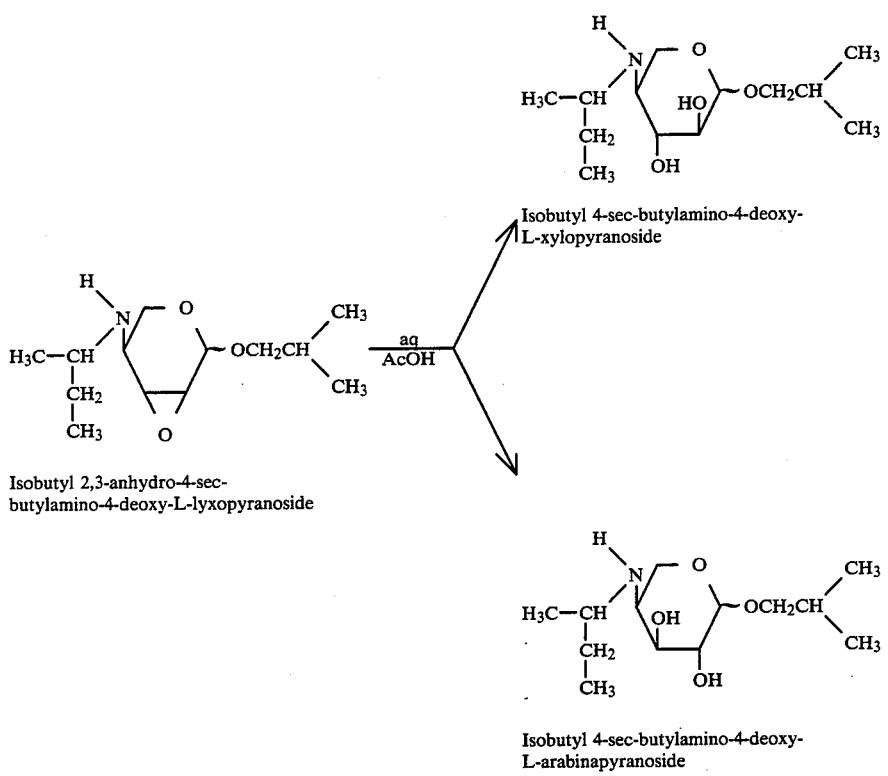
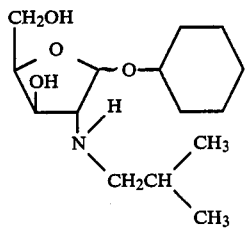

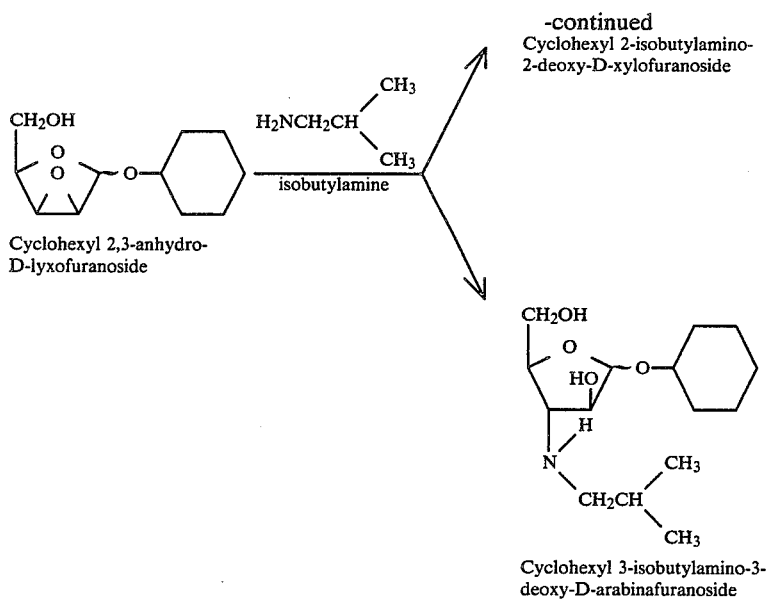

Cyclohexyl 2-isobutylamino-2-deoxy-D-xylofuranoside

Cyclohexyl 3-isobutylamino-3-deoxy-D-arabinafuranoside

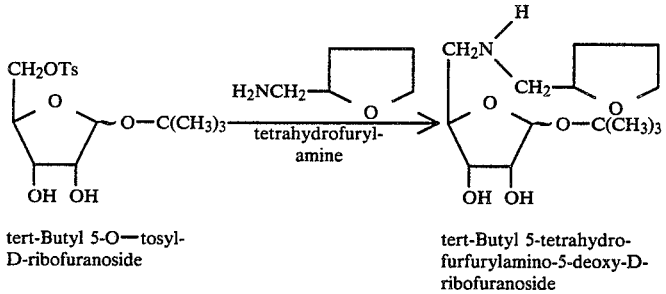

(S)

tert-Butyl 5-O—tosyl-D-ribofuranoside tert-Butyl 5-tetrahydrofurfurylamino-5-deoxy-D-ribofuranoside

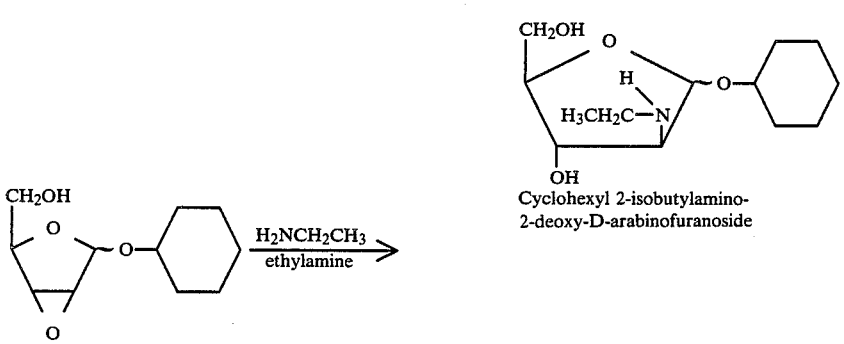

(T)

Cyclohexyl 2-isobutylamino-2-deoxy-D-arabinofuranoside

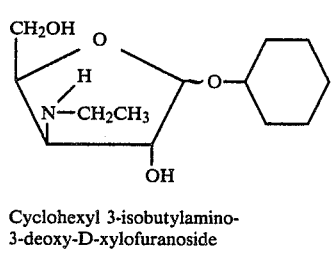

Cyclohexyl 3-isobutylamino-3-deoxy-D-xylofuranoside

The compounds of Formula IIa, IIb and IIc each involve the α-isomer, β-isomer, and mixtures thereof, which all can be used in Synthetic method 1 and Synthetic method 2 described later. The most desirable form of the starting material in Synthetic method 1 is an acid-addition salt of the basic compound (i.e. the secondary amino derivative) of Formulae IIa, IIb or IIc. This acid-addition salt must be capable of maintaining sufficient basidity of the reaction mixture to advance sufficiently the condensation replacement reaction with the compound of Formula III. Suitable acids for producing such acid-addition salts include organic acids such as formic acid, acetic acid, oxalic acid, lactic acid, fumaric acid, maleic acid, succinic acid, salicylic acid, and tartaric acid and inorganic acids such as carbonic acid and prussic acid, of which carbonic acid is most suitable.

Raw material compounds represented by Formula III, readily obtainable by known methods, are stable at low temperatures.

These compounds III include o-nitro or p-nitrophenyl N-(2-chloroethyl)-N-nitrosocarbamate and o-cyano or p-cyanophenyl N-(2-chloroethyl)-N-nitrosocarbamate, of which o-substituted compounds are preferred in order to achieve good yields of the objective products Ia, Ib and Ic and ease of purification of the products.

The condensation replacement reaction of the compound IIa, IIb or IIc with the compound III is desirably carried out in a suitable solvent at a temperature of $-20°$ to $80°$ C., preferably $-15°$ to $50°$ C. Said solvent is at least one selected from the group consisting of aliphatic, alicyclic, and aromatic mono- or poly-hydric alcohols having 1 to 12 carbon atoms, furans, nitriles, ketones, esters, ethers, amides, nitro compounds, sulfur-containing compounds, and phosphorus-containing compounds. These solvents may be used either after being dehydrated or in a state containing up to 10% by weight of water. It is preferable to use solvents among them which are capable of dissolving or suspending both of the raw materials, (IIa, IIb or IIc) and (III). Such a preferred solvent is one selected from methanol, ethanol, isopropanol (these are referred to as lower alcohols, hereinafter), tetrahydrofuran, toluene, dioxane, ethyl acetate, dimethylformamide, dimethylsulfoxide, (these six solvents will hereinafter be called "tetrahydrofuran and others"), benzene, acetonitrile, methylene chloride, ethylene dichloride, monochlorobenzene, dimethylacetoamide, nitromethane, nitroethane, carbon disulfide, and hexamethylphosphoramide or a mixture of one selected from said lower alcohols with one selected from the group consisting of "tetrahydrofuran and others", benzene, acetonitrile, isopropyl ether, carbon tetrachloride, methylene chloride, ethylene dichloride, monochlorobenzene, nitromethane, nitroethane, dimethylacetoamide, carbon disulfide and hexamethylphosphoroamide. The latter mixed solvent is particularly favorable.

In Synthetic method 1, the objective compound (Ia, Ib or Ic) in the reaction product mixture, after removal of the solvent, can be purified by crystallization or recrystallization from a suitable solvent or by column chromatography using silica gel or Kiesel gel as packing material. For the purification, it is preferable to use a solvent selected from the above-cited lower alcohols or a mixture of methanol or ethanol with a solvent selected from ethyl ether, petroleum ether, chloroform, ligroin, n-hexane, acetone and methyl ethyl keton. In particular, when the substituent $R_1$ consists of two or more radicals each having four or more carbon atoms, absolute solvents are preferably used for purification of nitrosocompounds. Also solvents containing some amounts of water may be used; for instance, a mixed solvent of lower alcohol with water may be applicable to the recrystallization at low temperature.

The objective compounds (Ia, Ib and Ic) of this invention can also be prepared with ease by the following synthetic method 2.

Synthetic method 2

According to the synthetic method 2, the objective compounds (Ia, Ib and Ic) can be synthesized by condensation reactions of secondary amino derivatives of aldohexopyranose, aldopentopyranose, and aldopentofuranose represented by the above formulae IIa, IIb and IIc, respectively, with 2-chloroethylisocyanate of the formula $OCN-CH_2OH_2Cl$ (IV), followed by nitrosation of the resulting chloroethylurea derivatives of aldohexopyranose, aldopentopyranose, and aldopentofuranose represented by the following formulae Va, Vb and Vc

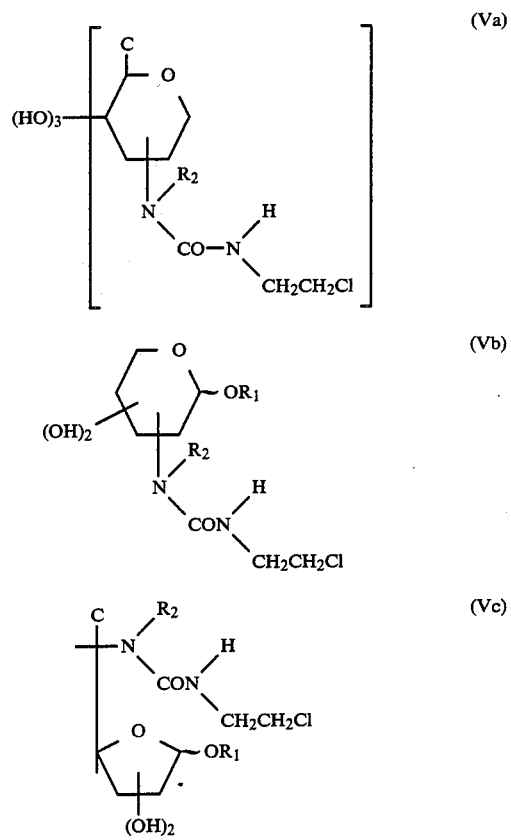

wherein $R_1$ and $R_2$ are as defined above.

The raw material compounds IIa, IIb and IIc, in the first stage reaction of this synthetic method 2, are preferably used in the form of free amine. Alternatively, they can also be used in the form of acid-addition salts (for example, besides salts of organic and inorganic weak acids as mentioned in the description of Synthetic method 1, salts of strong acids such as hydrochloric acid, sulfuric acids, phosphoric acid, and the like). In the latter case, it is desirable in particular to carry out the reaction in the presence of a deacidifying agent, which includes, for example, metal carbonates such as silver carbonate, alkaline earth metal carbonates, heavy metal carbonates, and the like, and tertiary amines such as trimethylamine, triethylamine, tripropylamines, tributylamines, tripentylamines, pyridines, quinolines, and the like. This condensation reaction is conducted in the same solvent as used in Synthetic method 1, within the temperature range $-10°$ to $100°$ C., preferably $0°$ to $50°$ C.

The second stage reaction, namely the nitrosation of compounds of Formula Va, Vb or Vc is carried out by contacting the compound with nitrous acid, dinitrogen trioxide, or dinitrogen tetraoxide in a suitable solvent. Nitrous acid for this purpose is obtainable by reaction of inorganic acids or organic acids (e.g. formic acid, acetic acid, hydrochloric acid, sulfuric acid, phosphoric acid, and the like) with an alkali metal nitrite (e.g. sodium nitrite or potassium nitrite) or an alkyl nitrite (e.g. butyl nitrite or pentyl nitrite), and is preferably used for the nitrosation during or just after this preparation reaction. Dinitrogen trioxide or dinitrogen tetraoxide, when used for the nitrosation, is preferably passed into a solution or suspension of the raw material of Formula Va, Vb or Vc in a suitable inert medium in the presence or absence of a deacidifying agent, which may be chosen suitably from sodium hydrogencarbonate, sodium carbonate, potassium hydrogencarbonate, potassium carbonate, sodium acetate and potassium acetate. Temperatures of this nitrosation are $-20°$ to $50°$ C., preferably $-10°$ to $40°$ C. Solvents suitable for this reaction are, besides the same solvents above-cited as in Synthetic method 1, absolute solvents. The objective compounds (Ia, Ib and Ic) thus obtained can be isolated and purified with ease by suitable known purification means such as recrystallization or washing with organic solvents, column chromatography, or ion exchange. The method 2 is more desirable than the method 1 in the reaction process and yield.

In Synthetic methods 1 and 2 of this invention, when starting compounds of Formula IIa, IIb or IIc are used in single forms of $\alpha$-anomer and $\beta$-anomer, objective compounds of Formula Ia, Ib or Ic are produced in single forms of $\alpha$-anomer and $\beta$-anomer, respectively. Similarly, when the starting compounds are used in a mixed form of $\alpha$- and $\beta$-anomers, the objective compounds are produced in the mixed form of $\alpha$- and $\beta$-anomers. This mixture can be resolved into $\alpha$- and $\beta$-anomers by known methods, for instance, column chromatography.

Pharmacological properties

Experiments were made for comparing pharmacological properties of the present objective compounds of Formulae Ia, Ib and Ic with those of known glucopyranose-(2-chloroethyl)-nitrosourea compounds, analogous with the present compounds. The following compounds, regarded as excellent in antitumor activity, were used as the known glucopyranose-(2-chloroethyl)-nitrosourea compounds:

3-(methyl $\alpha$-D-glucopyranose-2-yl)-1-(2-chloroethyl)-1-nitrosourea (hereinafter, shortened as 2MC$\alpha$G), 3-(methyl $\alpha$-D-glucopyranose-6-yl)-1-(2-chloroethyl)-1-nitrosourea (hereinafter, shortened as 6MC$\alpha$G), 3-(D-glucopyranose-2-yl)-1-(2-chloroethyl)-1-nitrosourea (hereinafter, shortened as DCNU), 3-($\beta$-D-glucopyranosyl)-1-(2-chloroethyl)-1-nitrosourea (hereinafter, shortened as GANU), 3-(methyl $\alpha$-D-glucopyranose-3-yl)-1-(2-chloroethyl)-1-nitrosourea (hereinafter, shortened as KCNUM), 3-(methyl $\alpha$-D-glucopyranose-6-yl)-1-(2-chloroethyl)-1-nitrosourea (hereinafter, abbreviated as 6MC$\alpha$GM)

3-n-butyl-3-(methyl $\alpha$-D-glucopyranose-6-yl)-1-(2-chloroethyl)-1-nitrosourea (hereinafter, abbreviated as 6MC$\alpha$GB), and 3-(2-hydroxyethyl)-3-(methyl $\alpha$-D-glucopyranose-6-yl)-1-(2-chloroethyl)-1-nitrosourea (hereinafter, shortened as 6MC$\alpha$GHE).

Antitumor activity

The compounds of Formulae Ia, Ib and Ic of this invention have a great antitumor effect on various tumor cells such as Ehrlich ascites carcinoma (EAC), Sarcoma 180 (S 180), Leukemia L-1210, P-388, Lewis lung tumor (L.L), Adenocarcinoma 755 (Ca 755), Melanoma B16, and rat ascites liver tumor, being capable of an increase in life span of warm-blooded animals suffering these tumors and/or capable of inhibiting proliferations of tumor cells in these animals. As example of antitumor effect thereof, the activity against Leukemia L1210 is shown below.

Activity against Leukemia L1210

Tests were conducted in accordance with the method for measuring antitumor activity of National Cancer Center Tokyo (A, Hoshi et al, Farumashia 9 464 (1973)). Test compounds were each intraperitoneally (referred to as ip) or orally (referred to as op) administered once a day for 5 successive days to a 6-membered group of femal mice (BDF$_1$ family, each weighing 20 to 23 g) 24 hours after $1 \times 10^5$ cells of Leukemia L1210 have been implantated into the abdominal cavities of the mice, and the effect was evaluated by comparing the survival days of treated groups with those of an untreated group of mice (control group) in 60-day observation. An increase percentage of life span (ILS%) was calculated from said average survival days compared with those of the control group. Further, therapeutic ratio (O.D./ILD30, referred to as T.R.) of each tested compound was calculated from the daily dosage of the compound necessary to increase said average survival days by 30% as compared with the control group (this dosage is referred to as ILS 30) and the daily dosage giving a maximum increase of life span to mice implantated with L1210 cells, namely an optimum dosage (referred to as O.D.). The results of five successive days intraperitoneal administrations of test compounds were shown in Tables I to III, and those of five successive oral administrations in Table IV.

From the results shown in Tables I to IV, it can be seen that the compounds of Formula I of this invention have excellent antitumor activities against Leukemia L1210 in both intraperitoneal and oral administrations, exhibiting therapeutic rate (T.R.) 3 to 9 times as great as known reference compounds, 6MC$\alpha$GM, 6MC$\alpha$G, 2MC$\alpha$G, KCNUM, DCNU, GANU, 6MC$\alpha$GB, and 6MC$\alpha$GHE.

TABLE I

| Compound No. | Glucopyranose nitroso compound | ILS$_{30}$ mg/kg | O.D. mg/kg | Therapeutic ratio TR | Survivors after 60 days Max. ILS % | LD$_{50}$ mg/kg |
| --- | --- | --- | --- | --- | --- | --- |
| 1 | 3-isobutyl-3-(n-propyl $\alpha$-D-glucopyranose-6-yl)-1-(2-chloroethyl)-1-nitrosourea | 2.96 | 120 | 40.5 | 6/6 >700 | 340 |
| 2 | 3-(2-methoxy-n-propyl)-3-(isopropyl $\alpha$-D-glucopyranose-6-yl)-1-(2-chloroethyl)-1-nitrosourea | 2.30 | 140 | 60.9 | 6/6 >700 | 420 |
| 3 | 3-methyl-3-(n-butyl$\alpha$-D-glucopyranose-6-yl)-1-(2-chloro- | 2.70 | 90 | 33.3 | 6/6 >700 | 260 |

TABLE I-continued

| Compound No. | Glucopyranose nitroso compound | ILS$_{30}$ mg/kg | O.D. mg/kg | Therapeutic ratio TR | Survivors after 60 days Max. ILS % | LD$_{50}$ mg/kg |
|---|---|---|---|---|---|---|
| | ethyl)-1-nitrosourea | | | | | |
| 4 | 3-methyl-3-(n-butyl β-D-glucopyranose-6-yl)-1-(2-chloroethyl)-1-nitrosourea | 2.70 | 80 | 29.6 | 6/6 >700 | 220 |
| 5 | 3-n-propyl-3-(n-butyl α-D-glucopyranose-6-yl)-1-(2-chloroethyl)-1-nitrosourea | 2.60 | 100 | 38.5 | 6/6 >700 | 325 |
| 6 | 3-n-butyl-3-(n-butyl α-D-glucopyranose-6-yl)-1-(2-chloroethyl)-1-nitrosourea | 3.00 | 120 | 40.0 | 6/6 >700 | 390 |
| 7 | 3-n-hexyl-3-(n-butyl α-D-glucopyranose-6-yl)-1-(2-chloroethyl)-1-nitrosourea | 5.20 | 140 | 26.9 | 5/6 >620 | 410 |
| 8 | 3-n-decyl-3-(n-butyl α-D-glucopyranose-6-yl)-1-(2-chloroethyl)-1-nitrosourea | 4.46 | 100 | 22.4 | 3/6 >450 | 315 |
| 9 | 3-isobutyl-3-(n-butyl α-D-glucopyranose-6-yl)-1-(2-chloroethyl)-1-nitrosourea | 3.33 | 150 | 45.0 | 6/6 >700 | 440 |
| 10 | 3-(3-methoxy-n-propyl)-3-n-butyl α-D-glucopyranose-6-yl)-1-(2-chloroethyl)-1-nitrosourea | 3.10 | 150 | 48.4 | 6/6 >700 | 480 |
| 11 | 3-(2-methoxy-n-propyl)-3-(n-butyl α-D-glucopyranose-6-yl)-1-(2-chloroethyl)-1-nitrosourea | 2.90 | 170 | 58.6 | 6/6 >700 | 495 |
| 12 | 3-[2-(2-hydroxyethoxy)ethyl]-3-(n-butyl α-D-glucopyranose-6-yl)-1-(2-chloroethyl)-1-nitrosourea | 2.85 | 170 | 59.6 | 6/6 >700 | 505 |
| 13 | 3-isopropyl-3-(isobutyl α-D-glucopyranose-6-yl)-1-(2-chloroethyl)-1-nitrosourea | 2.77 | 120 | 43.3 | 6/6 >700 | 375 |
| 14 | 3-isobutyl-3-(isobutyl α-D-glucopyranose-6-yl)-1-(2-chloroethyl)-1-nitrosourea | 3.32 | 170 | 51.2 | 6/6 >700 | 510 |
| 15 | 3-(2-methoxyethyl)-3-(isobutyl α-D-glucopyranose-6-yl)-1-(2-chloroethyl)-1-nitrosourea | 2.90 | 180 | 62.1 | 6/6 >700 | 570 |
| 16 | 3-(1-methyl-2-methoxyethyl)-3-(isobutyl α-D-glucopyranose-6-yl)-1-(2-chloroethyl)-1-nitrosourea | 2.90 | 190 | 65.6 | 6/6 >700 | 580 |
| 17 | 3-isobutyl-3-(sec-butyl α-D-glucopyranose-6-yl)-1-(2-chloroethyl)-1-nitrosourea | 3.55 | 170 | 47.9 | 6/6 >700 | 510 |
| 18 | 3-(2-methyl-2-propenyl)-3-(sec-butyl α-D-glucopyranose-6-yl)-1-(2-chloroethyl)-1-nitrosourea | 3.92 | 170 | 43.4 | 6/6 >700 | 515 |
| 19 | 3-(3-ethoxy-n-propyl)-3-(sec-butyl α-D-glucopyranose-6-yl)-1-(2-chloroethyl)-1-nitrosourea | 3.33 | 180 | 54.0 | 6/6 >700 | 560 |
| 20 | 3-(2-hydroxy-1-methylethyl)-3-(sec-butyl α-D-glucopyranose-6-yl)-1-(2-chloroethyl)-1-nitrosourea | 3.92 | 170 | 43.4 | 4/6 >430 | 560 |
| 21 | 3-(p-methoxybenzyl)-3-(isobutyl α-D-glucopyranose-6-yl)-1-(2-chloroethyl)-1-nitrosourea | 5.45 | 200 | 36.7 | 3/6 >360 | 585 |
| 22 | 3-benzyl-3-(isobutyl α-D-glucopyranose-6-yl)-1-(2-chloroethyl)-1-nitrosourea | 4.45 | 170 | 38.2 | 3/6 >350 | 510 |
| 23 | 3-tetrahydrofurfuryl-3-(isobutyl α-D-glucopyranose-6-yl)-1-(2-chloroethyl)-1-nitrosourea | 3.00 | 200 | 66.7 | 5/6 >630 | 620 |
| 24 | 3-furfuryl-3-(isobutyl α-D-glucopyranose-6-yl)-1-(2-chloroethyl)-1-nitrosourea | 3.10 | 180 | 58.1 | 5/6 >620 | 555 |
| 25 | 3-isobutyl-3-(isopentyl α-D-glucopyranose-6-yl)-1-(2-chloroethyl)-1-nitrosourea | 4.20 | 150 | 35.7 | 6/6 >700 | 450 |
| 26 | 3-isobutyl-3-(n-hexyl α-D-glucopyranose-6-yl)-1-(2-chloroethyl)-1-nitrosourea | 4.63 | 140 | 30.2 | 3/6 >370 | 415 |
| 27 | 3-(1-methyl-2-methoxyethyl)-3-(n-hexyl α-D-glucopyranose-6- | 4.67 | 170 | 36.4 | 5/6 >630 | 505 |

TABLE I-continued

| Compound No. | Glucopyranose nitroso compound | ILS$_{30}$ mg/kg | O.D. mg/kg | Therapeutic ratio TR | Survivors after 60 days Max. ILS % | LD$_{50}$ mg/kg |
|---|---|---|---|---|---|---|
| | yl)-1-(2-chloroethyl)-1-nitrosourea | | | | | |
| 28 | 3-isobutyl-3-(2-methyl-2-propyl α-D-glucopyranose-6-yl)-1-(2-chloroethyl)-1-nitrosourea | 3.00 | 130 | 43.2 | 6/6 >700 | 375 |
| 29 | 3-isobutyl-3-(2-butenyl α-D-glucopyranose-6-yl)-1-(2-chloroethyl)-1-nitrosourea | 3.64 | 140 | 38.5 | 5/6 >620 | 410 |
| 30 | 3-n-butyl-3-(3-methoxy-n-propyl-α-D-glucopyranose-6-yl)-1-(2-chloroethyl)-1-nitrosourea | 2.61 | 150 | 57.5 | 6/6 >700 | 450 |
| 31 | 3-isobutyl-3-(3-methoxy-n-propyl α-D-glucopyranose-6-yl)-1-(2-chloroethyl)-1-nitrourea | 2.65 | 170 | 64.2 | 6/6 >700 | 505 |
| 32 | 3-isobutyl-3-(3-ethoxy-n-propyl α-D-glucopyranose-6-yl)-1-(2-chloroethyl)-1-nitrosourea | 2.91 | 170 | 58.4 | 6/6 >700 | 495 |
| 33 | 3-isobutyl-3-(1-methyl-2-methoxyethyl α-D-glucopyranose-6-yl)-1-(2-chloroethyl)-1-nitrosourea | 2.62 | 170 | 64.9 | 6/6 >700 | 560 |
| 34 | 3-cyclopropylmethyl-3-(1-methyl-2-methoxyethyl α-D-glucopyranose-6-yl)-1-(2-chloroethyl)-1-nitrosourea | 2.34 | 150 | 64.1 | 6/6 >700 | 480 |
| 35 | 3-(2-methoxyethyl)-3-(1-methyl-2-methoxyethyl α-D-glucopyranose-6-yl)-1-(2-chloroethyl)-1-nitrosourea | 2.23 | 150 | 67.3 | 6/6 >700 | 470 |
| 36 | 3-isobutyl-3-(cyclohexylα-D-glucopyranose-6-yl)-1-(2-chloroethyl)-1-nitrosourea | 3.69 | 180 | 48.8 | 6/6 >700 | 580 |
| 37 | 3-sec-butyl-3-(cyclohexyl α-D-glucopyranose-6-yl)-1-(2-chloroethyl)-1-nitrosourea | 3.69 | 200 | 54.2 | 5/6 >620 | 605 |
| 38 | 3-(2-propenyl)-3-(cyclohexyl α-D-glucopyranose-6-yl)-1-(2-chloroethyl)-1-nitrosourea | 3.28 | 150 | 45.7 | 6/6 >700 | 430 |
| 39 | 3-(2-methoxyethyl)-3-(cyclohexyl α-D-glucopyranose-6-yl)-1-(2-chloroethyl)-1-nitrosourea | 2.47 | 170 | 68.8 | 6/6 >700 | 510 |
| 40 | 3-(2-ethoxyethyl)-3-(cyclohexyl α-D-glucopyranose-6-yl)-1-(2-chloroethyl)-1-nitrosourea | 2.66 | 170 | 63.9 | 6/6 >700 | 545 |
| 41 | 3-(2-methoxy-n-propyl)-3-(cyclohexyl α-D-glucopyranose-6-yl)-1-(2-chloroethyl)-1-nitrosourea | 2.72 | 180 | 66.2 | 6/6 >700 | 580 |
| 42 | 3-(1-methyl-2-methoxyethyl)-3-(cyclohexyl α-D-glucopyranose-6-yl)-1-(2-chloroethyl)-1-nitrosourea | 2.7 | 180 | 66.6 | 6/6 >700 | 595 |
| 43 | 3-(4-hydroxy-n-butyl)-3-(chlorohexyl α-D-glucopyranose-6-yl)-1-(2-chloroethyl)-1-nitrosourea | 4.68 | 160 | 34.2 | 4/6 >435 | 520 |
| 44 | 3-cyclopropylmethyl-3-(cyclohexyl α-D-glucopyranose-6-yl)-1-(2-chloroethyl)-1-nitrosourea | 3.32 | 150 | 45.2 | 6/6 >700 | 435 |
| 45 | 3-(2-cyclopentylethyl)-3-(cyclohexyl α-D-glucopyranose-6-yl)-1-(2-chloroethyl)-1-nitrosourea | 4.22 | 180 | 42.7 | 5/6 >625 | 560 |
| 46 | 3-benzyl-3-(cyclohexyl α-D-glucopyranose-6-yl)-1-(2-chloroethyl)-1-nitrosourea | 3.90 | 150 | 38.5 | 4/6 >425 | 510 |
| 47 | 3-(p-methylbenzyl)-3-(cyclohexyl α-D-glucopyranose-6-yl)-1-(2-chloroethyl)-1-nitrosourea | 4.97 | 170 | 34.2 | 4/6 >440 | 545 |
| 48 | 3-(p-methoxybenzyl)-3-(cyclohexyl α-D-glucopyranose-6-yl)-1-(2-chloroethyl)-1-nitrosourea | 4.64 | 170 | 36.6 | 4/6 >445 | 530 |
| 49 | 3-(2,3-dimethoxybenzyl)-3-(cyclohexyl α-D-glucopyranose)-6-yl)-1-(2-chloroethyl-1- | 4.74 | 170 | 35.9 | 4/6 >420 | 560 |

TABLE I-continued

| Compound No. | Glucopyranose nitroso compound | ILS$_{30}$ mg/kg | O.D. mg/kg | Therapeutic ratio TR | Survivors after 60 days Max. ILS % | LD$_{50}$ mg/kg |
| --- | --- | --- | --- | --- | --- | --- |
| | nitrosourea | | | | | |
| 50 | 3-tetrahydrofurfuryl-3-(cyclohexyl α-D-glucopyranose-6-yl)-1-(2-chloroethyl)-1-nitrosourea | 2.31 | 150 | 64.9 | 6/6 >700 | 450 |
| 51 | 3-isobutyl-3-(p-methoxybenzyl α-D-glucopyranose-6-yl)-1-(2-chloroethyl)-1-nitrosourea | 3.30 | 120 | 36.4 | 4/6 >430 | 350 |
| 52 | 3-isobutyl-3-(2,3-dimethoxybenzyl α-D-glucopyranose-6-yl)-1-(2-chloroethyl)-1-nitrosourea | 3.62 | 120 | 33.1 | 4/6 >420 | 360 |
| 53 | 3-isobutyl-3-(3,4,5-trimethoxybenzyl α-D-glucopyranose-6-yl)-1-(2-chloroethyl)-1-nitrosourea | 3.95 | 120 | 30.4 | 4/6 >425 | 350 |
| 54 | 3-isobutyl-3-(benzyl α-D-glucopyranose-6-yl)-1-(2-chloroethyl)-1-nitrosourea | 3.93 | 150 | 38.2 | 4/6 >450 | 450 |
| 55 | 3-n-butyl-3-(n-butyl α-D-glucopyranose-2-yl)-1-(2-chloroethyl)-1-nitrosourea | 6.05 | 180 | 29.8 | 3/6 >350 | 465 |
| 56 | 3-(2-methyl-2-propenyl)-3-(n-butyl α-D-glucopyranose-2-yl)-1-(2-chloroethyl)-1-nitrosourea | 5.38 | 170 | 31.6 | 3/6 >360 | 460 |
| 57 | 3-(3-methoxy-n-propyl)-3-(n-butyl α-D-glucopyranose-2-yl)-1-(2-chloroethyl)-1-nitrosourea | 5.50 | 190 | 34.5 | 3/6 >355 | 570 |
| 58 | 3-[2-(2-hydroxyethoxy)ethyl]-3-(n-butyl α-D-glucopyranose-2-yl)-1-(2-chloroethyl)-1-nitrosourea | 4.20 | 190 | 45.2 | 4/6 >422 | 585 |
| 59 | 3-isobutyl-3-(sec-butyl α-D-glucopyranose-2-yl)-1-(2-chloroethyl)-1-nitrosourea | 5.80 | 200 | 34.5 | 3/6 >348 | 605 |
| 60 | 3-(2-methyl-2-propenyl)-3-(sec-butyl α-D-glucopyranose-2-yl)-1-(2-chloroethyl)-1-nitrosourea | 7.15 | 200 | 28.0 | 3/6 >345 | 580 |
| 61 | 3-isobutyl-3-(isobutyl α-D-glucopyranose-2-yl)-1-(2-chloroethyl)-1-nitrosourea | 5.86 | 190 | 32.4 | 3/6 >340 | 595 |
| 62 | 3-benzyl-3-(isobutyl α-D-glucopyranose-2-yl)-1-(2-chloroethyl)-1-nitrosourea | 7.80 | 200 | 25.6 | 3/6 >340 | 565 |
| 63 | 3-tetrahydrofurfuryl-3-(n-butyl α-D-glucopyranose-2-yl)-1-(2-chloroethyl)-1-nitrosourea | 5.31 | 190 | 35.8 | 3/6 >350 | 595 |
| 64 | 3-(2-ethoxyethyl)-3-(cyclohexyl α-D-glucopyranose-2-yl)-1-(2-chloroethyl)-1-nitrosourea | 4.76 | 200 | 42.0 | 4/6 >450 | 650 |
| 65 | 3-(3-ethoxy-n-propyl)-3-(cyclohexyl α-D-glucopyranose-2-yl)-1-(2-chloroethyl)-1-nitrosourea | 4.44 | 200 | 45.0 | 5/6 >620 | 655 |
| 66 | 3-(4-hydroxy-n-butyl)-3-(cyclohexyl α-D-glucopyranose-2-yl)-1-(2-chloroethyl)-1-nitrosourea | 8.55 | 200 | 23.4 | 3/6 >345 | 620 |
| 67 | 3-(2-cyclopentylethyl)-3-(cyclohexyl α-D-glucopyranose-2-yl)-1-(2-chloroethyl)-1-nitrosourea | 7.5 | 200 | 28.6 | 3/6 >355 | 650 |
| 68 | 3-isobutyl-3-(3-methoxy-n-propyl α-D-glucopyranose-2-yl)-1-(2-chloroethyl)-1-nitrosourea | 4.43 | 170 | 38.4 | 4/6 >425 | 500 |
| 69 | 3-sec-butyl-3-(3-ethoxy-n-propyl α-D-glucopyranose-2-yl)-1-(2-chloroethyl)-1-nitrosourea | 4.50 | 180 | 400 | 4/6 >435 | 560 |
| 70 | 3-isobutyl-3-(1-methyl-2-methoxyethyl α-D-glucopyranose-2-yl)-1-(2-chloroethyl)-1-nitrosourea | 5.21 | 200 | 38.4 | 4/6 >420 | 645 |
| 71 | 3-(2-methoxyethyl)-3-(1-methyl-2-methoxyethyl α-D- | 4.17 | 180 | 43.2 | 6/6 >700 | 560 |

TABLE I-continued

| Compound No. | Glucopyranose nitroso compound | ILS$_{30}$ mg/kg | O.D. mg/kg | Therapeutic ratio TR | Survivors after 60 days Max. ILS % | LD$_{50}$ mg/kg |
|---|---|---|---|---|---|---|
| | glucopyranose-2-yl)-1-(2-chloroethyl)-1-nitrosourea | | | | | |
| 72 | 3-cyclopropylmethyl-3-(1-methyl-2-methoxyethyl α-D-glucopyranose-2-yl)-1-(2-chloroethyl)-1-nitrosourea | 4.53 | 180 | 39.7 | 5/6 >625 | 550 |
| 73 | 3-isobutyl-3-(cyclohexyl α-D-glucopyranose-2-yl)-1-(2-chloroethyl)-1-nitrosourea | 5.38 | 200 | 37.2 | 4/6 >420 | 670 |
| 74 | 3-(3-methoxy-n-propyl)-3-(isobutyl α-D-glucopyranose-2-yl)-1-(2-chloroethyl)-1-nitrosourea | 3.92 | 170 | 43.2 | 6/6 >700 | 560 |
| 75 | 3-cyclohexyl-3-(tetrahydrofurfuryl α-D-glucopyranose-2-yl)-1-(2-chloroethyl)-1-nitrosourea | 3.67 | 160 | 43.6 | 5/6 >625 | 505 |
| 76 | 3-n-butyl-3-(3-methoxy-n-propyl α-D-glucopyranose-3-yl)-1-(2-chloroethyl)-1-nitrosourea | 5.21 | 200 | 38.4 | 3/6 >360 | 650 |
| 77 | 3-isobutyl-3-(3-methoxy-n-propyl α-D-glucopyranose-3-yl)-1-(2-chloroethyl)-1-nitrosourea | 5.08 | 200 | 39.4 | 4/6 >425 | 685 |
| 78 | 3-isobutyl-3-(3-ethoxy-n-propyl α-D-glucopyranose-3-yl)-1-(2-chloroethyl)-1-nitrosourea | 5.33 | 200 | 37.5 | 3/6 >355 | 675 |
| 79 | 3-isobutyl-3-(1-methyl-2-methoxyethyl α-D-glucopyranose-3-yl)-1-(2-chloroethyl)-1-nitrosourea | 4.93 | 200 | 40.6 | 4/6 >430 | 690 |
| 80 | 3-(2-methoxyethyl)-3-(1-methoxyethyl α-D-glucopyranose-3-yl)-1-(2-chloroethyl)-1-nitrosourea | 4.17 | 200 | 48.0 | 5/6 >625 | 640 |
| 81 | 3-sec-butyl-3-(n-butyl β-D-glucopyranose-3-yl)-1-(2-chloroethyl)-1-nitrosourea | 5.80 | 200 | 34.5 | 3/6 >360 | 580 |
| 82 | 3-(3-methoxy-n-propyl)-3-(n-butyl α-D-glucopyranose-3-yl)-1-(2-chloroethyl)-1-nitrosourea | 5.50 | 200 | 30.4 | 3/6 >345 | 655 |
| 83 | 3-(2-methoxy-n-propyl)-3-(n-butyl α-D-glucopyranose-3-yl)-1-(2-chloroethyl)-1-nitrosourea | 5.03 | 200 | 39.8 | 4/6 >425 | 665 |
| 84 | 3-isobutyl-3-(sec-butyl α-D-glucopyranose-3-yl)-1-(2-chloroethyl)-1-nitrosourea | 5.80 | 220 | 37.9 | 3/6 >355 | 695 |
| 85 | 3-(2-methyl-2-propenyl)-3-(sec-butyl α-D-glucopyranose-3-yl)-1-(2-chloroethyl)-1-nitrosourea | 7.25 | 220 | 30.3 | 3/6 >360 | 685 |
| 86 | 3-(2-methoxy-n-propyl)-3-(cyclohexyl α-D-glucopyranose-3-yl)-1-(2-chloroethyl)-1-nitrosourea | 4.90 | 200 | 40.8 | 4/6 >430 | 695 |
| 87 | 3-(1-methyl-2-methoxyethyl)-3-(cyclohexyl α-D-glucopyranose-3-yl)-1-(2-chloroethyl)-1-nitrosourea | 4.24 | 200 | 47.2 | 6/6 >700 | 720 |
| 88 | 3-(2-cyclopentylethyl)-3-(cyclohexyl α-D-glucopyranose-3-yl)-1-(2-chloroethyl)-1-nitrosourea | 6.62 | 200 | 30.2 | 3/6 >360 | 710 |
| 89 | 3-(2-methoxyethyl)-3-(cyclohexyl α-D-glucopyranose-3-yl)-1-(2-chloroethyl)-1-nitrosourea | 2.66 | 170 | 63.9 | 6/6 >700 | 690 |
| 90 | 3-n-propyl-3-(isobutyl α-D-glucopyranose-4-yl)-1-(2-chloroethyl)-1-nitrosourea | 3.07 | 100 | 32.6 | 3/6 >350 | 325 |
| 91 | 3-(2-methyl-2-propenyl)-3-(sec-butyl α-D-glucopyranose-4-yl)-1-(2-chloroethyl)-1- | 4.65 | 150 | 32.3 | 3/6 >340 | 450 |

TABLE I-continued

| Compound No. | Glucopyranose nitroso compound | $ILS_{30}$ mg/kg | O.D. mg/kg | Therapeutic ratio TR | Survivors after 60 days Max. ILS % | $LD_{50}$ mg/kg |
|---|---|---|---|---|---|---|
| 92 | 3-isopropyl-3-(isobutyl α-D-glucopyranose-4-yl)-1-(2-chloroethyl)-1-nitrosourea | 3.14 | 100 | 31.8 | 3/6 >360 | 335 |
| 93 | 3-(2-methoxyethyl)-3-(isobutyl α-D-glucopyranose-4-yl)-1-(2-chloroethyl)-1-nitrosourea | 4.49 | 160 | 35.6 | 3/6 >370 | 530 |
| 94 | 3-(1-methyl-2-methoxyethyl)-3-(isobutyl α-D-glucopyranose-4-yl)-1-(2-chloroethyl)-1-nitrosourea | 4.43 | 160 | 36.1 | 3/6 >360 | 520 |
| 95 | 3-cyclopropylmethyl-3-(isobutyl α-D-glucopyranose-4-yl)-1-(2-chloroethyl)-1-nitrosourea | 3.82 | 120 | 31.4 | 3/6 >360 | 400 |
| 96 | 3-(1-methyl-2-methoxyethyl)-3-(sec-butyl α-D-glucopyranose-4-yl)-1-(2-chloroethyl)-1-nitrosourea | 4.46 | 150 | 33.6 | 3/6 >355 | 450 |
| 97 | 3-(2-methyl-2-propenyl)-3-(cyclohexyl α-D-glucopyranose-4-yl)-1-(2-chloroethyl)-1-nitrosourea | 3.72 | 120 | 32.3 | 3/6 >360 | 390 |

TABLE II

| Compound No. | Galactopyranose-nitroso compound | $ILS_{30}$ mg/kg | O.D. mg/kg | Therapeutic ratio TR | Survivors after 60 days | Max. ILS % | $LD_{50}$ mg/kg |
|---|---|---|---|---|---|---|---|
| 98 | 3-n-propyl-3-(cyclohexyl α-D-galactopyranose-6-yl)-1-(2-chloroethyl)-1-nitrosourea | 6.45 | 200 | 31.0 | 3/6 | >350 | 600 |
| 99 | 3-n-butyl-3-(cyclohexyl α-D-galactopyranose-6-yl)-1-(2-chloroethyl)-1-nitrosourea | 6.22 | 200 | 32.2 | 3/6 | >330 | 630 |
| 100 | 3-n-hexyl-3-(cyclohexyl α-D-galactopyranose-6-yl)-1-(2-chloroethyl)-1-nitrosourea | 6.41 | 200 | 31.2 | 3/6 | >330 | 580 |
| 101 | 3-(2-methoxyethyl)-3-(cyclohexyl α-D-galactopyranose-6-yl)-1-(2-chloroethyl)-1-nitrosourea | 3.66 | 200 | 54.6 | 6/6 | >700 | 660 |
| 102 | 3-(2-ethoxyethyl)-3-(cyclohexyl α-D-galactopyranose-6-yl)-1-(2-chloroethyl)-1-nitrosourea | 3.81 | 200 | 52.5 | 5/6 | >625 | 680 |
| 103 | 3-(2-methoxy-n-propyl)-3-(cyclohexyl α-D-galactopyranose-6-yl)-1-(2-chloroethyl)-1-nitrosourea | 3.63 | 200 | 55.1 | 5/6 | >625 | 685 |
| 104 | 3-(p-methoxybenzyl)-3-(cyclohexyl α-D-galactopyranose-6-yl)-1-(2-chloroethyl)-1-nitrosourea | 6.61 | 200 | 30.3 | 3/6 | >325 | 630 |
| 105 | 3-methyl-3-(n-butyl α-D-galactopyranose-6-yl)-1-(2-chloroethyl)-1-nitrosourea | 3.59 | 130 | 36.2 | 3/6 | >320 | 320 |
| 106 | 3-n-propyl-3-(n-butyl α-D-galactopyranose-6-yl)-1-(2-chloroethyl)-1-nitrosourea | 3.74 | 160 | 42.8 | 3/6 | >340 | 430 |
| 107 | 3-isobutyl-3-(isobutyl α-D-galactopyranose-6-yl)-1-(2-chloroethyl)-1-nitrosourea | 5.87 | 200 | 34.1 | 3/6 | >360 | 650 |
| 108 | 3-ethyl-3-(isobutyl α-D-galactopyranose-6-yl)-1-(2-chloroethyl)-1-nitrosourea | 4.24 | 130 | 30.7 | 3/6 | >320 | 390 |
| 109 | 3-(2-ethoxyethyl)-3-(isobutyl α-D-galactopyranose-6-yl)-1-(2-chloroethyl)-1-nitrosourea | 3.74 | 200 | 53.5 | 4/6 | >430 | 655 |
| 110 | 3-(1-methyl-2-methoxyethyl)-3-(isobutyl α-D-galactopyranose-6-yl)-1-(2-chloroethyl)-1-nitrosourea | 3.69 | 200 | 54.2 | 4/6 | >435 | 680 |
| 111 | 3-(p-methylbenzyl)-3-(isobutyl α-D-galactopyranose-6-yl)-1-(2-chloroethyl)-1-nitrosourea | 7.04 | 200 | 28.4 | 3/6 | >345 | 600 |
| 112 | 3-(thiophene-2-yl-methyl)-3-(isobutyl α-D-galactopyranose-6-yl)-1-(2-chloroethyl)-1-nitrosourea | 4.17 | 180 | 43.2 | 3/6 | >350 | 480 |

TABLE II-continued

| Compound No. | Galactopyranose-nitroso compound | $ILS_{30}$ mg/kg | O.D. mg/kg | Therapeutic ratio TR | Survivors after 60 days | Max. ILS % | $LD_{50}$ mg/kg |
|---|---|---|---|---|---|---|---|
| 113 | 3-isopropyl-3-(2-ethoxyethyl α-D-galactopyranose-6-yl)-1-(2-chloroethyl)-1-nitrosourea | 2.23 | 150 | 67.3 | 6/6 | >700 | 450 |
| 114 | 3-isobutyl-3-(2-ethoxyethyl α-D-galactopyranose-6-yl)-1-(2-chloroethyl)-1-nitrosourea | 2.86 | 180 | 62.9 | 6/6 | >700 | 580 |
| 115 | 3-sec-butyl-3-[2-(methoxymethoxy)ethyl]α-D-galactopyranose-6-yl)-1-(2-chloroethyl)-1-nitrosourea | 3.20 | 200 | 62.5 | 6/6 | >700 | 600 |
| 116 | 3-cyclopropylmethyl-3-(2-methoxy-n-propyl α-D-galactopyranose-6-yl)-1-(2-chloroethyl)-1-nitrosourea | 2.51 | 150 | 59.8 | 6/6 | >700 | 450 |
| 117 | 3-tetrahydrofurfuryl-3-(2-methoxy-n-propyl α-D-galactopyranose-6-yl)-1-(2-chloroethyl)-1-nitrosourea | 3.30 | 200 | 60.6 | 6/6 | >700 | 610 |
| 118 | 3-methyl-3-(n-butyl α-D-galactopyranose-2-yl)-1-(2-chloroethyl)-1-nitrosourea | 4.45 | 130 | 29.2 | 3/6 | >350 | 400 |
| 119 | 3-n-propyl-3-(n-butyl α-D-galactopyranose-2-yl)-1-(2-chloroethyl)-1-nitrosourea | 5.95 | 200 | 33.6 | 3/6 | >360 | 600 |
| 120 | 3-(p-methoxybenzyl)-3-(isobutyl α-D-galactopyranose-2-yl)-1-(2-chloroethyl)-1-nitrosourea | 6.59 | 170 | 25.8 | 3/6 | >340 | 550 |
| 121 | 3-ethyl-3-(isobutyl α-D-galactopyranose-2-yl)-1-(2-chloroethyl)-1-nitrosourea | 5.99 | 160 | 26.7 | 3/6 | >350 | 480 |
| 122 | 3-isobutyl-3-(isobutyl α-D-galactopyranose-2-yl)-1-(2-chloroethyl)-1-nitrosourea | 6.85 | 200 | 29.2 | 3/6 | >355 | 715 |
| 123 | 3-(2-ethoxyethyl)-3-(isobutyl α-D-galactopyranose-2-yl)-1-(2-chloroethyl)-1-nitrosourea | 4.98 | 200 | 40.2 | 3/6 | >365 | 730 |
| 124 | 3-(1-methyl-2-methoxyethyl)-3-(isobutyl α-D-galactopyranose-2-yl)-1-(2-chloroethyl)-1-nitrosourea | 5.30 | 210 | 39.6 | 3/6 | >360 | 745 |
| 125 | 3-isobutyl-3-(isobutyl α-D-galactopyranose-3-yl)-1-(2-chloroethyl)-1-nitrosourea | 7.67 | 250 | 32.6 | 3/6 | >350 | 780 |
| 126 | 3-(1-methyl-2-methoxyethyl)-3-(isobutyl α-D-galactopyranose-3-yl)-1-(2-chloroethyl)-1-nitrosourea | 6.22 | 250 | 40.2 | 3/6 | >355 | 785 |
| 127 | 3-isoamyl-3-(isobutyl α-D-galactopyranose-3-yl)-1-(2-chloroethyl)-1-nitrosourea | 6.56 | 200 | 30.5 | 3/6 | >340 | 600 |
| 128 | 3-cyclohexylmethyl-3-(cyclohexyl α-D-galactopyranose-3-yl)-1-(2-chloroethyl)-1-nitrosourea | 5.99 | 200 | 33.4 | 3/6 | >350 | 650 |
| 129 | 3-isobutyl-3-(isobutyl α-D-garactopyranose-4-yl)-1-(2-chloroethyl)-1-nitrosourea | 5.21 | 200 | 38.4 | 3/6 | >350 | 600 |
| 130 | 3-(2-methyl-2-propenyl)-3-(2,3-dimethoxy-n-propyl α-D-galactopyranose-4-yl)-1-(2-chloroethyl)-1-nitrosourea | 5.06 | 160 | 31.6 | 3/6 | >340 | 525 |
| 131 | 3-isobutyl-3-(2-ethoxyethyl α-D-galacropyranose-4-yl)-1-(2-chloroethyl)-1-nitrosourea | 3.98 | 160 | 40.2 | 4/6 | >430 | 565 |
| 132 | 3-(1-methyl-2-methoxyethyl)-3-(n-butyl α-D-galactopyranose-4-yl)-1-(2-chloroethyl)-1-nitrosourea | 3.86 | 160 | 41.5 | 4/6 | >420 | 550 |
| 133 | 3-n-propyl-3-(isobutyl α-L-galactopyranose-6-yl)-1-(2-chloroethyl)-1-nitrosourea | 4.11 | 150 | 36.5 | 3/6 | >360 | 495 |
| 134 | 3-n-butyl-3-(cyclopropylmethyl α-L-galactopyranose-6-yl)-1-(2-chloroethyl)-1-nitrosourea | 3.73 | 150 | 40.2 | 3/6 | >365 | 490 |

TABLE III

| Compound No. | Nitroso Compound | ILS₃₀ mg/kg | O.D. mg/kg | Therapeutic ratio TR | Survivors after 60 days | Max. ILS % | LD₅₀ mg/kg |
|---|---|---|---|---|---|---|---|
| 135 | 3-(2-methoxyethyl)-3-(isobutyl α-D-mannopyranose-6-yl)-1-(2-chloroethyl)-1-nitrosourea | 2.92 | 200 | 68.5 | 6/6 | >700 | 620 |
| 136 | 3-(isobuty)-3-(tetrahydrofurfuryl α-D-mannopyranose-6-yl)-1-(2-chloroethyl)-1-nitrosourea | 2.94 | 200 | 68.0 | 6/6 | >700 | 600 |
| 137 | 3-cyclohexyl-3-(isobutyl α-D-mannopyranose-4-yl)-1-(2-chloroethyl)-1-nitrosourea | 3.74 | 170 | 45.5 | 4/6 | >425 | 550 |
| 138 | 3-sec-butyl-3-(benzylα-D-mannopyranose-4-yl)-1-(2-chloroethyl)-1-nitrosourea | 4.26 | 120 | 28.2 | 3/6 | >350 | 370 |
| 139 | 3-isobutyl-3-(benzyl α-D-altropyranose-6-yl)-1-(2-chloroethyl)-1-nitrosourea | 4.58 | 130 | 28.4 | 3/6 | >340 | 420 |
| 140 | 3-tetrahydrofurfuryl-3-(isobutyl α-D-altropyranose-6-yl)-1-(2-chloroethyl)-1-nitrosourea | 2.8 | 180 | 64.3 | 6/6 | >700 | 540 |
| 141 | 3-(1-methyl-2-methoxyethyl)-3-(phenyl-β-ethyl α-D-altropyranose-6-yl)-1-(2-chloroethyl)-1-nitrosourea | 4.4 | 160 | 36.4 | 3/6 | >360 | 480 |
| 142 | 3-(2-methoxyethyl)-3-(phenyl-β-ethyl α-D-altropyranose-2-yl)-1-(2-chloroethyl)-1-nitrosourea | 4.16 | 160 | 38.5 | 3/6 | >350 | 500 |
| 143 | 3-tetrahydrofurfuryl-3-(phenyl-β-ethyl α-D-altropyranose-3-yl)-1-(2-chloroethyl)-1-nitrosourea | 3.52 | 150 | 42.6 | 4/6 | >425 | 460 |
| 144 | 3-isobutyl-3-(1-methyl-2-methoxyethyl α-D-altropyranose-6-yl)-1-(2-chloroethyl)-1-nitrosourea | 2.8 | 160 | 57.1 | 6/6 | >700 | 580 |
| 145 | 3-(1-methyl-2-methoxyethyl)-3-(cyclohexyl α-D-talopyranose-6-yl)-1-(2-chloroethyl)-1-nitrosourea | 2.91 | 170 | 58.4 | 6/6 | >700 | 580 |
| 146 | 3-(3-methoxy-n-propyl)-3-(isobutyl α-D-talopyranose-6-yl)-1-(2-chloroethyl)-1-nitrosourea | 3.19 | 180 | 56.4 | 5/6 | >620 | 595 |
| 147 | 3-n-propyl-3-(cyclohexyl α-D-xylopyranose-3-yl)-1-(2-chloroethyl)-1-nitrosourea | 3.91 | 150 | 38.4 | 3/6 | >350 | 430 |
| 148 | 3-isopropyl-3-(cyclohexyl α-D-xylopyranose-4-yl)-1-(2-chloroethyl)-1-nitrosourea | 3.81 | 160 | 42.0 | 4/6 | >425 | 480 |
| 149 | 3-(2-ethoxyethyl)-3-(cyclohexyl α-D-xylopyranose-3-yl)-1-(2-chloroethyl)-1-nitrosourea | 2.9 | 170 | 58.6 | 6/6 | >700 | 540 |
| 150 | 3-isobutyl-3-(cyclohexyl α-D-xylopyranose-3-yl)-1-(2-chloroethyl)-1-nitrosourea | 3.12 | 150 | 48.1 | 4/6 | >420 | 505 |
| 151 | 3-isobutyl-3-(cyclohexyl α-D-xylopyranose-4-yl)-1-(2-chloroethyl)-1-nitrosourea | 3.21 | 150 | 46.7 | 4/6 | >425 | 490 |
| 152 | 3-cyclohexyl-3-(isobutyl α-L-arabinopyranose-4-yl)-1-(2-chloroethyl)-1-nitrosourea | 4.31 | 170 | 43.1 | 4/6 | >425 | 550 |
| 153 | 3-(2-methoxy-n-propyl)-3-(isobutyl α-L-arabinopyranose-4-yl)-1-(2-chloroethyl)-1-nitrosourea | 2.57 | 150 | 58.4 | 5/6 | >625 | 480 |
| 154 | 3-(3-methoxy-n-propyl)-3-(isobutyl α-L-arabinopyranose-4-yl)-1-(2-chloroethyl)-1-nitrosourea | 2.85 | 160 | 56.1 | 5/6 | >620 | 500 |
| 155 | 3-(2-methoxyethyl)-3-(cyclohexyl α-L-arabinopyranose-2-yl)-1-(2-chloroethyl)-1-nitrosourea | 2.64 | 160 | 60.6 | 6/6 | >700 | 520 |
| 156 | 3-tetrahydrofurfuryl-3-(cyclohexyl α-L-arabinopyranose-2-yl)-1-(2-chloroethyl)-1-nitrosourea | 2.45 | 150 | 61.2 | 6/6 | >700 | 480 |
| 157 | 3-(3-ethoxy-n-propyl)-3-(sec- | 2.94 | 170 | 57.8 | 6/6 | >700 | 550 |

TABLE III-continued

| Compound No. | Nitroso Compound | ILS$_{30}$ mg/kg | O.D. mg/kg | Therapeutic ratio TR | Survivors after 60 days | Max. ILS % | LD$_{50}$ mg/kg |
|---|---|---|---|---|---|---|---|
| | butyl α-L-arabinopyranose-2-yl)-1-(2-chloroethyl)-1-nitrosourea | | | | | | |
| 158 | 3-(3-methoxy-n-propyl)-3-(sec-butyl α-L-arabinopyranose-2-yl)-1-(2-chloroethyl)-1-nitrosourea | 3.21 | 170 | 53.0 | 6/6 | >700 | 530 |
| 159 | 3-(2-methoxy-n-propyl)-3-(iso-butyl α-D-arabinopyranose-2-yl)-1-(2-chloroethyl)-1-nitrosourea | 2.61 | 160 | 61.3 | 6/6 | >700 | 520 |
| 160 | 3-(3-methoxy-n-propyl)-3-(cyclohexyl α-D-arabinopyranose-4-yl)-1-(2-chloroethyl)-1-nitrosourea | 3.10 | 180 | 58.1 | 6/6 | >700 | 550 |
| 161 | 3-isobutyl-3-(cyclohexyl β-D-arabinofuranose-5-yl)-1-(2-chloroethyl)-1-nitrosourea | 3.18 | 150 | 47.2 | 4/6 | >440 | 460 |
| 162 | 3-isobutyl-3-(cyclohexyl β-D-arabinofuranose-2-yl)-1-(2-chloroethyl)-1-nitrosourea | 5.63 | 160 | 28.4 | 3/6 | >350 | 500 |
| 163 | 3-isobutyl-3-(cyclohexyl β-D-arabinofuranose-3-yl)-1-(2-chloroethyl)-1-nitrosourea | 4.91 | 160 | 32.6 | 3/6 | >365 | 550 |
| 164 | 3-(3-methoxy-n-propyl)-3-(isobutyl α-D-xylofuranose-5-yl)-1-(2-chloroethyl)-1-nitrosourea | 2.72 | 160 | 58.8 | 6/6 | >700 | 520 |
| 165 | 3-(3-methoxy-n-propyl)-3-(isobutyl α-D-xylofuranose-3-yl)-1-(2-chloroethyl)-1-nitrosourea | 5.57 | 160 | 28.7 | 3/6 | >340 | 480 |
| 166 | 3-isobutyl-3-(cyclohexyl α-D-xylofuranose-2-yl)-1-(2-chloroethyl)-1-nitrosourea | 4.75 | 150 | 31.6 | 3/6 | >345 | 450 |
| 167 | 3-isobutyl-3-(3-methoxy-n-propyl β-D-ribofuranose-5-yl)-1-(2-chloroethyl)-1-nitrosourea | 3.17 | 160 | 50.5 | 4/6 | >430 | 510 |
| 168 | 3-(3-methoxy-n-propyl)-3-(3-methoxy-n-propyl β-D-ribofuranose-5-yl)-1-(2-chloroethyl)-1-nitrosourea | 3.30 | 160 | 48.5 | 4/6 | >425 | 500 |
| 169 | 3-isobutyl-3-(cyclohexyl β-D-ribofuranose-5-yl)-1-(2-chloroethyl)-1-nitrosourea | 3.90 | 180 | 46.2 | 4/6 | >420 | 550 |
| 170 | 3-isobutyl-3-(tetrahydrofurfuryl β-D-ribofuranose-5-yl)-1-(2-chloroethyl)-1-nitrosourea | 3.00 | 160 | 53.3 | 5/6 | >620 | 505 |
| 171 | 3-isobutyl-3-(cyclohexyl α-L-lyxofuranose-5-yl)-1-(2-chloroethyl)-1-nitrosourea | 3.30 | 150 | 45.5 | 4/6 | >440 | 450 |
| 172 | 3-(1-methy-2-methoxyethyl)-3-(cyclopentyl α-D-glucopyranose-6-yl)-1-(2-chloroethyl)-1-nitrosourea | 2.67 | 180 | 67.3 | 6/6 | >700 | 600 |
| 173 | 3-cyclohexyl-3-(tert-butyl α-D-glucopyranose-6-yl)-1-(2-chloroethyl)-1-nitrosourea | 3.16 | 160 | 50.6 | 5/6 | >630 | 510 |
| 174 | 3-cyclohexyl-3-(3-methoxy-n-propyl α-D-glucopyranose-6-yl)-1-(2-chloroethyl)-1-nitrosourea | 2.78 | 180 | 64.8 | 6/6 | >700 | 610 |
| 175 | 3-tert-butyl-3-(isobutyl β-D-glucopyranose-6-yl)-1-(2-chloroethyl)-1-nitrosourea | 3.33 | 170 | 51.0 | 6/6 | >700 | 550 |
| 176 | 3-tert-butyl-3-(isobutyl β-D-glucopyranose-2-yl)-1-(2-chloroethyl)-1-nitrosourea | 5.90 | 180 | 30.5 | 6/6 | >700 | 620 |
| 177 | 3-tert-butyl-3-(2-methyl-2-propenyl α-D-glucopyranose-6-yl)-1-(2-chloroethyl)-1-nitrosourea | 2.75 | 180 | 65.4 | 6/6 | >700 | 550 |
| 178 | 3-tert-butyl-3-(methoxy-2-n-butyl β-D-glucopyranose-6-yl)-1-(2-chloroethyl)-1-nitrosourea | 2.71 | 180 | 66.5 | 6/6 | >700 | 570 |
| 179 | 3-tert-butyl-3-(3-methoxy-n-propyl α-D-glucopyranose-6-yl)-1-(2-chloroethyl)-1- | 2.79 | 180 | 64.4 | 6/6 | >700 | 560 |

TABLE III-continued

| Compound No. | Nitroso Compound | ILS$_{30}$ mg/kg | O.D. mg/kg | Therapeutic ratio TR | Survivors after 60 days | Max. ILS % | LD$_{50}$ mg/kg |
|---|---|---|---|---|---|---|---|
| 180 | 3-tert-butyl-3-(morpholino α-D-glucopyranose-6-yl)-1-(2-chloroethyl)-1-nitrosourea | 2.66 | 160 | 60.1 | 6/6 | >700 | 515 |
| 181 | 3-tert-butyl-3-(2-morpholinoethyl α-D-glucopyranose-6-yl)-1-(2-chloroethyl)-1-nitrosourea | 2.89 | 160 | 55.4 | 6/6 | >700 | 530 |
| 182 | 3-tert-butyl-3-(p-methoxybenzyl α-D-glucopyranose-6-yl)-1-(2-chloroethyl)-1-nitrosourea | 3.49 | 140 | 40.1 | 5/6 | >620 | 420 |
| 183 | 3-neopentyl-3-(isobutyl α-D-glucopyranose-6-yl)-1-(2-chloroethyl)-1-nitrosourea | 3.01 | 170 | 56.4 | 6/6 | >700 | 520 |
| 184 | 3-neopentyl-3-(isobutyl β-D-glucopyranose-6-yl)-1-(2-chloroethyl)-1-nitrosourea | 2.93 | 170 | 58.0 | 6/6 | >700 | 540 |
| 185 | 3-neopentyl-3-(1-methoxy-2-n-butyl α-D-glucopyranose-6-yl)-1-(2-chloroethyl)-1-nitrosourea | 2.69 | 170 | 63.1 | 6/6 | >700 | 550 |
| 186 | 3-neopentyl-3-(3-methoxy-n-propyl α-D-glucopyranose-6-yl)-1-(2-chloroethyl)-1-nitrosourea | 2.49 | 160 | 64.3 | 6/6 | >700 | 520 |
| 187 | 3-neopentyl-3-(2-ethoxyethyl α-D-glucopyranose-6-yl)-1-(2-choroethyl)-1-nitrosourea | 2.66 | 160 | 60.2 | 6/6 | >700 | 510 |
| 188 | 3-neopentyl-3-(tetrahydrofurfuryl α-D-glucopyranose-6-yl)-1-(2-chloroethyl)-1-nitrosourea | 2.72 | 170 | 62.5 | 6/6 | >700 | 550 |
| 189 | 3-(3,3-dimethyl-n-butyl)-2-(isobutyl β-D-glucopyranose-6-yl)-1-(2-chloroethyl)-1-nitrosourea | 3.10 | 150 | 48.4 | 6/6 | >700 | 480 |
| 190 | 3-(3,3-dimethyl-n-butyl)-3-(sec-butyl α-D-glucopyranose-6-yl)-1-(2-chloroethyl)-1-nitrosourea | 3.12 | 150 | 48.1 | 6/6 | >700 | 470 |
| 191 | 3-(3,3-dimethyl-n-butyl)-3-(1-methoxy-n-butyl α-D-glucopyranose-6-yl)-1-(2-chloroethyl)-1-nitrosourea | 2.64 | 160 | 60.6 | 6/6 | >700 | 560 |
| 192 | 3-(3,3-dimethyl-n-butyl)-3-(2-ethoxyethyl α-D-glucopyranose-2-yl)-1-(2-chloroethyl)-1-nitrosourea | 2.74 | 160 | 58.4 | 6/6 | >700 | 515 |
| 193 | 3-tert-butyl-3-(tetrahydrofurfuryl α-D-glucopyranose-6-yl)-1-(2-chloroethyl)-1-nitrosourea | 2.52 | 160 | 63.4 | 6/6 | >700 | 550 |
| 194 | 3-neopentyl-3-(tetrahydrofurfuryl α-D-glucopyranose-6-yl)-1-(2-chloroethyl)-1-nitrosourea | 2.56 | 160 | 62.6 | 6/6 | >700 | 560 |
| 195 | 3-tert-butyl-3-(1-methoxy-2-methoxyethyl α-D-glucopyranose-6-yl)-1-(2-chloroethyl)-1-nitrosourea | 2.89 | 160 | 55.4 | 6/6 | >700 | 540 |
| 196 | 3-neopentyl-3-(1-methoxy-sec-butyl α-D-glucopyranose-6-yl)-1-(2-chloroethyl)-1-nitrosourea | 2.52 | 160 | 63.4 | 6/6 | >700 | 560 |
| 197 | 3-tert-butyl-3-[2-(2-methoxyethoxy)ethyl]α-D-glucopyranose-6-yl)-1-(2-chloroethyl)-1-nitrosourea | 2.70 | 160 | 59.2 | 6/6 | >700 | 530 |
| 198 | 3-tert-butyl-3-(3-methoxy-n-butyl α-D-glucopyranose-6-yl)-1-(2-chloroethyl)-1-ntirosourea | 2.76 | 180 | 65.3 | 6/6 | >700 | 570 |
| 199 | 3-isobutyl-3-(2-morpholinoethyl β-D-glucopyranose-6-yl)-1-(2-chloroethyl)-1-nitrosourea | 3.20 | 160 | 50.0 | 6/6 | >700 | 520 |
| 200 | 3-tert-butyl-3-(1-morpholinoisopropyl β-D-glucopyranose-6-yl)-1-(2-chloroethyl)-1-nitrosourea | 3.11 | 150 | 48.2 | 6/6 | >700 | 480 |

TABLE III-continued

| Compound No. | Nitroso Compound | ILS₃₀ mg/kg | O.D. mg/kg | Therapeutic ratio TR | Survivors after 60 days | Max. ILS % | LD₅₀ mg/kg |
|---|---|---|---|---|---|---|---|
| 201 | 3-tert-butyl-3-(α-cyclopropyl-benzyl α-D-glucopyranose-6-yl)-1-(2-chloroethyl)-1-nitrosourea | 4.78 | 150 | 31.4 | 6/6 | >700 | 460 |
| Known Compound | 6MCαGM | 1.45 | 29.1 | 20.1 | 4/6 | >450 | 88 |
| Known Compound | 6MCαG | 0.53 | 13.5 | 25.5 | 6/6 | >700 | 40 |
| Known Compound | 2MCαG | 1.15 | 15.2 | 13.2 | 5/6 | >625 | 46 |
| Known Compound | KCNUM | 1.38 | 25.4 | 18.4 | 4/6 | >425 | 130 |
| Known Compound | DCNU | 0.70 | 6.2 | 8.9 | 5/6 | >625 | 39 |
| Known Compound | GANU | 0.45 | 6.2 | 13.8 | 4/6 | >425 | 35 |
| Known Compound | 6MCαGB | 1.34 | 30 | 22.4 | 4/6 | >440 | 92 |
| Known Compound | 6MCαGHE | 1.40 | 30 | 21.4 | 4/6 | >440 | 90 |

TABLE IV

| Compound No. | ILS₃₀ mg/kg | O.D. mg/kg | Therapeutic ratio TR | Survivors after 60 days | Max. ILS % |
|---|---|---|---|---|---|
| 2 | 7.35 | 180 | 24.5 | 6/6 | >700 |
| 11 | 9.57 | 220 | 23.0 | 6/6 | >700 |
| 16 | 8.82 | 240 | 27.2 | 6/6 | >700 |
| 23 | 8.74 | 250 | 28.6 | 5/6 | >625 |
| 39 | 7.43 | 220 | 29.6 | 5/6 | >635 |
| 42 | 7.88 | 230 | 29.2 | 6/6 | >700 |
| 64 | 13.2 | 240 | 18.2 | 4/6 | >460 |
| 71 | 13.1 | 220 | 16.8 | 4/6 | >440 |
| 75 | 11.6 | 200 | 17.2 | 4/6 | >450 |
| 83 | 16.8 | 240 | 14.3 | 3/6 | >360 |
| 89 | 12.5 | 210 | 16.8 | 4/6 | >450 |
| 101 | 11.2 | 250 | 22.3 | 4/6 | >460 |
| 113 | 7.32 | 180 | 24.6 | 6/6 | >700 |
| 114 | 9.05 | 210 | 23.2 | 6/6 | >700 |
| 123 | 13.2 | 240 | 18.2 | 3/6 | >360 |
| 126 | 15.4 | 240 | 15.6 | 3/6 | >350 |
| 132 | 14.0 | 200 | 14.3 | 3/6 | >345 |
| 135 | 9.92 | 240 | 24.2 | 6/6 | >700 |
| 136 | 10.1 | 240 | 23.8 | 5/6 | >625 |
| 140 | 9.69 | 220 | 22.7 | 5/6 | >620 |
| 145 | 10.9 | 200 | 18.3 | 4/6 | >450 |
| 149 | 12.8 | 210 | 16.4 | 4/6 | >440 |
| 153 | 10.8 | 180 | 16.7 | 4/6 | >425 |
| 156 | 9.78 | 180 | 18.4 | 4/6 | >460 |
| 159 | 10.9 | 180 | 16.5 | 5/6 | >625 |
| 161 | 12.7 | 180 | 14.2 | 3/6 | >350 |
| 164 | 14.5 | 185 | 12.8 | 5/6 | >620 |
| 167 | 12.0 | 180 | 15.0 | 4/6 | >450 |
| 170 | 13.4 | 190 | 14.2 | 4/6 | >440 |
| 171 | 11.7 | 190 | 16.2 | 4/6 | >450 |
| 174 | 9.66 | 230 | 23.8 | 5/6 | >620 |
| 178 | 9.38 | 210 | 22.4 | 5/6 | >625 |
| 183 | 13.2 | 200 | 15.2 | 4/6 | >460 |
| 185 | 8.16 | 200 | 24.5 | 5/6 | >625 |
| 186 | 8.55 | 200 | 23.4 | 5/6 | >620 |
| 192 | 9.85 | 200 | 20.3 | 5/6 | >625 |
| 195 | 8.51 | 200 | 23.5 | 5/6 | >620 |
| 197 | 9.26 | 200 | 21.6 | 5/6 | >625 |
| 198 | 9.69 | 220 | 22.7 | 5/6 | >640 |
| 200 | 10.1 | 190 | 18.9 | 4/6 | >460 |
| 6MCαG | 2.45 | 16.8 | 6.86 | 6/6 | >700 |
| DCNU | — | 100 | — | 0/6 | 20 |
| GANU | 2.50 | 6.35 | 2.54 | 0/6 | 94 |

Growth-Inhibiting Effect against Ehrlich Acites carcinoma

Ehrlich acites carcinoma ($1 \times 10^7$ cells) was implantated into the abdominal cavities of a 6-membered group of male mice. Test compounds (solutions or suspensions in 1% Nikohl HCO-60) were each intraperioneally administered once a day 5 successive days to the mice 24 hrs. after the implantation. Total packed cell volumes [TPCV, namely, total packed volumes of Acites carcinoma] were determined 7 days after the implantation to calculate growth ratio of tumor [T/C%; T: packed volume of Acites carcinoma in treated groups, C: packed volume of Acites carcinoma in an untreated group]. Acitivity is represented by — when T/C% is 100—66, by + when T/C% 65—41, by + + when T/C% 40—11, and by + + + when T/C% 10—0. Tables IV-1 and IV-2 show these results. The compound No. in these Tables shows compound having the same No. in Tables I-IV. These result reveals that the compounds of the present invention have excellent effect also against Ehrlich acites carcinoma.

TABLE IV-1

| Test Compound No. | Dosage mg/kg day | TPCV T/C ml | T/C % | Activity |
|---|---|---|---|---|
| 3 | 50 | 0.30/1.34 | 22.4 | ++ |
|  | 200 | 0/1.34 | 0 | +++ |
| 4 | 50 | 0.40/1.34 | 30.2 | ++ |
|  | 200 | 0.03/1.34 | 2.3 | +++ |
| 10 | 25 | 0/1.34 | 0 | +++ |
|  | 100 | 0/1.34 | 0 | +++ |
| 11 | 25 | 0/1.34 | 0 | +++ |
|  | 100 | 0/1.34 | 0 | +++ |
| 12 | 25 | 0/1.34 | 0 | +++ |
|  | 100 | 0/1.34 | 0 | +++ |
| 15 | 25 | 0/1.34 | 0 | +++ |
|  | 100 | 0/1.34 | 0 | +++ |
| 16 | 25 | 0/1.34 | 0 | +++ |
|  | 100 | 0/1.34 | 0 | +++ |
| 19 | 25 | 0/1.34 | 0 | +++ |
|  | 100 | 0/1.34 | 0 | +++ |
| 20 | 25 | 0/1.34 | 0 | +++ |
|  | 100 | 0/1.34 | 0 | +++ |
| 23 | 25 | 0/1.34 | 0 | +++ |
|  | 100 | 0/1.34 | 0 | +++ |
| 30 | 25 | 0/1.34 | 0 | +++ |
|  | 100 | 0/1.34 | 0 | +++ |
| 31 | 25 | 0/1.34 | 0 | +++ |
|  | 100 | 0/1.34 | 0 | +++ |
| 35 | 25 | 0/1.34 | 0 | +++ |
|  | 100 | 0/1.34 | 0 | +++ |
| 39 | 25 | 0/1.34 | 0 | +++ |
|  | 100 | 0/1.34 | 0 | +++ |
| 40 | 25 | 0/1.34 | 0 | +++ |
|  | 100 | 0/1.34 | 0 | +++ |
| 41 | 25 | 0/1.34 | 0 | +++ |

TABLE IV-1-continued

| Test Compound No. | Dosage mg/kg day | TPCV T/C ml | T/C % | Activity |
|---|---|---|---|---|
| | 100 | 0/1.34 | 0 | +++ |
| 42 | 25 | 0/1.34 | 0 | +++ |
| | 100 | 0/1.34 | 0 | +++ |
| 50 | 25 | 0/1.34 | 0 | +++ |
| | 100 | 0/1.34 | 0 | +++ |
| 52 | 25 | 0/1.34 | 0 | +++ |
| | 100 | 0/1.34 | 0 | +++ |
| 57 | 25 | 0/1.34 | 0 | +++ |
| | 100 | 0/1.34 | 0 | +++ |
| 6MCαG | 3.2 | 0/1.34 | 0 | +++ |
| | 12.5 | 0/1.34 | 0 | Toxic (2/6) |
| GANU | 3.2 | 0/1.34 | 0 | +++ |
| | 25.0 | — | — | Toxic (6/6) |

TABLE IV-2

| Test Compound No. | Dosage mg/kg/day | TPCV T/C ml | T/C % | Activity |
|---|---|---|---|---|
| 63 | 25 | 0/1.41 | 0 | +++ |
| | 100 | 0/1.41 | 0 | +++ |
| 65 | 25 | 0/1.41 | 0 | +++ |
| | 100 | 0/1.41 | 0 | +++ |
| 71 | 25 | 0/1.41 | 0 | +++ |
| | 100 | 0/1.41 | 0 | +++ |
| 74 | 25 | 0/1.41 | 0 | +++ |
| | 100 | 0/1.41 | 0 | +++ |
| 75 | 25 | 0/1.41 | 0 | +++ |
| | 100 | 0/1.41 | 0 | +++ |
| 82 | 25 | 0/1.41 | 0 | +++ |
| | 100 | 0/1.41 | 0 | +++ |
| 86 | 25 | 0/1.41 | 0 | +++ |
| | 100 | 0/1.41 | 0 | +++ |
| 93 | 25 | 0/1.41 | 0 | +++ |
| | 100 | 0/1.41 | 0 | +++ |
| 94 | 25 | 0/1.41 | 0 | +++ |
| | 100 | 0/1.41 | 0 | +++ |
| 101 | 25 | 0/1.41 | 0 | +++ |
| | 100 | 0/1.41 | 0 | +++ |
| 105 | 50 | 0.08/1.41 | 5.7 | +++ |
| | 200 | 0/1.41 | 0 | +++ |
| 108 | 50 | 0.11/1.41 | 7.8 | +++ |
| | 200 | 0/1.41 | 0 | +++ |
| 109 | 25 | 0/1.41 | 0 | +++ |
| | 100 | 0/1.41 | 0 | +++ |
| 110 | 25 | 0/1.41 | 0 | +++ |
| | 100 | 0/1.41 | 0 | +++ |
| 114 | 25 | 0/1.41 | 0 | +++ |
| | 100 | 0/1.41 | 0 | +++ |
| 115 | 25 | 0/1.41 | 0 | +++ |
| | 100 | 0/1.41 | 0 | +++ |
| 117 | 25 | 0/1.41 | 0 | +++ |
| | 100 | 0/1.41 | 0 | +++ |
| 124 | 25 | 0/1.41 | 0 | +++ |
| | 100 | 0/1.41 | 0 | +++ |
| 132 | 25 | 0/1.41 | 0 | +++ |
| | 100 | 0/1.41 | 0 | +++ |
| 135 | 25 | 0/1.41 | 0 | +++ |
| | 100 | 0/1.41 | 0 | +++ |
| 136 | 25 | 0/1.41 | 0 | +++ |
| | 100 | 0/1.41 | 0 | +++ |
| 140 | 25 | 0/1.41 | 0 | +++ |
| | 100 | 0/1.41 | 0 | +++ |
| 146 | 25 | 0/1.41 | 0 | +++ |
| | 100 | 0/1.41 | 0 | +++ |
| 149 | 25 | 0/1.41 | 0 | +++ |
| | 100 | 0/1.41 | 0 | +++ |
| 157 | 25 | 0/1.41 | 0 | +++ |
| | 100 | 0/1.41 | 0 | +++ |
| 164 | 25 | 0/1.41 | 0 | +++ |
| | 100 | 0/1.41 | 0 | +++ |
| 170 | 25 | 0/1.41 | 0 | +++ |
| | 100 | 0/1.41 | 0 | +++ |
| 178 | 25 | 0/1.41 | 0 | +++ |
| | 100 | 0/1.41 | 0 | +++ |
| 179 | 25 | 0/1.41 | 0 | +++ |
| | 100 | 0/1.41 | 0 | +++ |
| 180 | 25 | 0/1.41 | 0 | +++ |
| | 100 | 0/1.41 | 0 | +++ |

TABLE IV-2-continued

| Test Compound No. | Dosage mg/kg/day | TPCV T/C ml | T/C % | Activity |
|---|---|---|---|---|
| 181 | 25 | 0/1.41 | 0 | +++ |
| | 100 | 0/1.41 | 0 | +++ |
| 188 | 25 | 0/1.41 | 0 | +++ |
| | 100 | 0/1.41 | 0 | +++ |
| 193 | 25 | 0/1.41 | 0 | +++ |
| | 100 | 0/1.41 | 0 | +++ |
| 200 | 25 | 0/1.41 | 0 | +++ |
| | 100 | 0/1.41 | 0 | +++ |
| 6MCαG | 6.3 | 0/1.41 | 0 | +++ |
| | 12.5 | 0/1.41 | 0 | Toxic (2/6) |
| GANU | 12.5 | 0/1.41 | 0 | +++ |
| | 25.0 | — | — | Toxic (6/6) |

Acute toxicity

Test compounds, dissolved or suspended in 0.5% aqueous CMC, were each intraperitoneally administered to ICR mice in a dose of 0.1 ml per 10 g body weight. $LD_{50}$ (mg/kg) value of each test compound was calculated from the mortality of mice during 30 days by the Behrens-Kärber method. The results were shown in Tables I and III. As is evident from these results, the compounds of this invention are antitumor substances excellent in safety, being less toxic than expected, that is, only ¼ to 1/15 times as toxic as compared with known antitumor compounds 6MCαGM, 6MCαG, 2MCαG, KCNUM, GANU, 6MCαGB, and 6MCαGHE.

The compounds of this invention are additionally useful for diuretic, since they are capable of diuresis against mammal.

Diuretic activity

The diuretic activity of the compounds of this invention was assayed by the diuresis screening test referred to as "acute sodium loaded mouse". This test was carried out by the following method.

The acute sodium loaded mouse screening test was carried out by using a 10-membered group of male mice (each weighing 18 to 24 g). Test compounds were incorporated in 1% saline (NaCl) solution and orally administered in a volume of 10 ml/kg. The mice were placed in metabolic cages. Each treated group consisted of 10-members. Five members were placed in one cage. Tests were conducted by oral administrations of (A) 1% saline (NaCl) solution to the control group and (B) 1% saline (NaCl) solution containing a test compound according to this invention.

The determination was carried out for sodium, potassium, and chlorine in each pooled urine sample. The determination of sodium and potassium was carried out by flame photometer. Chlorine was determined by chloride analysis apparatus. The analytical values of sodium, potassium, and chlorine were shown with an average mg equivalent (m Eq)/Kg/5 hours, and the diuretic activity was shown with an average urine volume (ml)/Kg/5 hours.

Table IV-3 shows the diuretic activity of the typical compounds of this invention. The compound No. in this table shows the compound having the same compound No. in Tables I~IV.

The results reveal that the compounds of this invention have excellent effect also as diuretic.

TABLE IV-2

| Compound No. | Dosage mg/kg | Urine volume (ml/kg/5 hrs.) | Na+ | K+ | Cl− |
|---|---|---|---|---|---|
| Control | — | 5.4 | 0.3 | 0.6 | 0.4 |
| 4 | 50 | 8.6 | 0.5 | 0.9 | 0.6 |
| 10 | 50 | 8.7 | 0.5 | 0.8 | 0.6 |
| 15 | 50 | 9.2 | 0.6 | 0.9 | 0.7 |
| 19 | 50 | 9.1 | 0.6 | 0.8 | 0.7 |
| 23 | 50 | 10.2 | 0.7 | 1.0 | 0.8 |
| 35 | 50 | 8.8 | 0.5 | 0.9 | 0.6 |
| 39 | 50 | 9.2 | 0.6 | 0.8 | 0.7 |
| 57 | 50 | 9.7 | 0.7 | 0.9 | 0.8 |
| 65 | 50 | 8.8 | 0.6 | 0.8 | 0.7 |
| 74 | 50 | 9.4 | 0.6 | 0.8 | 0.7 |
| 86 | 50 | 10.2 | 0.7 | 1.0 | 0.9 |
| 93 | 50 | 9.6 | 0.6 | 0.9 | 0.7 |
| 110 | 50 | 8.8 | 0.5 | 0.8 | 0.6 |
| 117 | 50 | 8.4 | 0.5 | 0.9 | 0.7 |
| 135 | 50 | 9.7 | 0.7 | 0.9 | 0.8 |
| 157 | 50 | 10.5 | 0.8 | 1.0 | 1.1 |
| 175 | 50 | 9.4 | 0.6 | 0.9 | 0.8 |
| 180 | 50 | 12.8 | 1.0 | 1.3 | 1.4 |
| 181 | 50 | 13.1 | 1.1 | 1.2 | 1.3 |

The compounds of this invention are available for medical purposes in any form of pharmaceutical preparations suitable for oral or parenteral administration, that is, they can be made up into pharmaceutical compositions, like other useful conventional anti-tumor and/or diuresis compounds, by mixing with solid or liquid carriers physiologically innocuous. These compositions may take any form of tablets, coated tablets, capsules, powders, granules, injections, emulsions, suspensions, and suppositories. Said carriers include, for example, excipients (binders) or disintegrants such as lactose, glucose, sucrose, starch, dextrine, methylcellulose, calcium carboxymethyl cellulose, crystalline cellulose, magnesium stearate, sodium alginate, Witepsol W35, Witepsol E85, and poly(vinyl alcohol); lubricants such as talc, stearic acid, waxes, hydroxypropyl cellulose, and boric acid; coating materials such as Shellac, poly(vinyl acetal) diethylamino acetate, and cellulose acetatephthalate; solubilizers such as glycerol, propylene glycol and mannitol; emulsifiers or suspending agents such as polyoxyethylene cetyl alcohol ether, polyoxyethylene stearate, gum arabic, and sodium soap; stabilizers such as Tween 80, Span 80, sorbitol, and fats and oils; and various kinds of solvents.

Said anti-tumor and/or diuresis pharmaceutical compositions are applied, for example, to animals (including human being) of weight 60 kg according to the following schedule in doses of the present compound Ia, Ib or Ic contained therein: once in every 1 to 6 weeks in a dosage of 20 to 4000 mg/time; 2 to 3 times in every 2 to 3 weeks in a dosage of 1 to 2000 mg/time; every day for 1 to 3 weeks in a daily dosage of 1 to 2000 mg; and so on. However, it is a matter of course that said dosages may be varied appropriately depending upon the mode of administration; the age, body weight, and condition of patient, the kind of tumor to be treated, the form of pharmaceutical composition, etc.

Formulations of the pharmaceutical compositions using compounds of Formulae Ia, Ib and Ic of this invention will be exemplified below.

Tablets:
i Compound No. 178 shown in Table III  100 mg
  Lactose                                158 mg
  Magnesium stearate                       2 mg
  Total                                  260 mg ii Compound No. 185 shown in Table III   200 mg
   Crystalline cellulose                  50 mg
   Starch                                 30 mg
   Lactose                                28 mg
   Glucose                                20 mg
   Calcium Carboxymethyl cellulose        30 mg
   Hydroxypropyl cellulose                10 mg
   Magnesium stearate                      2 mg
   Total                                 370 mg Suppostory:
Compound No. 31 shown in Table I        340 mg
Witepsol W 35                           830 mg
Witepsol E 85                            82 mg
Polyoxyethylene stearate                 48 mg
Total                                  1300 mg Capsules:
i. Compound No. 179 shown in Table III  150 mg
   Crystalline cellulose                 30 mg
   Starch                                18 mg
   Glucose                               50 mg
   Calcium carboxymethyl cellulose       20 mg
   Hydroxypropyl cellulose               10 mg
   Magnesium stearate                     2 mg
   Total                                280 mg
ii. Compound No. 113 shown in Table II  100 mg
    Crystalline cellulose                20 mg
    Starch                               18 mg
    Lactose                              40 mg
    Calcium carboxymethyl cellulose      15 mg
    Hydroxypropyl cellulose               5 mg
    Magnesium stearate                    2 mg
    Total                               200 mg Granule:
Compound No. 16 shown in Table III      150 mg
Crystalline cellulose                    20 mg
Starch                                   20 mg
Lactose                                  40 mg
Calcium Carboxymethyl cellulose          15 mg
Hydroxypropyl cellulose                   5 mg
Total                                   250 mg Injections:
Compound No. 136 shown in Table III     100 mg
Saline                                   10 ml Dropping injection preparation:
Compound No. 115 shown in Table II      100 mg
Sorbitol                                150 mg
Saline                                  300 ml Suspension:
Compound No. 23 shown in Table I         30 mg
Sodium carboxylmethyl cellulose           2 mg
Deionized water                          68 mg
Total                                   100 mg Emulsion:
Compound No. 41 shown in Table I         40 mg
Gum arabic                                3 mg
Cotton seed oil                          20 mg
Deionized water                          87 mg
Total                                   150 mg

EXAMPLE 1

A solution of n-butyl 6-methylamino-6-deoxy-α-D-glucopyranoside (7.11 g, 28.5 mmol) in ethanol (60 ml) was dropped into a solution of o-nitrophenyl N-2-(chloroethyl)-N-nitrosocarbamate (8.18 g, 29.9 mmol) in tetrahydrofuran (50 ml) with good stirring at 0°–5° C. spending 15 minutes, and reaction was conducted for further 2 hours at the same temperature. After completion of the reaction was confirmed by thin layer chromatography (hereinafter, shortened as TLC; precoat; silica gel 60; eluent: chloroform/ethanol 10:1), the resulting reaction mixture was vacuum-concentrated. The residue was washed with chloroform and crystallized from ethanol and water, giving 8.60 g of 3-methyl-3-(n- butyl α-D-glycopyranose-6-yl)-1-(2-chloroethyl)-1-nitrosourea; yield 78.6%; m.p. 70°–72° C.; $[\alpha]_D^{20} + 70.5°$ (C 1.0, methanol).

Elementary analysis, for $C_{14}H_{26}N_3O_7Cl$ (mol.wt. 383.83): Calcd. (%): C 43.81, H 6.83, N 10.95, Cl 9.23; Found (%): C 43.88, H 6.78, N 10.92, Cl 9.34.

IR $\nu_{max}^{KBr}$ (cm$^{-1}$): 3400 (OH), 1700 (CO), 1490 (NO), 1050 (C—O—C).

NMR (d$_6$-DMSO)δ: 0.8 (s, 3H, O—(CH$_2$)$_3$CH$_3$), 0.6–1.6 (t, protons of butyl group), 3.24 (s, $\overline{3H}$, N—CH$_3$), 3.6 (t, 2H, N—CH$_2$CH$_2$Cl), 4.09 (t, 2H, N—$\overline{CH_2}$—CH$_2$Cl), 4.66 (d, 1$\overline{H}$, C$_1$—$\underline{H}$).

EXAMPLE 2

A solution of n-butyl 6-methylamino-6-deoxy-β-D-glycopyranoside (6.61 g, 26.5 mmol) in a mixture of methanol (40 ml) and dioxide (40 ml), after 2 g of dry ice was added, was dropped into a solution of O-nitrophenyl N-(2-chloroethyl)-N-nitrosocarbamate (7.69 g, 28.1 mmol) in tetrahydrofuran (50 ml) with efficient stirring at 0°–5° C. in the course of 10 minutes, and the reaction was continued for 2 more hours at the same temperature. After completion of the reaction was confirmed by TLC, the reaction mixture was vacuum-concentrated at 30° C. The resulting residue was washed with chloroform and recrystallized from ethanol and water, giving 8.42 g of 3-methyl-3-(N-butyl β-D-glucopyranose-6-yl)-1-(2-chloroethyl)-1-nitrosourea; yield 82.8%; m.p. 106°–108° C. (decomposition); $[\alpha]_D^{20}$ −15.1° (C 1.0, methanol).

Elementary analysis as $C_{14}H_{26}N_3O_7Cl$ (mol.wt. 383.83): Calcd. (%): C 43.81, H 6.83, N 10.95, Cl 9.23; Found (%): C 43.72, H 6.77, N 10.99, Cl 9.32.

EXAMPLE 3

A solution of n-butyl 6-n-butylamino-6-deoxy-D-glycopyranoside (8.25 g, 28.3 mmol) in a mixture of methanol (50 ml) and dimethylsulfoxide (50 ml), after adjustment to pH 9.5 by adding succinic acid with stirring, was dropped into a solution of O-nitrophenyl N-(2-chloroethyl)-N-nitrosocarbamate (8.51 g, 31.1 mmol) in a mixed solvent (tetrahydrofuran 100 ml and dioxane 50 ml) with well stirring at 0°–5° C. (spending 10 minutes), and reaction was conducted for further 2 hours at the same temperature. After completion of the reaction was confirmed by TLC, the reaction mixture was vacuum-concentrated at 30° C. The residue was separated by column chromatography (packing: Kiesel gel 60; eluent: chloroform→chloroform/ethanol 8:1) into fractions of objective α- and β- form products, which were each vacuum-concentrated at 30° C. The residues were recrystallized from ethanol and petroleum ether, thereby giving 4.64 g of 3-n-butyl-3-(n-butyl α-D-glucopyranose-6-yl)-1-(2-chloroethyl)-1-nitrosourea; yield 38.5%; m.p. 80°–82° C.; $[\alpha]_D^{20} + 68.5°$ (C 1.0, methanol); and 3.90 g of 3-n-butyl-3-(n-butyl β-D-glucopyranose-6-yl)-1-(2-chloroethyl)-1-nitrosourea; yield 32.4%; m.p. 104°–106° C. (decomposition); $[\alpha]_D^{20} - 14.0°$ (C 1.0, methanol).

Elementary analysis, for $C_{17}H_{32}N_3O_7Cl$ (mol.wt. 425.91): Calcd. (%): C 47.94, H 7.57, N 9.87, Cl 8.32; Found (%): α-form: C 48.06, H 7.51, N 9.82, Cl 8.27; β-form: C 47.98, H 7.49, N 9.79, Cl 8.35.

EXAMPLE 4

A solution of n-butyl 6-n-hexylamino-6-deoxy-D-glycopyranoside (9.10 g, 28.5 mmol) in methanol (50 ml), after 2 g of dry ice was added, was dropped into a solution of p-nitro-phenyl N-(2-chloroethyl)-N-nitrosocarbamate (8.59 g, 31.4 mmol) in a mixture of tetrahydrofuran (30 ml), ethanol (10 ml), and hexane (10 ml) with well stirring at −5° to +5° C. spending 10 minutes, and reaction was continued at 5°–10° C. for 2 further hours. The reaction mixture was concentrated at 30° C. under reduced pressure and separated into fractions of objective α- and β-form products by column chromatography (packing: Kiesel gel 60; eluent: chloroform→chloroform/methanol 9:1). The fractionated solutions were each vacuum-concentrated at 25° C. and recrystallized from ethanol and petroleum ether, giving 3.20 g of 3-n-hexyl-3-(n-butyl α-D-glycopyranose-6-yl)-1-(2-chloroethyl)-1-nitrosourea; yield 24.7%, m.p. 75°–77° C. $[\alpha]_D^{20} + 67.4°$ (C 1.0, methanol); and 2.77 g of 3-n-hexyl-3-(n-butyl β-D-glycopyranose-6-yl)-1-(2-chloroethyl)-1-nitrosourea; yield 21.4%, m.p. 95°–97° C. (decomposition), $[\alpha]_D^{20} - 13.5°$ (C 1.0, methanol).

Elementary analysis, for $C_{19}H_{36}N_3O_7Cl$ (mol.wt. 453.96): Calcd. (%): C 50.27, H 7.99, N 9.26, Cl 7.81; Found (%): α-form: C 50.34, H 7.92, N 9.22, Cl 7.89; β-form: C 50.22, H 7.93, N 9.34, Cl 7.72.

EXAMPLE 5

A solution of n-butyl 6-n-propylamino-6-deoxy-α-D-glycopyranoside (7.57 g, 27.3 mmol) in a mixture of ethanol (50 ml) and dioxane (50 ml), after 3 g of dry ice was added, was dropped into a solution of O-nitrophenyl N-(2-chloroethyl)-N-nitrosocarbamate (7.96 g, 29.1 mmol) in a mixture of tetrahydrofuran (100 ml) and toluene (20 ml) with well stirring at 5°–0° C. spending 10 minutes, and reaction was continued for further 3 hours at the same temperature. After completion of the reaction was confirmed by TLC, the reaction fluid was vacuum-concentrated at 25° C., and the resulting residue was washed with chloroform and recrystallized from ethanol and water, giving 8.95 g of 3-n-propyl-3-(n-butyl α-D-glycopyranose-6-yl)-1-(2-chloroethyl)-1-nitrosourea; yield 79.6%, m.p. 64°–66° C., $[\alpha]_D^{20} + 68.8°$ (C1.0, methanol).

Elementary analysis, for $C_{16}H_{30}N_3O_7Cl$ (mol.wt. 411.88): Calcd. (%): C 46.66, H 7.34, N 10.20, Cl 8.61; Found (%): C 46.73, H 7.28, N 10.28, Cl 8.53.

EXAMPLE 6

A solution of n-butyl 2-n-butylamino-2-deoxy-D-glycopyranoside (7.61 g, 26.1 mmol) in a mixture of ethanol (50 ml) and dioxane (50 ml) was dropped into a solution of p-nitrophenyl N-(2-chloroethyl)-N-nitrosocarbamate (7.85 g, 28.7 mmol) in a mixture of tetrahydrofuran (100 ml) and methyl ethyl keton (30 ml) with well stirring at −5° to 10° C. spending 10 minutes, and reaction was continued at 10° to 20° C. for further 2 hours. After confirmation by TLC of the reaction completion, the reaction fluid was vacuum-concentrated at 25° C. The residue was separated into fractions of objective α- and β-forms by column chromatography (packing: Kiesel gel 60; eluent: chloroform→chloroform/methanol 9:1). The fractionated solutions were each vacuum-concentrated at 25° C. and recrystallized from ethanol and petroleum ether, giving 2.38 g of 3-n-butyl-3-(n-butyl α-D-glycopyranose-2-yl)-1-(2-chloroethyl)-1-nitrosourea; yield 21.4%, m.p. 98°–100° C. (decompostion), $[\alpha]_D^{20} + 74.2°$ (C 1.0, methanol); and 1.96 g of 3-n-butyl-3-(n-butyl β-D-glycopyranose-2-yl)-1-(2-chloroethyl)-1-nitrosourea; yield 17.6%, m.p. 115°–117° C. (decomposition), $[\alpha]_D^{20} - 17.3°$ (C 1.0, methanol).

Elementary analysis, for $C_{17}H_{32}N_3O_7Cl$ (mol.wt. 425.91): Calcd (%): C 47.94, H 7.57, N 9.87, Cl 8.32; Found (%): α-form: C 47.91, H 7.46, N 9.93, Cl 8.45; β-form: C 47.87, H 7.63, N 9.81, Cl 8.38.

EXAMPLE 7

A solution of n-butyl 2-ethylamino-α-deoxy-α-D-glycopyranoside (7.98 g, 30.3 mmol) in a mixture of tetrahydrofuran (30 ml) and methanol (10 ml), after 3 g of dry ice was added, was dropped into a solution of O-nitrophenyl-N-(2-chloroethyl)-N-nitrosocarbamate (9.11 g, 33.3 mmol) in a mixture of acetone (30 ml) and methyl ethyl keton (20 ml) with well stirring at 0° to 5° C. spending 20 minutes, and reaction was contained at 5° to 25° C. for further 2 hours. After confirmation by TLC of the reaction completion, the reaction fluid was vacuum-concentrated at 25° C., and the residue was recrystallized from methanol and water, giving 9.69 g of 3-ethyl-3-(n-butyl α-D-glucopyranose-2-yl)-1-(2-chloroethyl)-1-nitrosourea; yield 80.4%, m.p. 87°–89° C., $[\alpha]_D^{20} + 77.5°$ (C 1.0, methanol).

Elementary analysis, for $C_{15}H_{28}N_3O_7Cl$ (mol.wt. 397.86): Calcd. (%): C 45.28, H 7.10, N 10.56, Cl 8.91; Found (%): C 45.34, H 7.18, N 10.52, Cl 8.86.

EXAMPLE 8

A solution of n-butyl 3-ethylamino-3-deoxy-D-glucopyranoside (7.69 g, 29.2 mmol) in a mixture of tetrahydrofuran (20 ml) and ethanol (40 ml), after 3 g of dry ice was added, was dropped into a solution of O-nitrophenyl N-(2-chloroethyl)-N-nitrocarbamate (8.79 g, 32.1 mmol) in tetranhdrofuran (50 ml) with well stirring at 0° to 5° C. spending 20 minutes, and reaction was conducted at the same temperature for further 2 hours. After confirmation by TLC of the reaction completion, the reaction fluid was vacuum-concentrated at 25° C., and the objective α-form was separated from the residue by column chromatography (packing: Kiesel gel 60; eluent: chloroform→chlorform:methanol 9:1). The α-form-containing fraction was vacuum-concentrated at 25° C., and recrystallized from methanol and water, giving 3.93 g of 3-ethyl-3-(n-butyl α-D-glucopyranose-3-yl)-1-(2-chloroethyl)-1-nitrosourea; yield 33.8%, m.p. 63°–65° C., $[\alpha]_D^{20} + 41.3°$ (C 1.0, methanol).

Elementary analysis, for $C_{15}H_{28}N_3O_7Cl$ (mol.wt. 397.86): Calcd. (%): C 45.28, H 7.10, N 10.56, Cl 8.91; Found (%): C 45.22, H 7.15, N 10.64, Cl 8.78.

EXAMPLE 9

A solution of n-butyl 4-ethylamino-4-deoxy-D-glucopyranoside (6.66 g, 25.3 mmol) in a mixture of methanol (40 ml) and isopropanol (10 ml) was adjusted to pH 9.1 by adding succinic acid in a fine powder with stirring. The solution was dropped into a solution of O-nitrophenyl N-(2-chloroethyl)-N-nitrosocarbamate (7.61 g, 27.8 mmol) in a mixture of tetrahydrofuran (30 ml) and acetone (10 ml) with stirring at 0° to 10° C. spending 10 minutes. After being stirred at the said temperature for further 2 hours, the reaction mixture was filtered, and the filtrate was vacuum-concentrated at 30° C. From the residue, fractions containing the objective α-form of product were separated by column chromatography (packing: Kiesel gel 60; eluent: chloroform→chloroform/methanol 9:1) and vacuum-concentrated at 25° C. The residue was recrystallized from methanol and water, giving 3.10 g of 3-ethyl-3-(n-butyl α-D-glucopyranose-4-yl)-1-(2-chloroethyl)-1-nitrosourea; yield 30.8%, m.p. 75°–77° C., $[\alpha]_D^{20} + 60.7°$ (C 1.0, methanol).

Elementary analysis, for $C_{15}H_{28}N_3O_7Cl$ (mol.wt. 397.86): Calcd. (%): C 45.28, H 7.10, N 10.56, Cl 8.91; Found (%): C 45.36, H 7.15, N 10.49, Cl 8.83.

EXAMPLE 10

A solution of n-butyl 6-n-decylamino-6-deoxy-D-glycopyranoside (10.48 g, 27.9 mmol) in a mixture of methanol (25 ml) and dioxane (50 ml) was adjusted pH 9.2 by adding phthalic acid fine powder with stirring. The solution was dripped into a solution of p-nitrophenyl N-(2-chloroethyl)-N-nitrosocarbamate (8.40 g, 30.7 mmol) in a mixture of tetrahydrofuran (20 ml) and methyl ethyl ketone (5 ml) with well stirring at −5° to −10° C. spending 15 minutes. After being stirred at −5° to +10° C. for further 2 hours, the reaction fluid was filtered, and the filtrate was vacuum-concentrated at 25° C. The residue was separated into fractions of objective α- and β-form products by column chromatography (packing: Kiesel gel 60; eluent: chloroform→chloroform/methanol 9:1). The fractions, vacuum-concentrated at 25° C., were each recrystallized from methanol and water, giving 3.07 g of 3-n-decyl-3-(n-butyl α-D-glycopyranose-6-yl)-1-(chloroethyl)-1-nitrosourea; yield 21.6%, m.p. 80°–82° C., $[\alpha]_D^{20} + 60.8°$ (C 1.0, methanol); and 2.64 g of 3-n-decyl-3-(n-butyl β-D-glycopyranose-6-yl)-1-(2-chloroethyl)-1-nitrosourea; yield 18.6%, m.p. 103°–105° C. (decomposition), $[\alpha]_D^{20} - 11.4°$ (C 1.0, methanol).

Elementary analysis, for $C_{23}H_{44}N_3O_7Cl$ (mol.wt. 510.07): Calcd. (%): C 54.16, H 8.69, N 8.24, Cl 6.95; Found (%): α-form: C 54.24, H 8.62, N 8.37 Cl 6.82; β-form: C 54.24, H 8.62, N 8.18 Cl 6.97.

EXAMPLE 11

A solution of n-butyl 2-n-decylamino-2-deoxy-α-D-glycopyranoside (7.62 g, 20.3 mmol) in a mixture of methanol (30 ml) and tetrahydrofuran (30 ml) was dropped into a solution of O-cyanophenyl N-(2-chloroethyl)-N-nitrosocarbamate (5.88 g, 23.2 mmol) in a mixture of tetrahydrofuran (50 ml), acetone (30 ml), and hexane (10 ml) with well stirring at −5° to +5° C. spending 15 minutes, and reaction was conducted at the same temperature for further 2 hours. After confirmation by TLC of the reaction completion, the reaction fluid was vacuum-concentrated at 25° C., washed with benzene, and recrystallized from methanol and water, giving 7.10 g of 3-n-decyl-3-(n-butyl α-D-glucopyranose-2-yl)-1-(2-chloroethyl)-1-nitrosourea; yield 68.6%, m.p. 96°–98° C. (decomposition), $[\alpha]_D^{20} + 67.3°$ (C 1.0, methanol).

Elementary analysis, for $C_{23}H_{44}N_3O_7Cl$ (mol.wt. 510.07): Calcd. (%): C 54.16, H 8.69, N 8.24, Cl 6.95; Found (%): C 54.24, H 8.57, N 8.32, Cl 6.88.

EXAMPLE 12

A solution of n-butyl 3-n-decylamino-3-deoxy-D-glycopyranoside (7.96 g, 21.2 mmol) in a mixture of methanol (40 ml) and isopropanol (20 ml) was dropped into a solution of p-cyanophenyl N-(2-chloroethyl)-N-nitrosocarbamate (5.91 g, 23.3 mmol) in a mixture of tetrahydrofuran (50 ml), dioxane (30 ml), and acetone (20 ml) at −5° to −10° C. spending 10 minutes, and reaction was conducted at −5° to 15° C. for further 2 hours. After confirmation by TLC of the reaction completion, the reaction fluid was vacuum-concentrated at 25° C. and fractionated by column chromatography (packing: Kiesel gel 60; eluent: chloroform→chloroform/ethanol 9:1). The fraction of objective α-form product was vacuum-concentrated at 25° C., and recrystallized from methanol and water, giving 1.86 g of 3-n-decyl-3-(n-butyl α-D-glycopyranose-3-yl)-1-(2-chloroethyl)-1-nitrosourea; yield 17.2%, m.p. 81°–83° C., $[\alpha]_D^{20}+40.2°$ (C 1.0, methanol).

Elementary analysis, for $C_{23}H_{44}N_3O_7Cl$ (mol.wt. 510.07): Calcd. (%): C 54.16, H 8.69, N 8.24, Cl 6.95; Found (%): C 54.22, H 8.74, N 8.17, Cl 6.88.

EXAMPLE 13

A solution of n-butyl 4-n-decylamino-4-deoxy-α-D-glycopyranoside (7.21 g, 19.2 mmol) in methanol (50 ml) was dropped into a solution of p-nitrophenyl N-(2-chloroethyl)-N-nitrosocarbamate (5.77 g, 21.1 mmol) in tetrahydrofuran (60 ml) with well stirring at 0° to −5° C. spending 10 minutes, and reaction was conducted at the same temperature for further 2 hours. After confirmation by TLC of the reaction completion, the reaction fluid was vacuum-concentrated at 25° C. and fractionated by column chromatography (packing: Kiesel gel 60; eluent: chloroform→chloroform/ethanol 9:1). The fraction of objective α-form product was vacuum-concentrated at 25° C. and recrystallized from methanol and water, giving 3.81 g of 3-n-decyl-3-(n-butyl α-D-glycopyranose-4-yl)-1-(2-chloroethyl)-1-nitrosourea; yield 38.9%, m.p. 88°–90° C., $[\alpha]_D^{20}+53.8°$ (C 1.0, methanol).

Elementary analysis, for $C_{23}H_{44}N_3O_7Cl$ (mol.wt. 510.07): Calcd. (%): C 54.16, H 8.69, N 8.24, Cl 6.95; Found (%): C 54.28, H 8.72, N 8.18, Cl 6.89.

EXAMPLE 14

A solution of n-butyl 6-isobutylamino-6-deoxy-D-glycopyranoside (6.03 g, 20.7 mmol) in a mixture of methanol (50 ml) and acetone (20 ml), after adjustment to pH 9.0 by adding succinic acid fine powder, was dropped into a solution of p-nitrophenyl N-(2-chloroethyl)-N-nitrosocarbamate (6.21 g, 22.7 mmol) in a mixture of tetrahydrofuran (60 ml) and isopropanol (20 ml) with well stirring at 0° to −5° C. spending 15 minutes, and reaction was conducted at the same temperature for further 2 hours. After confirmation by TLC of the reaction completion, the reaction fluid was vacuum-concentrated at 25° C. and separated by column chromatography (packing Kiesel gel 60; eluent: benzene→chloroform/methanol 9:1) into fractions of objective α- and β-form products, which were each vacuum-concentrated at 25° C. and recrystallized from methanol and water, giving 1.63 g of 3-isobutyl-3-(n-butyl-α-D-glucopyranose-6-yl)-1-(2-chloroethyl)-1-nitrosourea; yield 18.5%, m.p. 73°–75° C., $[\alpha]_D^{20}+68.1°$ (C 1.0, methanol); and 1.34 g of 3-isobutyl-3-(n-butyl β-D-glycopyranose-6-yl)-1-(2-chloroethyl)-1-nitrosourea; yield 15.2%, m.p. 99°–101° C. (decomposition), $[\alpha]_D^{20}-14.8°$ (C 1.0, methanol).

Elementary analysis, for $C_{17}H_{32}N_3O_7Cl$ (mol.wt. 425.91): Calcd. (%): C 47.94, H 7.57, N 9.87, Cl 8.32; Found (%): α-form: C 47.99, H 7.51, N 9.84, Cl 8.38; β-form: C 48.08, H 7.51, N 9.79, Cl 8.44.

EXAMPLE 15

A solution of isobutyl 6-methylamino-6-deoxy-D-glycopyranoside (5.29 g, 21.2 mmol) in methanol (50 ml), after adjustment to pH 9.0 by adding salicylic acid fine powder, was dropped into a solution of O-nitrophenyl N-(2-chloroethyl)-N-nitrosocarbamate (6.40 g, 23.4 mmol) in a mixture of tetrahydrofuran (40 ml), dioxane (20 ml), and isopropanol (20 ml) with well stirring at 0° to −5° C. spending 10 minutes, and reaction was conducted at the same temperature for further 1.5 hours. After confirmation by TLC of the reaction completion, the reaction fluid was vacuum-concentrated at 25° C. and separated by column chromatography (packing: Kiesel gel 60; eluent: chloroform→chloroform/methanol 9:1) into fractions of objective α- and β-form products, which were each vacuum-concentrated at 30° C. and recrystallized from methanol and water, giving 3.07 g of 3-methyl-3-(isobutyl α-D-glucopyranose-6-yl)-1-(2-chloroethyl)-1-nitrosourea; yield 37.7%, m.p. 65°–67° C., $[\alpha]_D^{20}+73.4°$ (C 1.0, methanol); and 2.57 g of 3-methyl-3-(isobutyl β-D-glucopyranose-6-yl)-1-(2-chloroethyl)-1-nitrosourea; yield 31.6%, m.p. 94°–96° C. (decomposition), $[\alpha]_D^{20}-15.6°$ (C 1.0, methanol).

Elementary analysis, for $C_{14}H_{26}N_3O_7Cl$ (mol.wt. 383.83): Calcd.(%): C 43.81, H 6.83, N 10.95, Cl 9.23; Found (%): α-form: C 43.93, H 6.76, N 10.88, Cl 9.27; β-form: C 43.76, H 6.92, N 10.92, Cl 9.18.

EXAMPLE 16

A solution of isobutyl 6-isobutylamino-6-deoxy-D-glucopyranoside (6.85 g, 23.5 mmol) in a mixture of methanol (50 ml) and acetone (30 ml), after 4 g of dry ice was added, was dropped into a solution of O-nitrophenyl N-(2-chloroethyl)-N-nitrosocarbamate (7.09 g, 25.9 mmol) in a mixture of tetrahydrofuran (50 ml), ethanol (10 ml), and nitromethane (10 ml) with well stirring at −5° to −15° C. spending 15 minutes, and reaction was conducted at the same temperature for further 2 hours. After confirmation by TLC of the reaction completion, the reaction fluid was vacuum-concentrated at 25° C. and separated by column chromatography (packing: Kiesel gel 60; eluent: chloroform→chloroform/methanol 9:1) into fractions of α- and β-form products, which were each vacuum-concentrated at 25° C. and recrystallized from methanol and water, giving 3.57 g of 3-isobutyl-3-(isobutyl α-D-glucopyranose-6-yl)-1-(2-chloroethyl)-1-nitrosourea; yield 35.7%, m.p. 72°–74° C., $[\alpha]_D^{20}+72.5°$ (C 1.0, methanol); and 3.14 g of 3-isobutyl-3-(isobutyl β-D-glucopyranose-6-yl)-1-(2-chloroethyl)-1-nitrosourea; yield 31.4%, m.p. 96°–98° C. (decomposition), $[\alpha]_D^{20}-14.2°$ (C 1.0, methanol).

Elementary analysis, for $C_{17}H_{32}N_3O_7Cl$ (mol.wt. 425.91): Calcd.(%): C 47.94, H 7.57, N 9.87, Cl 8.32; Found (%): α-form C 47.98, H 7.49, N 9.92, Cl 8.26; β-form C 48.06, H 7.53, N 9.94, Cl 8.27.

EXAMPLE 17

A solution of isobutyl 2-isobutylamino-2-deoxy-D-glucopyranoside (6.21 g, 21.3 mmol) in a mixture of ethanol (30 ml), dioxane (10 ml), and isopropyl ether (10 ml) was dropped into a solution of p-cyanophenyl N-(2-chloroethyl)-N-nitrosocarbamate (5.94 g, 23.4 mmol) in a mixture of tetrahydrofuran (30 ml) and dioxane (20 ml) with stirring at 0° to −5° C. for 5 minutes, and stirring was continued at the same temperature for further 2 hours. After confirmation by TLC of completion of the reaction, the reaction fluid was vacuum-concentrated at 30° C. and separated by column chromatography (packing: Kiesel gel 60; eluent: chloroform→chloroform/methanol 8:1) into fractions of objective α- and β-form products, which were each vacuum-concentrated at 25° C. and recrystallized from methanol and water, giving 1.22 g of 3-isobutyl-3-(isobutyl α-D- glucopyranose-2-yl)-1-(2-chloroethyl)-1-nitrosourea; yield 13.5%, m.p. 84°–86° C., $[\alpha]_D^{20}+78.9°$ (C 1.0, methanol); and 0.98 g of 3-isobutyl-3-(isobutyl β-D-glucopyranose-2-yl)-1-(2-chloroethyl)-1-nitrosourea; yield 10.8%, m.p. 106°–108° C. (decomposition), $[\alpha]_D^{20}-20.4°$ (C 1.0, methanol).

Elementary analysis, for $C_{17}H_{32}N_3O_7Cl$ (mol.wt. 425.91): Calcd.(%): C 47.94, H 7.57, N 9.87, Cl 8.32; Found (%): α-form C 48.02, H 7.49, N 9.88, Cl 8.38; β-form C 48.08, H 7.49, N 9.94, Cl 8.22.

EXAMPLE 18

A solution of isobutyl 3-sec-butylamino-3-deoxy-D-glucopyranoside (6.59 g, 22.6 mmol) in a mixture of methanol (50 ml) and dioxane (30 ml), after 5 g of dry ice was added, was dropped into a solution of O-nitrophenyl N-(2-chloroethyl)-N-nitrosocarbamate (6.81 g, 24.9 mmol) in a mixture of tetrahydrofuran (50 ml) and isopropanol (20 ml) with well stirring at 0° to −5° C. spending 10 minutes, and stirring was continued at 0° to 5° C. for further 2 hours. After confirmation by TLC of the reaction completion, the reaction fluid was vacuum-concentrated at 25° C., washed with benzene, and fractionated by column chromatography (packing: Kiesel gel 60; eluent: chloroform/methanol 9:1) to separate objective α- and β-forms. The fractions were each vacuum-concentrated at 25° C. and recrystallized from methanol and petroleum ether, giving 3.54 g of 3-sec-butyl-3-(isobutyl α-D-glucopyranose-3-yl)-1-(2-chloroethyl)-1-nitrosourea; yield 36.8%, m.p. 65°–67° C., $[\alpha]_D^{20}+46.5°$ (C 1.0, methanol); and 3.00 g of 3-sec-butyl-3-(isobutyl β-D-glucopyranose-3-yl)-1-(2-chloroethyl)-1-nitrosourea; yield 31.2%, m.p. 87°–89° C., $[\alpha]_D^{20}-15.2°$ (C 1.0, methanol).

Elementary analysis, for $C_{17}H_{32}N_3O_7Cl$ (mol.wt. 425.91): Calcd.(%): C 47.94, H 7.57, N 9.87, Cl 8.32; Found (%): α-form C 48.06, H 7.51, N 9.93, Cl 8.27; β-form C 47.99, H 7.63, N 9.81, Cl 8.36.

EXAMPLE 19

A solution of isobutyl 2-isopropylamino-2-deoxy α-D-glucopyranoside (7.04 g, 25.4 mmol) in a mixture of methanol (50 ml) and tetrahydrofuran (15 ml), after adjusted to pH 8.9 by adding succinic acid fine powder with well stirring, was dropped into a solution of p-nitrophenyl N-(2-chloroethyl)-N-nitrosocarbamate (7.63 g, 27.9 mmol) in a mixture of acetone (40 ml) and isopropanol (20 ml) with well stirring at 0° to 5° C. spending 5 minutes, and reaction was continued at the same temperature for further 2 hours. After confirmation by TLC of the reaction completion, the reaction fluid was vacuum-concentrated at 25° C. and recrystallized from methanol and water, giving 2.56 g of 3-isopropyl-3-(isobutyl α-D-glucopyranose-2-yl)-1-(2-chloroethyl)-1-nitrosourea; yield 24.5%, m.p. 83°–85° C., $[\alpha]_D^{20}+81.5°$ (C 1.0, methanol).

Elementary analysis, for $C_{16}H_{30}N_3O_7Cl$ (mol.wt. 411.88): Calcd.(%): C 46.66, H 7.34, N 10.20, Cl 8.61; Found (%): C 46.74, H 7.28, N 10.28, Cl 8.53.

EXAMPLE 20

A solution of isobutyl 6-(2-methoxyethylamino)-6-deoxy-D-glucopyranoside (7.54 g, 25.7 mmol) in a mixture of methanol (50 ml) and dioxane (30 ml), after 4 g of dry ice was added, was dropped into a solution of O-cyanophenyl N-(2-chloroethyl)-N-nitrosocarbamate (7.15 g, 28.2 mmol) in a mixture of tetrahydrofuran (50 ml) and acetone (30 ml) with well stirring at −5° to −15° C., and reaction was conducted at the same temperature for 2 hours. After confirmation by TLC of the reaction completion, the reaction fluid was vacuum-concentrated at 25° C. and fractionated by column chromatography (packing: Kiesel gel 60; eluent: chloroform→chloroform/methanol 9:1) to separate ojective α- and β-forms. The fractionated solutions were each vacuum-concentrated at 25° C. and recrystallized from methanol and water, giving 2.66 g of 3-(2-methoxyethyl)-3-(isobutyl α-D-glucopyranose-6-yl)-1-(2-chloroethyl)-1-nitrosourea; yield 24.2%, m.p. 52°–54° C., $[\alpha]_D^{20}+70.7°$ (C 1.0, methanol); and 2.12 g of 3-(2-methoxyethyl)-3-(isobutyl β-D-glucopyranose-6-yl)-1-(2-chloroethyl)-1-nitrosourea; yield 19.3%, m.p. 81°–83° C., $[\alpha]_D^{20}-13.6°$ (C 1.0, methanol).

Elementary analysis, for $C_{16}H_{30}N_3O_8Cl$ (mol.wt. 427.88): Calcd.(%): C 44.91, H 7.07, N 9.82, Cl 8.29; Found (%): α-form C 44.98, H 7.02, N 9.76, Cl 8.34; β-form C 44.83, H 7.15, N 9.89, Cl 8.22.

EXAMPLE 21

A solution of cyclohexyl 6-isobutylamino-6-deoxy-D-glucopyranoside (7.84 g, 24.7 mmol) in a mixture of ethanol (50 ml) and dioxane (30 ml), after 4 g of dry ice was added, was dropped into a solution of O-nitrophenyl N-(2-chloroethyl)-N-nitrosocarbamate (7.44 g, 27.2 mmol) in tetrahydrofuran (50 ml) with well stirring at −10° to −15° C. spending 10 minutes, and reaction was continued at the same temperature for further 2 hours. After confirmation by TLC of the reaction completion, the reaction fluid was vacuum-concentrated at 25° C. and fractionated by column chromatography (packing: Kiesel gel 60; eluent: chloroform→chloroform/methanol 39:1) to separate objective α- and β-forms. The fractionated solutions were each vacuum-concentrated at 25° C. and recrystallized from methanol and water, giving 3.99 g of 3-isobutyl-3-(cyclohexyl α-D-glucopyranose-6-yl)-1-(2-chloroethyl)-1-nitrosourea; yield 35.7%, m.p. 61°–63° C., $[\alpha]_D^{20}+74.8°$ (C 1.0, methanol); and 3.63 g of 3-isobutyl-3-(cyclohexyl β-D-glucopyranose-6-yl)-1-(2-chloroethyl)-1-nitrosourea; yield 32.5%, m.p. 82°–83° C., $[\alpha]_D^{20}-13.6°$ (C 1.0, methanol).

Elementary analysis, for $C_{19}H_{34}N_3O_7Cl$ (mol.wt. 451.95): Calcd.(%): C 50.49, H 7.58, N 9.30, Cl 7.85; Found (%): α-form C 50.55, H 7.49, N 9.42, Cl 7.77; β-form C 50.56, H 7.51, N 9.22, Cl 7.79.

$IR\nu_{max}^{KBr}$ ($cm^{-1}$): α-form 3350, 1700, 1490; β-form 3330, 1710, 1480.

NMR ($d_6$-DMSO)δ: α-form 3.46 (t, 2H, —NCH$_2$CH$_2$Cl), 4.12 (t, 2H, —NCH$_2$CH$_2$Cl), 4.85 (d, 1H, C$_1$—H); β-form 3.45 (t, 2H, —$\overline{\text{N}}$CH$_2$CH$_2$Cl), 4.08 (t, 2H, —NCH$_2$CH$_2$Cl), 4.31 (d, 1H, C$_1$—$\overline{\text{H}}$).

EXAMPLE 22

A solution of cyclohexyl 6-n-propylamino-6-deoxy-α-D-galactopyranoside (6.16 g, 20.3 mmol) in methanol (50 ml) was dropped into a solution of O-nitrophenyl N-(2-chloroethyl)-N-nitrosocarbamate (6.10 g, 22.3 mmol) in a mixture of tetrahydrofuran (50 ml) and acetone (30 ml) with well stirring at −5° to −10° C. spending 5 minutes, and reaction was continued at the same temperature for further 2 hours. After confirmation by TLC of the reaction completion, the reaction fluid was vacuum-concentrated at 25° C. and purified by column chromatography (packing: Kiesel gel 60; eluent: chloroform→chloroform/ethanol 9:1). The purified solution was vacuum-concentrated at 25° C. and crystallized from methanol and water, giving 6.45 g of 3-n-propyl-3-(cyclohexyl α-D-galactopyranose-6-yl)-1-(2-chloroethyl)-1-nitrosourea; yield, 72.5%, m.p. 59°–61° C., $[\alpha]_D^{20}+19.2°$ (C 1.0, methanol).

Elementary analysis, for $C_{18}H_{32}N_3O_7Cl$ (mol.wt. 437.92): Calcd.(%): C 49.37, H 7.37, N 9.59, Cl 8.10; Found (%): C 49.42, H 7.30, N 9.64, Cl 8.04.

EXAMPLE 23

A solution of cyclohexyl 6-(3-ethoxy-n-propylamino)-deoxy-α-D-galactopyranoside (7.57 g, 21.8 mmol) in a mixture of methanol (50 ml) and isopropanol (30 ml), after 4 g of dry ice was added, was dropped into a solution of O-nitrophenyl N-(2-chloroethyl)-N-nitrosocarbamate (6.59 g, 24.1 mmol) in tetrahydrofuran (50 ml) with well stirring at −5° to −10° C. spending 10 minutes, and the reaction mixture was allowed to stand in a refregierator at 0° to 5° C. for 18 hours. After confirmation by TLC of the reaction completion, the reaction fluid was vacuum-concentrated at 25° C. and crystallized from methanol and petroleum ether, giving 8.07 g of 3-(ethoxy-n-propyl)-3-(cyclohexyl α-D-galactopyranose-6-yl)-1-(2-chloroethyl)-1-nitrosourea; yield 76.8%, m.p. 60°–63° C., $[\alpha]_D^{20}+14.8°$ (C 1.0, methanol).

Elementary analysis, for $C_{20}H_{36}N_3O_8Cl$ (mol.wt. 481.97): Calcd.(%): C 49.84, H 7.53, N 8.72, Cl 7.35; Found (%): C 49.93, H 7.47, N 8.79, Cl 7.30.

EXAMPLE 24

A solution of n-butyl 2-(2,3-dimethoxybenzyl α-D-galactopyranoside (7.63 g, 19.8 mmol) in a mixture of methanol (20 ml), dioxane (20 ml), and isopropyl ether (10 ml), after 3 g of dry ice was added, was dropped into a solution of p-nitrophenyl N-(2-chloroethyl)-N-nitrosocarbamate (6.13 g, 22.4 mmol) in tetrahydrofuran (30 ml) with well stirring at 0° to −5° C. spending 5 minutes, and reaction was continued at the same temperature for further 2 hours. After confirmation by TLC of the reaction completion, the reaction fluid was vacuum-concentrated at 25° C., and dissolved in ethanol, and crystallized by addition of ethyl ether and n-hexane, giving 7.39 g of 3-(2,3-dimethylbenzyl)-3-(n-butyl α-D-galactopyranose-2-yl)-1-(2-chloroethyl)-1-nitrosourea; yield 71.8%, m.p. 90°–92° C., $[\alpha]_D^{20}+12.4°$ (C 1.0, methanol)

Elementary analysis, for $C_{22}H_{34}N_3O_9Cl$ (mol.wt. 519.98): Calcd.(%): C 50.82, H 6.59, N 8.08, Cl 6.82; Found (%): C 50.95, H 6.55, N 8.12, Cl 6.77.

EXAMPLE 25

A solution of 2-methoxy-n-propyl 6-tetrahydrofurfurylamino-6-deoxy-α-D-galactopyranoside (8.52 g, 25.4 mmol) in methanol (50 ml) was dropped into a solution of O-nitrophenyl N-(2-chloroethyl)-N-nitrosocarbamate (7.69 g, 28.1 mmol) in tetrahydrofuran (50 ml) with well stirring at −5° to −10° C. spending 5 minutes, and stirring was continued for further 2 hours at 0° to 10° C. The resulting reaction mixture was vacuum-concentrated at 25° C. and crystallized from methanol and water, giving 9.25 g of 3-tetrahydrofurfuryl-3-(2-methoxy-n-propyl α-D-galactopyranose-6-yl)-1-(2-chloroethyl)-1-nitrosourea; yield 77.5%, m.p. 63°–65° C., $[\alpha]_D^{20}+12.7°$ (C 1.0, methanol).

Elementary analysis, for $C_{18}H_{32}N_3O_9Cl$ (mol.wt. 469.92): Calcd.(%): C 46.01, H 6.86, N 8.94, Cl 7.55; Found (%): C 46.13, H 6.82, N 8.88, Cl 7.62.

EXAMPLE 26

A solution of isobutyl 6-isobutylamino-6-deoxy-α-L-galactopyranoside (6.32 g, 21.7 mmol) in a mixture of methanol (50 ml) and tetrahydrofuran (20 ml), adjusted to pH 9.0 by adding succinic acid fine powder with well stirring, was dropped into a solution of p-nitrophenyl N-(2-chloroethyl)-N-nitrosocarbamate (6.54 g, 23.9 mmol) in acetone (50 ml) with thorough stirring at 0° to 5° C. spending 10 minutes, and reaction was conducted at the same temperature for further 2 hours. After confirmation by TLC of the reaction completion, the reaction mixture was vacuum-concentrated at 25° C. and fractionated by column chromatography (packing: Kiesel gel 60; eluent: benzene→chloroform/acetone 4:1) to separate the objective product of α-form. The objective fractionated solution was vacuum-concentrated at 25° C. and crystallized from methanol and water, giving 6.27 g of 3-isobutyl-3-(isobutyl α-L-galactopyranose-6-yl)-1-(2-chloroethyl)-1-nitrosourea; yield 67.8%, m.p. 75°–77° C., $[\alpha]_D^{20}-34.5°$ (C 1.0, methanol).

Elementary analysis, for $C_{17}H_{32}N_3O_7Cl$ (mol.wt. 425.91): Calcd.(%): C 47.94, H 7.57, N 9.87, Cl 8.32; Found (%): C 47.86, H 7.64, N 9.76, Cl 8.38.

EXAMPLE 27

A solution of benzyl 6-isobutylamino-6-deoxy-α-D-mannopyranoside (7.35 g, 22.6 mmol) in a mixture of methanol (50 ml) and tetrahydrofuran (20 ml), after 4 g of dry ice was added, was dropped into a solution of O-nitrophenyl N-(2-chloroethyl)-N-nitrosocarbamate (6.87 g, 25.1 mmol) in acetone (50 ml) with well stirring at 0° to −10° C. spending 5 minutes, and reaction was conducted at 0° to 5° C. for further 2 hours. After confirmation by TLC that the reaction finished, the reaction mixture was vacuum-concentrated at 25° C., dissolved in ethanol, and crystallized by addition of ethyl ether and n-hexane mixture, giving 7.93 g of 3-isobutyl-3-(benzyl α-D-mannopyranose-6-yl)-1-(2-chloroethyl)-1-nitrosourea; yield 76.3%, m.p. 55°–57° C., $[\alpha]_D^{20}+19.3°$ (C 1.0, methanol).

Elementary analysis, for $C_{20}H_{30}N_3O_7Cl$ (mol.wt. 459.93): Calcd.(%): C 52.23, H 6.57, N 9.14, Cl 7.71; Found (%): C 52.28, H 6.51, N 9.21, Cl 7.65.

EXAMPLE 28

A solution of isobutyl 6-cyclopropylmethylamino-6-deoxy-α-D-mannopyranoside (7.18 g, 24.8 mmol) in a mixture of methanol (50 ml), dioxane (20 ml), and acetone (20 ml) was dropped into a solution of O-nitrophenyl N-(2-chloroethyl)-N-nitrosocarbamate (7.50 g, 27.4 mmol) in tetrahydrofuran (50 ml) with well stirring at 0° to −5° C. spending 5 minutes, and the reaction mixture was allowed to stand in a refrigerator at 0° to 5° C. for 18 hours. After confirmation by TLC that the reaction was finished, the reaction mixture was vacuum-concentrated at 25° C., dissolved in chloroform (50 ml), and washed twice with 50 ml each of water. The chloroform solution was dehydrated, vacuum-concentrated at 20° C., and crystallized from a methanol-ethyl ether-n-hexane mixture, giving 7.63 g of a 3-cyclopropylmethyl-3-(isobutyl α-D-mannopyranose-6-yl)-1-(2-chloroethyl)-1-nitrosourea; yield 72.6%, m.p. 60°–62° C., $[\alpha]_D^{20}+21.9°$ (C 1.0, methanol).

Elementary analysis, for $C_{17}H_{30}N_3O_7Cl$ (mol.wt. 423.89): Calcd.(%): C 48.17, H 7.13, N 9.91, Cl 8.37; Found (%): C 48.28, H 7.05, N 9.85, Cl 8.43.

EXAMPLE 29

A solution of β-phenylethyl 6-(1-methyl-2-methoxyethylamino)-6-deoxy-α-D-altropyranoside (6.65 g, 18.7 mmol) in a mixture of methanol (30 ml), dioxane (20 ml), and benzene (10 ml) was dropped into a solution of p-nitrophenyl N-(2-chloroethyl)-N-nitrosocarbamate (5.64 g, 20.6 mmol) in a mixture of acetone (50 ml) and isopropyl ether (20 ml) with well stirring at 0° to 5° C. spending 5 minutes, and reaction was continued for further 2 hours at the same temperature. After confirmation by TLC that the reaction was finished, the reaction mixture was vacuum-concentrated at 25° C. and fractionated by column chromatography (packing: Kiesel gel 60; eluent: chloroform→chloroform/methanol 39:1) to separate the objective product of α-form. The objective fractionated solution was vacuum-concentrated at 25° C. and crystallized from methanol and water, giving 6.03 g of 3-(1-methyl-2-methoxyethyl)-3-(β-phenylethyl α-D-altropyranose-6-yl)-1-(2-chloroethyl)-1-nitrosourea; yield 65.8%, m.p. 55°–57° C., $[\alpha]_D^{20}+17.8°$ (C 1.0, methanol).

Elementary anaylisis for $C_{21}H_{32}N_3O_8Cl$ (mol.wt. 489.95): Calcd.(%): C 51.48, H 6.58, N 8.58, Cl 7.24; Found (%): C 51.42, H 6.65, N 8.64, Cl 7.18.

EXAMPLE 30

A solution of isobutyl 2-cyclohexylamino-2-deoxy-α-D-altropyranoside (6.89 g, 21.7 mmol) in a mixture of methanol (20 ml) and dioxane (20 ml), after 2 g of dry ice was added, was dropped into a solution of O-nitrophenyl N-(2-chloroethyl)-N-nitrosocarbamate (6.54 g, 23.9 mmol) in tetrahydrofuran (40 ml) with well stirring at 0° to 5° C. spending 5 minutes, and reaction was continued for further 2 hours with stirring at the same temperature. After confirmation by TLC that the reaction finished, the reaction mixture was vacuum-concentrated at 25° C. and crystallized from methanol and water, giving 7.11 g of 3-cyclohexyl-3-(isobutyl α-D-altropyranose-2-yl)-1-(2-chloroethyl)-1-nitrosourea; yield 72.5%, m.p. 87°–89° C., $[\alpha]_D^{20}+22.5°$ (C 1.0, methanol).

Elementary analysis, for $C_{19}H_{34}N_3O_7Cl$ (mol.wt. 451.95): Calcd.(%): C 50.49, H 7.58, N 9.30, Cl 7.85; Found (%): C 50.56, H 7.51, N 9.21, Cl 7.88.

EXAMPLE 31

A solution of benzyl 6-n-propylamino-6-deoxy-α-D-altropyranoside (6.73 g, 21.6 mmol) in a mixture of methanol (20 ml) and tetrahydrofuran (20 ml) was dropped into a solution of p-nitrophenyl N-(2-chloroethyl)-N-nitrosocarbamate (6.51 g, 23.8 mmol) in a mixture of acetone (20 ml) and isopropyl ether (15 ml) with well stirring at −5° to −10° C. spending 10 minutes, and stirring was continued for further 2 hours at 0° to 10° C. After confirmation of TLC that the reaction finished, the reaction mixture was vacuum-concentrated at 30° C. and fractionated by column chromatography (packing: Keisel gel 60; eluent: chloroform→chloroform/acetone 4:1) to separate the objective product of α-form. The objective fractionated solution was vacuum-concentrated at 25° C. and crystallized from an ethanol-ethyl ether-n hexane mixture, giving 2.06 g of 3-(n-propyl)-3-(benzyl α-D-altropyranose-6-yl)-1-(2-chloroethyl)-1-nitrosourea; yield 21.4%, m.p. 54°–56° C., $[\alpha]_D^{20}+23.8°$ (C 1.0, methanol).

Elementary analysis, for $C_{19}H_{28}N_3O_7Cl$ (mol.wt. 445.90): Calcd.(%): C 51.18, H 6.33, N 9.42, Cl 7.95; Found (%): C 51.12, H 6.42, N 9.35, Cl 7.99.

EXAMPLE 32

A solution of isobutyl 3-(1-methyl-2-methoxyethylamino-3-deoxy-α-D-altropyranoside (6.24 g, 20.3 mmol) in a mixture of methanol (30 ml) and tetrahydrofuran (20 ml), after adjusted to pH 8.8 by adding succinic acid fine powder with well stirring, was dropped into a solution of p-nitrophenyl N-(2-chloroethyl)-N-nitrosocarbamate (6.13 g, 22.4 mmol) in a mixture of acetone (30 ml) and tetrahydrofuran (20 ml) with well stirring at 0° to −5° C. spending 10 minutes, and reaction was conducted at the same temperature for further 2 hours. After confirmation by TLC that the reaction was finished, the reaction mixture was vacuum-concentrated at 25° C. and fractionated by column chromatography (packing: Kiesel gel 60; eluent: benzene→chloroform/methanol 10:1) to separate the objective product of α-form. The objective fractionated solution was vacuum concentrated at 25° C. and crystallized from methanol and water, giving 1.70 g of 3-(1-methyl-2-methoxyethyl)-3-(isobutyl α-D-altropyranose-3-yl)-1-(2-chloroethyl)-1-nitrosourea; yield 18.9%, m.p. 66°–68° C., $[\alpha]_D^{20}+10.6°$ (C 1.0, methanol).

Elementary analysis, for $C_{17}H_{32}N_3O_8Cl$ (mol.wt. 441.91): Calcd.(%): C 46.21, H 7.30, N 9.51, Cl 8.02; Found (%): C 46.29, H 7.24, N 9.45, Cl 7.94.

EXAMPLE 33

Using cyclohexyl 6-isobutylamino-6-deoxy-α-D-talopyranoside (6.86 g, 21.6 mmol), 7.15 g of 3-isobutyl-3-(cyclohexyl α-D-talopyranose-6-yl)-1-(2-chloroethyl)-1-nitrosourea was prepared in the same manner as in Example 23; yield 73.2%, m.p. 62°–64° C., $[\alpha]_D^{20}+17.2°$.

Elementary analysis, for $C_{19}H_{34}N_3O_7Cl$ (mol.wt. 451.95): Calcd.(%): C 50.49, H 7.58, N 9.30, Cl 7.85; Found (%): C 50.58, H 7.43, N 9.27, Cl 7.94.

EXAMPLE 34

Using isobutyl 6-(3-methoxy-n-propylamino)-6-deoxy-β-D-talopyranoside (5.81 g, 18.9 mmol), 6.16 g of 3-(3-methoxy-n-propyl)-3-(isobutyl β-D-talopyranose-6-yl)-1-(2-chloroethyl)-1-nitrosourea was prepared in the same manner as in Example 22; yield 73.8%, m.p. 51°–53° C., $[\alpha]_D^{20}+8.2°$ (C 1.0, methanol).

Elementary analysis, for $C_{17}H_{32}N_3O_8Cl$ (mol.wt. 441.91): Calcd.(%): C 46.21, H 7.30, N 9.51, Cl 8.02; Found (%): C 46.29, N 7.22, N 9.58, Cl 7.95.

EXAMPLE 35

Using tetrahydrofurfuryl 6-isobutylamino-6-deoxy-α-D-talopyranoside (6.29 g, 19.7 mmol), 6.31 g of 3-isobutyl-3-(tetrahydrofurfuryl α-D-talopyranose-6-yl)-1-(2-chloroethyl)-1-nitrosourea was obtained in the same manner as in Example 22; yield 70.6%, m.p. 58°–60° C., $[\alpha]_D^{20}+15.4°$ (C 1.0, methanol).

Elementary analysis, for $C_{18}H_{32}O_8Cl$ (mol.wt. 453.92): Calcd. (%): C 47.63, H 7.11, N 9.26, Cl 7.81; Found (%): C 47.76, H 7.04, N 9.34, Cl 7.73.

EXAMPLE 36

Using cyclohexyl 3-isopropylamino-3-deoxy-α-D-xylopyranoside (5.41 g, 19.8 mmol), 4.75 g of 3-isopropyl-3-(cyclohexyl α-D-xylopyranose-3-yl)-1-(2-chloroethyl)-1-nitrosourea was obtained in the same manner as in Example 22; yield 65.4%, m.p. 47°–49° C., $[\alpha]_D^{20}$ +17.3° (C 1.0, methanol).

Elementary analysis, for $C_{17}H_{30}N_3O_6Cl$ (mol.wt. 407.90): Calcd. (%): C 50.06, H 7.42, N 10.30, Cl 8.69; Found (%): C 49.98, H 7.48, N 10.36, Cl 8.68.

EXAMPLE 37

Using cyclohexyl 4-isobutylamino-4-deoxy-α-D-xylopyranoside (5.43 g, 18.9 mmol), 5.52 g of 3-isobutyl-3-(cyclohexyl α-D-xylopyranose-4-yl)-1-2-(chloroethyl)-1-nitrosourea was obtained in the same manner as in Example 22; yield 69.2%, m.p. 70°–72° C., $[\alpha]_D^{20}$ +15.2° (C 1.0, methanol).

Elementary analysis, for $C_{18}H_{32}N_3O_6Cl$ (mol.wt. 421.92): Calcd. (%): C 51.24, H 7.64, N 9.96, Cl 8.41; Found (%): C 51.33, H 7.58, N 9.93, Cl 8.28.

EXAMPLE 38

Using cyclohexyl 4-(2-ethoxyethylamino)-4-deoxy-α-D-xylopyranoside (6.01 g, 19.8 mmol), 5.02 g of 3-(2-ethoxyethyl)-3-(cychlohexyl α-D-xylopyranose-4-yl)-1-(2-chloroethyl)-1-nitrosourea was obtained in the same manner as in Example 22; yield 68.7%, m.p. 60°–62° C., $[\alpha]_D^{20}$ +12.8° (C1.0, methanol).

Elementary analysis, for $C_{18}H_{32}N_3O_7Cl$ (mol.wt. 437.92): Calcd. (%): C 49.37, H 7.37, N 9.59, Cl 8.10; Found (%): C 49.42, H 7.33, N 9.68, Cl 8.03.

EXAMPLE 39

Using 3-methoxy-n-propyl 4-isobutylamino-4-deoxy-α-D-xylopyranoside (5.49 g, 19.8 mmol), 5.22 g of 3-isobutyl-3-(3-methoxy-n-propyl α-D-xylopyranose-4-yl)-1-(2-chloroethyl)-1-nitrosourea was obtained in the same manner as in Example 22; yield 69.3%, m.p. 61°–63° C., $[\alpha]_D^{20}$ +12.8° (C 1.0, methanol).

Elementary analysis, for $C_{16}H_{30}N_3O_7Cl$ (mol.wt. 411.88): Calcd. (%): C 46.66, H 7.34, H 10.20, Cl 8.61; Found (%): C 46.78, H 7.28, N 10.27, Cl 8.57.

EXAMPLE 40

Using isobutyl 4-tetrahydrofurfurylamino-4-deoxy-α-D-xylopyranoside (7.21 g, 26.2 mmol), 8.01 g of 3-tetrahydrofurfuryl-3-(isobutyl α-D-xylopyranose-4-yl)-1-(2-chloroethyl)-1-nitrosourea was obtained in the same manner as in Example 2; yield 74.6%, m.p. 69°–71° C., $[\alpha]_D^{20}$ +10.4° (C 1.0, methanol).

Elementary analysis, for $C_{16}H_{28}N_3O_7Cl$ (mol.wt. 409.87): Calcd. (%): C 46.89, H 6.89, N 10.25, Cl 8.65; Found (%): C 46.94, H 6.82, N 10.34, Cl 8.60.

EXAMPLE 41

Using isobutyl 4-(3-methoxy-n-propylamino)-4-deoxy-α-L-arabinopyranoside (7.82 g, 28.2 mmol), 7.94 g of 3-(3-methoxy-n-propyl)-3-(isobutyl α-L-arabinopyranose-4-yl)-1-(2-chloroethyl)-1-nitrosourea was obtained in the same manner as in Example 1; yield 68.4%, m.p. 67°–69° C., $[\alpha]_D^{20}$ +60.2° (C 1.0, methanol).

Elementary analysis, for $C_{16}H_{30}N_3O_7Cl$ (mol.wt. 411.88): Calcd. (%): C 46.66, H 7.34, N 10.20, Cl 8.61; Found (%): C 46.74, H 7.28, N 10.15, Cl 8.68.

EXAMPLE 42

Using sec-butyl 4-isobutylamino-4-deoxy-α-L-arabinopyranoside (10.26 g, 28.4 mmol), 8.02 g of 3-isobutyl-3-(sec-butyl α-L-arabinopyranose-4-yl)-1-(2-chloroethyl)-1-nitrosourea was obtained in the same manner as in Example 1; yield 71.3%, m.p. 63°–65° C., $[\alpha]_D^{20}$ +66.2° (C 1.0, methanol).

Elementary analysis, for $C_{16}H_{30}N_3O_6Cl$ (mol.wt. 395.88): Calcd. (%): C 48.54, H 7.64, N 10.61, Cl 8.96; Found (%): C 48.62, H 7.57, N 10.68, Cl 9.02.

EXAMPLE 43

Using cyclohexyl 2-cyclopropylmethylamino-2-deoxy-α-L-arabinopyranoside (7.53 g, 26.4 mmol) 7.37 g of 3-cyclopropyl-3-(cyclohexyl α-L-arabinopyranose-2-yl)-1-(2-chloroethyl)-1-nitrosourea was obtained in the same manner as in Example 2; yield 66.5%, m.p. 62°–64° C., $[\alpha]_D^{20}$ +82.7° (C 1.0, methanol).

Elementary analysis, for $C_{18}H_{30}N_3O_6Cl$ (mol.wt. 419.91): Calcd. (%): C 51.49, H 7.20, N 10.01, Cl 8.44; Found (%): C 51.42, H 7.28, N 10.09, Cl 8.36.

EXAMPLE 44

Using isobutyl 3-methoxy-n-propylamino-2-deoxy-α-D-arabinopyranoside (7.77 g, 28.0 mmol), 7.80 g of 3-methoxy-n-propyl-3-(isobutyl α-D-arabinopyranose-2-yl)-1-(2-chloroethyl)-1-nitrosourea was obtained in the same manner as in Example 1; yield 67.6%, m.p. 84°–86° C., $[\alpha]_D^{20}$ −38.6° (C 1.0, methanol).

Elementary analysis, for $C_{16}H_{30}N_3O_7Cl$ (mol.wt. 411.88): Calcd. (%): C 46.66, H 7.34, N 10.20, Cl 8.61; Found (%): C 46.58, H 7.38, N 10.13, Cl 8.68.

EXAMPLE 45

Using isobutyl 4-cyclohexylmethylamino-4-deoxy-α-D-arabinopyranoside (8.08 g, 28.1 mmol), 7.81 g of 3-cyclohexyl-3-(isobutyl α-D-arabinopyranose-4-yl)-1-(2-chloroethyl)-1-nitrosourea was obtained in the same manner as in Example 1; yield 65.9%, m.p. 68°–70° C., $[\alpha]_D^{20}$ −28.4° (C 1.0, methanol).

Elementary analysis, for $C_{18}H_{32}N_3O_6Cl$ (mol.wt. 421.92): Calcd. (%): C 51.24, H 7.64, N 9.96, Cl 8.41; Found (%): C 51.18, H 7.71, N 9.99, Cl 8.37.

EXAMPLE 46

Using 2-methoxyethyl 5-sec-butylamino-5-deoxy-β-D-ribofuranoside (6.95 g, 26.4 mmol), the crystallization of objective product was attempted in the same manner as in Example 2, without success. Thus, 7.64 g sirupy 3-sec-butyl-3-(2-methoxy-ethyl β-D-ribofuranose-5-yl)-1-(2-chloroethyl)-1-nitrosourea was obtained; yield 75.8%, $[\alpha]_D^{20}$ −15.4° (C 1.0, methanol).

Elementary analysis, for $C_{15}H_{28}N_3O_7Cl$ (mol.wt. 397.86): Calcd. (%): C 45.28, H 7.10, N 10.56, Cl 8.91; Found (%): C 45.23, H 7.18, N 10.64, Cl 8.84.

EXAMPLE 47

Using cyclohexyl 5-isobutylamino-5-deoxy-β-D-ribofuranoside (8.10 g, 28.2 mmol), the crystallization of objective product was attempted in the same manner as in Example 1, without success. Thus, 8.73 g of sirupy 3-isobutyl-3-(cyclohexyl β-D-ribofuranose-5-yl)-1-(2-chloroethyl)-1-nitrosourea was obtained; yield 73.4%, $[\alpha]_D^{20}$ −12.8° (C 1.0, methanol).

Elementary analysis, for $C_{18}H_{32}N_3O_6Cl$ (mol.wt. 421.92): Calcd. (%): C 51.24, H 7.64, N 9.96, Cl 8.41; Found (%): C 51.32, H 7.58, N 9.92, Cl 8.47.

EXAMPLE 48

Using sec-butyl 5-methylamino-5-deoxy-β-D-ribofuranoside (5.77 g, 26.3 mmol), the crystallization of objective product was attempted in the same manner as in Example 2, but without success. Thus, 6.63 g of sirupy 3-methyl-3-(sec-butyl β-D-ribofuranose-5-yl)-1-(2-chloroethyl)-1-nitrosourea was obtained; yield 71.2%, $[α]_D^{20}$ −18.5° (C 1.0, methanol).

Elementary analysis, for $C_{13}H_{24}N_3O_6Cl$ (mol.wt. 353.80): Calcd. (%): C 44.13, H 6.84, N 11.88, Cl 10.02; Found (%): C 44.04, H 6.82, N 11.92, Cl 10.08.

EXAMPLE 49

Using chlorohexyl 5-isobutylamino-5-deoxy-β-D-arabinofuranoside (8.10 g, 28.2 mmol), 8.83 g of 3-isobutyl-3-(cyclohexyl β-D-arabinopyranose-5-yl)-1-(2-chloroethyl)-1-nitrosourea was obtained in the same manner as in Example 1; yield 74.2%, m.p. 74°–76° C., $[α]_D^{20}$ −36.8° (C 1.0, methanol).

Elementary analysis, for $C_{18}H_{32}N_3O_6Cl$ (mol.wt. 421.92): Calcd. (%): C 51.24, H 7.64, N 9.96, Cl 8.41; Found (%): C 51.18, H 7.68, N 9.92, Cl 8.54.

EXAMPLE 50

Using isobutyl 2-isobutylamino-2-deoxy-β-D-arabinofuranoside (6.93 g, 26.5 mmol), 7.73 g of 2-isobutyl-3-(isobutyl β-D-arabinofuranose-5-yl)-1-(2-chloroethyl)-1-nitrosourea was obtained in the same manner as in Example 2; yield 73.7%, m.p. 95°–97° C. (decomposition), $[α]_D^{20}$ −42.4° (C 1.0, methanol).

Elementary analysis, for $C_{16}H_{30}N_3O_6Cl$ (mol.wt. 395.88): Calcd. (%): C 48.54, H 7.64, N 10.61, Cl 8.96; Found (%): C 48.47, H 7.72, N 10.66, Cl 8.90.

EXAMPLE 51

Using isobutyl 5-(3-methoxy-n-propylamino)-5-deoxy-α-D-xylofuranoside (7.77 g, 28.0 mmol), 7.89 g of 3-(3-methoxy-n-propyl)-3-(isobutyl α-D-xylofuranose-5-yl)-1-(2-chloroethyl)-1-nitrosourea was obtained in the same manner as in Example 1; yield 68.4%, m.p. 66°–68° C., $[α]_D^{20}$ +14.4° (C 1.0, methanol).

Elementary analysis, for $C_{16}H_{30}N_3O_7Cl$ (mol.wt. 411.88): Calcd. (%): C 46.66, H 7.34, N 10.20, Cl 8.61; Found (%): C 46.73, H 7.28, N 10.19, Cl 8.69.

EXAMPLE 52

Using cyclohexyl 2-isobutylamino-2-deoxy-α-D-xylofuranoside (7.56 g, 26.3 mmol), 7.36 g of 3-isobutyl-3-(cyclohexyl α-D-xylofuranose-2-yl)-1-(2-chloroethyl)-1-nitrosourea was obtained in the same manner as in Example 2; yield 66.3%, m.p. 70°–72° C., $[α]_D^{20}$ +22.4° (C 1.0, methanol).

Elementary analysis, for $C_{18}H_{32}N_3O_6Cl$ (mol.wt. 421.92): Calcd. (%): C 51.24, H 7.64, N 9.96, Cl 8.41; Found (%): C 51.28, H 7.57, N 9.91, Cl 8.37.

EXAMPLE 53

Using cyclohexyl 3-(2-ethoxyethylamino)-3-deoxy-α-D-xylofuranoside (8.56 g, 28.2 mmol), 7.93 g of 3-(2-ethoxyethyl)-3-(cyclohexyl α-D-xylofuranose-3-yl)-1-(2-chloroethyl)-1-nitrosourea was obtained in the same manner as in Example 1; yield 64.2%, m.p. 62°–64° C., $[α]_D^{20}$ +10.2° (C 1.0, methanol).

Elementary analysis, for $C_{18}H_{32}N_3O_7Cl$ (mol.wt. 437.92): Calcd. (%): C 49.37, H 7.37, N 9.59, Cl 8.10; Found (%): C 49.45, H 7.31, N 9.52, Cl 8.17.

EXAMPLE 54

Using cyclohexyl 5-isobutylamino-5-deoxy-α-L-lyxofuranoside (8.16 g, 28.4 mmol), 7.01 g of 3-isobutyl-3-(cyclohexyl α-L-lyxofuranose-5-yl)-1-(2-chloroethyl)-1-nitrosourea was obtained in the same manner as in Example 1; yield 58.2%, m.p. 83°–85° C., $[α]_D^{20}$ −18.6° (C 1.0, methanol).

Elementary analysis, for $C_{18}H_{32}N_3O_6Cl$ (mol.wt. 421.92): Calcd. (%): C 51.24, H 7.64, N 9.96, Cl 8.41; Found (%): C 51.16, H 7.73, N 10.04, Cl 8.37.

EXAMPLE 55

Using tetrahydrofurfuryl 5-isobutylamino-5-deoxy-α-L-lyxofuranoside (7.82 g, 28.4 mmol), 6.24 g of 3-isobutyl-3-(tetrahydrofurfuryl α-L-lyxofuranose-5-yl)-1-(2-chloroethyl)-1-nitrosourea was obtained in the same manner as in Example 1; yield 53.6%, m.p. 65°–67° C., $[α]_D^{20}$ −16.5° (C 1.0, methanol).

Elementary analysis, for $C_{16}H_{28}N_3O_7Cl$ (mol.wt. 409.87): Calcd. (%): C 46.89, H 6.89, N 10.25, Cl 8.65; Found (%): C 46.81, H 6.93, N 10.21, Cl 8.73.

EXAMPLE 56

Using sec-butyl 5-isobutylamino-5-deoxy-α-L-lyxofuranoside (7.37 g, 28.2 mmol), 5.75 g of 3-isobutyl-3-(sec-butyl α-L-lyxofuranose-5-yl)-1-(2-chloroethyl)-1-nitrosourea was obtained in the same manner as in Example 1; yield 51.5%; m.p. 80°–82° C., $[α]_D^{20}$ −20.4° (C 1.0, methanol).

Elementary analysis, for $C_{16}H_{30}N_3O_6Cl$ (mol.wt. 395.88): Calcd. (%): C 48.54, H 7.64, N 10.61, Cl 8.96; Found (%): C 48.46, H 7.69, N 10.57, Cl 9.08.

EXAMPLE 57

(1) A solution of 2-chloroethyl isocyanate (6.61 g) in tetrahydrofuran (10 ml) was dropped into a solution of n-butyl 6-sec-butylamino-6-deoxy-D-glucopyranoside (15.2 g, 52.2 mmol) in methanol (50 ml) with thorough stirring at 0° to 5° C., and stirring was continued for further 1.5 hours at 20° to 25° C. After confirmation by TLC that the reaction was finished, the reaction mixture was vacuum-concentrated at 25° C. and separated by column chromatography (packing: Kiesel gel 60; eluent: chloroform:methanol 10:1) into fractions of objective α- and β-form products, which were each vacuum-concentrated at 25° C. and crystallized from ethanol and water, giving 6.94 g of 3-sec-butyl-3-(n-butyl α-D-glucopyranose-6-yl)-1-(2-chloroethyl)urea; yield 33.5%, m.p. 94°–96° C., $[α]_D^{20}$ +52.2° (C 1.0, methanol); and 6.26 g of 3-sec-butyl-3-(n-butyl β-D-glucopyranose-6-yl)-1-(2-chloroethyl)urea; yield 30.2%, m.p. 107°–109° C. $[α]_D^{20}$ −21.4° (C 1.0, methanol).

Elementary analysis, for $C_{17}H_{33}N_2O_6Cl$ (mol.wt. 396.91): Calcd. (%): C 51.44, H 8.38, N 7.06, Cl 8.93 Found (%): α-form C 51.38, H 8.45, N 7.14, Cl 8.88; β-form C 51.52, H 8.32, N 7.01, Cl 8.99.

(2) Sodium nitrite fine powder (0.6 g) was slowly added to a solution of 3-sec-butyl-3-(n-butyl α-D-glucopyranose-6-yl)-1-(2-chloroethyl)urea (2.24 g, 5.64 mmol) in formic acid (10 ml) with thorough stirring at 0° to 5° C. spending 1 hour, and stirring was continued for further 2 hours at the same temperature. After confirmation by TLC that the reaction was finished, 20 g of an ion exchange resin (H+ form, registered trade mark: Amberlite IR-120) was added to the reaction mixture at 0° to 5° C., and the mixture was thoroughly stirred for 30 minutes. The ion exchange resin was filtered off, and the filtrate was vacuum-concentrated at 25° C. and crystallized from methanol and water, giving 1.41 g of 3-sec-butyl-3-(n-butyl α-D-glucopyranose-6-yl)-1-(2-chloroethyl)-1-nitrosourea; yield 58.7%, m.p. 68°–70° C., $[α]_D^{20}$ +67.5° (C 1.0, methanol).

Elementary analysis, for $C_{17}H_{32}N_3O_7Cl$ (mol.wt. 425.91): Calcd. (%): C 47.94, H 7.57, N 9.87, Cl 8.32; Found (%): C 47.90, H 7.69, N 9.82, Cl 8.36.

(3) Sodium nitrite (0.85 g) was slowly added to a suspension of 3-sec-butyl-3-(n-butyl β-D-glucopyranose-6-yl)-1-(2-chloroethyl)urea (3.25 g, 8.19 mmol) in 80% aqueous acetic acid (40 ml) with thoroughly stirring at 0° to 5° C., and stirring was continued for further 2 hours at the same temperature. After confirmation by TLC that the reaction finished, 15 ml of the same ion exchange resin as mentioned above was added to the reaction mixture at 0° to 5° C., and the mixture was stirred for 30 minutes. The ion exchange resin was filtered off, and the filtrate was vacuum-concentrated at 25° C. and crystallized from methanol and water, giving 2.39 g of 3-sec-butyl-3-(n-butyl β-D-glucopyranose-6-yl)-1-(2-chloroethyl)-1-nitrosourea; yield 68.4%, m.p. 92°–95° C. (decomposition). $[\alpha]_D^{20}$ −14.2° (C 1.0, methanol).

Elementary analysis, for $C_{17}H_{32}N_3O_7Cl$ (mol.wt. 425.91): Calcd. (%): C 47.94, H 7.57, N 9.87, Cl 8.32; Found (%): C 48.02, H 7.57, N 9.89, Cl 8.27.

EXAMPLE 58

(1) 2-Chloroethyl isocyanate (1.35 g) and silver carbonate (2.14 g) were added to a solution of n-butyl 6-(2-methyl-2-propenylamino)-6-deoxy-α-D-glucopyranoside hydrochloride (3.47 g, 10.6 mmol) in a mixture of water (25 ml) and acetonitrile (40 ml) at 0° to 5° C., and the mixture was heated under reflux on a water bath for 1 hour. Then, the reaction mixture was filtered while hot to remove the insoluble silver salt. The filtrate was vacuum-concentrated and crystallized from ethanol and water, giving 2.73 g of 3-(2-methyl-2-propenyl)-3-(n-butyl α-D-glucopyranose-6-yl)-1-(2-chloroethyl)urea; yield 65.2%, m.p. 110°–112° C., $[\alpha]_D^{20}$ +59.2° (C 1.0, methanol).

Elementary analysis, for $C_{17}H_{31}N_2O_6Cl$ (mol.wt. 394.90): Calcd. (%): C 51.71, H 7.91, N 7.09, Cl 8.98; Found (%): C 51.78, H 7.85, N 7.14, Cl 8.92.

(2) Sodium nitrile powder (1.20 g) was slowly added to a solution of the thus prepared 3-(2-methyl-2-propenyl)-3-(n-butyl α-D-glucopyranose-6-yl)-1-(2-chloroethyl)urea (4.58 g, 11.6 mmol) in formic acid (40 ml) with thoroughly stirring at 0° to 5° C. spending 1 hour, and stirring was continued for further 4 hours at the same temperature. The resulting solution, after addition of 30 ml of the same ion exchange resin as mentioned above, was stirred for 20 minutes and filtered to remove the ion exchange resin. The filtrate was vacuum-concentrated at or below 30° C., and crystallized from ethanol and water, giving 3.67 g of 3-(2-methyl-2-propenyl)-3-(n-butyl α-D-glucopyranose-6-yl)-1-(2-chloroethyl)-1-nitrosourea; yield 74.6%, m.p. 80°–82° C., $[\alpha]_D^{20}$ +68.0° (C 1.0, methanol).

Elementary analysis, for $C_{17}H_{30}N_3O_7Cl$ (mol.wt. 423.89): Calcd. (%): C 48.17, H 7.13, N 9.91, Cl 8.37; Found (%): C 48.11, H 7.24, N 9.98, Cl 8.32.

EXAMPLE 59

(1) Using n-butyl 2-(2-methyl-2-propenylamino)-2-deoxy-α-D-glucopyranoside (6.25 g, 19.2 mmol), 5.13 g of 3-(2-methyl-2-propenyl)-3-(n-butyl α-D-glucopyranose-2-yl)-1-(2-chloroethyl)urea was prepared in the same manner as used in Example 57(1); yield 67.6%, m.p. 121°–123° C., $[\alpha]_D^{20}$ −64.8° (C 1.0, methanol).

Elementary analysis, for $C_{17}H_{31}N_2O_6Cl$ (mol.wt. 394.90): Calcd. (%): C 51.71, H 7.91, N 7.09, Cl 8.98; Found (%): C 51.64, H 7.96, N 7.02, Cl 9.05.

(2) Using 3-(2-methyl-2-propenyl)-3-(n-butyl α-D-glucopyranose-2-yl)-1-(2-chloroethyl)urea (3.24 g, 8.20 mmol). 2.65 g of 3-(2-methyl-2-propenyl)-3-(n-butyl α-D-glucopyranose-2-yl)-1-(2-chloroethyl)-1-nitrosourea was prepared in the same manner as Example 57(2); yield 76.3%, m.p. 97°–99° C. (decomposition), $[\alpha]_D^{20}$ +74.5° (C 1.0, methanol).

Elementary analysis, for $C_{17}H_{30}N_3O_7Cl$ (mol.wt. 423.89): Calcd. (%): C 48.17, H 7.13, N 9.91, Cl 8.37; Found (%): C 48.05, H 7.22, N 9.87, Cl 8.43.

EXAMPLE 60

(1) 2-Chloroethyl isocyanate (1.33 g) and barium carbonate (2.5 g) were added to a solution of n-butyl 6-(3-methoxy-n-propylamino)-6-deoxy-D-glucopyranoside ½ sulfate (3.64 g, 10.5 mmol) in a mixture of water (10 ml) and methanol (30 ml) at 0° to 5° C., and the mixture was heated under reflux on a water bath for 1 hour. The reaction mixture was then filtered while hot, to remove the insoluble barium salt. The filtrate was vacuum-concentrated and fractionated by column chromatography (packing: Kiesel gel 60; eluent: chloroform/methanol 10:1) to separate the α- and β-form of products. The objective α- and β-form product fractions were each vacuum-concentrated at 25° C. and crystallized from aqueous isopropanol, giving 1.40 g of 3-(3-methoxy-n-propyl)-3-(n-butyl α-D-glucopyranose-6-yl)-1-(2-chloroethyl)-urea; yield 32.2%, m.p. 103°–105° C., $[\alpha]_D^{20}$ +50.8° (C 1.0, methanol); and 1.32 g of 3-(3-methoxy-n-propyl)-3-(n-butyl β-D-glucopyranose-6-yl)-1-(2-chloroethyl)urea; yield 30.4%, m.p. 109°–111° C., $[\alpha]_D^{20}$ −4.7° (C 1.0, methanol).

Elementary analysis, for $C_{17}H_{33}N_2O_7Cl$ (mol.wt. 412.91): Calcd. (%): C 49.45, H 8.06, N 6.78, Cl 8.59; Found (%): α-form C 49.53, H 8.12, N 6.71, Cl 8.64; β-form C 49.53, H 8.14, N 6.72, Cl 8.64.

(2) Anhydrous sodium carbonate (15 g) was added to a solution of the above obtained 3-(3-methoxy-n-propyl)-3-(n-butyl α-D-glucopyranose-6-yl)-1-(2-chloroethyl)urea (3.14 g, 7.60 mmol) in a mixture of tetrahydrofuran (80 ml) and methylene chloride (50 ml). Dinitrogen tetraoxide gas (5 g) was introduced into the mixture with stirring at 0° to 5° C. spending 10 minutes, and stirring was continued for further 10 minutes at the same temperature. Methanol (15 ml) and water (3 ml) were then added to the resulting mixture, which was stirred for 5 seconds, dehydrated, and dried up at 25° C. under reduced pressure. The residue was purified by column chromatography (packing: silica gel; eluent: ethyl acetate/chloroform/methanol (5:2:1), giving 1.51 g of 3-(3-methoxy-n-propyl)-3-(n-butyl α-D-glucopyranose-6-yl)-1-(2-chloroethyl)-1-nitrosourea; yield 44.8%, m.p. 80°–83° C., $[\alpha]_D^{20}$ +60.2° (C 1.0, methanol).

Elementary analysis, for $C_{17}H_{32}N_3O_8Cl$ (mol.wt. 441.91): Calcd. (%): C 46.21, H 7.30, N 9.51, Cl 8.02; Found (%): C 46.29, H 7.24, N 9.48, Cl 7.98.

(3) Using 3-(3-methoxy-n-propyl)-3-(n-butyl β-D-glucopyranose-6-yl)-1-(2-chloroethyl)urea (4.54 g, 11.0 mmol), 2.26 g of 3-(3-methoxy-n-propyl)-3-(n-butyl β-D-glucopyranose-6-yl)-1-(2-chloroethyl)-1-nitrosourea was prepared in the same manner as (2) of this Example; yield 46.5%, m.p. 95°–97° C., $[\alpha]_D^{20}$ −12.4° (C 1.0, methanol).

Elementary analysis, for $C_{17}H_{32}N_3O_8Cl$ (mol.wt. 441.91): Calcd. (%): C 46.21, H 7.30, N 9.51, Cl 8.02; Found (%): C 46.19, H 7.35, N 9.57, Cl 7.98.

EXAMPLE 61

(1) A solution of 2-chloroethyl isocyanate (2.57 g) in tetrahydrofuran (10 ml) was slowly dropped into a solution of n-butyl 3-cyclohexylmethylamino-3-deoxy-α-D-glucopyranoside (6.73 g, 20.3 mmol) in methanol (60 ml) at 0° to 5° C., and stirring was continued for further 2 hours at the same temperature. After completion of the reaction, the resulting reaction mixture was vacuum-concentrated, dissolved in methanol, and crystallized from a mixture of ethyl acetate-diethyl ether, giving 5.01 g of 3-cyclohexylmethyl-3-(n-butyl α-D-glucopyranose-3-yl)-1-(2-chloroethyl)urea; yield 56.5%, m.p. 87°–89° C., $[\alpha]_D^{20}$ +39.7° (C 1.0, methanol).

Elementary analysis, for $C_{20}H_{37}N_2O_6Cl$ (mol.wt. 436.98): Calcd. (%): C 54.97, H 8.54, N 6.41, Cl 8.11 Found (%): C 54.91, H 8.62, N 6.48, Cl 8.03

(2) Anhydrous sodium acetate (15 g) was added to a solution of 3-cyclohexylmethyl-3-(n-butyl α-D-glucopyranose-3-yl)-1-(2-chloroethyl)urea (3.94 g, 9.02 mmol) in a mixture of tetrahydrofuran (120 ml) and acetic acid (20 ml), and dinitrogen tetraoxide gas (4 g) was introduced into the mixture with well stirring at 0° to 5° C. spending 5 minutes. After the mixture was stirred at the same temperature for further 30 minutes to complete reaction, n-hexane (200 ml) was added and insoluble matter was filtered off. The filtrate was vacuum-concentrated at 25° C. and fractionated by column chromatography (packing: silica gel; eluent: ethyl acetate/chloroform/methanol (2:10:1) to isolate the objective product. Thus, 1.62 g of 3-cyclohexylmethyl-3-(n-butyl α-D-glucopyranose-3-yl)-1-(2-chloroethyl)-1-nitrosourea was obtained; yield 38.5%, m.p. 75°–77° C., $[\alpha]_D^{20}$ +47.2° (C 1.0, methanol).

Elementary analysis, for $C_{20}H_{36}N_3O_7Cl$ (mol.wt. 465.98): Calcd. (%) C 51.55, H 7.79, N 9.02, Cl 7.61; Found (%): C 51.63, H, 7.71, N 8.95, Cl 7.68.

EXAMPLE 62

(1) 2-Chloroethyl isocyanate (2.39 g) and triethylamine (1.22 g) were added to a solution of n-butyl 6-(p-methoxybenzylamino)-6-deoxy-α-D-glucopyranoside hydrochloride (7.41 g, 18.9 mmol) in a mixture of water (10 ml) and tetrahydrofuran (50 ml), while well stirring the solution at 0° to 5° C. After stirring at 25° C. for further 1 hour to complete reaction, which was confirmed by TLC, the reaction mixture was vacuum-concentrated at or below 30° C. and crystallized from ethanol and water, giving 4.91 g of 3-(p-methoxybenzyl)-3-(n-butyl α-D-glucopyranose-6-yl)-1-(2-chloroethyl)urea; yield 56.3%, m.p. 101°–102° C., $[\alpha]_D^{20}$+47.2° (C 1.0, methanol).

Elementary analysis, for $C_{21}H_{33}N_2O_7Cl$ (mol.wt. 460.96): Calcd.(%): C 54.72, H 7.22, N 6.07, Cl 7.69; Found (%): C 54.65, H 7.28, N 6.15, Cl 7.64.

(2) Potassium nitrite (2 g) was added at 0° to 5° C. to a solution of the above synthesized 3-(p-methoxybenzyl)-3-(n-butyl α-D-glucopyranose-6-yl)-1-(2-chloroethyl)urea (3.85 g, 8.35 mmol) in a mixture of tetrahydrofuran (100 ml) and 10% hydrochloric acid (10 ml). After stirring at the same temperature for 10 minutes, the reaction mixture was extracted with ethyl acetate. The extract was dried over anhydrous sodium sulfate, vacuum-concentrated at 25° C., and purified by column chromatography (packing: Kiesel gel 60; eluent: chloroform/methanol 10:1). Thus, 2.35 g of 3-(p-methoxybenzyl)-3-(n-butyl α-D-glucopyranose-6-yl)-1-(2-chloroethyl)-1-nitrosourea was obtained; yield 57.4%, m.p. 86°–88° C., $[\alpha]_D^{20}$+61.5° (C 1.0, methanol).

Elementary analysis, for $C_{21}H_{32}N_3O_8Cl$ (mol.wt. 489.95): Calcd.(%): C 51.48, H 6.58, N 8.58, Cl 7.24; Found (%): C 51.40, H 6.66, N 8.52, Cl 7.32.

EXAMPLE 63

(1) 2-Chloroethyl isocyanate (2.74 g) was dropped into a solution of isobutyl 6-n-propylamino-6-deoxy-α-D-glucopyranoside (5.98 g, 21.6 mmol) in a mixture of ethanol (20 ml) and tetrahydrofuran (50 ml), with good stirring at 5° to 15° C. After stirring at the same temperature for 2 hours to complete reaction, which was confirmed by TLC, the reaction mixture was vacuum-concentrated at 30° C. or below and crystallized from ethanol and water, giving 4.85 g of 3-n-propyl-3-(isobuyl α-D-glucopyranose-6-yl)-1-(2-chloroethyl)-urea; yield 58.7%, m.p. 84°–86° C., $[\alpha]_D^{20}$+56.5° (C 1.0, methanol).

Elementary analysis, for $C_{16}H_{31}N_2O_6Cl$ (mol.wt. 382.89): Calcd.(%): C 50.19, H 8.16, N 7.32, Cl 9.26; Found (%): C 50.15, H 8.24, N 7.28, Cl 9.35.

(2) Isoamyl nitrite (4 ml) was dropped into a solution of the above synthesized 3-n-propyl-3-(isobutyl α-D-glucopyranose-6-yl)-1-2-chloroethyl)urea (3.47 g, 9.06 mmol) in a mixture of methanol (50 ml), dioxane (150 ml), and 10% sulfuric acid (50 ml), with well stirring at 0° to 5° C. After stirring for further 3 hours to complete reaction, which was confirmed by TLC, the reaction mixture was vacuum-concentrated at 25° C. and crystallized from ethanol and water, giving 2.55 g of 3-n-propyl-3-(isobutyl α-D-glucopyranose-6-yl)-1-(2-chloroethyl)-1-nitrosourea; yield 68.4%, m.p. 58°–60° C., $[\alpha]_D^{20}$+71.7° (C 1.0, methanol).

Elementary analysis, for $C_{16}H_{30}N_3O_7Cl$ (mol.wt. 411.88); Calcd.(%): C 46.66, H 7.34, N 10.20, Cl 8.61; Found (%): C 46.73, H 7.28, N 10.28, Cl 8.56.

EXAMPLE 64

(1) Using isobutyl 3-isopentylamino-3-deoxy-α-D-glucopyranoside (6.35 g, 20.8 mmol), 4.91 g of 3-isopentyl-3-(isobutyl α-D-glucopyranose-3-yl)-1-(2-chloroethyl)urea was prepared in the same manner as Example 63(1); yield 57.5%, m.p. 82°–84° C., $[\alpha]_D^{20}$+37.2° (C 1.0, methanol).

Elementary analysis, for $C_{18}H_{35}N_2O_6Cl$ (mol.wt. 410.94): Calcd.(%): C 52.61, H 8.58, N 6.82, Cl 8.63; Found (%): C 52.55, H 8.64, N 6.76, Cl 8.71.

(2) Isobutyl nitrite (3.5 ml) was dropped into a solution of 3-isopentyl-3-(isobutyl α-D-glucopyranose-3-yl)-1-(2-chloroethyl)urea (3.48 g, 8.47 mmol) in a mixture of ethanol (50 ml), tetrahydrofuran (150 ml), and 2N hydrochloric acid (30 ml) with well stirring at 0° to 5° C. Thereafter, 2.51 g of 3-isopentyl-3-(isobutyl α-D-glucopyranose-3-yl)-1-(2-chloroethyl)-1-nitrosourea was obtained by the same operations of Example 63(2); yield 67.3%, m.p. 69°–71° C., $[\alpha]_D^{20}$+45.8° (C 1.0, methanol).

Elementary analysis, for $C_{18}H_{34}N_3O_7Cl$ (mol.wt. 439.94): Calcd.(%): C 49.14, H 7.79, N 9.55, Cl 8.06; Found (%): C 49.23, H 7.72, N 9.63, Cl 8.01.

EXAMPLE 65

(1) A mixture of 2-chloroethyl isocyanate (6.60 g), tripropylamine (4.3 g) and pyridine (2.4 g) was added to a solution of isobutyl 6-(2-hydroxy-n-propyl)-6-deoxy-D-glucopyranoside hydrochloride (16.48 g, 50.0 mmol) in a mixture of ethanol (50 ml) and tetrahydrofuran (80 ml), and the mixture was reacted with thorough stirring at 60° C. for 1.5 hours. The resulting solution was vacuum-concentrated and separated by column chromatography (packing: Kiesel gel 60; eluent: chloroform/methanol 10:1) into three fractions of the objective products of α-form, β-form and α,β-mixed form. The fractionated solutions of α-form product and of β-form product were each vacuum-concentrated at 25° C. and crystallized from ethanol and water, giving 4.10 g of 3-(2-hydroxy-n-propyl)-3-(isobutyl α-D-glucopyranose-6-yl)-1-(2-chloroethyl)urea; yield 21.4%, m.p. 88°–90° C., $[\alpha]_D^{20}+52.2°$ (C 1.0, methanol); and 3.50 g of 3-(2-hydroxy-n-propyl)-3-(isobutyl β-D-glucopyranose-6-yl)-1-(2-chloroethyl)urea; yield 18.3%, m.p. 100°–102° C., $[\alpha]_D^{20}-23.5°$ (C 1.0, methanol).

Elementary analysis, for $C_{16}H_{31}N_2O_7Cl$ (mol.wt. 382.89): Calcd.(%): C 50.19, H 8.16, N 7.32, Cl 9.26; Found (%): α-form C 50.12, H 8.24, N 7.24, Cl 9.34; β-form C 50.24, H 8.12, N 7.24, Cl 9.32.

(2) Sodium nitrite (2 g) was added to a solution of the above fractionated α,β-mixed form of 3-(2-hydroxy-n-propyl)-3-(isobutyl D-glucopyranose-6-yl)-1-(2-chloroethyl)urea (4.48 g, 11.7 mmol) in a mixture of ethanol (60 ml) and 80% aqueous acetic acid (30 ml) with well stirring at 0° to 5° C. spending 30 minutes. This reaction mixture was allowed to stand in a refrigerator at 0° to 5° C. for 18 hours to complete reaction, which was confirmed by TLC. An ion exchange resin (H+ form, registered trade mark: Amberlite IR-120) (20 ml) was added to the reaction mixture and the mixture was stirred at 0° to 5° C. for 1 hour. The ion exchange resin was filtered off, and the filtrate was vacuum-concentrated at 25° C. and fractionated by column chromatography (packing: Kiesel gel 60; eluent: chloroform/ethanol 9:1) to separate the α- and β-forms. Each fractionated solution was vacuum-concentrated at 25° C. and crystallized from ether and petroleum ether. Thus, there were obtained 1.43 g of 3-(2-hydroxy-n-propyl)-3-(isobutyl α-D-glucopyranose-6-yl)-1-(2-chloroethyl)-1-nitrosourea; yield 28.5%, m.p. 62°–64° C., $[\alpha]_D^{20}+66.9°$ (C 1.0, methanol); and 1.14 g of 3-(2-hydroxy-n-propyl)-3-(isobutyl β-D-glucopyranose-6-yl)-1-(2-chloroethyl)-1-nitrosourea; yield 22.7%, m.p. 80°–82° C., $[\alpha]_D^{20}-12.5°$ (C 1.0, methanol).

Elementary analysis, for $C_{16}H_{30}N_3O_8Cl$ (mol.wt. 427.88): Calcd.(%): C 44.91, H 7.07, N 9.82, Cl 8.29; Found (%): α-form C 44.86, H 7.12, N 9.77, Cl 8.34; β-form C 44.84, H 7.09, N 9.75, Cl 8.31.

EXAMPLE 66

(1) A solution of 2-chloroethyl isocyanate (2.38 g) in tetrahydrofuran (10 ml) was dropped into a solution of isobutyl 6-tetrahydrofurfurylamino-6-deoxy-α-D-glucopyranoside (6.01 g, 18.8 mmol) in a mixture of methanol (50 ml) and tetrahydrofuran (30 ml) at 0° to 5° C. After stirred at the same temperature for two hours to complete reaction, the reaction mixture was vacuum-concentrated and fractionated by column chromatography (packing: Kiesel gel 60; eluent: chloroform/methanol 9:1). The objective fractionated solution was vacuum-concentrated at 25° C. and crystallized from chloroform and petroleum ether, giving 4.57 g of 3-tetrahydrofurfuryl-3-(isobutyl α-D-glucopyranose-6-yl)-1-(2-chloroethyl)urea; yield 57.2%, m.p. 85°–87° C. $[\alpha]_D^{20}+49.7°$ (C 1.0, methanol).

Elementary analysis, for $C_{18}H_{33}N_2O_7Cl$ (mol.wt. 424.92): Calcd.(%): C 50.88, H 7.83, N 6.59, Cl 8.34; Found (%): C 50.94, H 7.76, N 6.64, Cl 8.28.

(2) From 3-tetrahydrofurfuryl-3-(isobutyl α-D-glucopyranose-6-yl)-1-(2-chloroethyl)urea (2.82 g, 6.64 mmol) obtained in the above way, 1.19 g of 3-tetrahydrofurfuryl-3-(isobutyl α-D-glucopyranose-6-yl)-1-(2-chloroethyl)-1-nitrosourea was by the same operations as Example 61(2); yield 39.4%, m.p. 68°–70° C., $[\alpha]_D^{20}+64.2°$ (C 1.0, methanol).

Elementary analysis, for $C_{18}H_{32}N_3O_8Cl$ (mol.wt. 453.92): Calcd.(%): C 47.63, H 7.11, N 9.26, Cl 7.81; Found (%): C 47.55, H 7.19, N 9.22, Cl 7.92.

EXAMPLE 67

(1) 2-Chloroethyl isocyanate (3.4 g) was dropped into a solution of n-butyl 6-isopropylamino-6-deoxy-α-D-glucopyranoside (7.25 g, 26.1 mmol) in a mixture of methanol (150 ml) and tetrahydrofuran (50 ml) with well stirring at 15° to 20° C. The mixture was stirred at the same temperature for two hours to complete reaction, which was confirmed by TLC. The product solution was vacuum-concentrated at 30° C. or below and purified by column chromatography (packing: Kiesel gel 60; eluent: chloroform/methanol 9:1), giving 5.64 g of 3-isobutyl-3-(n-butyl α-D-glucopyranose-6-yl)-1-(2-chloroethyl)urea; yield 56.4%, m.p. 101°–103° C., $[\alpha]_D^{20}+54.2°$ (C 1.0, methanol).

Elementary analysis, for $C_{16}H_{31}N_2O_6Cl$ (mol.wt. 382.89): Calcd.(%): C 50.19, H 8.16, N 7.32, Cl 9.26; Found (%): C 50.13, H 8.24, N 7.28, Cl 9.36.

(2) Sodium nitrite (0.74 g) was slowly added to a solution of 3-isopropyl-3-(n-butyl α-D-glucopyranose-6-yl)-1-(2-chloroethyl)urea (3.43 g, 8.96 mmol), obtained in the above way, in 40% aqueous acetic acid with well stirring at 0° to 5° C. After continuation of stirring for four hours at the same temperature, an ion exchange resin (13 ml, the same type as used in Example 65) was added to the resulting solution, and the mixture was stirred for 30 minutes. The ion exchange resin was filtered off, and the filtrate was vacuum-concentrated at 25° C. and purified by column chromotography (packing: Kiesel gel 60; eluent: chloroform/methanol 10:1). Thus, 2.39 g of 3-isopropyl-3-(n-butyl α-D-glucopyranose-6-yl)-1-(2-chloroethyl)-1-nitrosourea was obtained; yield 64.8%, m.p. 70°–72° C., $[\alpha]_D^{20}+69.8°$ (C 1.0, methanol).

Elementary analysis, for $C_{16}H_{30}N_3O_7Cl$ (mol.wt. 411.88): Calcd.(%): C 46.66, H 7.34, N 10.20, Cl 8.61; Found (%): C 46.58, H 7.41, N 10.28, Cl 8.56.

IR $\nu_{max}^{KBr}$ (cm$^{-1}$): 3400, 1700, 1495, 1050.

NMR (d$_6$-DMSO)δ: 3.61 (t, 2H, N—CH$_2$—CH$_2$—Cl) 4.12 (t, 2H, N—CH$_2$-CH$_2$—Cl)

(3) Dinitrogen trioxide gas (1.3 g) was introduced into a solution of the thus prepared 3-isopropyl-3-(n-butyl-α-D-glucopyranose-6-yl)-1-(2-chloroethyl)urea (3.58 g, 9.35 mmol) in dichloroethane (50 ml) with thorough stirring at 15°–20° C., and stirring was continued for further two hours at the same temperature. The reaction mixture was vacuum-concentrated concentrated at 25° C., and purified by column chromatography (packing: silica gel; eluent: hexane/ethyl acetate 4:1) to obtain 3-isopropyl-3-(n-butyl-α-D-glucopyranose-6-yl)-1-(2-chloroethyl)-1-nitrosourea (2.78 g, 6.75 mmol); yield 72.2%, m.p. 70°–72° C., $[\alpha]_D^{20}+69.7°$ (C 1.0, methanol).

Elementary analysis, for C₁₆H₃₀N₃O₇Cl (mol.wt. 411.88): Calcd.(%): C 46.66, H 7.34, N 10.20, Cl 8.61; Found (%): C 46.71, H 7.32, N 10.24, Cl 8.60.

EXAMPLE 68

(1) Using n-butyl 6-isopentylamino-6-deoxy-α-D-glucopyranoside (4.58 g, 15.0 mmol), 3.53 g of 3-isopentyl-3-(n-butyl α-D-glucopyranose-6-yl)-1-(2-chloroethyl)urea was prepared in the same manner as Example 67(1); yield 57.2% m.p. 80°–82° C., $[\alpha]_D^{20}+49.7°$ (C 1.0, methanol).

Elementary analysis, for C₁₈H₃₅N₂O₆Cl (mol. wt. 410.94): Calcd.(%): C 52.61, H 8.58, N 6.82, Cl 8.63; Found (%): C 52.56, H 8.63, N 6.78, Cl 8.69.

(2) Dinitrogen trioxide gas (0.6 g) was introduced into a solution of 3-isopentyl-3-(n-butyl α-D-glucopyranose-6-yl)-1-(2-chloroethyl)urea (2.15 g, 5.23 mmol), synthesized in the above-mentioned way, in a mixture of tetrahydrofuran (50 ml) and acetic acid (8 ml) with well stirring at 0° to 5° C. After continuation of stirring for 2 hours, the resulting solution was vacuum-concentrated at 25° C. and purified by column chromatography (packing: Kiesel gel 60; eluent: chloroform/methanol 10:1), giving 1.44 g of 3-isopentyl-3-(n-butyl α-D-glucopyranose-6-yl)-1-(2-chloroethyl)-1-nitrosourea; yield 62.6%, m.p. 66°–68° C., $[\alpha]_D^{20}+65.2°$ (C 1.0, methanol).

Elementary analysis, for C₁₈H₃₄N₃O₇Cl (mol.wt. 439.94): Calcd.(%): C 49.14, H 7.79, N 9.55, Cl 8.06; Found (%): C 49.23, H 7.71, N 9.48, Cl 8.13.

(3) Dinitrogen trioxide gas (1.5 g) was introduced into a solution of the thus prepared 3-isopentyl-3-(n-butyl-α-D-glucopyranose-6-yl)-1-(2-chloroethyl)urea (4.68 g, 11.38 mmol) in a mixture of dichloroethane (50 ml), dichloromethane (10 ml), and monochlorobenzene (10 ml) with thorough stirring at 10°–18° C., and stirring was continued for further one hour at the same temperature. The reaction mixture was vacuum-concentrated at 28° C. or below and purified by column chromatography (packing silica gel; eluent: octane/isopropyl acetate 4:1) to obtain 3-isopentyl-3-(n-butyl-α-D-glucopyranose-6-yl)-1-(2-chloroethyl)-1-nitrosourea (3.82 g, 8.68 mmol); yield 76.3%; m.p. 66°–68° C.; $[\alpha]_D^{20}+65.3°$ (C 1.0, methanol).

Elementary analysis, for C₁₈H₃₄N₃O₇Cl (mol.wt. 439.94): Calcd.(%): C 49.14, H 7.79, N 9.55, Cl 8.06; Found (%): C 49.08, H 7.82, N 9.62, Cl 8.11.

EXAMPLES 69–241

In the same way as Example 67, various 3-(R₂)-3-(R₁ α- or β-D-glucopyranose-6-yl)-1-(2-chloroethyl)ureas (referred to briefly as urea compound) and 3-(R₂)-3-(R₁ α- or β-D-glucopyranose-6-yl)-1-(2-chloroethyl)-1-nitrosoureas (referred to briefly as nitroso compound) were synthesized from various starting materials, R₁ 6-(R₂ amino)-6-deoxy-α- or β-D-glucopyranosides (referred to briefly as starting material). Table V shows R₁ and R₂ of starting material and yields (%), melting points (m.p. °C.), and specific rotations ($[\alpha]_D^{20}$ (C 1.0, methanol)) of urea and nitroso forms in each Example.

TABLE V

| | Starting Material | | | Urea Compound | | | Nitroso Compound | | |
|---|---|---|---|---|---|---|---|---|---|
| Example No. | Isomeric form | R₁ | R₂ | Yield % | MP °C. | $[\alpha]_D^{20}$ degree | Yield % | MP °C. | $[\alpha]_D^{20}$ degree |
| 69 | α | n-Butyl | 2-Ethylhexyl | 57.8 | 76–78 | +47.3 | 62.5 | 61–63 | +63.4 |
| 70 | α | " | 2-Propenyl | 55.3 | 102–104 | +59.1 | 61.8 | 70–72 | +68.7 |
| 71 | α | " | 2-Butenyl | 54.2 | 106–108 | +58.0 | 60.7 | 78–80 | +67.5 |
| 72 | α | " | 3-Butenyl | 56.4 | 105–107 | +59.2 | 59.1 | 76–78 | +68.1 |
| 73 | α | " | 2-Methoxyethyl | 54.3 | 86–89 | +37.4 | 58.4 | 62–64 | +62.8 |
| 74 | α | " | 2-Ethoxyethyl | 55.8 | 92–95 | +47.7 | 57.2 | 68–70 | +61.4 |
| 75 | α | " | 2-Methoxy-n-propyl | 56.2 | 84–86 | +45.8 | 58.5 | 61–63 | +60.6 |
| 76 | α | " | 1-Methyl-2-methoxyethyl | 55.7 | 93–95 | +45.4 | 57.6 | 70–72 | +60.1 |
| 77 | α | " | 3-Hydroxy-n-propyl | 56.8 | 81–83 | +38.8 | 56.8 | 58–60 | +53.5 |
| 78 | α | " | 2-(2-Hydroxyethoxy)ethyl | 58.4 | 86–88 | +44.2 | 55.9 | 67–69 | +59.8 |
| 79 | α | " | 4-Hydroxy-n-butyl | 55.6 | 83–85 | +41.6 | 57.4 | 63–65 | +56.2 |
| 80 | α | " | Cyclopropylmethyl | 57.5 | 89–91 | +54.8 | 56.3 | 66–68 | +68.3 |
| 81 | α | " | Cyclohexylmethyl | 53.8 | 91–93 | +52.2 | 54.5 | 77–79 | +67.5 |
| 82 | α | " | 2-Cyclopentylethyl | 57.2 | 86–87 | +51.3 | 55.8 | 72–74 | +66.3 |
| 83 | α | " | Benzyl | 55.3 | 93–95 | +49.2 | 54.7 | 79–81 | +64.7 |
| 84 | α | " | p-Methylbenzyl | 56.4 | 106–108 | +47.8 | 58.2 | 92–94 | +62.5 |
| 85 | α | " | 2,4,6-Trimethylbenzyl | 57.2 | 97–99 | +45.4 | 59.1 | 82–84 | +58.1 |
| 86 | α | " | Tetrahydrofurfuryl | 56.4 | 99–102 | +49.5 | 60.4 | 79–81 | +64.2 |
| 87 | α | " | Furfuryl | 55.6 | 84–86 | +47.5 | 57.2 | 64–66 | +63.4 |
| 88 | α | " | Thiophene-2-yl-methyl | 53.4 | 90–93 | +47.8 | 51.2 | 70–73 | +62.2 |
| 89 | α | Isobutyl | Ethyl | 56.4 | 92–94 | +57.5 | 60.8 | 61–63 | +72.5 |
| 90 | α | " | n-Butyl | 58.6 | 91–93 | +55.8 | 62.5 | 78–80 | +72.2 |
| 91 | α | " | n-Hexyl | 57.6 | 89–91 | +55.7 | 59.2 | 72–74 | +70.4 |
| 92 | α | " | n-Octyl | 56.4 | 82–84 | +53.8 | 60.4 | 68–70 | +68.5 |
| 93 | α | " | Isopropyl | 56.8 | 94–96 | +57.4 | 61.2 | 69–71 | +73.3 |
| 94 | α | " | sec-Butyl | 57.4 | 90–92 | +52.1 | 63.4 | 68–70 | +71.8 |
| 95 | β | " | sec-Butyl | 59.7 | 104–106 | −17.6 | 64.8 | 90–92 | −13.5 |
| 96 | α | " | Neopentyl | 56.4 | 68–70 | +55.6 | 61.2 | Yellow carmel | +70.4 |
| 97 | α | " | 2-Propenyl | 53.8 | 91–93 | +56.3 | 57.8 | 65–67 | +71.8 |
| 98 | α | " | Isobutenyl | 54.6 | 97–100 | +55.7 | 58.2 | 74–77 | +71.4 |
| 99 | α | " | 2-Butenyl | 54.6 | 94–66 | +55.2 | 56.5 | 71–73 | +70.8 |
| 100 | β | " | 2-Butenyl | 61.4 | 106–108 | −19.5 | 63.4 | 92–95 | −11.5 |
| 101 | α | " | 3-Butenyl | 57.2 | 95–97 | +55.6 | 56.8 | 72–74 | +70.2 |
| 102 | α | " | 3-Methoxy-n-propyl | 56.4 | 88–90 | +54.7 | 58.6 | 68–71 | +69.4 |
| 103 | α | " | 2-Ethoxyethyl | 58.6 | 77–79 | +55.6 | 59.2 | 58–60 | +70.2 |

TABLE V-continued

| | Starting Material | | | Urea Compound | | | Nitroso Compound | | |
|---|---|---|---|---|---|---|---|---|---|
| Example No. | Isomeric form | R₁ | R₂ | Yield % | MP °C. | $[\alpha]_D^{20}$ degree | Yield % | MP °C. | $[\alpha]_D^{20}$ degree |
| 104 | α | " | 1-Methyl-2-methoxy-ethyl | 55.7 | 89–91 | +54.8 | 58.6 | 69–71 | +69.2 |
| 105 | α | " | 3-Ethoxy-n-propyl | 56.2 | 80–82 | +54.0 | 59.2 | 63–65 | +69.71 |
| 106 | α | " | Cyclopropylmethyl | 57.6 | 78–80 | +56.6 | 64.2 | 57–59 | +71.0 |
| 107 | α | " | Cyclohexylmethyl | 56.8 | 82–84 | +54.3 | 61.7 | 68–70 | +70.8 |
| 108 | α | " | 2-Hydroxy-1-methyl-ethyl | 53.4 | 89–91 | +51.8 | 55.8 | 63–65 | +66.2 |
| 109 | α | " | 2-Hydroxy-1-ethyl-ethyl | 52.4 | 79–81 | +45.8 | 56.4 | 56–58 | +60.5 |
| 110 | α | " | Benzyl | 53.6 | 86–88 | +51.7 | 58.4 | 72–74 | +66.2 |
| 111 | α | " | p-Methylbenzyl | 55.8 | 99–102 | +50.4 | 59.5 | 85–87 | +65.2 |
| 112 | α | " | 2,4,6-Trimethyl-benzyl | 54.2 | 91–93 | +50.3 | 58.7 | 76–78 | +65.7 |
| 113 | α | " | p-Methoxybenzyl | 53.2 | 83–85 | +66.0 | 56.6 | 97–99 | +51.5 |
| 114 | α | " | 2,3-Dimethoxybenzyl | 51.4 | 80–83 | +50.8 | 55.8 | 68–70 | +60.3 |
| 115 | α | " | Furfuryl | 50.7 | 72–74 | +50.3 | 56.5 | 55–57 | +65.4 |
| 116 | α | " | Thiophene-2-yl-methyl | 51.3 | 77–79 | +49.2 | 55.3 | 63–65 | +63.7 |
| 117 | α | sec-Butyl | Metyly | 57.8 | 95–97 | +58.4 | 64.3 | 62–64 | +73.0 |
| 118 | α | " | Ethyl | 58.2 | 88–90 | +57.6 | 65.7 | 59–61 | +72.4 |
| 119 | α | " | n-Propyl | 59.5 | 83–85 | +56.8 | 66.3 | 57–59 | +72.0 |
| 120 | α | " | n-Butyl | 58.3 | 95–97 | +57.3 | 64.5 | 72–75 | +72.1 |
| 121 | α | " | n-Pentyl | 58.4 | 85–87 | +56.5 | 62.4 | 68–70 | +71.0 |
| 122 | α | " | n-Hexyl | 59.2 | 88–90 | +55.9 | 63.5 | 66–68 | +71.4 |
| 123 | α | " | n-Octyl | 60.4 | 76–78 | +55.4 | 61.8 | 62–64 | +70.8 |
| 124 | α | " | Isopropyl | 50.4 | 86–89 | +58.7 | 55.9 | 60–63 | +72.4 |
| 125 | α | " | Isobutyl | 57.2 | 89–91 | +55.7 | 58.7 | 64–66 | +71.7 |
| 126 | α | " | sec-Butyl | 56.3 | 81–83 | +56.2 | 56.7 | 58–60 | +70.9 |
| 127 | α | " | tert-Butyl | 53.2 | 86–88 | +57.4 | 59.4 | Yellow caramel | +71.2 |
| 128 | α | " | 2-Propenyl | 50.3 | 88–91 | +56.2 | 58.7 | 62–65 | +70.9 |
| 129 | α | " | Isobutenyl | 52.3 | 94–96 | +56.9 | 55.4 | 71–73 | +71.2 |
| 130 | α | " | 2-Butenyl | 51.9 | 91–93 | +55.6 | 54.6 | 69–71 | +70.4 |
| 131 | α | " | 3-Butenyl | 50.8 | 90–92 | +55.0 | 58.8 | 68–70 | +70.2 |
| 132 | α | " | 3-Methoxy-n-propyl | 52.4 | 85–87 | +54.7 | 54.2 | 66–68 | +69.3 |
| 133 | α | " | 3-Ethoxy-n-propyl | 53.2 | 75–77 | +49.7 | 51.3 | 58–60 | +68.5 |
| 134 | α | " | 1-Methyl-2-methoxy-ethyl | 53.6 | 84–86 | +48.8 | 53.2 | 64–66 | +69.3 |
| 135 | α | " | 2-Hydroxy-1-methyl-ethyl | 53.2 | 83–85 | +52.3 | 54.6 | 60–62 | +66.8 |
| 136 | α | " | Cyclohexylmethyl | 51.2 | 77–79 | +55.6 | 55.4 | 63–65 | +70.4 |
| 137 | α | " | p-Methylbenzyl | 54.5 | 94–96 | +53.7 | 56.4 | 80–82 | +68.2 |
| 138 | α | " | p-Methoxybenzyl | 51.4 | 92–94 | +54.7 | 51.2 | 78–81 | +68.0 |
| 139 | α | " | Furfuryl | 50.7 | 65–67 | +51.4 | 50.6 | 48–50 | +66.3 |
| 140 | α | " | Thiophene-2-yl-methyl | 50.4 | 72–74 | +50.1 | 50.2 | 54–56 | +65.8 |
| 141 | α | n-Propyl | n-Butyl | 57.6 | 65–67 | +57.4 | 64.3 | 42–44 | +73.2 |
| 142 | α | " | n-Octyl | 58.4 | 72–74 | +56.2 | 65.8 | 58–60 | +71.0 |
| 143 | α | " | Isopropyl | 52.4 | Caramel like | +57.3 | 52.8 | Caramel like | +72.8 |
| 144 | α | " | Isobutyl | 56.5 | 62–64 | +59.4 | 57.5 | Caramel like | +74.6 |
| 145 | α | " | Cyclohexyl | 52.3 | 65–67 | +60.4 | 52.4 | 48–50 | +75.2 |
| 146 | α | " | Cyclohexylmethyl | 54.2 | 60–62 | +58.6 | 54.5 | 45–47 | +73.2 |
| 147 | α | Isopropyl | 2-Methyl-2-propenyl | 53.4 | 62–65 | +58.8 | 53.6 | 39–42 | +73.4 |
| 148 | α | " | 2-Methoxy-n-propyl | 51.4 | Caramel like | +59.8 | 56.2 | Caramel like | +74.2 |
| 149 | α | " | n-Butyl | 53.6 | 65–67 | +60.4 | 57.8 | 42–43 | +75.3 |
| 150 | α | Isopentyl | Isobutyl | 53.4 | 89–91 | +58.8 | 56.7 | 63–65 | +69.3 |
| 151 | α | " | 3-Ethoxy-n-propyl | 55.2 | 80–82 | +41.6 | 57.4 | 59–61 | +65.2 |
| 152 | α | 2-Ethylhexyl | Isobutyl | 51.2 | 78–81 | +40.2 | 55.3 | 58–60 | +60.7 |
| 153 | α | " | p-Methoxybenzyl | 50.6 | 90–92 | +53.4 | 54.6 | 72–74 | +62.5 |
| 154 | α | " | Tetrahydrofurfuryl | 50.4 | 77–79 | +42.6 | 54.2 | 58–60 | +59.4 |
| 155 | α | n-Hexyl | Methyl | 57.7 | 91–93 | +53.4 | 59.2 | 60–62 | +67.8 |
| 156 | α | " | n-Butyl | 56.6 | 93–96 | +54.2 | 62.3 | 70–73 | +68.2 |
| 157 | α | " | Isopropyl | 52.3 | 86–88 | +52.6 | 53.4 | 60–62 | +67.5 |
| 158 | α | " | Isobutyl | 54.5 | 88–90 | +53.7 | 55.8 | 63–65 | +68.6 |
| 159 | α | " | sec-Butyl | 52.8 | 84–86 | +52.4 | 56.7 | 61–63 | +67.6 |
| 160 | α | " | 2-Methyl-2-propenyl | 50.7 | 93–95 | +50.7 | 58.4 | 70–73 | +65.2 |
| 161 | α | " | 2-Butenyl | 51.4 | 91–93 | +51.8 | 57.6 | 67–69 | +66.4 |
| 162 | α | " | 2-Ethoxyethyl | 55.2 | 74–76 | +50.3 | 56.5 | 53–55 | +64.3 |
| 163 | α | " | 1-Methyl-2-methoxy-ethyl | 53.4 | 83–85 | +48.8 | 55.8 | 63–65 | +63.6 |
| 164 | α | " | Cyclohexylmethyl | 54.5 | 76–78 | +51.8 | 56.4 | 62–64 | +67.4 |
| 165 | α | n-Octyl | n-Butyl | 60.4 | 90–92 | +53.6 | 67.6 | 66–68 | +67.2 |
| 166 | α | " | Isobutyl | 57.5 | 84–86 | +54.6 | 62.4 | 60–62 | +68.4 |
| 167 | α | " | Cyclopropylmethyl | 55.7 | 74–76 | +51.3 | 63.7 | 50–52 | +66.8 |
| 168 | α | " | p-Methylbenzyl | 52.4 | 94–96 | +52.6 | 58.7 | 80–82 | +67.5 |
| 169 | α | " | p-Methoxybenzyl | 51.7 | 89–91 | +50.5 | 56.5 | 75–77 | +64.2 |

TABLE V-continued

| Example No. | Starting Material Isomeric form | R₁ | R₂ | Urea Compound Yield % | MP °C. | $[\alpha]_D^{20}$ degree | Nitroso Compound Yield % | MP °C. | $[\alpha]_D^{20}$ degree |
|---|---|---|---|---|---|---|---|---|---|
| 170 | α | n-decyl | α-Methylbenzyl | 54.5 | 120–122 | +43.6 | 58.9 | 106–108 | +57.8 |
| 171 | α | " | Tetrahydrofurfuryl | 53.6 | 84–86 | +38.2 | 57.3 | 68–70 | +53.5 |
| 172 | α | " | Thiophene-1-yl-methyl | 52.3 | 75–77 | +38.8 | 56.7 | 55–57 | +53.2 |
| 173 | α | 2-Methyl-2-propenyl | n-Butyl | 51.4 | 100–102 | +53.8 | 57.8 | 76–78 | +68.2 |
| 175 | α | 2-Methyl-2-propenyl | Isobutyl | 50.8 | 92–94 | +52.4 | 58.3 | 68–71 | +67.3 |
| 176 | α | 2-Butenyl | " | 51.4 | 89–91 | +54.6 | 59.4 | 66–68 | +69.7 |
| 177 | α | 3-Butenyl | Cyclohexyl | 50.3 | 78–80 | +51.7 | 60.4 | 61–63 | +66.4 |
| 178 | α | " | 3-Methoxy-n-propyl | 50.6 | 95–97 | +51.2 | 58.3 | 74–76 | +65.3 |
| 179 | α | 2-Propenyl | Isobutyl | 51.7 | 85–87 | +53.8 | 51.1 | 62–64 | +69.6 |
| 180 | α | 2-Propynyl | " | 52.4 | 82–84 | +54.3 | 57.6 | 60–62 | +69.0 |
| 181 | α | 3-Methoxy-n-propyl | n-Butyl | 53.6 | 96–98 | +53.7 | 55.8 | 72–75 | +67.8 |
| 182 | α | 3-Methoxy-n-propyl | Isobutyl | 52.5 | 88–90 | +53.9 | 57.8 | 64–66 | +68.3 |
| 183 | α | 3-Methoxy-n-propyl | sec-Butyl | 51.6 | 81–83 | +54.2 | 56.5 | 59–60 | +68.7 |
| 184 | α | 3-Methoxy-n-propyl | Cyclohexylmethyl | 50.7 | 71–73 | +53.6 | 54.3 | 55–57 | +69.5 |
| 185 | α | 3-Methoxy-n-propyl | Tetrahydrofurfuryl | 51.4 | 70–72 | +49.9 | 53.8 | 53–55 | +64.2 |
| 186 | α | 3-Ethoxy-n-propyl | n-Butyl | 56.4 | 85–87 | +50.7 | 61.2 | 62–64 | +65.2 |
| 187 | α | 3-Ethoxy-n-propyl | Cyclohexyl | 51.6 | 75–77 | +52.6 | 58.8 | 58–60 | +67.4 |
| 188 | α | 3-Ethoxy-n-propyl | Isobutyl | 52.4 | 82–84 | +53.8 | 57.5 | 56–58 | +66.8 |
| 189 | α | 3-Ethoxy-n-propyl | sec-Butyl | 53.2 | 73–75 | +51.2 | 56.6 | 52–54 | +66.0 |
| 190 | α | 1-Methyl-2-methoxyethyl | n-Butyl | 51.3 | 93–95 | +53.6 | 57.3 | 70–72 | +68.3 |
| 191 | α | 1-Methyl-2-methoxyethyl | Isobutyl | 50.6 | 87–89 | +53.8 | 56.2 | 64–66 | +69.7 |
| 192 | α | 1-Methyl-2-methoxyethyl | sec-Butyl | 50.2 | 81–83 | +54.6 | 55.7 | 58–60 | +68.9 |
| 193 | α | 1-Methyl-2-methoxyethyl | Cyclopropylmethyl | 53.4 | 69–71 | +52.5 | 56.5 | 45–47 | +66.4 |
| 194 | α | 1-Methyl-2-methoxyethyl | 2-Methoxyethyl | 49.4 | 81–83 | +50.4 | 50.6 | 58–60 | +65.3 |
| 195 | α | Cyclohexylmethyl | Methyl | 56.6 | 89–91 | +61.8 | 58.7 | 57–58 | +76.4 |
| 196 | β | Cyclohexylmethyl | Methyl | 58.8 | 124–126 | −25.4 | 64.3 | 110–112 | −18.2 |
| 197 | α | Cyclohexyl | n-Propyl | 56.6 | 76–79 | +60.2 | 64.3 | 51–53 | +74.2 |
| 198 | α | " | n-Butyl | 57.6 | 91–93 | +60.8 | 62.4 | 67–69 | +75.8 |
| 199 | β | " | n-Butyl | 58.5 | 102–104 | −24.6 | 63.6 | 88–90 | −16.8 |
| 200 | α | " | n-Pentyl | 56.4 | 74–76 | +58.7 | 64.2 | 53–55 | +73.2 |
| 201 | α | 2-Cyclopentylethyl | n-Hexyl | 53.6 | 72–74 | +57.3 | 63.7 | 56–58 | +72.5 |
| 202 | β | 2-Cyclopentylethyl | n-Hexyl | 55.8 | 112–114 | −22.4 | 66.8 | 98–100 | −13.6 |
| 203 | α | Cyclohexyl | iso-Propyl | 53.4 | 83–85 | +60.6 | 65.7 | 57–59 | +75.4 |
| 204 | α | " | sec-Butyl | 52.6 | 70–72 | +60.2 | 64.3 | 56–58 | +74.6 |
| 205 | β | " | sec-Butyl | 51.3 | 91–93 | −20.7 | 62.7 | 77–79 | −12.6 |
| 206 | α | " | 2-Propenyl | 52.4 | 83–85 | +59.8 | 61.4 | 57–59 | +74.3 |
| 207 | α | " | 2-Methyl-2-propenyl | 51.0 | 90–92 | +56.3 | 60.6 | 67–69 | +72.6 |
| 208 | α | " | 2-Butenyl | 54.3 | 86–88 | +56.8 | 58.4 | 63–65 | +72.2 |
| 209 | α | " | 2-Methoxyethyl | 51.2 | 68–70 | +58.4 | 54.3 | 44–46 | +72.5 |
| 210 | α | " | 3-Methoxy-n-propyl | 50.4 | 82–84 | +57.2 | 55.7 | 62–64 | +73.4 |
| 211 | α | " | 2-Ethoxyethyl | 51.6 | 70–72 | +58.4 | 58.4 | 50–52 | +73.5 |
| 212 | α | " | 3-Ethoxy-n-propyl | 52.5 | 73–75 | +57.2 | 56.4 | 55–57 | +72.6 |
| 213 | α | " | 2-Methoxy-n-propyl | 51.3 | 64–66 | +57.3 | 59.8 | 43–44 | +72.9 |
| 214 | α | " | 1-Methyl-2-methoxyethyl | 50.4 | 82–84 | +56.4 | 61.4 | 61–62 | +71.7 |
| 215 | β | " | 1-Methyl-2-methoxyethyl | 54.4 | 98–100 | −19.9 | 60.7 | 84–86 | −12.8 |
| 216 | α | " | 4-Hydroxy-n-butyl | 52.8 | 76–78 | +50.7 | 57.5 | 54–56 | +64.6 |
| 217 | α | " | Cyclopropylmethyl | 54.7 | 72–74 | +58.7 | 56.3 | 49–51 | +73.8 |
| 218 | α | " | Cyclohexylmethyl | 56.4 | 75–77 | +58.2 | 58.7 | 60–62 | +73.2 |
| 219 | α | " | 2-Cyclopentylethyl | 55.8 | 70–72 | +57.7 | 57.6 | 55–57 | +73.4 |
| 220 | α | " | Cyclohexyl | 54.4 | 79–81 | +60.2 | 57.8 | 62–64 | +74.8 |
| 221 | α | " | Benzyl | 50.6 | 76–78 | +55.8 | 58.8 | 61–63 | +69.4 |
| 222 | α | " | p-Chlorobenzyl | 51.4 | 86–88 | +53.6 | 56.6 | 72–74 | +68.6 |
| 223 | α | " | p-Methylbenzyl | 52.6 | 90–92 | +52.7 | 57.8 | 75–77 | +67.4 |
| 224 | α | " | 2,4,6-Trimethylbenzyl | 50.7 | 79–81 | +54.4 | 56.7 | 65–68 | +68.9 |
| 225 | α | " | p-Methoxybenzyl | 51.2 | 85–87 | +53.6 | 55.7 | 72–74 | +68.2 |
| 226 | α | " | 2,3-Dimethoxybenzyl | 50.5 | 74–76 | +52.6 | 54.6 | 60–63 | +67.6 |

TABLE V-continued

| Example No. | Starting Material Isomeric form | R₁ | R₂ | Urea Compound Yield % | Urea Compound MP °C. | Urea Compound $[\alpha]_D^{20}$ degree | Nitroso Compound Yield % | Nitroso Compound MP °C. | Nitroso Compound $[\alpha]_D^{20}$ degree |
|---|---|---|---|---|---|---|---|---|---|
| 227 | α | " | 3,4,5-Trimethyl-benzyl | 51.7 | 96–98 | +50.2 | 58.7 | 85–87 | +65.2 |
| 228 | α | " | Phenetyl | 50.5 | 78–80 | +50.4 | 56.5 | 64–66 | +64.4 |
| 229 | α | " | α-Methylbenzyl | 51.4 | 84–86 | +53.2 | 54.6 | 70–72 | +68.6 |
| 230 | α | " | Tetrahydrofurfuryl | 52.4 | 78–80 | +50.9 | 57.6 | 61–63 | +66.8 |
| 231 | α | " | Furfuryl | 51.6 | 63–65 | +52.0 | 58.1 | 46–48 | +66.7 |
| 232 | α | " | Thiophene-2-yl-methyl | 50.7 | 74–76 | +51.4 | 57.6 | 56–58 | +66.4 |
| 233 | α | " | 4-Pyridylethyl | 50.4 | 83–85 | +50.7 | 56.8 | 69–71 | +65.2 |
| 234 | α | p-Methylbenzyl | Isobutyl | 54.2 | 95–97 | +47.8 | 59.3 | 73–75 | +62.2 |
| 235 | α | p-Methoxybenzyl | " | 51.8 | 91–93 | +47.5 | 57.6 | 71–73 | +62.6 |
| 236 | α | 2,3-Dimethoxy-benzyl | " | 50.1 | 76–78 | +45.4 | 53.8 | 54–56 | +60.2 |
| 237 | α | 3,4,5-trimethyl-benzyl | " | 48.3 | 108–111 | +43.6 | 52.3 | 85–87 | +55.7 |
| 238 | α | 2,4,6-trimethyl-benzyl | " | 49.7 | 87–89 | +41.9 | 53.4 | 63–65 | +57.8 |
| 239 | α | Benzyl | " | 50.4 | 80–82 | +45.3 | 51.7 | 57–59 | +61.2 |
| 240 | α | α-Methylbenzyl | " | 51.2 | 86–88 | +47.8 | 50.8 | 61–63 | +59.4 |
| 241 | α | Phenethyl | " | 50.4 | 83–85 | +47.2 | 57.4 | 58–60 | +59.2 |

EXAMPLES 242–388

In the same manner as Example 67, various 3-R₂-3-(R₁ α- or β-D-glucopyranose-2-yl)-1-(2-chloroethyl-)ureas (urea compound) and 3-R₂-3-(R₁ α- or β-D-glucopyranose-2-yl)-1-(2-chloroethyl)-1-nitrosoureas (nitroso compound) were prepared from corresponding R₁ 2-(R₂ amino)-2-deoxy-α- or β-D-glucopyranosides (starting material). Table VI shows the species of R₁ and R₂ and the yields, melting points, and specific rotations ($[\alpha]_D^{20}$ (C 1.0, methanol)) of the urea compounds and nitroso compounds.

TABLE VI

| Example No. | Starting Material Isomeric form | R₁ | R₂ | Urea Compound Yield % | Urea Compound MP °C. | Urea Compound $[\alpha]_D^{20}$ Degree | Nitroso Compound Yield % | Nitroso Compound MP °C. | Nitroso Compound $[\alpha]_D^{20}$ Degree |
|---|---|---|---|---|---|---|---|---|---|
| 242 | α | n-Butyl | Isobutyl | 56.1 | 104–106 | +60.7 | 62.8 | 90–92 | +74.3 |
| 243 | β | " | " | 54.8 | 125–127 | −23.5 | 61.9 | 111–113 | −16.7 |
| 244 | α | " | 3-Methoxy-n-propyl | 51.2 | 105–108 | +55.3 | 55.8 | 91–94 | +64.7 |
| 245 | α | " | 2-Methoxy-n-propyl | 50.8 | 90–92 | +59.4 | 57.6 | 76–79 | +68.8 |
| 246 | α | " | 3-Hydroxy-n-propyl | 54.7 | 87–89 | +45.6 | 59.2 | 71–73 | +58.4 |
| 247 | α | " | 2-(2-Hydroxyethoxy)-ethyl | 53.6 | 103–105 | +51.5 | 58.7 | 88–90 | +64.1 |
| 248 | α | " | 4-Hydroxy-n-butyl | 51.4 | 90–92 | +48.7 | 54.1 | 75–77 | +60.2 |
| 249 | α | " | Cyclopropylmethyl | 56.6 | 92–94 | +65.2 | 65.4 | 78–80 | +74.8 |
| 250 | α | " | Cyclohyxylmethyl | 52.4 | 101–103 | +56.4 | 62.7 | 87–89 | +71.8 |
| 251 | α | " | Benzyl | 51.8 | 104–105 | +59.4 | 58.6 | 89–91 | +68.3 |
| 252 | α | " | p-Methylbenzyl | 51.3 | 113–115 | +51.7 | 59.7 | 100–102 | +67.0 |
| 253 | α | " | 2,4,6-Trimethyl-benzyl | 50.7 | 101–104 | +61.4 | 56.6 | 90–92 | +73.5 |
| 254 | α | " | Tetrahydrofurfuryl | 48.1 | 104–106 | +60.3 | 51.2 | 87–89 | +69.7 |
| 255 | α | " | Furfuryl | 46.5 | 91–93 | +59.0 | 54.3 | 76–78 | +68.9 |
| 256 | α | " | Thiophene-2-methyl | 44.6 | 97–99 | +59.4 | 53.7 | 82–84 | +67.7 |
| 257 | α | Iso-Butyl | Methyl | 53.7 | 108–110 | +74.7 | 52.6 | 90–92 | +84.2 |
| 258 | α | " | n-Propyl | 57.1 | 89–91 | +69.5 | 53.3 | 73–75 | +79.2 |
| 259 | α | " | n-Butyl | 50.6 | 104–107 | +59.9 | 52.7 | 91–94 | +67.8 |
| 260 | α | " | n-Hexyl | 56.7 | 96–99 | +66.7 | 56.4 | 84–86 | +75.3 |
| 261 | α | " | n-Octyl | 58.4 | 87–89 | +64.2 | 60.7 | 76–78 | +73.6 |
| 262 | α | " | Isopentyl | 51.2 | 97–99 | +65.6 | 55.6 | 83–85 | +75.0 |
| 263 | α | " | Isobutenyl | 50.8 | 101–103 | +68.3 | 54.2 | 87–89 | +77.6 |
| 264 | α | " | 2-Butenyl | 51.2 | 97–99 | +68.4 | 56.7 | 83–85 | +77.2 |
| 265 | β | " | " | 54.5 | 116–118 | −25.6 | 66.4 | 102–104 | −17.4 |
| 266 | α | " | 2-Methoxyethyl | 52.1 | 81–83 | +69.2 | 57.4 | 67–69 | +78.6 |
| 267 | α | " | 3-Methoxy-n-propyl | 54.6 | 94–97 | +67.5 | 55.5 | 80–83 | +75.3 |
| 268 | α | " | 3-Ethoxyethyl | 50.8 | 87–89 | +66.7 | 54.3 | 75–77 | +75.9 |
| 269 | α | " | Cyclopropylmethyl | 56.4 | 83–85 | +66.9 | 58.4 | 69–71 | +77.5 |
| 270 | α | " | Cyclohexylmethyl | 55.7 | 91–93 | +66.4 | 57.6 | 79–81 | +75.3 |
| 280 | α | Isobutyl | Benzyl | 50.2 | 93–95 | +61.2 | 53.8 | 81–83 | +70.7 |
| 281 | α | " | 2,4,6-Trimethyl-benzyl | 48.6 | 91–93 | +58.4 | 54.6 | 82–84 | +70.8 |
| 282 | α | " | p-Methoxybenzyl | 46.2 | 102–104 | +61.7 | 48.8 | 91–93 | +70.2 |
| 283 | α | " | Tetrahydrofurfuryl | 43.7 | 90–92 | +61.5 | 47.2 | 81–83 | +70.4 |
| 284 | α | " | Furfuryl | 41.5 | 78–80 | +60.7 | 45.6 | 66–68 | +69.2 |
| 285 | α | " | Thiophene-2-yl-methyl | 38.4 | 86–88 | +60.1 | 40.3 | 74–76 | +68.9 |
| 286 | α | sec-Butyl | Methyl | 55.4 | 105–107 | +74.5 | 59.4 | 87–89 | +83.3 |
| 287 | α | " | n-Propyl | 57.2 | 88–90 | +59.4 | 60.6 | 72–74 | +78.0 |

TABLE VI-continued

| Example No. | Isomeric form | R₁ | R₂ | Urea Compound Yield % | Urea Compound MP °C. | Urea Compound $[\alpha]_D^{20}$ Degree | Nitroso Compound Yield % | Nitroso Compound MP °C. | Nitroso Compound $[\alpha]_D^{20}$ Degree |
|---|---|---|---|---|---|---|---|---|---|
| 288 | α | " | n-Butyl | 57.4 | 98–101 | +69.7 | 53.6 | 85–87 | +78.4 |
| 289 | α | " | n-Octyl | 55.7 | 80–82 | +64.7 | 59.4 | 70–72 | +75.6 |
| 290 | α | " | Isobutyl | 51.3 | 89–91 | +68.4 | 56.8 | 75–78 | +77.8 |
| 291 | α | " | 2-Propenyl | 50.7 | 93–95 | +66.7 | 57.5 | 77–80 | +77.2 |
| 292 | α | " | 2-Methyl-2-propenyl | 51.6 | 97–99 | +68.2 | 55.8 | 84–86 | +77.6 |
| 293 | α | " | 3-Butenyl | 50.1 | 93–95 | +72.8 | 53.6 | 79–81 | +81.7 |
| 294 | α | " | 3-Methoxy-n-propyl | 47.6 | 95–97 | +67.8 | 49.8 | 80–82 | +77.6 |
| 295 | α | " | 1-Methyl-2-methoxyethyl | 44.8 | 92–94 | +69.3 | 50.4 | 77–79 | +77.0 |
| 296 | α | " | 2-Hydroxy-1-methylethyl | 46.7 | 91–93 | +64.5 | 53.6 | 75–77 | +73.4 |
| 297 | α | " | Cyclohexylmethyl | 51.2 | 87–90 | +68.4 | 56.8 | 73–75 | +75.6 |
| 298 | α | " | p-Methoxybenzyl | 54.2 | 100–102 | +64.5 | 50.7 | 89–91 | +72.6 |
| 299 | α | " | Furfuryl | 46.8 | 70–72 | +64.8 | 53.6 | 58–60 | +73.5 |
| 300 | α | " | Thiophene-2-yl-methyl | 41.2 | 77–79 | +60.8 | 47.6 | 65–69 | +70.3 |
| 301 | α | n-Propyl | n-Butyl | 56.6 | 69–71 | +71.2 | 59.3 | 55–57 | +80.4 |
| 302 | α | " | n-Octyl | 50.2 | 76–78 | +67.5 | 57.6 | 66–68 | +75.6 |
| 303 | α | " | Isopropyl | 53.6 | Caramel like | +57.3 | 50.4 | Caramel like | +80.2 |
| 304 | α | " | Isobutyl | 51.7 | 67–69 | +64.7 | 53.4 | Caramel like | +80.5 |
| 305 | α | " | Cyclohexyl | 50.4 | 71–73 | +70.2 | 52.7 | 59–61 | +79.6 |
| 306 | α | " | Cyclohexylmethyl | 53.5 | 60–62 | +58.6 | 60.4 | 55–57 | +77.8 |
| 307 | α | " | 2-Methyl-2-propenyl | 51.7 | 66–68 | +70.2 | 56.3 | 52–54 | +80.4 |
| 308 | α | " | 2-Methoxy-n-propyl | 50.7 | 65–67 | +70.9 | 56.8 | 50–52 | +80.2 |
| 309 | α | Isopropyl | n-Butyl | 53.8 | 69–71 | +71.3 | 53.2 | 54–56 | +81.7 |
| 310 | α | Isopentyl | Isobutyl | 50.6 | 89–91 | +58.8 | 56.4 | 75–77 | +75.6 |
| 311 | α | 2-Ethylhexyl | " | 51.6 | 85–87 | +58.7 | 57.3 | 71–73 | +65.8 |
| 312 | α | n-Hexyl | Methyl | 55.8 | 104–106 | +67.9 | 60.7 | 85–87 | +78.3 |
| 313 | α | " | n-Butyl | 56.7 | 100–102 | +65.2 | 63.5 | 83–85 | +74.6 |
| 314 | α | " | Isopropyl | 52.4 | 89–92 | +65.7 | 60.6 | 72–74 | +75.0 |
| 315 | α | " | sec-Butyl | 51.6 | 86–88 | +64.8 | 58.3 | 73–76 | +73.4 |
| 316 | α | " | 2-Methyl-2-propenyl | 50.4 | 96–98 | +62.6 | 56.4 | 82–84 | +71.6 |
| 317 | α | " | 2-Butenyl | 51.3 | 94–96 | +64.3 | 57.8 | 80–82 | +73.0 |
| 318 | α | " | 1-Methyl-2-methoxyethyl | 48.6 | 89–91 | +61.5 | 53.5 | 75–77 | +70.2 |
| 319 | α | " | Cyclohexylmethyl | 47.4 | 83–85 | +62.4 | 51.2 | 71–73 | +71.8 |
| 320 | α | n-Octyl | n-Butyl | 52.8 | 93–95 | +65.7 | 63.7 | 78–80 | +74.6 |
| 321 | α | " | Isobutyl | 54.7 | 86–88 | +64.3 | 62.3 | 74–76 | +74.1 |
| 322 | α | " | Cyclopropylmethyl | 51.4 | 78–80 | +63.4 | 57.8 | 63–65 | +73.0 |
| 323 | α | " | p-Methylbenzyl | 54.6 | 98–100 | +62.9 | 58.9 | 88–90 | +71.8 |
| 324 | α | " | p-Methoxybenzyl | 51.4 | 93–95 | +58.7 | 57.2 | 83–85 | +68.7 |
| 325 | α | " | α-Methylbenzyl | 50.8 | 126–128 | +53.5 | 56.3 | 111–113 | +63.6 |
| 326 | α | " | Tetrahydrofurfuryl | 48.5 | 91–93 | +51.7 | 53.6 | 76–78 | +60.4 |
| 327 | α | " | Thiophene-2-yl-methyl | 37.8 | 80–82 | +51.2 | 42.5 | 67–69 | +60.1 |
| 328 | α | 2-Methyl-2-propenyl | n-Butyl | 47.3 | 104–106 | +60.7 | 54.6 | 88–90 | +74.8 |
| 329 | α | 2-Methyl-2-properyl | Isobutyl | 50.8 | 95–97 | +58.7 | 56.8 | 80–82 | +73.4 |
| 330 | α | 2-Butenyl | " | 46.8 | 90–92 | +54.6 | 49.3 | 78–80 | +75.0 |
| 331 | α | 3-Butenyl | Cyclohexyl | 53.5 | 94–96 | +66.8 | 57.7 | 72–74 | +70.8 |
| 332 | α | 3-Butenyl | 3-Methoxy-n-propyl | 55.4 | 100–102 | +63.7 | 62.8 | 76–78 | +72.6 |
| 333 | α | 3-Methoxy-n-propyl | n-Butyl | 54.2 | 99–101 | +64.4 | 58.6 | 85–87 | +73.8 |
| 334 | α | 3-Methoxy-n-propyl | Isobutyl | 48.4 | 91–93 | +66.4 | 51.4 | 76–78 | +74.7 |
| 335 | α | 3-Methoxy-n-propyl | sec-Butyl | 45.6 | 85–87 | +65.7 | 50.7 | 72–74 | +74.2 |
| 336 | α | 3-Methoxy-n-propyl | Cyclohexylmethyl | 51.6 | 76–78 | +64.5 | 55.8 | 64–66 | +73.8 |
| 337 | α | 3-Methoxy-n-propyl | Tetrahydrofurfuryl | 49.5 | 77–79 | +60.5 | 57.3 | 65–67 | +69.8 |
| 338 | α | 3-Ethoxy-n-propyl | n-Butyl | 52.7 | 85–87 | +50.7 | 50.6 | 74–76 | +69.6 |
| 339 | α | 3-Ethoxy-n-propyl | Cyclohexyl | 55.6 | 82–84 | +62.8 | 58.7 | 69–71 | +71.8 |
| 340 | α | 3-Ethoxy-n-propyl | Isobutyl | 53.1 | 86–88 | +64.3 | 56.4 | 70–72 | +73.6 |
| 341 | α | 3-Ethoxy-n-propyl | sec-Butyl | 51.7 | 79–81 | +63.4 | 55.6 | 64–66 | +72.4 |
| 342 | α | 1-Methyl-2-methoxyethyl | n-Butyl | 53.7 | 98–100 | +65.3 | 57.4 | 83–85 | +74.3 |

TABLE VI-continued

| | Starting Material | | | Urea Compound | | | Nitroso Compound | | |
|---|---|---|---|---|---|---|---|---|---|
| Example No. | Isomeric form | R₁ | R₂ | Yield % | MP °C. | $[\alpha]_D^{20}$ Degree | Yield % | MP °C. | $[\alpha]_D^{20}$ Degree |
| 343 | α | 1-Methyl-2-methoxyethyl | Isobutyl | 53.2 | 91–93 | +65.7 | 56.2 | 76–78 | +75.5 |
| 344 | α | 1-Methyl-2-methoxyethyl | sec-Butyl | 52.8 | 85–87 | +66.3 | 55.7 | 70–73 | +75.2 |
| 345 | α | 1-Methyl-2-methoxyethyl | Cyclopropylmethyl | 51.7 | 73–75 | +64.6 | 56.6 | 57–59 | +73.6 |
| 346 | α | 1-Methyl-2-methoxyethyl | 2-Methoxyethyl | 50.4 | 88–90 | +64.9 | 53.5 | 73–75 | +73.3 |
| 347 | α | Cyclohexylmethyl | Methyl | 48.6 | 100–102 | +77.9 | 51.4 | 82–84 | +86.7 |
| 348 | α | Cyclohexylmethyl | " | 58.5 | 134–136 | −24.2 | 64.7 | 120–122 | −17.4 |
| 349 | α | Cyclohexyl | n-Propyl | 56.4 | 83–85 | +73.4 | 61.5 | 66–68 | +82.7 |
| 350 | α | Cyclohexyl | n-Butyl | 55.3 | 93–95 | +76.3 | 60.4 | 79–81 | +85.6 |
| 351 | β | Cyclohexyl | " | 52.7 | 78–80 | −24.2 | 58.6 | 64–66 | −16.8 |
| 352 | α | 2-Cyclopentylethyl | n-Hexyl | 51.4 | 76–78 | +61.6 | 57.3 | 66–68 | +76.8 |
| 353 | β | 2-Cyclopentylethyl | " | 50.6 | 122–124 | −24.8 | 56.7 | 108–110 | −17.6 |
| 354 | α | Cyclohexyl | Isopropyl | 51.7 | 86–88 | +74.3 | 53.5 | 72–74 | +83.7 |
| 355 | α | " | Isobutyl | 56.3 | 88–90 | +71.8 | 59.8 | 73–75 | +80.6 |
| 356 | β | " | " | 54.2 | 108–110 | −25.4 | 57.1 | 94–96 | −17.2 |
| 357 | α | " | sec-Butyl | 52.7 | 74–76 | +70.6 | 56.3 | 68–70 | +80.4 |
| 358 | β | " | " | 57.4 | 103–105 | −25.4 | 62.2 | 89–91 | −17.6 |
| 359 | α | " | 2-Propenyl | 50.3 | 88–90 | +73.6 | 54.5 | 72–74 | +82.6 |
| 360 | α | " | 2-Methyl-2-propenyl | 43.6 | 64–66 | +70.3 | 50.7 | 79–81 | +78.4 |
| 361 | α | " | 2-Butenyl | 41.5 | 90–92 | +71.5 | 49.6 | 75–77 | +78.3 |
| 362 | α | " | 2-Methoxyethyl | 40.3 | 75–77 | +71.3 | 45.4 | 59–61 | +80.8 |
| 363 | α | " | 3-Methoxy-n-propyl | 51.3 | 88–90 | +70.4 | 56.7 | 74–76 | +79.6 |
| 364 | α | " | 2-Ethoxyethyl | 52.3 | 76–78 | +70.8 | 57.8 | 62–64 | +80.2 |
| 365 | α | " | 3-Ethoxy-n-propyl | 50.7 | 78–80 | +67.9 | 54.3 | 66–69 | +77.4 |
| 366 | α | " | 2-Methoxy-n-propyl | 51.7 | 69–71 | +68.8 | 55.4 | 55–57 | +78.5 |
| 367 | α | " | 4-Hydroxy-n-butyl | 49.3 | 91–93 | +62.6 | 56.6 | 76–78 | +71.3 |
| 368 | α | " | Cyclopropylmethyl | 46.8 | 77–79 | +70.9 | 52.5 | 61–63 | +80.1 |
| 369 | α | " | Cyclohexylmethyl | 53.5 | 82–84 | +68.9 | 56.6 | 69–71 | +77.6 |
| 370 | α | " | 2-Cyclopentylethyl | 51.2 | 76–78 | +67.5 | 54.3 | 64–66 | +77.0 |
| 371 | α | " | Cyclohexyl | 50.1 | 86–88 | +69.7 | 57.8 | 73–75 | +78.2 |
| 372 | α | " | Benzyl | 45.4 | 83–85 | +64.5 | 53.7 | 71–73 | +73.6 |
| 373 | α | " | p-Chlorobenzyl | 43.6 | 89–92 | +63.9 | 51.3 | 79–81 | +72.5 |
| 374 | α | " | p-Methylbenzyl | 41.7 | 94–96 | +62.7 | 48.4 | 84–86 | +71.2 |
| 375 | α | " | p-Methoxybenzyl | 38.4 | 91–93 | +64.5 | 45.6 | 80–82 | +73.6 |
| 376 | α | " | 2,3-Dimethoxybenzyl | 33.8 | 76–78 | +63.5 | 41.3 | 67–69 | +73.0 |
| 377 | α | " | 3,4,5-Trimethoxybenzyl | 36.2 | 104–106 | +61.4 | 42.6 | 93–95 | +70.4 |
| 378 | α | " | Phenethyl | 51.3 | 72–74 | +68.6 | 55.6 | 82–86 | +60.2 |
| 379 | α | " | Tetrahydrofurfuryl | 48.8 | 84–86 | +63.5 | 54.3 | 61–63 | +66.8 |
| 380 | α | " | Thiophene-2-yl-methyl | 47.4 | 80–82 | +63.3 | 56.8 | 68–70 | +72.1 |
| 381 | α | " | 4-Pyridylmethyl | 45.6 | 90–92 | +60.4 | 52.8 | 80–82 | +69.6 |
| 382 | α | p-Methylbenzyl | Isobutyl | 43.1 | 99–101 | +59.8 | 49.4 | 84–86 | +68.6 |
| 383 | α | p-n-Propylbenzyl | " | 44.6 | 88–90 | +46.6 | 52.6 | 72–74 | +63.4 |
| 384 | α | p-Methoxybenzyl | " | 41.0 | 96–98 | +61.7 | 48.7 | 83–85 | +69.8 |
| 385 | α | p-Ethoxybenzyl | " | 38.4 | 93–95 | +60.2 | 50.2 | 78–81 | +65.4 |
| 386 | α | 2,3-Dimethoxybenzyl | " | 42.7 | 82–84 | +57.4 | 56.4 | 67–69 | +66.7 |
| 387 | α | 3,4,5-Trimethoxybenzyl | " | 48.9 | 113–115 | +55.8 | 57.2 | 90–92 | +62.4 |
| 388 | α | α-Methylbenzyl | " | 51.4 | 94–96 | +60.7 | 56.7 | 76–78 | +65.9 |

EXAMPLES 389–525

Various 3-R₂-3-(R₁ α- or β-D-glucopyranose-3-yl)-1-(2-chloroethyl)urea (urea compound) and 3-R₂-3-(R₁ α- or β-D-glucopyranose-3-yl)-1-(2-chloroethyl)-1-nitrosourea (nitroso compound) were prepared from corresponding R₁ 3-(R₂ amino)-3-deoxy-α- or β-D-glucopyranosides (starting material) in the same manner as Example 67. In addition, homologous nitroso compounds were prepared from corresponding starting materials in the same manner as Example 2. Table VII shows the species of R₁ and R₂ and the yields, melting points, and specific rotations ($[\alpha]_D^{20}$ (C 1.0, methanol)) of the products.

TABLE VII

| Example No. | Starting Material Isomeric form | $R_1$ | $R_2$ | Urea Compound Yield % | MP °C. | $[\alpha]_D^{20}$ degree | Nitroso Compound Yield % | MP °C. | $[\alpha]_D^{20}$ degree |
|---|---|---|---|---|---|---|---|---|---|
| 389 | α | n-Butyl | n-Hexyl | 39.4 | 90–92 | +38.3 | 36.5 | 78–80 | +45.6 |
| 390 | β | " | " | 45.3 | 103–105 | −24.0 | 49.6 | 93–95 | −17.5 |
| 391 | α | " | sec-Butyl | 43.8 | 82–84 | +35.2 | 50.7 | 68–70 | +42.2 |
| 392 | β | " | " | 41.7 | 97–99 | −23.4 | 57.6 | 89–92 | −17.3 |
| 393 | α | " | 3-Butenyl | 36.4 | 93–95 | +35.6 | 45.6 | 79–81 | +42.7 |
| 394 | α | " | 3-Methoxy-n-propyl | 34.6 | 90–93 | +31.6 | 48.4 | 77–80 | +38.4 |
| 395 | α | " | " | 33.6 | 91–93 | +31.5 | 40.7 | 77–80 | +38.5 |
| 396 | α | " | 2-Methoxy-n-propyl | 40.7 | 71–73 | +25.7 | 42.6 | 57–59 | +32.3 |
| 397 | α | " | Cyclopropylmethyl | 44.5 | 77–79 | +35.4 | 48.9 | 63–65 | +42.6 |
| 398 | α | " | Benzyl | 30.8 | 90–92 | +35.8 | 43.8 | 77–79 | +43.8 |
| 399 | α | " | p-Methylbenzyl | 29.1 | 100–102 | +36.6 | 46.3 | 90–92 | +43.2 |
| 400 | α | " | Tetrahydrofurfuryl | 46.4 | 90–92 | +33.4 | 55.7 | 76–78 | +41.0 |
| 401 | α | " | Furfuryl | 37.6 | 74–77 | +32.7 | 43.5 | 60–63 | +39.6 |
| 402 | α | Isobutyl | Methyl | 41.5 | 78–80 | +36.4 | 49.5 | 59–61 | +40.6 |
| 403 | α | " | n-Propyl | 45.8 | 70–72 | +36.8 | 52.6 | 54–56 | +43.3 |
| 404 | α | " | n-Butyl | 43.7 | 98–100 | +33.6 | 51.7 | 75–77 | +47.4 |
| 405 | α | " | n-Hexyl | 38.8 | 81–83 | +40.2 | 48.6 | 69–71 | +47.6 |
| 406 | α | " | n-Octyl | | | | 70.3 | 66–68 | +47.3 |
| 407 | α | " | Isopropyl | | | | 78.7 | 64–66 | +45.4 |
| 408 | α | " | Isobutenyl | | | | 74.6 | 71–74 | +46.2 |
| 409 | α | " | 2-Butenyl | 42.0 | 83–85 | +33.4 | 53.8 | 69–72 | +45.6 |
| 410 | β | " | " | 36.6 | 97–99 | −25.4 | 48.7 | 83–85 | −18.2 |
| 411 | α | " | 2-Methoxyethyl | 41.4 | 62–64 | +37.4 | 50.3 | 48–50 | +42.8 |
| 412 | α | " | 3-Methoxy-n-propyl | 42.8 | 79–81 | +36.3 | 52.8 | 65–67 | +44.2 |
| 413 | α | " | 3-Ethoxy-n-propyl | 37.3 | 72–74 | +36.8 | 43.5 | 60–62 | +42.8 |
| 414 | α | " | Cyclopropylmethyl | 38.7 | 68–70 | +38.4 | 48.3 | 54–56 | +46.6 |
| 415 | α | " | Cyclohexylmethyl | 33.6 | 77–79 | +41.7 | 45.7 | 65–67 | +48.4 |
| 416 | α | " | 2-Hydroxy-n-propyl | 34.8 | 73–75 | +36.8 | 51.4 | 57–59 | +42.6 |
| 417 | α | " | 2-Hydroxy-1-methylethyl | 38.4 | 76–78 | +37.4 | 48.2 | 59–61 | +43.3 |
| 418 | α | " | 2-Hydroxy-1-ethylethyl | 40.6 | 67–69 | +32.4 | 47.5 | 53–55 | +39.8 |
| 419 | α | " | Benzyl | 31.2 | 82–84 | +38.7 | 46.3 | 70–72 | +45.6 |
| 420 | α | " | 2,4,6-Trimethylbenzyl | 34.5 | 83–85 | +37.2 | 43.8 | 74–76 | +44.7 |
| 421 | α | " | p-Methoxybenzyl | 28.9 | 89–92 | +38.8 | 41.6 | 79–81 | +46.0 |
| 422 | α | " | Tetrahydrofurfuryl | 29.4 | 77–79 | +34.2 | 38.4 | 65–67 | +41.3 |
| 423 | α | " | Furfuryl | 31.6 | 65–67 | +36.7 | 42.6 | 53–55 | +43.6 |
| 424 | α | " | Thiophene-2-yl-methyl | 28.4 | 72–74 | +33.8 | 40.7 | 60–62 | +40.7 |
| 425 | α | sec-Butyl | Methyl | 54.6 | 75–77 | +33.6 | 61.8 | 57–59 | +44.8 |
| 426 | α | " | n-Propyl | 50.1 | 69–71 | +31.4 | 56.4 | 53–55 | +42.9 |
| 427 | α | " | n-Butyl | 48.7 | 82–84 | +29.4 | 51.6 | 70–72 | +37.4 |
| 428 | α | " | n-Octyl | 41.3 | 71–73 | +42.6 | 48.4 | 60–62 | +43.7 |
| 429 | α | " | Isobutyl | 38.6 | 74–76 | +40.7 | 43.7 | 60–62 | +46.3 |
| 430 | α | " | 2-Propenyl | 34.5 | 73–75 | +37.3 | 41.8 | 59–61 | +42.4 |
| 431 | α | " | 2-Methyl-2-propenyl | 41.2 | 82–84 | +39.8 | 48.3 | 68–70 | +46.7 |
| 432 | α | " | 3-Butenyl | 38.7 | 79–81 | +35.6 | 51.6 | 64–66 | +43.5 |
| 433 | α | " | 3-Methoxy-n-propyl | 31.7 | 75–77 | +33.5 | 48.6 | 61–63 | +40.7 |
| 434 | α | " | 1-Methyl-2-methoxyethyl | 41.5 | 72–74 | +32.9 | 47.4 | 59–61 | +40.3 |
| 435 | α | " | Cyclohexylmethyl | 40.8 | 73–75 | +37.2 | 48.3 | 60–63 | +43.6 |
| 436 | α | " | p-Methoxybenzyl | 38.7 | 86–88 | +39.7 | 42.5 | 75–77 | +46.4 |
| 437 | α | " | Furfuryl | 37.6 | 55–57 | +30.8 | 39.4 | 42–44 | +38.6 |
| 438 | α | " | n-Butyl | 29.2 | 58–60 | +41.3 | 34.8 | Caramel like | +48.0 |
| 439 | α | " | n-Octyl | 37.2 | 64–66 | +43.5 | 45.4 | 53–55 | +47.6 |
| 440 | α | " | Isopropyl | 42.8 | Caramel like | +35.2 | 43.8 | Caramel like | +42.9 |
| 441 | α | " | Isobutyl | 37.4 | Caramel like | +41.8 | 42.6 | Caramel like | +49.3 |
| 442 | α | " | Cyclohexyl | 41.6 | 58–60 | +45.2 | 47.8 | 46–48 | +53.7 |
| 443 | α | " | Cyclohexylmethyl | 38.9 | 55–57 | +46.6 | 43.6 | 43–45 | +53.1 |
| 444 | α | Isopropyl | 2-Methyl-2-propenyl | 43.8 | 58–60 | +42.4 | 48.2 | Caramel like | +48.6 |
| 445 | α | " | 2-Methoxy-n-propyl | 33.6 | Caramel like | +42.8 | 34.2 | Caramel like | +49.5 |
| 446 | α | " | n-Butyl | 47.5 | 60–62 | +42.4 | 37.4 | Caramel like | +49.2 |
| 447 | α | Isopentyl | Isobutyl | 48.4 | 73–75 | +40.5 | 53.3 | 60–62 | +45.4 |
| 448 | α | " | 2-Ethoxy-n-propyl | 50.4 | 70–72 | +35.4 | 38.7 | 56–58 | +42.7 |
| 449 | α | " | p-Methoxybenzyl | 48.6 | 78–80 | +48.3 | 47.6 | 66–68 | +42.6 |
| 450 | α | " | Tetrahydrofurfuryl | 47.5 | 77–79 | +42.5 | 48.7 | 55–57 | +46.3 |
| 451 | α | 2-Ethylhexyl | p-Methoxybenzyl | 43.8 | 90–92 | +53.4 | 52.5 | 72–74 | +62.5 |
| 452 | α | " | Tetrahydrofurfuryl | 40.6 | 80–82 | +40.4 | 51.7 | 58–60 | +50.4 |
| 453 | α | n-Hexyl | Methyl | | | | 78.4 | 55–57 | +44.6 |

TABLE VII-continued

| Example No. | Starting Material Isomeric form | R₁ | R₂ | Urea Compound Yield % | MP °C. | $[\alpha]_D^{20}$ degree | Nitroso Compound Yield % | MP °C. | $[\alpha]_D^{20}$ degree |
|---|---|---|---|---|---|---|---|---|---|
| 454 | α | " | n-Butyl | | | | 73.4 | 66-68 | +43.7 |
| 455 | α | " | Isopropyl | 45.3 | 75-77 | +32.4 | 43.7 | 56-58 | +39.4 |
| 456 | α | " | Isobutyl | 46.7 | 74-76 | +36.2 | 48.4 | 60-62 | +43.6 |
| 457 | α | " | sec-Butyl | 48.3 | 72-74 | +34.3 | 49.6 | 57-59 | +41.5 |
| 458 | α | " | 2-Methyl-2-propenyl | 44.5 | 71-74 | +33.6 | 48.3 | 68-70 | +40.3 |
| 459 | α | " | 2-Butenyl | 41.2 | 78-81 | +34.3 | 28.4 | 64-67 | +41.6 |
| 460 | α | " | 1-Methyl-2-methoxyethyl | 38.6 | 74-76 | +30.5 | 39.2 | 60-62 | +38.4 |
| 461 | α | " | Cyclohexylmethyl | 33.7 | 72-74 | +35.7 | 41.8 | 61-63 | +45.0 |
| 462 | α | n-Octyl | n-Butyl | 43.6 | 77-79 | +34.6 | 36.4 | 63-65 | +42.6 |
| 463 | α | " | Isobutyl | 51.2 | 71-73 | +36.8 | 58.4 | 58-60 | +43.3 |
| 464 | α | " | Cyclopropylmethyl | 36.9 | 64-66 | +34.2 | 41.2 | 47-49 | +41.0 |
| 465 | α | " | p-Methylbenzyl | 35.8 | 87-89 | +40.3 | 40.7 | 77-79 | +47.2 |
| 466 | α | " | p-Methoxybenzyl | 31.7 | 85-87 | +35.4 | 41.7 | 73-75 | +43.8 |
| 467 | α | n-Decyl | α-Methylbenzyl | 32.4 | 110-112 | +31.7 | 36.6 | 100-102 | +39.2 |
| 468 | α | " | Tetrahydrofurfuryl | 28.9 | 75-77 | +26.4 | 21.4 | 62-65 | +32.7 |
| 469 | α | 2-Methyl-2-propenyl | n-Butyl | 36.8 | 87-89 | +37.3 | 38.8 | 73-75 | +43.6 |
| 470 | α | 2-Methyl-2-propenyl | Isobutyl | 34.5 | 79-81 | +35.8 | 38.9 | 65-67 | +42.6 |
| 471 | α | 2-Butenyl | " | 31.3 | 77-79 | +36.5 | 30.6 | 63-65 | +44.7 |
| 472 | α | 3-Butenyl | Cyclohexyl | 28.8 | 70-72 | +37.2 | 35.4 | 58-60 | +44.0 |
| 473 | α | " | 3-Methoxy-n-propyl | 36.4 | 84-86 | +34.6 | 38.6 | 70-73 | +41.2 |
| 474 | α | 3-Methoxy-n-propyl | n-Butyl | 41.6 | 81-83 | +34.8 | 48.8 | 68-71 | +42.7 |
| 475 | α | 3-Methoxy-n-propyl | Isobutyl | 43.7 | 75-77 | +36.4 | 51.7 | 61-63 | +43.4 |
| 476 | α | 3-Methoxy-n-propyl | sec-Butyl | 36.6 | 70-72 | +36.2 | 49.4 | 56-58 | +43.9 |
| 477 | α | 3-Methoxy-n-propyl | Cyclohexylmethyl | 31.4 | 66-68 | +39.6 | 37.6 | 53-55 | +46.4 |
| 478 | α | 3-Methoxy-n-propyl | Tetrahydrofurfuryl | 30.7 | 62-64 | +34.6 | 38.3 | 50-52 | +41.5 |
| 479 | α | 3-Ethoxy-n-propyl | n-Butyl | 29.6 | 74-76 | +38.5 | 36.5 | 60-62 | +43.6 |
| 480 | α | 3-Ethoxy-n-propyl | Cyclohexyl | 28.3 | 68-70 | +36.3 | 35.3 | 55-57 | +44.3 |
| 481 | α | 3-Ethoxy-n-propyl | Isobutyl | 36.4 | 69-71 | +35.4 | 41.3 | 56-58 | +42.0 |
| 482 | α | 3-Ethoxy-n-propyl | sec-Butyl | 33.5 | 63-65 | +34.5 | 40.6 | 49-51 | +41.4 |
| 483 | α | 1-Methyl-2-methoxyethyl | n-Butyl | 32.3 | 81-83 | +36.2 | 41.3 | 67-69 | +43.7 |
| 484 | α | 1-Methyl-2-methoxyethyl | Isobutyl | 31.4 | 76-78 | +37.4 | 38.7 | 61-63 | +44.1 |
| 485 | α | 1-Methyl-2-methoxyethyl | sec-Butyl | 35.8 | 69-71 | +34.2 | 41.3 | 55-57 | +43.6 |
| 486 | α | 1-Methyl-2-methoxyethyl | Cyclopropylmethyl | 31.7 | 55-57 | +33.8 | 40.4 | Caramel like | +41.7 |
| 487 | α | 1-Methyl-2-methoxyethyl | 2-Methoxyethyl | 29.4 | 68-70 | +30.2 | 38.7 | 54-56 | +37.4 |
| 488 | α | Cyclohexylmethyl | Methyl | 32.7 | 71-73 | +36.0 | 36.8 | 52-54 | +43.2 |
| 489 | β | Cyclohexylmethyl | " | 36.6 | 119-121 | -25.3 | 37.7 | 105-107 | -16.8 |
| 490 | α | Cyclohexyl | n-Propyl | 37.9 | 63-65 | +39.6 | 35.6 | 47-49 | +46.4 |
| 491 | α | Cyclohexyl | n-Butyl | 41.5 | 78-80 | +42.6 | 38.7 | 63-65 | +50.3 |
| 492 | β | " | " | 40.6 | 98-100 | -24.4 | 33.8 | 84-86 | -17.2 |
| 493 | α | 2-Cyclopentylethyl | n-Hexyl | 32.8 | 67-69 | +43.8 | 39.4 | 50-52 | +50.7 |
| 494 | β | 2-Cyclopentylethyl | " | 35.7 | 107-109 | -23.4 | 41.3 | 94-96 | -16.6 |
| 495 | α | Cyclohexyl | Isopropyl | 30.6 | 69-71 | +40.8 | 39.6 | 53-55 | +46.7 |
| 496 | α | " | Isobutyl | 36.7 | 72-74 | +43.6 | 42.4 | 58-60 | +50.8 |
| 497 | β | " | " | 39.4 | 93-95 | -24.2 | 43.6 | 78-80 | -16.4 |
| 498 | α | " | sec-Butyl | 41.6 | 67-69 | +42.5 | 51.3 | 53-54 | +49.3 |
| 499 | β | " | " | 42.8 | 87-89 | -24.3 | 50.8 | 73-75 | -16.3 |
| 500 | α | " | 2-Propenyl | 34.6 | 69-71 | +40.4 | 40.4 | 53-55 | +46.5 |
| 501 | α | " | 2-Methyl-2-propenyl | 31.4 | 78-80 | +40.6 | 38.7 | 64-66 | +47.7 |
| 502 | α | " | 2-Butenyl | 28.8 | 75-77 | +40.3 | 31.5 | 60-62 | +47.1 |
| 503 | α | " | 2-Methoxyethyl | 40.3 | 56-58 | +36.4 | 44.8 | 40-42 | +44.6 |
| 504 | α | " | 3-Methoxy-n-propyl | 30.7 | 73-75 | +40.6 | 38.6 | 59-61 | +47.2 |
| 505 | α | " | 2-Ethoxyethyl | 28.7 | 61-63 | +41.8 | 32.7 | 46-48 | +48.4 |
| 506 | α | " | 3-Ethoxy-n-propyl | 30.5 | 63-65 | +42.2 | 38.4 | 51-53 | +49.0 |
| 507 | α | " | 2-Methoxy-n-propyl | 25.7 | 55-57 | +37.5 | 31.4 | 40-42 | +45.2 |
| 508 | α | " | Cyclopropylmethyl | 31.4 | 59-61 | +41.8 | 38.7 | 45-48 | +48.6 |
| 509 | α | " | Cyclohexylmethyl | 28.6 | 69-71 | +41.3 | 39.3 | 57-59 | +48.2 |

TABLE VII-continued

| Example No. | Starting Material | | | Urea Compound | | | Nitroso Compound | | |
|---|---|---|---|---|---|---|---|---|---|
| | Isomeric form | $R_1$ | $R_2$ | Yield % | MP °C. | $[\alpha]_D^{20}$ degree | Yield % | MP °C. | $[\alpha]_D^{20}$ degree |
| 510 | α | " | 2-Cyclopentylethyl | 30.4 | 65–67 | +40.7 | 40.6 | 53–55 | +49.4 |
| 511 | α | " | Cyclohexyl | 28.7 | 72–74 | +42.6 | 36.4 | 60–62 | +50.6 |
| 512 | α | " | Benzyl | 32.4 | 70–72 | +40.3 | 36.5 | 59–61 | +47.8 |
| 513 | α | " | p-Chlorobenzyl | 24.2 | 80–82 | +39.7 | 41.9 | 70–73 | +46.5 |
| 514 | α | " | p-Methylbenzyl | 29.4 | 83–85 | +38.6 | 38.6 | 72–74 | +45.7 |
| 515 | α | " | 2,3-Dimethoxybenzyl | 28.4 | 69–71 | +41.4 | 36.4 | 58–61 | +48.2 |
| 516 | α | " | 3,4,5-Trimethoxybenzyl | 33.6 | 89–91 | +36.8 | 37.2 | 80–82 | +45.6 |
| 517 | α | " | Phenethyl | 30.3 | 71–73 | +37.2 | 36.4 | 61–63 | +44.3 |
| 518 | α | " | Tetrahydrofurfuryl | 38.2 | 69–71 | +35.8 | 39.6 | 57–59 | +43.6 |
| 519 | α | " | Thiophene-2-yl-methyl | 39.4 | 66–68 | +35.0 | 41.4 | 53–55 | +43.0 |
| 520 | α | " | 4-Pyridylethyl | 41.2 | 78–80 | +26.6 | 48.7 | 67–69 | +34.1 |
| 521 | α | p-Methylbenzyl | Isobutyl | | | | 67.4 | 68–70 | +37.8 |
| 522 | α | p-Methoxybenzyl | " | | | | 59.4 | 64–66 | +36.2 |
| 523 | α | 2,3-Dimethoxybenzyl | " | | | | 64.6 | 52–54 | +34.3 |
| 524 | α | 3,4,5-Trimethoxybenzyl | " | | | | 63.7 | 78–80 | +30.4 |
| 525 | α | α-Methylbenzyl | " | | | | 65.6 | 58–60 | +35.2 |

EXAMPLES 526–552

In the same manner as Example 67, various 3-$R_2$-3-($R_1$ α- or β-D-glucopyranose-4-yl)-1-(2-chloroethyl)ureas (urea compound) and 3-$R_2$-3-($R_1$ α- or β-D-glucopyranose-4-yl)-1-(2-chloroethyl)-1-nitrosourea (nitroso compound) were prepared from corresponding $R_1$ 4-($R_2$ amino)-4-deoxy α- or β-D-glucosides (starting material). Additionally, in the same manner as in Example 2, homologous nitroso compounds were prepared from corresponding starting materials. Table VIII shows the species of $R_1$ and $R_2$ and the yields, melting points, and specific rotations ($[\alpha]_D^{20}$ (C 1.0, methanol)) of the urea compounds and nitroso compounds.

TABLE VIII

| Example No. | Starting Material | | | Nitroso Compound | | |
|---|---|---|---|---|---|---|
| | Isomeric form | $R_1$ | $R_2$ | Yield % | MP °C. | $[\alpha]_D^{20}$ degree |
| 526 | α | n-Butyl | 3-Methoxy-n-propyl | 53.8 | 85–87 | +51.6 |
| 527 | α | " | 2-Methoxy-n-propyl | 48.1 | 68–70 | +52.0 |
| 528 | α | Isobutyl | n-Propyl | 61.4 | 60–62 | +58.9 |
| 529 | α | " | Isopropyl | 58.7 | 73–75 | +62.4 |
| 530 | α | " | Isopentyl | 56.4 | 77–79 | +58.6 |
| 531 | α | " | 2-Methoxyethyl | 61.4 | 59–61 | +60.4 |
| 532 | α | " | 3-Ethoxy-n-propyl | 55.6 | 68–70 | +60.8 |
| 533 | α | " | Cyclopropylmethyl | 60.7 | 58–60 | +60.4 |
| 534 | α | " | Cyclohexylmethyl | 51.6 | 73–75 | +61.2 |
| 535 | α | sec-Butyl | 2-Methyl-2-propenyl | 48.5 | 75–77 | +62.4 |
| 536 | α | " | 1-Methyl-2-methoxyethyl | 52.8 | 67–69 | +58.6 |
| 537 | α | Cyclohexyl | n-Propyl | 58.4 | 56–58 | +63.7 |
| 538 | α | " | n-Butyl | 56.7 | 71–73 | +68.8 |
| 539 | α | " | Isopropyl | 49.6 | 64–66 | +63.5 |
| 540 | α | " | Isobutyl | 53.8 | 65–67 | +65.3 |
| 541 | α | " | sec-Butyl | 52.7 | 60–62 | +61.7 |
| 542 | α | " | 2-Methyl-2-propenyl | 46.3 | 71–73 | +63.4 |
| 543 | α | " | 3-Methoxy-n-propyl | 53.2 | 66–68 | +62.5 |
| 544 | α | " | 2-Methoxy-n-propyl | 53.7 | 58–60 | +61.5 |
| 545 | α | " | Cyclohexylmethyl | 58.3 | 64–66 | +62.8 |
| 546 | α | " | 2-Cyclopentylethyl | 61.4 | 58–60 | +62.8 |
| 547 | α | " | Cyclohexyl | 57.5 | 67–69 | +64.7 |
| 548 | α | " | p-Methylbenzyl | 51.2 | 78–80 | +58.8 |
| 549 | α | " | p-Methoxybenzyl | 49.7 | 74–76 | +60.4 |
| 550 | α | " | 3,4,5-Trimethoxybenzyl | 53.4 | 86–88 | +60.8 |
| 551 | α | p-Methoxybenzyl | Isobutyl | 51.7 | 75–77 | +53.6 |
| 552 | α | α-Methylbenzyl | " | 55.6 | 64–66 | +50.2 |

EXAMPLES 553–617

In the same manner as Example 67, various 3-$R_2$-3-($R_1$ α- or β-D-galactopyranose-6-yl)-1-(2-chloroethyl)urea (urea compound) and 3-$R_2$-3-($R_1$ α- or β-D-galactopyranose-6-yl)-1-(2-chloroethyl)-1-nitrosoureas (nitroso compound) were prepared from corresponding $R_1$ 6-($R_2$ amino)-6-deoxy-α- or β-D-galactopyranosides (starting material). Additionally, in the same manner as Example 2, homologous nitroso compounds were prepared from corresponding starting materials. Table IX shows the species of $R_1$ and $R_2$ and the yields, melting points, and specific rotations ($[\alpha]_D^{20}$ (C 1.0, methanol)) of the urea compounds and nitroso compounds.

TABLE IX

| | Starting Material | | | Urea Compound | | | Nitroso Compound | | |
|---|---|---|---|---|---|---|---|---|---|
| Example No. | Isomeric form | $R_1$ | $R_2$ | Yield % | MP °C. | $[\alpha]_D^{20}$ degree | Yield % | MP °C. | $[\alpha]_D^{20}$ degree |
| 553 | α | n-Butyl | Methyl | 56.2 | 103–105 | +11.8 | 61.4 | 82–84 | +18.6 |
| 554 | α | " | n-Propyl | 51.4 | 91–93 | +10.7 | 62.3 | 73–75 | +17.5 |
| 555 | α | " | n-Butyl | 48.9 | 108–110 | +10.1 | 57.6 | 91–93 | +16.2 |
| 556 | α | " | n-Hexyl | 54.2 | 99–101 | +8.9 | 56.7 | 84–86 | +15.3 |
| 557 | α | " | n-Heptyl | 55.7 | 94–96 | +7.6 | 57.8 | 80–82 | +14.1 |
| 558 | α | " | Isopropyl | 51.4 | 98–100 | +12.8 | 56.9 | 80–82 | +19.3 |
| 559 | α | " | Isobutyl | 47.6 | 97–99 | +10.4 | 43.5 | 82–84 | +17.8 |
| 560 | α | " | sec-Butyl | 43.7 | 94–96 | +10.2 | 48.6 | 76–78 | +17.7 |
| 561 | α | " | Isoamyl | 48.4 | 90–92 | +8.3 | 60.7 | 74–76 | +15.8 |
| 562 | α | " | 2-Propenyl | 32.6 | 99–102 | +10.2 | 48.4 | 81–83 | +17.8 |
| 563 | α | " | 2-Methyl-2-propenyl | 31.7 | 107–109 | +9.3 | 47.7 | 90–92 | +16.7 |
| 564 | α | " | Cyclopropylmethyl | 42.6 | 88–90 | +10.6 | 46.6 | 71–73 | +17.2 |
| 565 | α | " | Cyclohexyl | 43.6 | 99–101 | +9.8 | 47.2 | 84–86 | +16.7 |
| 566 | α | " | Cyclohexylmethyl | 43.8 | 95–97 | +8.9 | 48.4 | 81–83 | +15.8 |
| 567 | α | " | Benzyl | 51.4 | 97–99 | +8.3 | 52.3 | 83–84 | +14.2 |
| 568 | α | " | p-Methylbenzyl | 52.6 | 109–111 | +6.8 | 48.6 | 96–98 | +12.8 |
| 569 | α | " | 2,3-Dimethoxybenzyl | 51.8 | 91–93 | +6.1 | 58.6 | 81–83 | +10.2 |
| 570 | α | " | 3-Methoxy-n-propyl | 50.6 | 101–103 | +9.8 | 64.2 | 85–88 | +14.6 |
| 571 | α | " | 1-Methyl-2-methoxyethyl | 54.7 | 90–92 | +9.2 | 61.4 | 75–77 | +14.8 |
| 572 | α | " | 2,2-Diethyoxyethyl | 53.6 | 76–78 | +8.4 | 60.7 | 63–65 | +13.0 |
| 573 | α | " | Tetrahydrofurfuryl | 60.4 | 98–100 | +9.2 | 67.4 | 83–85 | +14.8 |
| 574 | α | " | Furfuryl | 50.3 | 83–85 | +7.5 | 62.4 | 68–70 | +10.3 |
| 575 | α | Isobutyl | Ethyl | 48.4 | 83–85 | +13.8 | 57.6 | 64–66 | +20.4 |
| 576 | α | " | n-Butyl | 49.7 | 100–102 | +11.6 | 56.8 | 83–85 | +18.5 |
| 577 | β | " | " | 50.6 | — | — | 47.2 | 98–100 | −4.8 |
| 578 | α | " | n-Pentyl | 48.6 | 86–88 | +10.6 | 58.6 | 70–72 | +17.4 |
| 579 | α | " | n-Hexyl | 34.7 | 91–93 | +9.2 | 59.4 | 76–78 | +16.8 |
| 580 | α | " | Isobutyl | 47.5 | 94–96 | +11.6 | 46.4 | 77–79 | +18.4 |
| 581 | β | " | " | 45.2 | — | — | 40.5 | 89–91 | −5.2 |
| 582 | α | " | sec-Butyl | 46.3 | 90–92 | +10.2 | 43.2 | 73–75 | +18.6 |
| 583 | α | " | Isoamyl | 51.7 | 92–94 | +9.5 | 45.7 | 76–78 | +16.9 |
| 584 | α | " | 2-Butenyl | 50.6 | 94–96 | +11.6 | 57.3 | 77–79 | +18.4 |
| 585 | α | " | 2-Ethoxyethyl | 51.8 | 78–80 | +9.7 | 58.9 | 62–64 | +16.3 |
| 586 | α | " | 1-Methyl-2-Methoxyethyl | 54.4 | 91–93 | +8.9 | 56.3 | 74–76 | +15.9 |
| 587 | α | " | Cyclohexylmethyl | 56.7 | 90–92 | +10.4 | 61.2 | 76–78 | +17.2 |
| 588 | α | " | Cyclohexyl | 56.3 | 94–96 | +10.4 | 58.6 | 79–81 | +17.8 |
| 589 | α | " | p-Methylbenzyl | 46.4 | 101–103 | +7.5 | 56.6 | 88–91 | +14.2 |
| 590 | α | " | p-Methoxybenzyl | 50.6 | 99–101 | +6.8 | 51.8 | 85–87 | +12.3 |
| 591 | α | " | Tetrahydrofurfuryl | 41.4 | 87–89 | +8.3 | 48.6 | 73–75 | +15.9 |
| 592 | α | " | Furfuryl | 38.7 | 74–76 | +6.8 | 43.7 | 59–61 | +11.7 |
| 593 | α | " | Thiophene-2-yl-methyl | 36.9 | 82–84 | +6.4 | 50.4 | 67–69 | +11.0 |
| 594 | α | Cyclopropylmethyl | n-Butyl | 45.1 | 69–71 | +12.7 | 62.4 | 56–58 | +19.5 |
| 595 | α | Cyclopentylethyl | " | 47.2 | 72–74 | +9.4 | 57.7 | 62–64 | +14.2 |
| 596 | α | Cyclohexylmethyl | " | 56.4 | 85–87 | +8.4 | 51.3 | 65–67 | +15.4 |
| 597 | α | Cyclohexyl | n-Propyl | 51.4 | 77–79 | +12.3 | 58.5 | 59–61 | +19.2 |
| 598 | α | " | n-Butyl | 56.6 | 98–91 | +10.8 | 47.3 | 67–69 | +17.2 |
| 599 | α | " | n-Hexyl | 41.3 | 74–76 | +6.3 | 49.6 | 59–61 | +12.8 |
| 600 | α | " | Isopropyl | 55.6 | 81–83 | +14.3 | 53.5 | 63–65 | +21.5 |
| 601 | α | " | Isobutyl | 49.7 | 83–85 | +12.5 | 54.6 | 66–68 | +19.8 |
| 602 | α | " | sec-Butyl | 53.6 | 78–80 | +12.8 | 51.7 | 61–63 | +19.5 |
| 603 | α | " | Isopentyl | 48.9 | 76–78 | +10.8 | 61.3 | 60–62 | +15.2 |
| 604 | α | " | Isobutenyl | 43.4 | 89–91 | +11.5 | 58.6 | 72–74 | +16.5 |
| 605 | α | " | 2-Butenyl | 38.6 | 85–87 | +11.2 | 48.7 | 67–69 | +16.8 |
| 606 | α | " | 2-Methoxyethyl | 32.7 | 67–69 | +9.4 | 55.7 | 50–52 | +16.4 |
| 607 | α | " | 2-Methoxy-n-propyl | 44.6 | 64–66 | +9.7 | 48.6 | 48–50 | +15.3 |
| 608 | α | " | 1-Hydroxy-n-propyl | 41.2 | 62–64 | +9.8 | 48.7 | 44–47 | +16.4 |
| 609 | α | " | Cyclopropylmethyl | 51.8 | 71–73 | +10.4 | 61.9 | 54–56 | +16.8 |
| 610 | α | " | Cyclohexyl | 43.3 | 82–84 | +9.7 | 64.6 | 66–68 | +14.2 |
| 611 | α | " | Cyclohexylmethyl | 51.2 | 78–80 | +7.4 | 58.3 | 64–66 | +12.8 |
| 612 | α | " | Benzyl | 54.6 | 80–82 | +6.8 | 48.6 | 65–67 | +11.5 |
| 613 | α | " | p-Methylbenzyl | 50.7 | 90–92 | +5.8 | 46.4 | 77–79 | +10.7 |
| 614 | α | " | p-Methoxybenzyl | 43.6 | 88–90 | +5.7 | 38.9 | 76–78 | +9.7 |
| 615 | α | " | Furfuryl | 51.4 | 66–68 | +6.2 | 43.6 | 51–53 | +10.4 |
| 616 | α | " | Tetrahydrofurfuryl | 50.8 | 74–76 | +8.2 | 39.3 | 58–60 | +10.1 |
| 617 | α | " | Thiophene-2-yl-methyl | 46.8 | 76–78 | +5.2 | 36.7 | 61–63 | +9.4 |

EXAMPLES 618–695

In the same manner as Example 67, various 3-$R_2$-3-($R_1$ α-D-galactopyranose-2-yl)-1-(2-chloroethyl)ureas (urea compound) and 3-$R_2$-3-($R_1$α-D-galactopyranose-2-yl)-1-(2-chloroethyl)-1-nitrosourea (nitroso compound) were prepared from corresponding $R_1$ 2-($R_2$ amino)-6-deoxy-α-D-galactopyranosides (starting material). Additionally, in the same manner as Example 2, homologous nitroso compounds were prepared from corresponding starting materials. Table X shows the species of $R_1$ and $R_2$ and the yields, melting points, and specific rotations ($[\alpha]_D^{20}$ (1.0, methanol)) of the urea compounds and nitroso compounds.

TABLE X

| | Starting Material | | | Urea Compound | | | Nitroso Compound | | |
|---|---|---|---|---|---|---|---|---|---|
| Example No. | Isomeric form | $R_1$ | $R_2$ | Yield % | MP °C. | $[\alpha]_D^{20}$ degree | Yield % | MP °C. | $[\alpha]_D^{20}$ degree |
| 618 | α | n-Butyl | Methyl | 48.1 | 111–113 | +15.6 | 53.5 | 93–95 | +20.3 |
| 619 | α | " | n-Propyl | 49.1 | 98–100 | +14.6 | 50.4 | 82–84 | +19.4 |
| 620 | α | " | n-Butyl | 41.6 | 119–121 | +13.7 | 43.8 | 103–105 | +18.5 |
| 621 | α | " | n-Hexyl | 38.4 | 108–110 | +11.8 | 52.6 | 96–98 | +17.4 |
| 622 | α | " | n-Heptyl | 46.7 | 103–105 | +11.2 | 58.1 | 91–93 | +16.5 |
| 623 | α | " | Isopropyl | 39.8 | 102–104 | +16.4 | 50.7 | 86–88 | +21.6 |
| 624 | α | " | Isobutyl | 48.4 | 106–108 | +12.6 | 55.6 | 92–94 | +19.2 |
| 625 | α | " | sec-Butyl | 49.1 | 102–104 | +16.0 | 54.2 | 87–89 | +19.5 |
| 626 | α | " | Isoamyl | 50.3 | 97–99 | +11.7 | 56.4 | 83–85 | +17.2 |
| 627 | α | " | 2-Propenyl | 41.7 | 103–105 | +14.4 | 48.3 | 88–90 | +18.9 |
| 628 | α | " | 2-Methyl-2-propenyl | 51.0 | 116–118 | +14.0 | 51.6 | 101–103 | +18.6 |
| 629 | α | " | Cyclopropylmethyl | 38.2 | 98–100 | +14.8 | 49.3 | 83–85 | +19.6 |
| 630 | α | " | Cyclohexyl | 46.7 | 105–107 | +12.6 | 51.3 | 93–95 | +17.6 |
| 631 | α | " | Cyclohexyl | | | | 67.8 | 91–93 | +17.1 |
| 632 | α | " | Benzyl | | | | 64.3 | 89–91 | +16.7 |
| 633 | α | " | p-Methylbenzyl | | | | 58.6 | 104–106 | +14.6 |
| 634 | α | " | 2,3-Dimethylbenzyl | 41.5 | 98–100 | +8.6 | 50.7 | 90–92 | +12.4 |
| 635 | α | " | 3-Methoxy-n-propyl | 48.4 | 110–112 | +11.7 | 53.6 | 96–98 | +16.4 |
| 636 | α | " | 1-Methyl-2-methoxy-ethyl | 41.6 | 98–100 | +12.4 | 45.7 | 86–89 | +17.2 |
| 637 | α | " | 2,2-Diethoxyethyl | 43.7 | 78–80 | +9.8 | 43.6 | 68–70 | +14.7 |
| 638 | α | " | Tetrahydrofurfuryl | 38.9 | 106–108 | +11.4 | 37.1 | 94–96 | +16.4 |
| 639 | α | " | Furfuryl | 35.6 | 92–94 | +9.2 | 45.6 | 80–82 | +11.2 |
| 640 | α | Isobutyl | Ethyl | 41.7 | 86–88 | +18.6 | 52.6 | 70–72 | +23.6 |
| 641 | α | " | n-Butyl | 52.3 | 109–111 | +15.9 | 49.7 | 94–96 | +20.7 |
| 642 | α | " | n-Hexyl | 47.3 | 100–102 | +11.4 | 55.4 | 88–90 | +18.6 |
| 643 | α | " | Isobutyl | 55.6 | 105–107 | +16.4 | 54.2 | 89–91 | +20.2 |
| 644 | α | " | sec-Butyl | 43.8 | 96–98 | +16.6 | 53.6 | 81–83 | +21.4 |
| 645 | α | " | Isoamyl | 39.7 | 101–103 | +13.7 | 47.3 | 87–89 | +18.5 |
| 646 | α | " | 2-Butenyl | — | — | — | 70.4 | 86–88 | +20.6 |
| 647 | α | " | 2-Ethoxyethyl | — | — | — | 68.4 | 70–72 | +18.6 |
| 648 | α | " | 1-Methyl-2-methoxy-ethyl | — | — | — | 61.2 | 83–85 | +17.2 |
| 649 | α | " | Cyclohexylmethyl | — | — | — | 59.8 | 83–86 | +19.8 |
| 650 | α | " | Cyclohexyl | — | — | — | 61.6 | 87–89 | +20.2 |
| 651 | α | " | p-Methylbenzyl | — | — | — | 59.3 | 95–97 | +14.4 |
| 652 | α | " | p-Methoxybenzyl | — | — | — | 62.4 | 93–95 | +14.1 |
| 653 | α | " | Tetrahydrofurfuryl | — | — | — | 63.6 | 83–85 | +17.2 |
| 654 | α | " | Furfuryl | — | — | — | 62.7 | 70–72 | +18.9 |
| 655 | α | Cyclopropyl-methyl | n-Butyl | 38.9 | 77–79 | +17.6 | 42.6 | 67–70 | +22.8 |
| 656 | α | Cyclopentyl-methyl | " | 41.4 | 92–94 | +13.8 | 52.8 | 88–90 | +18.9 |
| 657 | α | Cyclohexyl-methyl | " | 40.8 | 108–110 | +14.6 | 51.4 | 90–92 | +19.5 |
| 658 | α | Cyclohexyl | n-Propyl | 47.5 | 86–88 | +17.8 | 56.4 | 72–74 | +22.9 |
| 659 | α | " | n-Butyl | 39.8 | 108–110 | +16.2 | 49.8 | 93–95 | +21.7 |
| 660 | α | " | n-Hexyl | 43.8 | 82–84 | +11.4 | 56.7 | 70–72 | +16.2 |
| 661 | α | " | Isopropyl | 37.9 | 91–93 | +19.6 | 48.6 | 75–78 | +24.2 |
| 662 | α | " | Isobutyl | 42.7 | 94–96 | +17.8 | 52.6 | 79–81 | +22.4 |
| 663 | α | " | sec-Butyl | 37.2 | 88–91 | +16.7 | 47.3 | 73–75 | +21.6 |
| 664 | α | " | Isopentyl | — | — | — | 58.4 | 70–72 | +17.4 |
| 665 | α | " | Isobutenyl | — | — | — | 61.4 | 84–86 | +18.6 |
| 666 | α | " | 2-Butenyl | — | — | — | 55.8 | 80–82 | +19.2 |
| 667 | α | " | 2-Methoxyethyl | — | — | — | 56.3 | 65–67 | +18.6 |
| 668 | α | " | 2-Methoxy-n-propyl | — | — | — | 57.7 | 59–61 | +17.2 |
| 669 | α | " | Cyclopropylmethyl | — | — | — | 59.4 | 66–68 | +18.3 |
| 670 | α | " | Cyclohexyl | 43.5 | 89–92 | +11.3 | 55.6 | 77–79 | +16.4 |
| 671 | α | " | Cyclohexylmethyl | 38.9 | 85–87 | +9.6 | 48.4 | 73–75 | +14.3 |

TABLE X-continued

| Example No. | Starting Material Isomeric form | R₁ | R₂ | Urea Compound Yield % | MP °C. | $[\alpha]_D^{20}$ degree | Nitroso Compound Yield % | MP °C. | $[\alpha]_D^{20}$ degree |
|---|---|---|---|---|---|---|---|---|---|
| 672 | α | " | Benzyl | 32.7 | 86–88 | +8.2 | 47.2 | 75–77 | +13.4 |
| 673 | α | " | p-Methylbenzyl | 28.9 | 96–98 | +7.5 | 38.7 | 86–88 | +12.5 |
| 674 | α | " | p-Methoxybenzyl | 37.4 | 95–97 | +7.8 | 45.8 | 84–86 | +11.3 |
| 675 | α | " | Furfuryl | 40.4 | 78–80 | +8.6 | 56.8 | 66–68 | +12.4 |
| 676 | α | 2-Ethoxyethyl | Isopropyl | 38.6 | 84–86 | +14.6 | 51.4 | 68–70 | +19.6 |
| 677 | α | 2-Ethoxyethyl | n-Butyl | 41.5 | 99–101 | +10.7 | 48.9 | 84–86 | +17.5 |
| 678 | α | 2-Ethoxyethyl | Isobutyl | 44.6 | 93–95 | +11.3 | 54.6 | 78–80 | +17.6 |
| 679 | α | 2-(methoxymethoxy)ethyl | sec-Butyl | 41.0 | 88–90 | +11.5 | 54.3 | 73–76 | +17.4 |
| 680 | α | 2-(methoxymethoxy)ethyl | Cyclohexyl | 37.6 | 79–81 | +9.9 | 46.4 | 67–69 | +16.7 |
| 681 | α | 2-Methoxy-n-propyl | Cyclopropylmethyl | 29.4 | 74–76 | +11.8 | 39.7 | 59–61 | +18.5 |
| 682 | α | 2,3-Dimethoxy-n-propyl | Tetrahydrofurfuryl | 33.8 | 82–84 | +6.3 | 46.8 | 70–72 | +11.7 |
| 683 | α | 2,3-Dimethoxy-n-propyl | 2-Methoxyethyl | 42.9 | 75–77 | +7.2 | 47.7 | 58–60 | +11.9 |
| 684 | α | 2,3-Dimethoxy-n-propyl | 3-Methoxy-n-propyl | 37.6 | 91–93 | +6.8 | 48.2 | 77–79 | +10.4 |
| 685 | α | 2,3-Dimethoxy-n-propyl | 2-Methyl-2-propenyl | — | — | — | 49.4 | 90–92 | +18.4 |
| 686 | α | Tetrahydrofurfuryl | n-Butyl | 45.7 | 101–103 | +14.4 | 38.4 | 86–88 | +19.3 |
| 689 | α | Tetrahydrofurfuryl | Isobutyl | 52.7 | 95–97 | +16.8 | 58.7 | 80–82 | +21.5 |
| 690 | α | Tetrahydrofurfuryl | sec-Butyl | 43.7 | 91–93 | +16.5 | 55.6 | 76–78 | +21.4 |
| 691 | α | Tetrahydrofurfuryl | tert-Butyl | 25.2 | 75–77 | +18.3 | 29.2 | 59–61 | +23.6 |
| 692 | α | Tetrahydrofurfuryl | Cyclohexyl | 39.8 | 83–85 | +14.5 | 46.3 | 71–73 | +19.3 |
| 693 | α | Tetrahydrofurfuryl | Cyclopropylmethyl | 41.8 | 77–79 | +17.8 | 49.7 | 62–64 | +22.3 |
| 694 | α | Tetrahydrofurfuryl | 1-Methyl-2-methoxyethyl | 39.7 | 87–89 | +15.4 | 47.3 | 73–75 | +20.7 |
| 695 | α | Tetrahydrofurfuryl | 3-Methoxy-n-propyl | 43.8 | 94–96 | +11.9 | 51.6 | 79–81 | +16.8 |

EXAMPLES 696–714

In the same manner as Example 2, various 3-R₂-3-(R₁ α-D-galactopyranose-3-yl)-1-(2-chloroethyl)-1-nitrosoureas (nitroso compound) were prepared from R₁ 3-(R₂amino)-3-deoxy-α-D-galactopyranosides (starting material). Table XI shows the species of R₁ and R₂ and the yields, melting points, and specific rotations ($[\alpha]_D^{20}$ (C 1.0, methanol)) of the nitroso compounds.

TABLE XI

| Example No. | Starting Material Isomeric form | R₁ | R₂ | Nitroso Compound Yield % | MP °C. | $[\alpha]_D^{20}$ Degree |
|---|---|---|---|---|---|---|
| 696 | α | n-Butyl | n-Propyl | 49.2 | 69–71 | +12.6 |
| 697 | α | " | n-Butyl | 58.4 | 85–87 | +11.8 |
| 698 | α | " | Isopropyl | 55.6 | 74–76 | +14.2 |
| 699 | α | " | Isobutyl | 61.7 | 76–78 | +13.8 |
| 700 | α | " | sec-Butyl | 68.1 | 72–74 | +14.6 |
| 701 | α | " | 2-Methyl-2-propenyl | 62.6 | 84–86 | +12.4 |
| 702 | α | " | 1-Methyl-2-methoxyethyl | 57.2 | 71–73 | +10.2 |
| 703 | α | " | Tetrahydrofurfuryl | 56.7 | 78–80 | +10.3 |
| 704 | α | Isobutyl | n-Butyl | 46.8 | 79–81 | +15.2 |
| 705 | α | " | Isobutyl | 54.3 | 72–74 | +12.4 |
| 706 | α | " | Isoamyl | 49.3 | 71–73 | +11.6 |
| 707 | α | " | 2-Butenyl | 50.4 | 73–75 | +13.6 |
| 708 | α | " | 1-Methyl-2-methoxyethyl | 43.7 | 69–71 | +10.4 |
| 709 | α | Cyclopentylethyl | n-Butyl | 49.7 | 59–61 | +12.1 |
| 710 | α | Cyclohexyl | " | 53.5 | 64–66 | +14.4 |
| 711 | α | " | Isobutyl | 41.6 | 63–65 | +15.6 |

TABLE XI-continued

| Example No. | Starting Material | | | Nitroso Compound | | |
|---|---|---|---|---|---|---|
| | Isomeric form | $R_1$ | $R_2$ | Yield % | MP °C. | $[\alpha]_D^{20}$ Degree |
| 712 | α | " | sec-Butyl | 48.4 | 58–60 | +16.4 |
| 713 | α | 2-Ethoxyethyl | Isobutyl | 56.7 | 63–65 | +10.4 |
| 714 | α | 2,3-Dimethoxy-n-propyl | 2-Methyl-2-propenyl | 49.2 | 73–75 | +10.1 |

EXAMPLES 715–743

In the same manner as Example 2, various 3-$R_2$-3-($R_1$ α-D-galactopyranose-4-yl)-1-(2-chloroethyl)-1-nitrosoureas (nitroso compound) were prepared from $R_1$ 4-($R_2$ amino)-4-deoxy-α-D-galactopyranosides (starting material). Table XII shows the species of $R_1$ and $R_2$ and the yields, melting points, and specific rotations ($[\alpha]_D^{20}$ (1.0, methanol)) of the nitroso compounds.

EXAMPLES 744–749

In the same manner as Example 2, various 3-$R_2$($R_1$-α-L-galactopyranose-6-yl)-1-(2-chloroethyl)-1-nitrosoureas (nitroso compound) were prepared from $R_1$ 6-($R_2$ amino)-6-deoxy-α-L-galactopyranosides (starting material). Table XIII shows the species of $R_1$ and $R_2$ and the yields, melting points, and specific rotation ($[\alpha]_D^{20}$ (1.0, methanol)) of the nitroso compounds.

TABLE XII

| Example No. | Starting Material | | | Nitroso Compound | | |
|---|---|---|---|---|---|---|
| | Isomeric form | $R_1$ | $R_2$ | Yield % | MP °C. | $[\alpha]_D^{20}$ degree |
| 715 | α | n-Butyl | n-Propyl | 57.5 | 76–78 | +13.8 |
| 716 | α | " | n-Butyl | 64.8 | 94–96 | +13.3 |
| 717 | α | " | Isopropyl | 62.7 | 84–86 | +16.6 |
| 718 | α | " | Isobutyl | 66.5 | 86–88 | +15.4 |
| 719 | α | " | sec-Butyl | 57.4 | 79–81 | +16.2 |
| 720 | α | " | 1-Methyl-2-methoxyethyl | 53.8 | 78–80 | +10.3 |
| 721 | α | " | Tetrahydrofurfuryl | 45.3 | 86–88 | +12.3 |
| 722 | α | Isobutyl | n-Butyl | 51.7 | 87–89 | +16.8 |
| 723 | α | " | Isobutyl | 52.6 | 80–82 | +16.4 |
| 724 | α | " | Isoamyl | 54.1 | 80–82 | +15.0 |
| 725 | α | " | 2-Butenyl | 41.2 | 79–81 | +16.4 |
| 726 | α | Isobutyl | 1-Methyl-2-methoxyethyl | 38.2 | 76–78 | +13.6 |
| 727 | α | " | Cyclohexyl | 44.6 | 82–84 | +16.4 |
| 728 | α | " | p-Methoxybenzyl | 32.7 | 89–91 | +11.7 |
| 729 | α | n-Butyl | n-Propyl | 48.4 | 76–78 | +13.8 |
| 730 | α | " | n-Butyl | 55.6 | 94–96 | +13.6 |
| 731 | α | " | Isopropyl | 51.4 | 84–86 | +16.4 |
| 732 | α | " | Isobutyl | 53.6 | 86–88 | +15.6 |
| 733 | α | " | sec-Butyl | 61.4 | 79–81 | +16.2 |
| 734 | α | " | 1-Methyl-2-methoxyethyl | 66.8 | 78–80 | +13.1 |
| 735 | α | " | Tetrahydrofurfuryl | 43.6 | 86–88 | +12.4 |
| 736 | α | Cyclohexylmethyl | n-Butyl | 42.8 | 78–80 | +16.3 |
| 737 | α | Cyclopentylethyl | " | 51.7 | 83–85 | +13.7 |
| 738 | α | Cyclohexyl | Isobutyl | 48.3 | 70–72 | +18.4 |
| 739 | α | " | sec-Butyl | 55.6 | 65–67 | +17.6 |
| 740 | α | Cyclohexyl | 3-Ethoxy-n-propyl | 54.2 | 64–66 | +13.8 |
| 741 | α | " | Cyclohexyl | 41.2 | 68–70 | +13.2 |
| 742 | α | " | Cyclohexylmethyl | 46.6 | 67–69 | +11.8 |
| 743 | α | " | p-Methoxybenzyl | 43.7 | 78–80 | +9.2 |

TABLE XIII

| Example No. | Starting Material | | | Nitroso Compound | | |
|---|---|---|---|---|---|---|
| | Isomeric form | $R_1$ | $R_2$ | Yield % | MP °C. | $[\alpha]_D^{20}$ degree |
| 744 | α | Isobutyl | n-Propyl | 55.8 | 62–64 | −36.4 |
| 745 | α | n-Butyl | Isobutyl | 58.7 | 80–82 | −35.7 |
| 746 | α | Cyclopropylmethyl | n-Butyl | 64.2 | 58–60 | −33.5 |
| 747 | α | Cyclohexylmethyl | " | 63.7 | 65–67 | −28.4 |
| 748 | α | 2-Methoxy-n-propyl | Isobutyl | 57.9 | 64–66 | −30.6 |
| 749 | α | Tetrahydrofurfuryl | Cyclohexyl | 65.4 | 62–64 | −28.2 |

EXAMPLES 750-752

In the same manner as Example 2, 3-$R_2$-3-($R_1$ α-L-galactopyranose-2-yl)-1-(2-chloroethyl)-1-nitrosoureas (nitroso compound) were prepared from $R_1$ 2-($R_2$ amino)-2-deoxy-α-L-galactopyranosides (starting material). Table XIV shows the species of $R_1$ and $R_2$ and the yields, melting points, and specific rotations ([α]$_D^{20}$ (1.0, methanol)) of the nitroso compounds.

TABLE XIV

| Example No. | Starting Material Isomeric form | $R_1$ | $R_2$ | Nitroso Compound Yield % | MP °C. | [α]$_D^{20}$ degree |
|---|---|---|---|---|---|---|
| 750 | α | Isobutyl | Isobutyl | 51.8 | 85–87 | −38.8 |
| 751 | α | " | n-Propyl | 49.7 | 68–70 | −40.6 |
| 752 | α | " | 2-Methoxy-n-propyl | 58.3 | 75–77 | −36.3 |

EXAMPLES 753-763

In the same manner as Example 67, various 3-$R_2$-3-($R_1$ α-D-mannopyranose-6-yl)-1-(2-chloroethyl)ureas (urea compound) and 3-$R_2$-3-($R_1$ α-D-mannopyranose-6-yl)-1-(2-chloroethyl)-1-nitrosoureas (nitroso compound) were prepared from $R_1$ 6-($R_2$ amino)-6-deoxy-α-D-mannopyranosides (starting material). Table XV shows the species of $R_1$ and $R_2$ and the yields, melting points, and specific rotations ([α]$_D^{20}$ (1.0, methanol)) of the urea form and nitroso form products.

TABLE XV

| Example No. | Starting Material Isomeric form | $R_1$ | $R_2$ | Urea Compound Yield % | MP °C. | [α]$_D^{20}$ degree | Nitroso Compound Yield % | MP °C. | [α]$_D^{20}$ degree |
|---|---|---|---|---|---|---|---|---|---|
| 753 | α | Benzyl | n-Butyl | 47.3 | 80–82 | +13.4 | 52.8 | 60–62 | +17.8 |
| 754 | α | " | sec-Butyl | 41.5 | 70–72 | +16.3 | 53.6 | 50–52 | +20.7 |
| 755 | α | α-Methylbenzyl | 1-methyl-2-methoxyethyl | 45.7 | 76–78 | +11.3 | 55.2 | 54–56 | +15.2 |
| 756 | α | " | Cyclohexylmethyl | 29.4 | 74–76 | +12.5 | 43.8 | 53–55 | +15.2 |
| 757 | α | " | Tetrahydrofurfuryl | 52.7 | 61–63 | +11.8 | 52.4 | Caramel like | +13.6 |
| 758 | α | Isobutyl | Cyclohexyl | 48.4 | 93–85 | +16.8 | 54.6 | 72–74 | +20.6 |
| 759 | α | " | 2-Methoxyethyl | 37.5 | 76–78 | +15.9 | 32.4 | 55–57 | +19.8 |
| 760 | α | " | Isobutyl | 34.6 | 93–95 | +17.6 | 42.7 | 75–77 | +21.4 |
| 761 | α | " | n-Butyl | 41.7 | 103–105 | +19.2 | 48.5 | 81–83 | +23.6 |
| 762 | α | " | Thiophene-2-yl-methyl | 40.2 | 87–89 | +14.4 | 43.7 | 66–68 | +18.2 |
| 763 | α | Tetrahydrofurfuryl | Isobutyl | 37.1 | 95–97 | +14.1 | 35.6 | 77–79 | +18.0 |

EXAMPLES 764-777

In the same manner as Example 67, various 3-$R_2$-3-($R_1$ α-D-mannopyranose-4-yl)-1-(2-chloroethyl)ureas (urea compound) and 3-$R_2$-3-($R_1$α-D-mannopyranose-4-yl)-1-(2-chloroethyl)-1-nitrosoureas (nitroso compound) were prepared from $R_1$ 4-($R_2$ amino)-4-deoxy-α-D-mannopyranosides (starting material). Table XVI shows the species of $R_1$ and $R_2$ and the yields, melting points, and specific rotations ([α]$_D^{20}$ (1.0 methanol)) of the urea compounds and nitroso compounds.

TABLE XVI

| Example No. | Starting Material Isomeric form | $R_1$ | $R_2$ | Urea Compound Yield % | MP °C. | [α]$_D^{20}$ degree | Nitroso Compound Yield % | MP °C. | [α]$_D^{20}$ degree |
|---|---|---|---|---|---|---|---|---|---|
| 764 | α | Benzyl | n-Butyl | 36.4 | 75–77 | +10.2 | 38.7 | 56–58 | +13.4 |
| 765 | α | " | Isobutyl | 41.2 | 69–71 | +12.6 | 45.6 | 50–52 | +15.8 |
| 766 | α | " | sec-Butyl | 38.5 | 64–66 | +11.5 | 41.4 | 45–47 | +15.2 |
| 767 | α | α-Methylbenzyl | 1-Methyl-2-methoxyethyl | 45.3 | 63–65 | +9.6 | 47.6 | 42–44 | +13.4 |
| 768 | α | " | Cyclohexylmethyl | 43.7 | 70–72 | +10.4 | 35.3 | 50–52 | +12.7 |
| 769 | α | " | Tetrahydrofurfuryl | 38.6 | 55–57 | +9.2 | 45.7 | Caramel like | +12.2 |
| 770 | α | Isobutyl | Cyclohexyl | 43.1 | 88–90 | +13.4 | 48.5 | 67–69 | +18.4 |
| 771 | α | " | 2-Methoxyethyl | 36.4 | 72–74 | +12.2 | 45.3 | 51–53 | +16.7 |
| 772 | α | " | Isobutyl | 45.8 | 88–90 | +13.7 | 51.3 | 71–73 | +18.9 |
| 773 | α | " | n-Butyl | 40.7 | 96–98 | +14.6 | 47.5 | 77–79 | +18.8 |
| 774 | α | " | Cyclopropylmethyl | 33.8 | 77–79 | +13.2 | 42.8 | 56–58 | +17.4 |
| 775 | α | Isobutyl | Thiophene-2-yl-methyl | 29.5 | 81–83 | +8.2 | 34.6 | 62–64 | +10.4 |
| 776 | α | Tetrahydrofurfuryl | Isobutyl | 44.8 | 90–92 | +13.7 | 47.5 | 73–75 | +16.6 |
| 777 | α | Tetrahydrofurfuryl | 2-Ethoxy-n-propyl | 41.3 | 73–75 | +12.4 | 46.7 | 58–60 | +15.2 |

EXAMPLES 778-785

In the same manner as Example 2, various 3-$R_2$-3-($R_1$ α-D-altropyranose-6-yl)-1-(2-chloroethyl)-1-nitrosoureas (nitroso compound) were prepared from $R_1$ 6-($R_2$ amino)-6-deoxy-α-D-altropyranosides (starting material). Table XVII shows the species of $R_1$ and $R_2$ and the yields, melting points, and specific rotations ([α]$_D^{20}$ (C 1.0, methanol)) of the nitroso compounds.

TABLE XVII

| Example No. | Starting Material | | | Nitroso Compound | | |
|---|---|---|---|---|---|---|
| | Isomeric form | R₁ | R₂ | Yield % | MP °C. | $[\alpha]_D^{20}$ degree |
| 778 | α | Benzyl | n-Butyl | 64.6 | 63–65 | +21.2 |
| 779 | α | " | Isobutyl | 62.4 | 56–68 | +22.9 |
| 780 | α | " | sec-Butyl | 63.3 | 51–53 | +22.5 |
| 781 | α | β-Phenylethyl | 2-Methoxyethyl | 55.7 | Caramel like | +19.6 |
| 782 | α | " | Cyclopropylmethyl | 53.6 | " | +19.9 |
| 783 | α | " | Tetrahydrofurfuryl | 43.8 | 50–52 | +17.8 |
| 784 | α | Isobutyl | Cyclohexyl | 39.2 | 79–81 | +20.9 |
| 785 | α | 1-Methyl-2-methoxyethyl | Isobutyl | 44.6 | 70–72 | +23.1 |

EXAMPLES 786–795

In the same manner as Example 2, various 3-R₂-3-(R₁ α-D-altropyranose-2-yl)-1-(2-chloroethyl)-1-nitrosoureas (nitroso compound) were prepared from R₁ 2-(R₂ amino)-2-deoxy-α-D-altropyranosides (starting material). Table XVIII shows the species of R₁ and R₂ and the yields, melting points, and specific rotations of ($[\alpha]_D^{20}$ (C 1.0, methanol)) of the nitroso compounds.

TABLE XVIII

| Example No. | Starting Material | | | Nitroso Compound | | |
|---|---|---|---|---|---|---|
| | Isomeric form | R₁ | R₂ | Yield % | MP °C. | $[\alpha]_D^{20}$ degree |
| 786 | α | Benzyl | n-Propyl | 58.9 | 66–68 | +25.7 |
| 787 | α | " | n-Butyl | 61.4 | 83–85 | +24.9 |
| 788 | α | " | Isobutyl | 60.2 | 68–70 | +25.2 |
| 789 | α | " | sec-Butyl | 57.6 | 64–66 | +24.8 |
| 790 | α | β-Phenylethyl | 1-Methyl-2-methoxyethyl | 56.8 | 69–71 | +19.9 |
| 791 | α | " | 2-Methoxyethyl | 58.4 | 55–57 | +21.3 |
| 792 | α | " | Cyclopropyl-methyl | 62.4 | 57–59 | +21.4 |
| 793 | α | " | Tetrahydro-furfuryl | 57.8 | 61–63 | +20.2 |
| 794 | α | Isobutyl | Isobutyl | 61.7 | 84–86 | +23.8 |
| 795 | α | 1-Methyl-2-methoxyethyl | " | 59.8 | 79–81 | +25.1 |

EXAMPLES 796–807

In the same manner as Example 2, various 3-R₂-3-(R₁ α-D-altropyranose-3-yl)-1-(2-chloroethyl)-1-nitrosoureas (nitroso compound) were prepared from R₁ 3-(R₂ amino)-3-deoxy-α-D-altropyranosides (starting material). Table XIX shows the R₁ and R₂ species and the yields, melting points, and specific rotations ($[\alpha]_D^{20}$ (C 1.0, methanol)) of the products.

TABLE XIX

| Example No. | Starting Material | | | Nitroso Compound | | |
|---|---|---|---|---|---|---|
| | Isomeric form | R₁ | R₂ | Yield % | MP °C. | $[\alpha]_D^{20}$ degree |
| 797 | α | Cyclohexyl | n-Propyl | 39.4 | 62–64 | +16.3 |
| 798 | α | " | n-Butyl | 48.3 | 70–72 | +15.4 |
| 799 | α | " | Isobutyl | 44.7 | 63–65 | +14.9 |
| 800 | α | " | sec-Butyl | 46.5 | 58–60 | +13.2 |
| 801 | α | α-Methyl-benzyl | 1-Methyl-2-methoxyethyl | 38.4 | 63–65 | +11.8 |
| 802 | α | α-Methyl-benzyl | 2-Methoxyethyl | 32.7 | Caramel like | +10.9 |
| 803 | α | α-Methyl-benzyl | Cyclopropyl-methyl | 43.9 | 52–54 | +9.8 |
| 804 | α | α-Methyl-benzyl | Tetrahydro-furfuryl | 34.5 | 60–62 | +17.8 |
| 805 | α | Isobutyl | Cyclohexyl | 43.2 | 76–78 | +12.4 |
| 806 | α | " | Isobutyl | 40.7 | 72–74 | +11.7 |
| 807 | α | 1-Methyl-2-methoxy-ethyl | Isobutyl | 37.6 | 66–68 | +10.6 |

EXAMPLES 808–813

In the same manner as Example 2, various 3-R₂-3-(R₁ α-D-talopyranose-6-yl)-1-(2-chloroethyl)-1-nitrosoureas (nitroso compound) were prepared from R₁ 6-(R₂ amino)-6-deoxy-α-D-talopyranosides (starting material). Table XX shows the R₁ and R₂ species and

TABLE XX

| Example No. | Starting Material Isomeric form | R₁ | R₂ | Nitroso Compound Yield % | MP °C. | $[\alpha]_D^{20}$ degree |
|---|---|---|---|---|---|---|
| 808 | α | Cyclohexyl | n-Propyl | 52.4 | 60–62 | +18.4 |
| 809 | α | " | sec-Butyl | 51.8 | 56–58 | +16.8 |
| 810 | α | " | 1-Methyl-2-methoxyethyl | 48.7 | 60–62 | +15.4 |
| 811 | α | Isobutyl | n-Butyl | 46.8 | 76–78 | +20.2 |
| 812 | α | " | 3-Methoxy-n-propyl | 48.2 | 61–63 | +18.3 |
| 813 | α | 1-Methyl-2-methoxyethyl | Isobutyl | 34.6 | 63–65 | +17.2 |

EXAMPLES 814–818

In the same manner as Examples 67, various 3-R₂-3-(R₁ α-D-xylopyranose-3-yl)-1-(2-chloroethyl)ureas (urea compound) and 3-R₂-3-(R₁ α-D-xylopyranose-3-yl)-1-(2-chloroethyl)-1-nitrosoureas (nitroso compound) were prepared from R₁ 3-(R₂ amino)-3-deoxy-α-D-xylopyranosides (starting material). Table XXI shows the R₁ and R₂ species and the yields, melting points, and specific rotations ($[\alpha]_D^{20}$ (1.0, methanol)) of the products.

TABLE XXI

| Example No. | Starting Material Isomeric form | R₁ | R₂ | Urea Compound Yield % | MP °C. | $[\alpha]_D^{20}$ degree | Nitroso Compound Yield % | MP °C. | $[\alpha]_D^{20}$ degree |
|---|---|---|---|---|---|---|---|---|---|
| 814 | α | Cyclohexyl | n-Propyl | 41.5 | 68–70 | +9.5 | 48.9 | 52–54 | +16.7 |
| 815 | α | " | n-Butyl | 48.3 | 80–82 | +8.7 | 55.4 | 66–68 | +15.2 |
| 816 | α | " | Isobutyl | 45.7 | 76–78 | +9.8 | 51.3 | 62–64 | +16.4 |
| 817 | α | " | sec-Butyl | 38.3 | 73–75 | +8.2 | 44.6 | 57–59 | +15.8 |
| 818 | α | " | 2-Ethoxyethyl | 36.9 | 66–68 | +6.8 | 47.5 | 51–53 | +13.4 |

EXAMPLES 819–822

In the same manner as Example 2, different 3-R₂-3-(R₁ α-D-xylopyranose-4-yl)-1-(2-chloroethyl)-1-nitrosoureas (nitroso compound) were prepared from R₁ 4-(R₂ amino)-4-deoxy-α-D-xylopyranosides (starting material). Table XXII shows the R₁ and R₂ species and the yield, melting points, and specific rotations ($[\alpha]_D^{20}$ (C 1.0, methanol)) of the products.

TABLE XXII

| Example No. | Starting Material Isomeric form | R₁ | R₂ | Nitroso Compound Yield % | MP °C. | $[\alpha]_D^{20}$ degree |
|---|---|---|---|---|---|---|
| 819 | α | Cyclohexyl | n-Propyl | 58.7 | 60–62 | +15.4 |
| 820 | α | " | Isopropyl | 61.4 | 56–58 | +14.4 |
| 821 | α | " | n-Butyl | 60.7 | 73–75 | +13.1 |
| 822 | α | " | sec-Butyl | 56.9 | 65–67 | +14.2 |

EXAMPLES 823–827

In the same manner as Example 2, different 3-R₂-3-(R₁ α-L-arabinopyranose-4-yl)-1-(2-chloroethyl)-1-nitrosoureas (nitroso compound) were prepared from R₁ 4-(R₂ amino)-4-deoxy)-α-L-arabinopyranosides (starting material). Table XXIII shows the R₁ and R₂ species and the yields, melting points, and specific rotations ($[\alpha]_D^{20}$ (C 1.0, methanol)) of the products.

TABLE XXIII

| Example No. | Starting Material Isomeric form | R₁ | R₂ | Nitroso Compound Yield % | MP °C. | $[\alpha]_D^{20}$ degree |
|---|---|---|---|---|---|---|
| 823 | α | Isobutyl | Cyclohexyl | 71–73 | | +62.8 |
| 824 | α | Isobutyl | Cyclopropyl-methyl | 57–59 | | +64.2 |
| 825 | α | Isobutyl | 3-Methoxy-n-propyl | 64–66 | | +58.4 |
| 826 | α | Isobutyl | Isobutyl | 69–71 | | +60.6 |
| 827 | α | Isobutyl | n-Butyl | 77–79 | | +65.2 |

EXAMPLES 828–846

In the same manner as Example 67, various 3-R₂-3-(R₁ α-L-arabinopyranose-2-yl)-1-(2-chloroethyl)ureas (urea compound) and 3-R₂-3-(R₁ α-L-arabinopyranose-2-yl)-1-(2-chloroethyl)-1-nitrosoureas (nitroso compound) were prepared from R₁ 2-(R₂ -amino)-2-deoxy-α-L-arabinopyranosides (starting material). Table XXIV shows the R₁ and R₂ species and the yields, melting points, and specific rotations ($[\alpha]_D^{20}$ (C 1.0, methanol)) of the products.

TABLE XXIV

| Example No. | Starting Material Isomeric form | R₁ | R₂ | Urea Compound Yield % | MP °C. | $[\alpha]_D^{20}$ degree | Nitroso Compound Yield % | MP °C. | $[\alpha]_D^{20}$ degree |
|---|---|---|---|---|---|---|---|---|---|
| 828 | α | Cyclohexyl | n-Propyl | 43.7 | 82–84 | +74.6 | 35.6 | 66–68 | +83.4 |
| 829 | α | " | Isobutyl | 47.5 | 89–91 | +73.4 | 44.8 | 73–75 | +82.9 |
| 830 | α | " | Benzyl | 45.8 | 57–59 | +65.2 | 54.6 | 69–71 | +75.8 |
| 831 | α | " | p-Methoxybenzyl | 43.7 | 69–71 | +65.0 | 52.8 | 80–82 | +74.1 |
| 832 | α | " | 2-Methoxyethyl | 39.6 | 75–77 | +74.4 | 47.5 | 59–61 | +82.9 |
| 833 | α | " | 3-Methoxy-n-propyl | 40.3 | 89–91 | +71.6 | 49.8 | 74–76 | +81.8 |
| 834 | α | " | Tetrahydrofurfuryl | 41.8 | 86–88 | +63.8 | 39.2 | 72–74 | +74.0 |
| 835 | α | Isobutyl | Isobutyl | 39.4 | 101–103 | +71.6 | 52.8 | 86–88 | +81.4 |

TABLE XXIV-continued

| Example No. | Starting Material Isomeric form | $R_1$ | $R_2$ | Urea Compound Yield % | MP °C. | $[\alpha]_D^{20}$ degree | Nitroso Compound Yield % | MP °C. | $[\alpha]_D^{20}$ degree |
|---|---|---|---|---|---|---|---|---|---|
| 386 | α | " | sec-Butyl | 44.6 | 97–99 | +68.2 | 67.4 | 83–85 | +78.0 |
| 837 | α | sec-Butyl | Isobutyl | 51.3 | 91–93 | +69.8 | 58.7 | 77–79 | +79.4 |
| 838 | α | " | sec-Butyl | 48.2 | 85–87 | +68.5 | 51.4 | 70–72 | +78.3 |
| 839 | α | " | n-Butyl | 52.4 | 99–101 | +72.2 | 57.6 | 84–86 | +82.4 |
| 840 | α | Isobutyl | 3-Ethoxy-n-propyl | 43.6 | 81–83 | +68.8 | 49.5 | 69–71 | +77.8 |
| 841 | α | " | 3-Methoxy-n-propyl | 41.7 | 87–89 | +69.7 | 54.3 | 77–79 | +76.7 |
| 842 | α | " | 2-Ethoxyethyl | 38.3 | 91–93 | +70.4 | 42.6 | 65–67 | +79.7 |
| 843 | α | " | 2-Methoxy-n-propyl | 39.8 | 86–88 | +70.1 | 47.5 | 60–62 | +76.8 |
| 844 | α | " | Cyclopropylmethyl | 40.6 | 76–78 | +72.3 | 52.8 | 61–63 | +80.4 |
| 845 | α | " | Cyclohexyl | 43.4 | 87–89 | +73.3 | 61.4 | 75–77 | +79.5 |
| 846 | α | " | Tetrahydrofurfuryl | 37.8 | 77–79 | +67.6 | 64.3 | 65–67 | +76.2 |

EXAMPLES 847–848

In the same manner as Example 2, 3-$R_2$-3-($R_1$ α-D-arabinopyranose-2-yl)-1-(2-chloroethyl)-1-nitrosoureas (nitroso compound) were prepared from $R_1$ 2-($R_2$ amino)-2-deoxy-α-D-arabinopyranosides (starting material). Table XXV shows the $R_1$ and $R_2$ species and the yields, melting points, and specific rotations ($[\alpha]_D^{20}$ (C 1.0, methanol)) of the products.

TABLE XXV

| Example No. | Starting Material Isomeric form | $R_1$ | $R_2$ | Nitroso Compound Yield % | MP °C. | $[\alpha]_D^{20}$ degree |
|---|---|---|---|---|---|---|
| 847 | α | Isobutyl | Isobutyl | 50.4 | 89–91 | −42.3 |
| 848 | α | Cyclohexyl | Isobutyl | 48.6 | 74–76 | −39.2 |

EXAMPLES 849–850

In the same manner as Example 2, 3-$R_2$-3-($R_1$ α-D-arabinopyranose-4-yl)-1-(2-chloroethyl)-1-nitrosoureas (nitroso compound) were prepared from $R_1$ 4-($R_2$ amino)-4-deoxy-α-D-arabinopyranosides (starting material). Table XXVI shows the $R_1$ and $R_2$ species and the yields, melting points, and specific rotations ($[\alpha]_D^{20}$ (C 1.0, methanol)) of the products.

TABLE XXVI

| Example No. | Starting Material Isomeric form | $R_1$ | $R_2$ | Nitroso Compound Yield % | MP °C. | $[\alpha]_D^{20}$ degree |
|---|---|---|---|---|---|---|
| 849 | α | Isobutyl | Isobutyl | 57.6 | 82–84 | −30.2 |
| 850 | α | Cyclohexyl | 3-Methoxy-n-propyl | 51.4 | 70–72 | −26.8 |

EXAMPLES 851–859

In the same manner as Example 67, 3-$R_2$-3-($R_1$ β-D-ribofuranose-5-yl)-1-(2-chloroethyl)ureas (urea compound) and 3-$R_2$-3-($R_1$ β-D-ribofuranose-5-yl)-1-(2-chloroethyl)-1-nitrosoureas (nitroso compound) were prepared from $R_1$ 5-($R_2$ amino)-5-deoxy-β-D-ribofuranosides (starting material). Additionally, in the same manner as Example 2, homologous nitroso compounds were prepared from corresponding starting materials. Table XXVII shows the $R_1$ and $R_2$ species and the yields, melting points, and specific rotations ($[\alpha]_D^{20}$ (C 1.0, methanol)) of the products.

TABLE XXVII

| Example No. | Starting Material Isomeric form | $R_1$ | $R_2$ | Urea Compound Yield % | MP °C. | $[\alpha]_D^{20}$ degree | Nitroso Compound Yield % | MP °C. | $[\alpha]_D^{20}$ degree |
|---|---|---|---|---|---|---|---|---|---|
| 851 | α | 2-Methoxyethyl | Isobutyl | 62.5 | Sirupy | −10.4 | 63.8 | Sirupy | −14.8 |
| 852 | α | Isobutyl | 2-Methoxyethyl | 63.8 | " | −9.2 | 64.4 | " | −14.1 |
| 853 | α | 3-Methoxy-n-propyl | 3-Methoxy-n-propyl | 58.7 | " | −9.5 | 61.2 | " | −15.4 |
| 854 | α | 3-Methoxy-n-propyl | 2-Isobutenyl | 59.4 | " | −10.2 | 60.7 | " | −13.6 |
| 855 | α | Cyclohexyl | sec-Butyl | 60.5 | " | −7.8 | 59.8 | " | −10.7 |
| 856 | α | " | Cyclopentylethyl | 59.6 | " | −8.2 | 57.3 | " | −11.4 |
| 857 | α | Tetrahydrofurfuryl | Isobutyl | 57.7 | " | −7.4 | 56.4 | " | −9.7 |
| 858 | α | Tetrahydrofurfuryl | 2-Butenyl | 60.4 | " | −6.4 | 57.9 | " | −8.8 |
| 859 | α | Tetrahydrofurfuryl | n-Propyl | 58.3 | " | −10.8 | 61.5 | " | −13.2 |

EXAMPLES 860–863

In the same manner as Example 2, 3-$R_2$-3-($R_1$ β-D-arabinofuranose-2, 3, or 5-yl)-1-(2-chloroethyl)-1-nitrosoureas (nitroso compound) were prepared from corresponding starting materials $R_1$ 2-, 3-, or 5-($R_2$ amino)-2, 3, or 5-deoxy-β-D-arabinofuranosides. Table XXVIII shows the starting material and product names and the yields, melting points, and specific rotations ($[\alpha]_D^{20}$ (C 1.0, methanol)) of the products.

TABLE XXVIII

| Example No. | Starting Material | Nitroso Compound | Nitroso Compound Yield % | MP °C. | $[\alpha]_D^{20}$ degree |
|---|---|---|---|---|---|
| 860 | Cyclohexyl-2-isobutyl-amino-2-deoxy-β-D-arabinofuranoside | 3-Isobutyl-3-(cyclohexyl β-D-arabinofuranose-2-yl)-1-(2-chloroethyl)-1-nitrosourea | 54.5 | 83–85 | −40.2 |
| 861 | Cyclohexyl-3-isobutyl-amino-2-deoxy-β-D-arabinofuranoside | 3-Isobutyl-3-(cyclo-hexyl β-D-arabinofuranose-3-yl)-1-(2-chloroethyl)-1-nitrosourea | 51.7 | 71–73 | −24.5 |
| 862 | Isobutyl 5-isobutyl-amino-5-deoxy-β-D-arabinofuranoside | 3-Isobutyl-3-(isobutyl β-D-arabinofuranose-5-yl)-1-(2-chloroethyl)-1-nitrosourea | 48.6 | 86–88 | −38.4 |
| 863 | Isobutyl 3-isobutyl-amino-3-deoxy-β-D-arabinofuranoside | 3-Isobutyl-3-(isobutyl β-D-arabinofuranose-3-yl)-1-(2-chloroethyl)-1-nitrosourea | 49.4 | 81–83 | −26.2 |

EXAMPLES 864–869

In the same manner as Example 2, 3-R$_2$-3-(R$_1$ α-D-xylofuranose-2, 3, or 5-yl)-1-(2-chloroethyl)-1-nitrosoureas (nitroso compound) were prepared from R$_1$ 2-, 3-, or 5-(R$_2$ amino)-2, 3, or 5-deoxy-α-D-xylofuranoside (starting material). Table XXIX shows the starting material and product names and the yields, melting points, and specific rotations ([$\alpha$]$_D^{20}$ (C 1.0, methanol)) of the products.

TABLE XXIX

| Example No. | Starting Material | Nitroso Compound | Nitroso Compound Yield % | MP °C. | $[\alpha]_D^{20}$ degree |
|---|---|---|---|---|---|
| 864 | Cyclohexyl 5-isobutyl-amino-5-deoxy-α-D-xylofuranoside | 3-Isobutyl-3-(cyclo-hexyl α-D-xylofuranose-5-yl)-1-(2-chloro-ethyl)-1-nitrosourea | 61.4 | 62–64 | +16.8 |
| 865 | Cyclohexyl 3-isobutyl-amino-3-deoxy-α-D-xylofuranoside | 3-Isobutyl-3-(cyclo-hexyl α-D-xylo-furanose-3-yl)-1-(2-chloroethyl)-1-nitrosourea | 57.8 | 58–60 | +14.2 |
| 866 | Cyclohexyl 5-sec-butyl-amino-5-deoxy-α-D-xylofuranoside | 3-sec-Butyl-3-(cyclo-hexyl α-D-xylo-furanose-5-yl)-1-(2-chloroethyl)-1-nitroso-urea | 59.3 | 56–58 | +16.2 |
| 867 | Cyclohexyl 2-sec-butyl-amino-2-deoxy-α-D-xylofuranoside | 3-sec-Butyl-3-(cyclo-hexyl α-D-xylo-furanose-2-yl)-1-(2-chloroethyl)-1-nitrosourea | 60.6 | 65–67 | +23.4 |
| 868 | Isobutyl 2-(3-methoxy-n-propylamino)-2-deoxy-α-D-xylofuranoside | 3-(3-Methoxy-n-propyl)-3-(isobutyl α-D-xylo-furanose-2-yl)-1-(2-chloroethyl)-1-nitroso-urea | 56.8 | 74–76 | +18.8 |
| 869 | Cyclohexyl 3-sec-butyl-amino-3-deoxy-α-D-xylo-furanoside | 3-sec-Butyl-3-(cyclo-hexyl α-D-xylofuranose-3-yl)-1-(2-chloroethyl)-1-nitrosourea | 63.4 | 52–54 | +13.9 |

EXAMPLE 870

In the same manner as Example 2,3-sec-butyl-3-(cyclohexyl α-L-lyxofuranose-5-yl)-1-(2-chloroethyl)-1-nitrosourea was prepared from the starting material cyclohexyl 5-sec-butylamino-5-deoxy-α-L-lyxofuranoside; yield 55.7%, m.p. 78°–80° C., [$\alpha$]$_D^{20}$ −18.4° (C 1.0, methanol).

Elementary analysis, for C$_{18}$H$_{32}$N$_3$O$_6$Cl (mol. wt. 421.92): Calcd. (%): C 51.24, H 7.64, N 9.96, Cl 8.41; Found (%): C 51.32, H 7.58, N 9.93, Cl 8.46.

EXAMPLES 871–885

In the same manner as Example 67, 3-R$_2$-3-(R$_1$ α- or β-D-glucopyranose-6,2, or 3-yl)-1-(2-chloroethyl)urea (urea compound) and 3-R$_2$-3-(R$_1$ α- or β-D-glucopyranose-6,2, or 3-yl)-1-(2-chloroethyl)-1-nitrosourea (nitroso compound) were prepared from starting materials R$_1$ 6-, 2-, or 3-(R$_2$ amino)-6, 2, or 3-deoxy-α or β-glucopyranosides. Tables XXX and XXXI show the names, yiels, melting points, and specific rotations ([$\alpha$]$_D^{20}$ (C 1.0, methanol)) of the products.

TABLE XXX

| Example No. | Urea Compound | Yield % | MP °C. | $[\alpha]_D^{20}$ degree |
|---|---|---|---|---|
| 871 | 3-(2-Ethoxyethyl)-3-(cyclopentyl α-D-glucopyranose-6-yl)-1-(2-chloroethyl)urea | 60.8 | 67–69 | +60.3 |
| 872 | 3-(2-Ethoxyethyl)-3-(cyclopentyl β-D-glucopyranose-6-yl)-1-(2-chloroethyl)urea | 63.9 | 84–86 | −22.4 |
| 873 | 3-(1-Methyl-2-methoxyethyl)-3-(cyclopentyl α-D-glucopyranose-6-yl)-1-(2-chloroethyl)urea | 59.4 | 79–82 | +58.2 |
| 874 | 3-(1-Methyl-2-methoxyethyl)-3-(cyclopentyl β-D-glucopyranose-6-yl)-1-(2-chloroethyl)urea | 62.7 | 97–99 | −20.6 |
| 875 | 3-(3-Methoxy-n-propyl)-3-(cyclopentyl α-D-glucopyranose-2-yl)-1-(2-chloroethyl)urea | 64.5 | 84–86 | +69.3 |
| 876 | 3-Isobutyl-3-(cyclopentyl α-D-glucopyranose-6-yl)-1-(2-chloroethyl)urea | 57.5 | 78–80 | +58.6 |
| 877 | 3-Cyclohexyl-3-(tert-butyl α-D-glucopyranose-6-yl)-1-(2-chloroethyl)urea | 34.2 | 77–79 | +56.3 |
| 878 | 3-Cyclopropyl-3-(2-methoxyethyl α-D-glucopyranose-6-yl)-1-(2-chloroethyl)urea | 48.6 | 65–67 | +58.4 |
| 879 | 3-Cyclohexyl-3-(2-methoxyethyl α-D-glucopyranose-6-yl)-1-(2-chloroethyl)urea | 54.6 | 78–80 | +53.7 |
| 880 | 3-Cyclohexyl-3-(2-ethoxyethyl β-D-glucopyranose-6-yl)-1-(2-chloroethyl)urea | 52.4 | 91–93 | −18.4 |
| 881 | 3-Cyclopentyl-3-(3-methoxy-n-propyl α-D-glucopyranose-6-yl)-1-(2-chloroethyl)urea | 54.7 | 68–70 | +54.6 |
| 882 | 3-Cyclohexyl-3-(3-methoxy-n-propyl α-D-glucopyranose-6-yl)-1-(2-chloroethyl)urea | 56.3 | 76–78 | +52.8 |
| 883 | 3-Cyclohexyl-3-(3-methoxy-n-propyl β-D-glucopyranose-6-yl)-1-(2-chloroethyl)urea | 61.5 | 91–93 | −20.6 |
| 884 | 3-Tetrahydrofurfuryl-3-(cyclopentyl α-D-glucopyranose-6-yl)-1-(2-chloroethyl)urea | 55.7 | 76–79 | +48.4 |
| 885 | 3-Tetrahydrofurfuryl-3-(cyclopropyl α-D-glucopyranose-6-yl)-1-(2-chloroethyl)urea | 57.4 | 73–75 | +52.6 |

TABLE XXXI

| Example No. | Nitroso Compound | Yield % | MP °C. | $[\alpha]_D^{20}$ degree |
|---|---|---|---|---|
| 871 | 3-(2-Ethoxyethyl)-3-(cyclopentyl α-D-glucopyranose-6-yl)-1-(2-chloroethyl)-1-nitrosourea | 48.6 | 47–49 | +75.4 |
| 872 | 3-(2-Ethoxyethyl)-3-(cyclopentyl β-D-glucopyranose-6-yl)-1-(2-chloroethyl)-1-nitrosourea | 53.5 | 70–72 | −14.5 |
| 873 | 3-(1-Methyl-2-methoxyethyl)-3-(cyclopentyl α-D-glucopyranose-6-yl)-1-(2-chloroethyl)-1-nitrosourea | 46.7 | 57–59 | +73.4 |
| 874 | 3-(1-Methyl-2-methoxyethyl)-3-(cyclopentyl β-D-glucopyranose-6-yl)-1-(2-chloroethyl)-1-nitrosourea | 54.8 | 82–84 | −13.6 |
| 875 | 3-(3-Methoxy-n-propyl)-3-(cyclopentyl α-D-glucopyranose-2-yl)-1-(2-chloroethyl)-1-nitrosourea | 48.3 | 72–74 | +80.5 |
| 876 | 3-Isobutyl-3-(cyclohexyl α-D-glucopyranose-6-yl)-1-(2-chloroethyl)-1-nitrosourea | 46.7 | 62–64 | +46.3 |
| 877 | 3-Cyclohexyl-3-(tert-butyl α-D-glucopyranose-6-yl)-1-(2-chloroethyl)-1-nitrosourea | 28.2 | 55–58 | +72.3 |
| 878 | 3-Cyclopentyl-3-(2-methoxyethyl α-D-glucopyranose-6-yl)-1-(2-chloroethyl)-1-nitrosourea | 49.6 | 50–52 | +71.6 |
| 879 | 3-Cyclohexyl-3-(2-methoxyethyl α-D-glucopyranose-6-yl)-1-(2-chloroethyl)-1-nitrosourea | 59.2 | 56–58 | +69.5 |
| 880 | 3-Cyclohexyl-3-(2-ethoxyethyl β-D-glucopyranose-6-yl)-1-(2-chloroethyl)-1-nitrosourea | 50.6 | 76–78 | −13.2 |
| 881 | 3-Cyclopentyl-3-(3-methoxy-n-propyl α-D-glucopyranose-6-yl)-1-(2-chloroethyl)-1-nitrosourea | 42.8 | 46–48 | +69.2 |
| 882 | 3-Cyclohexyl-3-(3-methoxy-n-propyl α-D-glucopyranose-6-yl)-1-(2-chloroethyl)-1-nitrosourea | 51.7 | 54–56 | +67.4 |
| 883 | 3-Cyclohexyl-3-(3-methoxy-n-propyl β-D-glucopyranose-6-yl)-1-(2-chloroethyl)-1-nitrosourea | 58.4 | 76–79 | −12.8 |
| 884 | 3-Tetrahydrofurfuryl-3-(cyclopentyl α-D-glucopyranose-6-yl)-1-(2-chloroethyl)-1-nitrosourea | 53.5 | 58–60 | +65.2 |
| 885 | 3-Tetrahydrofurfuryl-3-(cyclopropyl α-D-glucopyranose-6-yl)-1-(2-chloroethyl)-1-nitrosourea | 54.2 | 55–57 | +68.4 |

EXAMPLES 886–1031

In the same manner as Example 67, various 3-$R_2$-3-($R_1$ α- or β-D-glucopyranose-6,2,3, or 4-yl)-1-(2-chloroethyl)-urea (urea compound) and 3-$R_2$-3-($R_1$ α- or β-D-glucopyranose-6,2,3,4-yl)-1-(2-chloroethyl)-1-nitrosoureas (nitroso compound) were prepared from corresponding starting materials $R_1$ 6-, 2-, 3-, or 4-($R_2$ amino)-6,2,3, or 4-deoxy-α or β-D-glucopyranosides. Tables XXXII and XXXIII show the $R_1$ and $R_2$ species and the yields, melting points, and specific rotations ($[\alpha]_D^{20}$ (C 1.0, methanol)) of the products.

TABLE XXXII

| Example No. | Isomeric form | Position of the substituent $R_2$ amino | $R_1$ | $R_2$ | Urea Compound Yield % | MP °C. | $[\alpha]_D^{20}$ degree |
|---|---|---|---|---|---|---|---|
| 886 | β | 6 | tert-Butyl | Ethyl | 54.6 | 104–106 | −26.4 |
| 887 | α | 6 | " | n-Propyl | 56.3 | 98–100 | +62.3 |
| 888 | β | 6 | " | " | 54.5 | 118–120 | −24.5 |
| 889 | α | 6 | " | n-Butyl | 58.7 | 114–116 | +62.0 |
| 890 | β | 6 | " | " | 59.4 | 132–134 | −22.7 |
| 891 | α | 2 | " | " | 61.6 | 119–121 | +73.4 |
| 892 | α | 3 | " | " | 48.4 | 95–97 | +44.3 |
| 893 | α | 4 | " | " | 44.2 | 107–109 | +63.4 |
| 894 | α | 6 | " | Isobutyl | 60.8 | 103–105 | +62.3 |
| 895 | β | 6 | " | " | 62.4 | 119–121 | −24.7 |
| 896 | α | 2 | " | " | 57.5 | 109–111 | +72.6 |
| 897 | β | 2 | " | " | 56.1 | 139–141 | −26.8 |
| 898 | α | 3 | tert-Butyl | Isobutyl | 58.4 | 92–94 | +44.8 |
| 899 | α | 4 | " | " | 53.6 | 84–86 | +63.1 |
| 900 | α | 6 | " | sec-Butyl | 54.9 | 96–98 | +62.3 |
| 901 | β | 6 | " | " | 47.3 | 111–113 | −22.4 |
| 902 | α | 3 | " | " | 46.5 | 87–89 | +37.6 |
| 903 | α | 6 | " | 2-Methyl-2-propenyl | 43.9 | 115–117 | +58.4 |
| 904 | α | 6 | " | 3,3-Dimethyl-sec-butyl | 39.7 | 95–97 | +48.3 |
| 905 | α | 6 | " | 2-(2-Hydroxyethoxy-ethyl | 40.1 | 94–96 | +46.7 |
| 906 | α | 6 | " | 1-Methoxy-sec-butyl | 47.4 | 89–91 | +50.8 |
| 907 | β | 6 | " | " | 48.2 | 116–118 | −21.4 |
| 908 | α | 6 | " | 3-Isopropoxy-n-propyl | 47.5 | 73–75 | +39.3 |
| 909 | α | 6 | " | 2,2-Dimethyl-3-hydroxy-n-propyl | 38.4 | 75–77 | +34.5 |
| 910 | α | 6 | " | 1-Hydroxy-sec-butyl | 43.6 | 81–83 | +42.4 |
| 911 | α | 6 | " | 2-Methoxy-n-propyl | 54.2 | 108–111 | +58.9 |
| 912 | α | 6 | " | 2-Ethoxyethyl | 52.6 | 93–95 | +59.4 |
| 913 | α | 2 | " | 2-Ethoxyethyl | 47.8 | 103–105 | +71.5 |
| 914 | α | 3 | " | " | 40.2 | 84–86 | +43.1 |
| 915 | α | 6 | " | 1-Methyl-2-methoxy-ethyl | 42.6 | 98–100 | +57.6 |
| 916 | β | 6 | " | 1-Methyl-2-methoxy-ethyl | 51.4 | 111–113 | −20.8 |
| 917 | α | 6 | " | Morpholino | 46.6 | 90–92 | +52.4 |
| 918 | α | 6 | " | 2-Morpholinoethyl | 43.5 | 87–89 | +50.2 |
| 919 | α | 6 | " | 3-Morpholinopropyl | 54.3 | 82–84 | +49.3 |
| 920 | α | 6 | " | 2-Piperidinoethyl | 48.7 | 86–88 | +52.5 |
| 921 | α | 6 | " | 2-(4-Pyridyl)ethyl | 43.6 | 76–78 | +65.7 |
| 922 | α | 6 | " | Cyclopropyl | 51.1 | 73–75 | +67.8 |
| 923 | α | 6 | " | Cycloheptyl | 43.5 | 80–82 | +61.5 |
| 924 | α | 6 | " | Cyclooctyl | 52.3 | 86–88 | +59.8 |
| 925 | α | 6 | " | 2-Cyclopentylethyl | 47.5 | 93–95 | +57.2 |
| 926 | α | 6 | " | Cyclohexylmethyl | 43.2 | 98–100 | +53.8 |
| 927 | α | 6 | " | Benzyl | 54.3 | 100–102 | +50.4 |
| 928 | α | 6 | " | p-Methoxybenzyl | 41.4 | 104–106 | +48.3 |
| 929 | α | 6 | " | Tetrahydrofurfuryl | 55.7 | 106–108 | +50.8 |
| 930 | α | 6 | Neopentyl | n-Propyl | 57.8 | 103–105 | +59.5 |
| 931 | β | 6 | " | " | 59.3 | 122–124 | −22.4 |
| 932 | α | 6 | " | n-Butyl | 51.6 | 119–121 | +59.7 |
| 933 | β | 6 | " | " | 49.7 | 137–139 | −21.5 |
| 934 | α | 6 | " | Isobutyl | 42.7 | 112–114 | +58.8 |
| 935 | β | 6 | " | " | 46.9 | 125–127 | −23.2 |
| 936 | α | 2 | " | " | 49.7 | 115–117 | +68.7 |
| 937 | β | 2 | " | " | 53.4 | 145–147 | −24.5 |
| 938 | α | 3 | " | " | 45.8 | 100–102 | +42.6 |
| 939 | α | 6 | " | sec-Butyl | 51.3 | 103–105 | +59.8 |
| 940 | β | 6 | " | " | 48.6 | 118–120 | −21.6 |
| 941 | α | 3 | " | " | 43.4 | 92–94 | +36.2 |
| 942 | β | 3 | " | " | 47.6 | 115–117 | −23.1 |
| 943 | α | 6 | " | 2-Methyl-2-propenyl | 48.3 | 114–116 | +58.4 |
| 944 | α | 6 | " | 3,3-Dimethyl-sec-butyl | 42.6 | 100–102 | +46.8 |
| 945 | α | 6 | " | 2-(2-Hydroxyethoxy)-ethyl | 46.8 | 99–101 | +45.7 |
| 946 | α | 6 | " | 1-Methoxy-sec-butyl | 43.5 | 95–97 | +48.2 |
| 947 | β | 6 | " | " | 46.7 | 120–122 | −20.4 |
| 948 | α | 6 | " | 3-Isopropoxy-n-propyl | 47.4 | 81–83 | +38.1 |
| 949 | α | 6 | " | 2,2-Dimethyl-3- | 42.8 | 82–84 | +34.2 |

TABLE XXXII-continued

| Example No. | Isomeric form | Position of the substituent R₂ amino | R₁ | R₂ | Urea Compound Yield % | MP °C. | $[\alpha]_D^{20}$ degree |
|---|---|---|---|---|---|---|---|
| 950 | α | 6 | " | hydroxy-n-propyl 3-Methoxy-n-propyl | 49.6 | 114–116 | +55.8 |
| 951 | α | 6 | " | 2-Ethoxyethyl | 51.4 | 103–105 | +57.2 |
| 952 | α | 2 | " | " | 44.4 | 116–118 | +67.8 |
| 953 | α | 6 | " | 1-Methyl-2-methoxyethyl | 48.6 | 107–109 | +54.2 |
| 954 | β | 6 | " | 1-Methyl-2-methoxyethyl | 51.3 | 125–127 | −20.1 |
| 955 | α | 6 | " | 2-Cyclopentylethyl | 49.7 | 98–100 | +55.7 |
| 956 | α | 6 | " | Cyclohexylmethyl | 52.3 | 105–107 | +52.6 |
| 957 | α | 6 | " | Benzyl | 43.8 | 103–105 | +49.4 |
| 958 | α | 6 | " | p-Methoxybenzyl | 48.4 | 111–113 | +46.2 |
| 959 | α | 6 | " | Tetrahydrofurfuryl | 52.6 | 105–107 | +50.8 |
| 960 | α | 6 | 3,3-Dimethyl-n-butyl | n-Propyl | 43.7 | 95–97 | +57.9 |
| 961 | β | 6 | 3,3-Dimethyl-n-butyl | " | 48.4 | 111–113 | −20.4 |
| 962 | α | 6 | 3,3-Dimethyl-n-butyl | n-Butyl | 51.6 | 106–108 | +58.3 |
| 963 | β | 6 | 3,3-Dimethyl-n-butyl | " | 58.3 | 124–126 | −20.1 |
| 964 | α | 6 | 3,3-Dimethyl-n-butyl | Isobutyl | 46.5 | 99–101 | +56.2 |
| 965 | β | 6 | 3,3-Dimethyl-n-butyl | " | 54.4 | 112–124 | −21.8 |
| 966 | α | 2 | 3,3-Dimethyl-n-butyl | " | 52.6 | 102–104 | +66.4 |
| 967 | β | 2 | 3,3-Dimethyl-n-butyl | " | 49.2 | 131–133 | −22.3 |
| 968 | α | 3 | 3,3-Dimethyl-n-butyl | " | 46.3 | 89–91 | +41.6 |
| 969 | α | 6 | 3,3-Dimethyl-n-butyl | sec-Butyl | 48.6 | 82–84 | +57.2 |
| 970 | β | 6 | 3,3-Dimethyl-n-butyl | " | 43.5 | 103–105 | −20.8 |
| 971 | α | 3 | 3,3-Dimethyl-n-butyl | " | 51.2 | 78–80 | +34.7 |
| 972 | β | 3 | 3,3-Dimethyl-n-butyl | " | 40.8 | 99–101 | −20.4 |
| 973 | α | 6 | 3,3-Dimethyl-n-butyl | 2-Methyl-2-propenyl | 43.7 | 104–106 | +56.5 |
| 974 | α | 6 | 3,3-Dimethyl-n-butyl | 3,3-Dimethyl-sec-butyl | 46.1 | 87–89 | +44.3 |
| 975 | α | 6 | 3,3-Dimethyl-n-butyl | 2-(2-Hydroxyethoxy)-ethyl | 37.3 | 85–87 | +44.6 |
| 976 | α | 6 | 3,3-Dimethyl-n-butyl | 1-Methoxy-sec-butyl | 47.6 | 80–82 | +46.2 |
| 977 | β | 6 | 3,3-Dimethyl-n-butyl | 1-Methoxy-sec-butyl | 51.4 | 106–108 | −18.8 |
| 978 | α | 6 | 3,3-Dimethyl-n-butyl | 3-Isopropoxy-n-propyl | 38.6 | 70–72 | +36.9 |
| 979 | α | 6 | 3,3-Dimethyl-n-butyl | 3-Methoxy-n-propyl | 49.7 | 111–113 | +53.6 |
| 980 | α | 6 | 3,3-Dimethyl-n-butyl | 2-Ethoxyethyl propyl | 53.6 | 98–100 | +55.6 |
| 981 | α | 2 | 3,3-Dimethyl-n-butyl | 2-Ethoxyethyl | 51.4 | 108–110 | +66.1 |
| 982 | α | 6 | 3,3-Dimethyl-n-butyl | 1-Ethyl-2-Methoxyethyl | 48.7 | 103–105 | +50.4 |
| 983 | β | 6 | 3,3-Dimethyl-n-butyl | 1-Ethyl-2-Methoxyethyl | 50.3 | 131–133 | −19.5 |
| 984 | α | 6 | 3,3-Dimethyl-n-butyl | Cyclopentylethyl | 53.4 | 97–99 | +53.8 |
| 985 | α | 6 | 3,3-Dimethyl-n-butyl | Cyclohexylmethyl | 52.6 | 103–105 | +51.7 |
| 986 | α | 6 | 3,3-Dimethyl-n-butyl | Benzyl | 46.4 | 101–103 | +49.0 |
| 987 | α | 6 | 3,3-Dimethyl-n-butyl | p-Methoxybenzyl | 43.1 | 108–110 | +44.5 |
| 988 | α | 6 | 3,3-Dimethyl-n-butyl | Tetrahydrofurfuryl | 51.3 | 107–109 | +46.2 |
| 989 | α | 6 | Tetrahydrofurfuryl | tert-Butyl | 45.6 | 101–103 | +54.3 |
| 990 | α | 6 | Tetrahydrofurfuryl | Neopentyl | 43.7 | 106–108 | +52.4 |
| 991 | α | 6 | Tetrahydrofurfuryl | 3,3-Dimethyl-n-butyl | 40.5 | 94–96 | +51.3 |

TABLE XXXII-continued

| Example No. | Isomeric form | Position of the substituent R₂ amino | R₁ | R₂ | Urea Compound Yield % | MP °C. | $[\alpha]_D^{20}$ degree |
|---|---|---|---|---|---|---|---|
| 992 | α | 6 | Tetrahydrofurfuryl | n-Butyl | 47.6 | 98–100 | +50.2 |
| 993 | α | 6 | Tetrahydrofurfuryl | Isobutyl | 55.4 | 92–94 | +53.8 |
| 994 | α | 6 | Tetrahydrofurfuryl | sec-Butyl | 49.6 | 88–90 | +54.3 |
| 995 | α | 6 | 3-Methoxy-n-propyl | tert-Butyl | 51.2 | 102–104 | +50.4 |
| 996 | α | 2 | 3-Methoxy-n-propyl | " | 53.4 | 106–108 | +63.2 |
| 997 | α | 3 | 3-Methoxy-n-propyl | " | 48.6 | 81–83 | +33.6 |
| 998 | α | 4 | " | " | 37.5 | 91–93 | +48.5 |
| 999 | α | 6 | 1-Methoxy-2-methoxyethyl | " | 43.6 | 99–101 | +50.2 |
| 1000 | α | 6 | 1-Methoxy-2-methoxyethyl | Neopentyl | 45.7 | 104–106 | +48.7 |
| 1001 | α | 6 | 1-Methoxy-2-methoxyethyl | 3,3-Dimethyl-n-butyl | 44.8 | 93–95 | +46.4 |
| 1002 | α | 6 | 1-Methoxy-sec-butyl | tert-Butyl | 54.6 | 107–109 | +49.2 |
| 1003 | α | 6 | 1-Methoxy-sec-butyl | Neopentyl | 50.7 | 111–113 | +47.6 |
| 1004 | α | 6 | 1-Methoxy-sec-butyl | 3,3-Dimethyl-n-butyl | 48.3 | 100–102 | +45.3 |
| 1005 | α | 6 | 2-Ethoxyethyl | tert-Butyl | 52.7 | 95–97 | +49.6 |
| 1006 | α | 6 | 2-(2-Methoxyethoxy)ethyl | " | 47.6 | 90–92 | +47.2 |
| 1007 | α | 6 | 3-Methoxy-n-butyl | " | 48.5 | 103–105 | +48.1 |
| 1008 | α | 6 | Neopentyl | " | 51.3 | 112–114 | +60.4 |
| 1009 | α | 6 | 3,3-Dimethyl-n-butyl | " | 49.3 | 103–105 | +58.2 |
| 1010 | α | 6 | Neopentyl | 2-Butenyl | 47.5 | 106–108 | +58.4 |
| 1011 | α | 6 | 3,3-Dimethyl-n-butyl | " | 46.4 | 100–102 | +56.3 |
| 1012 | β | 6 | 2-Morpholinoethyl | Isobutyl | 59.6 | 92–94 | −14.6 |
| 1013 | β | 6 | 3-Morpholino-n-propyl | " | 47.8 | 85–86 | −13.8 |
| 1014 | β | 6 | 1-Morpholino-2-propyl | " | 40.4 | 83–86 | −14.2 |
| 1015 | β | 6 | 2-Piperidinoethyl | " | 45.3 | 100–102 | −16.4 |
| 1016 | β | 6 | 2-Piperidinoethyl | tert-Butyl | 49.6 | 106–108 | −17.8 |
| 1017 | β | 6 | 3-Morpholino-n-propyl | tert-Butyl | 48.7 | 93–95 | −14.0 |
| 1018 | β | 6 | 1-Morpholino-2-propyl | " | 44.3 | 90–92 | −14.5 |
| 1019 | β | 6 | 2-Morpholinoethyl | " | 56.6 | 96–98 | −14.7 |
| 1020 | β | 6 | 3-Cyclopentyl-n-propyl | Isobutyl | 51.4 | 91–93 | −17.9 |
| 1021 | β | 6 | 3-Cyclopentyl-n-propyl | tert-Butyl | 53.2 | 96–98 | −18.6 |
| 1022 | β | 6 | 2-Cyclohexylethyl | Isobutyl | 54.2 | 92–94 | −15.5 |
| 1023 | β | 6 | " | tert-Butyl | 47.5 | 99–101 | −16.4 |
| 1024 | β | 6 | α-Methylcyclopropylmethyl | Isobutyl | 43.6 | 78–80 | −18.6 |
| 1025 | β | 6 | α-Methylcyclopropylmethyl | tert-Butyl | 45.3 | 84–86 | −19.2 |
| 1026 | β | 6 | Cycloheptyl | Isobutyl | 56.2 | 86–89 | −17.4 |
| 1027 | β | 6 | " | tert-Butyl | 47.1 | 91–93 | −18.0 |
| 1028 | β | 6 | Cyclooctyl | Isobutyl | 53.5 | 97–99 | −14.6 |
| 1029 | β | 6 | " | tert-Butyl | 51.6 | 103–105 | −16.8 |
| 1030 | α | 6 |  | Isobutyl | 49.3 | 83–85 | +43.7 |
| 1031 | α | 6 |  | tert-Butyl | 52.4 | 89–91 | +45.6 |

TABLE XXXIII

| Example No. | Nitroso Compound Yield % | MP °C. | $[\alpha]_D^{20}$ degree |
|---|---|---|---|
| 886 | 51.4 | 86–88 | −16.2 |
| 887 | 48.7 | 73–75 | +76.7 |
| 888 | 49.2 | 93–95 (decomp.) | −14.1 |
| 889 | 50.4 | 91–93 (decomp.) | +74.2 |
| 890 | 52.5 | 109–111 (decomp.) | −17.5 |
| 891 | 61.3 | 107–109 (decomp.) | +80.3 |
| 892 | 42.5 | 83–85 | +52.4 |
| 893 | 39.7 | 95–97 (decomp.) | +70.3 |
| 894 | 59.1 | 83–85 | +76.2 |
| 895 | 54.6 | 104–106 (decomp.) | −14.8 |
| 896 | 60.7 | 94–96 (decomp.) | +77.6 |
| 897 | 58.9 | 115–117 (decomp.) | −19.2 |

TABLE XXXIII-continued

| Example No. | Nitroso Compound Yield % | MP °C. | $[\alpha]_D^{20}$ degree |
|---|---|---|---|
| 898 | 55.7 | 78–80 | +52.4 |
| 899 | 46.3 | 69–71 | +70.3 |
| 900 | 45.8 | 76–78 | +76.6 |
| 901 | 49.2 | 98–100 (decomp.) | −14.9 |
| 902 | 51.3 | 73–75 | +44.6 |
| 903 | 48.7 | 91–93 (decomp.) | +73.7 |
| 904 | 43.5 | 71–73 | +74.3 |
| 905 | 49.7 | 67–69 | +58.2 |
| 906 | 52.6 | 66–68 | +60.4 |
| 907 | 51.7 | 90–92 | −14.5 |
| 908 | 43.6 | 50–52 | +49.8 |
| 909 | 39.2 | 53–55 | +46.7 |
| 910 | 44.5 | 58–60 | +56.3 |
| 911 | 47.7 | 84–86 | +75.4 |
| 912 | 52.1 | 73–75 | +76.2 |
| 913 | 49.7 | 88–90 | +78.5 |
| 914 | 40.6 | 69–71 | +50.4 |
| 915 | 51.5 | 75–77 | +72.5 |
| 916 | 47.3 | 97–99 (decomp.) | −14.2 |
| 917 | 50.4 | 76–78 | +68.4 |
| 918 | 49.8 | 73–75 | +66.7 |
| 919 | 45.6 | 68–70 | +65.4 |
| 920 | 47.3 | 73–75 | +66.8 |
| 921 | 43.1 | 68–70 | +76.3 |
| 922 | 39.4 | 76–78 | +75.8 |
| 923 | 48.7 | 71–73 | +74.2 |
| 924 | 47.2 | 80–82 | +73.4 |
| 925 | 49.5 | 77–79 | +70.2 |
| 926 | 50.1 | 84–86 | +70.4 |
| 927 | 45.7 | 85–88 | +65.3 |
| 928 | 43.3 | 90–92 (decomp.) | +64.3 |
| 929 | 53.8 | 84–86 | +67.7 |
| 930 | 44.4 | 78–80 | +74.2 |
| 931 | 46.8 | 99–102 (decomp.) | −15.6 |
| 932 | 51.3 | 96–98 (decomp.) | +72.8 |
| 933 | 54.1 | 114–116 (decomp.) | −16.3 |
| 934 | 49.4 | 88–90 | +74.1 |
| 935 | 47.4 | 110–112 (decomp.) | −14.0 |
| 936 | 42.6 | 100–102 (decomp.) | +76.3 |
| 937 | 48.3 | 121–123 (decomp.) | −18.0 |
| 938 | 50.7 | 84–86 | +48.8 |
| 939 | 46.3 | 82–84 | +74.2 |
| 940 | 51.4 | 104–106 (decomp.) | −13.8 |
| 941 | 49.6 | 78–80 | +43.1 |
| 942 | 44.7 | 101–103 (decomp.) | −18.4 |
| 943 | 46.3 | 98–100 (decomp.) | +71.2 |
| 944 | 50.4 | 76–78 | +72.4 |
| 945 | 32.4 | 72–74 | +56.4 |
| 946 | 46.8 | 70–72 | +57.6 |
| 947 | 50.4 | 96–98 (decomp.) | −13.4 |
| 948 | 38.5 | 57–59 | +47.2 |
| 949 | 32.7 | 58–60 | +45.1 |
| 950 | 47.6 | 89–91 | +70.3 |
| 951 | 51.7 | 78–80 | +70.8 |
| 952 | 42.4 | 93–95 (decomp.) | +78.1 |
| 953 | 45.6 | 81–83 | +68.5 |
| 954 | 47.1 | 102–104 (decomp.) | −13.8 |
| 955 | 43.5 | 83–85 | +68.2 |
| 956 | 57.3 | 90–92 | +68.0 |
| 957 | 43.1 | 91–93 | +63.9 |
| 958 | 50.2 | 95–95 (decomp.) | +62.7 |
| 959 | 51.0 | 90–92 | +63.2 |
| 960 | 49.4 | 70–72 | +72.5 |
| 961 | 43.7 | 86–88 | −13.6 |
| 962 | 54.2 | 83–85 | +71.6 |
| 963 | 56.7 | 102–104 (decomp.) | −15.8 |
| 964 | 44.5 | 75–77 | +72.4 |
| 965 | 46.7 | 98–100 (decomp.) | −13.5 |
| 966 | 42.8 | 86–88 | +74.6 |
| 967 | 47.2 | 107–109 (decomp.) | −16.8 |
| 968 | 54.6 | 70–72 | +46.7 |
| 969 | 56.3 | 68–70 | +69.4 |
| 970 | 53.1 | 90–92 | −12.2 |
| 971 | 45.0 | 64–66 | +41.2 |
| 972 | 47.6 | 84–86 | −17.2 |
| 973 | 48.1 | 80–82 | +70.1 |
| 974 | 43.9 | 63–65 | +70.6 |
| 975 | 40.2 | 62–64 | +54.5 |
| 976 | 48.7 | 57–59 | +55.6 |
| 977 | 46.3 | 82–84 | −12.1 |
| 978 | 31.0 | 46–48 | +45.8 |
| 979 | 47.9 | 86–88 | +69.0 |
| 980 | 40.4 | 76–78 | +68.2 |
| 981 | 42.6 | 90–92 | +76.4 |
| 982 | 44.7 | 78–80 | +66.4 |
| 983 | 40.1 | 99–101 (decomp.) | −13.0 |
| 984 | 36.7 | 80–82 | +66.8 |
| 985 | 45.3 | 88–90 | +67.2 |
| 986 | 40.7 | 82–84 | +63.1 |
| 987 | 41.2 | 91–93 | +61.2 |
| 988 | 50.4 | 86–88 | +61.7 |
| 989 | 52.6 | 77–79 | +66.4 |
| 990 | 49.7 | 82–84 | +65.2 |
| 991 | 47.5 | 71–73 | +64.0 |
| 992 | 50.4 | 74–76 | +63.7 |
| 993 | 51.6 | 68–70 | +65.1 |
| 994 | 46.7 | 64–66 | +66.2 |
| 995 | 45.2 | 78–80 | +68.5 |
| 996 | 48.1 | 90–92 | +73.2 |
| 997 | 40.4 | 73–75 | +43.4 |
| 998 | 41.3 | 82–84 | +57.1 |
| 999 | 40.8 | 75–77 | +68.8 |
| 1000 | 40.1 | 80–82 | +67.2 |
| 1001 | 44.5 | 69–71 | +65.4 |
| 1002 | 50.6 | 82–84 | +69.2 |
| 1003 | 47.1 | 86–88 | +67.5 |
| 1004 | 43.6 | 74–76 | +63.8 |
| 1005 | 48.1 | 70–72 | +67.2 |
| 1006 | 44.6 | 65–67 | +65.4 |
| 1007 | 45.2 | 78–80 | +67.2 |
| 1008 | 52.8 | 88–90 | +74.6 |
| 1009 | 54.5 | 80–82 | +72.2 |
| 1010 | 46.1 | 82–84 | +70.4 |
| 1011 | 45.7 | 76–78 | +68.2 |
| 1012 | 52.3 | 76–78 | −8.4 |
| 1013 | 52.4 | 72–74 | −7.6 |
| 1014 | 51.6 | 70–72 | −7.7 |
| 1015 | 53.5 | 86–88 | −9.4 |
| 1016 | 48.1 | 92–94 (decomp.) | −10.4 |
| 1017 | 47.2 | 79–81 | −7.8 |
| 1018 | 50.1 | 76–78 | −8.0 |
| 1019 | 51.4 | 82–84 | −8.6 |
| 1020 | 52.3 | 76–78 | −10.6 |
| 1021 | 50.5 | 82–84 | −11.5 |
| 1022 | 46.7 | 78–80 | −9.0 |
| 1023 | 51.2 | 78–87 | −9.2 |
| 1024 | 48.0 | 64–66 | −11.3 |
| 1025 | 47.9 | 70–72 | −11.9 |
| 1026 | 40.4 | 72–74 | −10.4 |
| 1027 | 41.3 | 77–79 | −10.6 |
| 1028 | 50.2 | 83–85 | −8.0 |
| 1029 | 51.4 | 89–91 | −9.2 |
| 1030 | 40.2 | 60–62 | +57.8 |
| 1031 | 41.6 | 66–68 | +58.5 |

EXAMPLES 1032–1046

In the same manner as Example 67, vaious 3-$R_2$-3-($R_1$ α- or β-D-galactopyranose-6,2,3, or 4-yl)-1-(2-chloroethyl)ureas (urea compound) and 3-$R_2$-3-($R_1$ α- or β-D-galactopyranose-6,2,3, or 4-yl)-1-(2-chloroethyl)-1-nitrosoureas (nitroso compound) were prepared from corresponding starting materials $R_1$ 6-, 2-, 3-, or 4-($R_2$ amino)-6, 2,3, or 4-deoxy-α- or β-D-galactopyranosides. Tables XXXIV and XXXV show the $R_1$ and $R_2$ species and the yields, melting points, and specific rotations ($[\alpha]_D^{20}$ (C 1.0, methanol)) of the products.

TABLE XXXIV

| Example No. | Isomeric form | Position of the substituent R$_2$ amino | R$_1$ | R$_2$ | Urea Compound Yield % | MP °C. | $[\alpha]_D^{20}$ degree |
|---|---|---|---|---|---|---|---|
| 1032 | α | 6 | tert-Butyl | Isobutyl | 60.4 | 90–92 | +15.6 |
| 1033 | α | 6 | " | sec-Butyl | 58.6 | 85–87 | +15.3 |
| 1034 | α | 6 | " | 3-Ethoxy-n-propyl | 43.5 | 80–82 | +11.2 |
| 1035 | α | 6 | " | p-Methoxybenzyl | 44.6 | 110–112 | +6.4 |
| 1036 | α | 2 | " | " | 46.8 | 115–117 | +9.8 |
| 1037 | α | 3 | " | " | 40.2 | 98–100 | +7.1 |
| 1038 | α | 4 | " | " | 40.6 | 104–106 | +8.0 |
| 1039 | α | 6 | " | 2-Methoxy-n-propyl | 41.7 | 79–81 | +11.2 |
| 1040 | α | 6 | Neopentyl | Isobutyl | 57.6 | 97–99 | +14.8 |
| 1041 | α | 6 | " | sec-Butyl | 56.5 | 91–93 | +14.2 |
| 1042 | α | 6 | " | 1-Methoxy-sec-butyl | 42.6 | 94–96 | +9.7 |
| 1043 | α | 6 | " | 2-Methoxy-n-propyl | 40.1 | 86–88 | +10.4 |
| 1044 | α | 6 | Tetrahydrofurfuryl | tert-Butyl | 54.3 | 95–97 | +8.9 |
| 1045 | α | 6 | 3,3-Dimethyl-n-butyl | Isobutyl | 48.5 | 94–96 | +14.3 |
| 1046 | α |  | Cyclohexyl | tert-Butyl | 54.6 | 88–90 | +15.0 |

TABLE XXXV
Nitroso Compound

| Example No. | Yield % | MP °C. | $[\alpha]_D^{20}$ degree |
|---|---|---|---|
| 1032 | 51.2 | 73–75 | +22.4 |
| 1033 | 50.6 | 68–70 | +21.6 |
| 1034 | 45.4 | 65–67 | +16.8 |
| 1035 | 40.1 | 96–98 (decomp.) | +11.4 |
| 1036 | 46.7 | 104–106 (decomp.) | +15.6 |
| 1037 | 41.6 | 90–92 (decomp.) | +10.2 |
| 1038 | 35.7 | 94–96 (decomp.) | +11.3 |
| 1039 | 40.8 | 61–63 | +17.2 |
| 1040 | 53.4 | 79–81 | +21.8 |
| 1041 | 54.6 | 74–76 | +21.3 |
| 1042 | 41.0 | 76–78 | +15.7 |
| 1043 | 42.7 | 68–70 | +16.9 |
| 1044 | 52.3 | 78–80 | +17.5 |
| 1045 | 55.6 | 67–69 | +20.6 |
| 1046 | 49.4 | 71–73 | +21.4 |

EXAMPLES 1047–1061

In the same manner as Example 2, 3-R$_2$-3-(R$_1$ α-D-mannopyranose-6-yl)-1-(2-chloroethyl)-1-nitrosoureas were prepared from R$_1$ 6-(R$_2$ amino)-6-deoxy-α-D-mannopyranosides (Examples 1047–1053), 3-R$_2$-3-(R$_1$ α-D-altropyranose-6-yl)-1-(2-chloroethyl)-1-nitrosoureas from R$_1$ 6-(R$_2$ amino)-6-deoxy-α-D-altropyranosides (Examples 1054–1058), and 3-R$_2$-3-(R$_1$ α-D-talopyranose-6-yl)-1-(2-chloroethyl)-1-nitrosoureas from R$_1$ 6-(R$_2$ amino)-6-deoxy-α-D-talopyranosides (Examples 1059–1061). Table XXXVI shows the R$_1$ and R$_2$ species and the yields, melting points, and specific rotations ($[\alpha]_D^{20}$ (C 1.0, methanol)) of the products.

TABLE XXXVI

| Example No. | Nitroso Compound R$_1$ | R$_2$ | Yield % | MP °C. | $[\alpha]_D^{20}$ degree |
|---|---|---|---|---|---|
| 1047 | tert-Butyl | Isobutyl | 64.1 | 65–67 | +22.3 |
| 1048 | " | sec-Butyl | 63.4 | 59–62 | +21.7 |
| 1049 | " | 1-Methyl-sec-butyl | 54.6 | 64–66 | +20.2 |
| 1050 | " | 2-Methoxyethyl | 43.8 | 57–59 | +19.4 |
| 1051 | Neopentyl | Isobutyl | 56.4 | 73–75 | +21.8 |
| 1052 | " | sec-Butyl | 58.9 | 67–69 | +20.5 |
| 1053 | " | 1-Methyl-2-methoxyethyl | 47.5 | 58–60 | +18.4 |
| 1054 | tert-Butyl | 1-Methyl-2-methoxyethyl | 43.6 | 65–67 | +17.8 |
| 1055 | " | Tetrahydrofurfuryl | 51.7 | 60–62 | +17.6 |
| 1056 | " | Cyclohexyl | 53.4 | 71–73 | +18.4 |
| 1057 | Neopentyl | Isobutyl | 53.6 | 72–74 | +21.0 |
| 1058 | " | 3-Methoxy-n-propyl | 48.7 | 67–69 | +20.1 |
| 1059 | tert-Butyl | Isobutyl | 52.4 | 64–66 | +19.2 |
| 1060 | " | Tetrahydrofurfuryl | 57.3 | 60–62 | +16.4 |
| 1061 | Neopentyl | Isobutyl | 53.6 | 70–72 | +18.3 |

EXAMPLES 1062–1069

In the same manner as Example 2, 3-R$_2$-3-(R$_1$ α-D-xylopyranose-6-yl)-1-(2-chloroethyl)-1-nitrosoureas were prepared from R$_1$ 6- or 4-(R$_2$ amino)-6 or 4-deoxy-α-D-xylopyranosides (Examples 1062 and 1063), 3-R$_2$-3-(R$_1$ α-D-xylopyranose-4-yl)-1-(2-chloroethyl)-1-nitrosoureas from R$_1$ 4-(R$_2$ amino)-4-deoxy-α-D-xylopyranosides (Examples 1064 and 1065), 3-R$_2$-(R$_1$ α-L-arabinopyranose-2-yl)-1-(2-chloroethyl)-1-nitrosoureas from R$_1$ 2-(R$_2$ amino)-2-deoxy-α-L-arabinopyranosides (Examples 1066 and 1067), and 3-R$_2$-3-(R$_1$ α-L-arabinopyranose-4-yl)-1-(2-chloroethyl)-1-nitrosoureas from R$_1$ 4-(R$_2$amino)-4-deoxy-α-L-arabinopyranosides (Examples 1068 and 1069). Table XXXVII shows the R$_1$ and R$_2$ species and the yields, melting points, and specific rotations ($[\alpha]_D^{20}$ (C 1.0, methanol)) of the products.

TABLE XXXVII

| Example No. | Nitroso Compound R$_1$ | R$_2$ | Yield % | MP °C. | $[\alpha]_D^{20}$ degree |
|---|---|---|---|---|---|
| 1062 | tert-Butyl | Isobutyl | 51.4 | 68–70 | +18.8 |
| 1063 | " | Tetrahydrofurfuryl | 42.0 | 64–66 | +17.9 |
| 1064 | " | Isobutyl | 48.7 | 62–64 | +17.4 |

TABLE XXXVII-continued

| | Nitroso Compound | | | | |
|---|---|---|---|---|---|
| Example No. | $R_1$ | $R_2$ | Yield % | MP °C. | $[\alpha]_D^{20}$ degree |
| 1065 | Neopentyl | " | 49.2 | 74–76 | +16.7 |
| 1066 | tert-Butyl | " | 50.7 | 80–82 | +83.4 |
| 1067 | Neopentyl | 3-Methoxy-n-propyl | 41.3 | 81–83 | +81.2 |
| 1068 | tert-Butyl | Tetrahydrofurfuryl | 43.1 | 75–77 | +60.5 |
| 1069 | Neopentyl | Isobutyl | 50.6 | 79–81 | +62.4 |

What is claimed is:

1. A compound of the structural formula $$\begin{array}{c} \text{CHX} \overset{O}{\diagup}\diagdown \\ \diagdown \quad \quad \text{---}OR_{11} \\ \text{CHY}\text{---}(\text{CHY})_n \end{array} \quad (I)$$

wherein n is 1 or 2;

X is $CH_2Y$ where n is 1, and

X is $CH_2Y$ or H where n is 2, and one of the radicals Y is Z and all other radicals Y are OH;

$$Z \text{ is } -NR_{12}-\underset{\underset{NO}{|}}{CON}-CH_2-CH_2Cl;$$

$R_{11}$ is a $C_2$–$C_4$ linear or $C_3$–$C_4$ branched alkyl substituted by $C_1$–$C_4$ alkoxy, methoxymethoxy, methoxyethoxy, or hydroxyethoxy radicals;

$C_{3-8}$ cycloalkyl;

$C_{1-3}$ alkyl substituted with $C_{3-8}$ cycloalkyl groups;

benzyl;

benzyl having 1 to 3 substituents selected from the group consisting of $C_{1-4}$ alkyl, $C_{1-4}$ alkoxy and cyclopropyl;

phenethyl;

tetrahydrofurfuryl, furfuryl;

morpholinoethyl, morpholinopropyl;

pieridinoethyl; and $R_{12}$ is a $C_1$–$C_{10}$ linear or $C_{3-10}$ branched alkyl;

$C_3$–$C_5$ linear or branched alkenyl or alkynyl;

$C_{3-6}$ hydroxyalkyl;

$C_{2-4}$ linear or $C_{3-4}$ branched alkyl substituted by $C_{1-4}$ alkoxy or $C_{1-4}$ hydroxyalkoxy;

$C_{3-8}$ cycloalkyl;

$C_{1-3}$ alkyl substituted by a $C_{3-8}$ cycloalkyl radical;

benzyl, chlorobenzyl;

benzyl having 1 to 3 substituents selected from the group consisting of $C_{1-4}$ alkyl and $C_{1-4}$ alkoxy;

tetrahydrofurfuryl;

furfuryl;

morpholino;

morpholino ethyl;

morpholinopropyl;

thiophen-2-yl-methyl;

pyridylethyl; and piperidinoethyl.

2. A compound of claim 1, which is a compound of D- or L-aldohexopyranose, D- or L-aldopentopyranose, or D- or L-aldopentofuranose.

3. A compound of claim 1, wherein $R_{11}$ and $R_{12}$ are defined as in claim 1, which is 3-($R_{12}$)-3-($R_{11}$D-glucopyranose-6-yl)-1-(2-chloroethyl)-1-nitrosourea, 3-($R_{12}$)-3-($R_{11}$D-glucopyranose-2-yl)-1-(2-chloroethyl)-1-nitrosourea, 3-($R_{12}$)-3-($R_{11}$D-glucopyranose-3-yl)-1-(2-chloroethyl)-1-nitrosourea, 3-($R_{12}$)-3-($R_{11}$D-glucopyranose-4-yl)-1-(2-chloroethyl)-1-nitrosourea, 3-($R_{12}$)-3-($R_{11}$D-galactopyranose-6-yl)-1-(2-chloroethyl)-1-nitrosourea, 3-($R_{12}$)-3-($R_{11}$D-galactopyranose-2-yl)-1-(2-chloroethyl)-1-nitrosourea, 3-($R_{12}$)-3-($R_{11}$D-galactopyranose-3-yl)-1-(2-chloroethyl)-1-nitrosourea, 3-($R_{12}$)-3-($R_{11}$D-galactopyranose-4-yl)-1-(2-chloroethyl)-1-nitrosourea, 3-($R_{12}$)-3-($R_{11}$L-galactopyranose-6-yl)-1-(2-chloroethyl)-1-nitrosourea, 3-($R_{12}$)-3-($R_{11}$L-galactopyranose-2-yl)-1-(2-chloroethyl)-1-nitrosourea, 3-($R_{12}$)-3-($R_{11}$D-mannopyranose-6-yl)-1-(2-chloroethyl)-1-nitrosourea, 3-($R_{12}$)-3-($R_{11}$D-mannopyranose-4-yl)-1-(2-chloroethyl)-1-nitrosourea, 3-($R_{12}$)-3-($R_{11}$D-altropyranose-6-yl)-1-(2-chloroethyl)-1-nitrosourea, 3-($R_{12}$)-3-($R_{11}$D-altropyranose-2-yl)-1-(2-chloroethyl)-1-nitrosourea, 3-($R_{12}$)-3-($R_{11}$D-altropyranose-3-yl)-1-(2-chloroethyl)-1-nitrosourea, 3-($R_{12}$)-3-($R_{11}$D-talopyranose-6-yl)-1-(2-chloroethyl)-1-nitrosourea, 3-($R_{12}$)-3-($R_{11}$D-talopyranose-4-yl)-1-(2-chloroethyl)-1-nitrosourea;

3-($R_{12}$)-3-($R_{11}$D-xylopyranose-3-yl)-1-(2-chloroethyl)-1-nitrosourea, 3-($R_{12}$)-3-($R_{11}$D-xylopyranose-4-yl)-1-(2-chloroethyl)-1-nitrosourea, 3-($R_{12}$)-3-($R_{11}$D-arabopyranose-2-yl)-1-(2-chloroethyl)-1-nitrosourea, 3-($R_{12}$)-3-($R_{11}$D-arabopyranose-4-yl)-1-(2-chloroethyl)-1-nitrosourea, 3-($R_{12}$)-3-($R_{11}$L-arabopyranose-2-yl)-1-(2-chloroethyl)-1-nitrosourea, 3-($R_{12}$)-3-($R_{11}$L-arabopyranose-4-yl)-1-(2-chloroethyl)-1-nitrosourea, 3-($R_{12}$)-3-($R_{11}$D-ribofuranose-5-yl)-1-(2-chloroethyl)-1-nitrosourea, 3-($R_{12}$)-3-($R_{11}$L-lyxofuranose-5-yl)-1-(2-chloroethyl)-1-nitrosourea, 3-($R_{12}$)-3-($R_{11}$D-arabofuranose-5-yl)-1-(2-chloroethyl)-1-nitrosourea, 3-($R_{12}$)-3-($R_{11}$D-arabofuranose-2-yl)-1-(2-chloroethyl)-1-nitrosourea, 3-($R_{12}$)-3-($R_{11}$D-arabofuranose-3-yl)-1-(2-chloroethyl)-1-nitrosourea, 3-($R_{12}$)-3-($R_{11}$D-xylofuranose-5-yl)-1-(2-chloroethyl)-1-nitrosourea, 3-($R_{12}$)-3-($R_{11}$D-xylofuranose-2-yl)-1-(2-chloroethyl)-1-nitrosourea, 3-($R_{12}$)-3-($R_{11}$D-xylofuranose-3-yl)-1-(2-chloroethyl)-1-nitrosourea.

4. A compound of claim 1, 2 or 3, wherein $R_{11}$ is a radical selected from the group consisting of 2-propenyl, 2-butenyl, 3-butenyl, and 2-methyl-2-propenyl.

5. A compound of claim 1, 2 or 3, wherein $R_{11}$ is a radical selected from the group consisting of 2-propynyl, 2-n-butynyl, and 2-methyl-3-n-butynyl.

6. A compound of claim 1, 2 or 3, wherein $R_{11}$ is a radical selected from the group consisting of 2-methoxyethyl, 2-methoxy-n-propyl, 3-methoxy-n-propyl, 2,2-dimethoxyethyl, 1-methyl-2-methoxyethyl, 2-(2-methoxy-ethoxy)ethyl, 2,3-dimethoxy-n-propyl, 2-ethoxyethyl, 3-ethoxy-n-propyl, and 2-methoxy-n-butyl.

7. A compound of claim 1, 2 or 3, wherein $R_{11}$ is a radical selected from the group consisting of cyclopropylmethyl, 1-cyclopropylethyl, 2-cyclopentylethyl, 3-cyclopentyl-n-propyl, cyclohexylmethyl, 2-cyclohexylethyl, cyclopropyl, cyclopentyl, cyclohexyl, cycloheptyl, and cyclooctyl.

8. A compound of claim 1, 2 or 3, wherein $R_{11}$ is a radical selected from the group consisting of benzyl, α-methylbenzyl, α-ethylbenzyl, phenethyl, p-methylbenzyl, p-n-propylbenzyl, 2,4,6-trimethylbenzyl, p-methoxybenzyl, p-ethoxybenzyl, 2,3-dimethoxybenzyl, 3,4,5-trimethoxybenzyl, and α-cyclopropylbenzyl.

9. A compound of claim 1, 2 or 3, wherein $R_{11}$ is a radical selected from the group consisting of tetrahydrofurfuryl, furfuryl, 2-morpholinoethyl, 3-morpholinopropyl, 1-morpholino isopropyl, and 2-piperidinoethyl.

10. A compound of claim 1, 2 or 3, wherein $R_{12}$ is a radical selected from the group consisting of methyl, ethyl, n-propyl, n-butyl, n-pentyl, n-hexyl, n-octyl, and n-decyl.

11. A compound of claim 1, 2 or 3, wherein $R_{12}$ is a radical selected from the group consisting of isopropyl, isobutyl, sec-butyl, tert-butyl, isopentyl, neopentyl, 3,3-dimethyl-n-butyl, and 2-ethylhexyl.

12. A compound of claim 1, 2 or 3, wherein $R_{12}$ is a radical selected from the group consisting of 2-propenyl, 2-methyl-2-propenyl, 2-butenyl and 3-butenyl.

13. A compound of claim 1, 2 or 3, wherein $R_{12}$ is a radical selected from the group consisting of 2-propynyl, 2-n-butynyl, and n-methyl-3-n-butynyl.

14. A compound of claim 1, 2 or 3, wherein $R_{12}$ is a radical selected from the group consisting of 2-methoxyethyl, 2-methoxy-n-propyl, 3-methoxy-n-propyl, 1-methyl-2-methoxyethyl, 2-ethoxyethyl, 3-ethoxy-n-propyl, 2,2-dimethoxy-ethyl, 2,2-diethoxyethyl, 2-(2-hydroxyethoxy)ethyl, 3-isopropyloxy-n-propyl, and 1-methoxy-2-butyl.

15. A compound of claim 1, 2 or 3, wherein $R_{12}$ is a radical selected from the group consisting of 2-hydroxy-1-methylethyl, 2,2-dimethyl-3-hydroxy-n-propyl, 2-(2-hydroxyethoxy)ethyl, 2-hydroxy-n-propyl, 3-hydroxy-n-propyl, 1-hydroxy-n-butyl, 2-hydroxy-n-butyl, and 4-hydroxy-n-butyl.

16. A compound of claim 1, 2 or 3, wherein $R_{12}$ is a radical selected from the group consisting of cyclopropylmethyl, cyclopentylethyl, cyclohexylmethyl, cyclopropyl, cyclopentyl, cyclohexyl, cycloheptyl, and cyclooctyl.

17. A compound of claim 1, 2 or 3, wherein $R_{12}$ is a radical selected from the group consisting of benzyl, 1-phenylethyl, p-methylbenzyl, 2,4,6-trimethylbenzyl, p-ethylbenzyl, p-methoxybenzyl, p-ethoxybenzyl, 2,3-dimethoxybenzyl, 3,4,5-trimethoxybenzyl, and p-chlorobenzyl.

18. A compound of claim 1, 2 or 3, wherein $R_{12}$ is a radical selected from the group consisting of tetrahydrofurfuryl, furfuryl, thiophene-2-yl-methyl, morpholino, 2-morpholinoethyl, 3-morpholinopropyl, 2-piperidinoethyl, and 2-(4-pyridyl)ehtyl.

* * * * *